US011633488B2

(12) United States Patent
Pattabiraman et al.

(10) Patent No.: US 11,633,488 B2
(45) Date of Patent: Apr. 25, 2023

(54) MODIFIED IL-2 POLYPEPTIDES AND USES THEREOF

(71) Applicant: Bright Peak Therapeutics AG, Basel (CH)

(72) Inventors: Vijaya Raghavan Pattabiraman, Basel (CH); Roberto Iacone, Basel (CH); Jean-Philippe Carralot, Basel (CH); Matilde Arévalo-Ruiz, Basel (CH); Jeffrey William Bode, Basel (CH); Alexander Mayweg, Basel (CH); Fränzi Weibel, Basel (CH); Anna Haydn, Basel (CH); Régis Boehringer, Basel (CH); Görkem Kurtuldu Sahin, Basel (CH); Claudia Fetz, Basel (CH); Camille Delon, Basel (CH); Eric Armentani, Basel (CH); Alexander Flohr, Basel (CH); Giorgio Ottaviani, Basel (CH)

(73) Assignee: Bright Peak Therapeutics AG, Basel (CH)

(*) Notice: Subject to any disclaimer, the term of this patent is extended or adjusted under 35 U.S.C. 154(b) by 91 days.

(21) Appl. No.: 17/144,537

(22) Filed: Jan. 8, 2021

(65) Prior Publication Data
US 2021/0252157 A1 Aug. 19, 2021

Related U.S. Application Data

(60) Provisional application No. 62/959,382, filed on Jan. 10, 2020.

(51) Int. Cl.
*A61K 38/20* (2006.01)
*A61K 47/60* (2017.01)

(52) U.S. Cl.
CPC .......... *A61K 47/60* (2017.08); *A61K 38/2013* (2013.01)

(58) Field of Classification Search
CPC .............................. A61K 38/20; A61K 47/60
See application file for complete search history.

(56) References Cited

U.S. PATENT DOCUMENTS

| | | |
|---|---|---|
| 6,689,353 B1 | 2/2004 | Wang et al. |
| 6,906,170 B1 | 6/2005 | Lider et al. |
| 7,186,804 B2 | 3/2007 | Gillies et al. |
| 7,507,406 B2 | 3/2009 | Gilles et al. |
| 7,517,526 B2 | 4/2009 | Gilles et al. |
| 7,569,215 B2 | 8/2009 | Wittrup et al. |
| 7,667,076 B2 | 2/2010 | Bode et al. |
| 7,888,071 B2 | 2/2011 | Gillies et al. |
| 8,012,465 B2 | 9/2011 | Elias et al. |
| 8,906,356 B2 | 12/2014 | Wittrup et al. |
| 9,206,243 B2 | 12/2015 | Leon et al. |
| 9,266,938 B2 | 2/2016 | Ast et al. |
| 9,428,567 B2 | 8/2016 | Garcia et al. |
| 9,732,134 B2 | 8/2017 | Gavin et al. |
| 9,844,582 B2 | 12/2017 | Wittrup et al. |
| 9,861,705 B2 | 1/2018 | Bossard et al. |
| 10,035,836 B1 | 7/2018 | Greve |
| 10,150,802 B2 | 12/2018 | Garcia et al. |
| 10,294,287 B2 | 5/2019 | Greve |
| 2017/0204154 A1 | 7/2017 | Greve |
| 2017/0313753 A1 | 11/2017 | Gavin et al. |
| 2017/0367981 A1 | 12/2017 | Little et al. |
| 2018/0125941 A1 | 5/2018 | Greve |
| 2018/0200338 A1 | 7/2018 | Umana et al. |
| 2018/0228842 A1 | 8/2018 | Garcia et al. |
| 2018/0326010 A1 | 11/2018 | Codarri Deak et al. |
| 2018/0340014 A1 | 11/2018 | Viney et al. |
| 2018/0344810 A1 | 12/2018 | Addepalli et al. |
| 2019/0023760 A1 | 1/2019 | Bode et al. |
| 2019/0054145 A1 | 2/2019 | Wittrup et al. |
| 2019/0062395 A1 | 2/2019 | Merchant et al. |
| 2019/0077881 A1 | 3/2019 | Ast et al. |
| 2019/0083635 A1 | 3/2019 | Xie et al. |
| 2019/0241638 A1 | 8/2019 | Bernett et al. |
| 2019/0248860 A1 | 8/2019 | Garcia et al. |
| 2020/0317787 A1 | 10/2020 | Li et al. |
| 2020/0330601 A1 | 10/2020 | Ptacin et al. |

(Continued)

FOREIGN PATENT DOCUMENTS

| | | |
|---|---|---|
| EP | 0405467 A2 | 1/1991 |
| EP | 1076704 B1 | 1/2007 |

(Continued)

OTHER PUBLICATIONS

Asahina, Yuya, et al., "Chemical Synthesis of O-Glycosylated Human Interleukin-2 by the Reverse Polarity Protection Strategy," Angewandte Chemie International Edition 54.28, 2015, pp. 8226-8230.

Harmand, Thibault J., et al., "Protein chemical synthesis by α-ketoacid-hydroxylamine ligation," *Nature Protocols*, vol. 11, No. 6, May 26, 2016, pp. 1130-1147.

Ju, Grace, et al., "Structure-Function Analysis of Human Interleukin-2. Identification of Amino Acid Residues Required for Biological Activity," *Journal of Biological Chemistry*, vol. 262, Issue 12, Apr. 25, 1987, pp. 5723-5731.

(Continued)

Primary Examiner — Prema M Mertz
(74) Attorney, Agent, or Firm — Eversheds Sutherland (US) LLP

(57) ABSTRACT

The present disclosure relates to modified IL-2 polypeptides, compositions comprising modified IL-2 polypeptides, methods of making the same, and methods of using the modified IL-2 polypeptides for treatment of diseases. In one aspect, the disclosure relates to the treatment of cancer using the modified IL-2 polypeptides. In some embodiments, the disclosed IL-2 polypeptides exhibit preferential binding characteristics to IL-2 receptor βγ complex (IL-2Rβ) over IL-2 receptor αβγ complex (IL-2Rα). In some embodiments, the molecular weight distribution of the modified IL-2 polypeptides is monodispersed.

20 Claims, 25 Drawing Sheets

Specification includes a Sequence Listing.

(56) References Cited

U.S. PATENT DOCUMENTS

| | | |
|---|---|---|
| 2021/0046160 A1 | 2/2021 | Ptacin et al. |
| 2021/0221863 A1 | 7/2021 | Kang et al. |
| 2021/0340207 A1 | 11/2021 | Abrahams et al. |
| 2022/0056093 A1 | 2/2022 | Chen et al. |

FOREIGN PATENT DOCUMENTS

| | | |
|---|---|---|
| EP | 1370280 B1 | 6/2010 |
| EP | 2723380 A4 | 10/2015 |
| EP | 3180020 A4 | 1/2018 |
| EP | 3508496 A1 | 7/2019 |
| EP | 3280725 B1 | 8/2020 |
| WO | WO2005016969 A2 | 2/2005 |
| WO | WO2012065086 A1 | 5/2012 |
| WO | WO-2016025642 A1 | 2/2016 |
| WO | WO-2016025645 A1 | 2/2016 |
| WO | WO-2018091003 A1 | 5/2018 |
| WO | WO-2018089669 A3 | 6/2018 |
| WO | WO-2018119114 A1 | 6/2018 |
| WO | WO-2018189220 A1 | 10/2018 |
| WO | WO2019028419 A1 | 2/2019 |
| WO | WO-2019028419 A1 | 2/2019 |
| WO | WO-2019028425 A1 | 2/2019 |
| WO | WO-2019036031 A3 | 5/2019 |
| WO | WO-2019104092 A1 | 5/2019 |
| WO | WO-2019112852 A1 | 6/2019 |
| WO | WO2019125732 A1 | 6/2019 |
| WO | WO2019173832 A2 | 9/2019 |
| WO | WO2019226538 A1 | 11/2019 |
| WO | WO2020057646 A1 | 3/2020 |
| WO | WO2020233515 A1 | 11/2020 |
| WO | WO2020252421 A2 | 12/2020 |
| WO | WO2021030374 A1 | 2/2021 |
| WO | WO2021030633 A1 | 2/2021 |
| WO | WO2021119516 A1 | 6/2021 |
| WO | WO2021236474 A1 | 11/2021 |
| WO | WO2022140797 A1 | 6/2022 |
| WO | WO2022159771 A1 | 7/2022 |

OTHER PUBLICATIONS

Levin, Aron M., et al., "Exploiting a natural conformational switch to engineer an interieukin-2 'superkine'," *Nature*, vol. 484, Apr. 26, 2012, pp. 529-533.

Murar, Claudia Elena. *Chemical Synthesis of Betrophin, Interleukin-2 and Protein Aldehydes by α-Ketoacid-Hydroxylamine (KAHA) Ligation*. ETH Zurich University, Ph.D. Thesis, 2017, 338 pages.

International Search Report from PCT/IB2021/000004, dated Jun. 7, 2021 (8 pages).

Klein, Christian, et al. "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines." *Oncoimmunology*, vol. 6, No. 3, Jan. 11, 2017.

Gillies, Stephen D., et al. "An anti-CD20-IL-2 immunocytokine is highly efficacious in a SCID mouse model of established human B lymphoma." *Blood*, vol. 105, No. 10, May 15, 2005: 3972-3978.

Wang, Xingxing, et al. "T Cell-Signaling-Responsive Conjugate of Antibody with siRNA to Overcome Acquired Resistance to anti-PD-1 Immunotherapy." *Advanced Therapeutics*, vol. 5, No. 1, Oct. 5, 2021: 2100161.

Chen, Xi, et al. "Therapeutic efficacy of an anti-PD-L1 antibody based immunocytokine in a metastatic mouse model of colorectal cancer." *Biochemical and biophysical research communications*, vol. 480, No. 2, Oct. 5, 2016: 160-165.

Dougan, Michael, and Stephanie K. Dougan. "Targeting immunotherapy to the tumor microenvironment." *Journal of cellular biochemistry*, 118.10. Nov. 2016: 3049-3054.

Marusic, Carla, et al. "N-glycan engineering of a plant-produced anti-CD20-hIL-2 immunocytokine significantly enhances its effector functions." *Biotechnology and bioengineering* 115.3, Nov. 20, 2017: 565-576.

Singh, Harjeet et al. "Combining adoptive cellular and immunocytokine therapies to improve treatment of B-lineage malignancy." *Cancer Research*, 67.6 Mar. 15, 2007: 2872-2880.

Stauber, Deborah J., et al. "Crystal structure of the IL-2 signaling complex: paradigm for a heterotrimeric cytokine receptor." *Proceedings of the National Academy of Sciences*, vol. 103, No. 8, Feb. 21, 2006: 2788-2793.

International Search Report for PCT/IB2022/056361, dated Oct. 18, 2022, 8 pages.

International Search Report for PCT/IN2022/056364, dated Oct. 10, 2022. 4 pages.

Invitation to Pay Additional Fees and Partial International Search Report for PCT/IB2022/056363, dated Oct. 5, 2022, 38 pages.

International Search Report and Written Opinion for PCT/IB2022056362, dated Oct. 26, 2022, 32 pages.

SEQUENCE LISTING

```
<160> NUMBER OF SEQ ID NOS: 23

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

```
<210> SEQ ID NO 2
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 3
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30
```

```
Asn Pro Lys Leu Thr Arg Leu Leu Ser Tyr Lys Phe Tyr Leu Pro Lys
            35                  40                  45

Lys Ala Thr Glu Leu Lys His Leu Gln Cys Leu Glu Glu Leu Lys
     50                  55                  60

Pro Leu Glu Glu Val Leu Ser Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 4
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 4

Ala Pro Thr Ser Ser Ser Thr Lys Lys Thr Gln Leu Gln Leu Glu His
 1               5                  10                  15

Leu Leu Leu Asp Leu Gln Leu Ile Leu Asn Gly Ile Asn Asn Tyr Lys
                20                  25                  30

Asn Pro Lys Leu Thr Arg Leu Leu Ser Phe Lys Phe Tyr Leu Pro Lys
            35                  40                  45

Lys Ala Thr Glu Leu Lys His Leu Gln Cys Leu Glu Glu Leu Lys
     50                  55                  60

Pro Leu Glu Glu Val Leu Ser Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
                100                 105                 110

Thr Ile Val Glu Phe Leu Asn Arg Trp Ile Thr Phe Ser Gln Ser Ile
```

```
                     115                 120                 125

Ile Ser Thr Leu Thr
        130

<210> SEQ ID NO 5
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30

Asn Pro Lys Leu Thr Arg Leu Leu Ser Tyr Lys Phe Tyr Leu Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Ser Tyr Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 6
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
```

```
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30

Asn Pro Lys Leu Thr Arg Leu Leu Ser Phe Lys Phe Tyr Leu Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Ser Tyr Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 7
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
```

```
<221> NAME/KEY: MOD_RES
<222> LOCATION: (104)..(104)
<223> OTHER INFORMATION: Hse

<400> SEQUENCE: 7

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
                20                  25                  30

Asn Pro Lys Leu Thr Arg Leu Leu Ser Tyr Lys Phe Tyr Leu Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Ser Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 8
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 8

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
                20                  25                  30

Asn Pro Lys Leu Thr Arg Leu Leu Ser Tyr Lys Phe Tyr Leu Pro Lys
            35                  40                  45

Lys Ala Thr Glu Leu Lys His Leu Gln Cys Leu Glu Glu Glu Leu Lys
        50                  55                  60
```

```
Tyr Leu Glu Glu Val Leu Ser Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 9
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 9

Ala Pro Thr Ser Ser Ser Thr Lys Lys Thr Gln Leu Gln Leu Glu His
 1               5                  10                  15

Leu Leu Leu Asp Leu Gln Leu Ile Leu Asn Gly Ile Asn Asn Tyr Lys
                 20                  25                  30

Asn Pro Lys Leu Thr Arg Leu Leu Ser Phe Lys Phe Tyr Leu Pro Lys
             35                  40                  45

Lys Ala Thr Glu Leu Lys His Leu Gln Cys Leu Glu Glu Glu Leu Lys
    50                  55                  60

Tyr Leu Glu Glu Val Leu Ser Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

```
<210> SEQ ID NO 10
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30

Asn Pro Lys Leu Thr Tyr Leu Leu Ser Tyr Lys Phe Tyr Leu Pro Lys
        35                  40                  45

Lys Ala Thr Glu Leu Lys His Leu Gln Cys Leu Glu Glu Tyr Leu Lys
    50                  55                  60

Tyr Leu Glu Glu Val Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 11
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
```

```
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 11
```

Ala Pro Thr Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
                20                  25                  30

Asn Pro Lys Leu Thr Arg Leu Leu Ser Phe Lys Phe Tyr Leu Pro Lys
            35                  40                  45

Lys Ala Thr Glu Leu Lys His Leu Gln Cys Leu Glu Glu Tyr Leu Lys
50                  55                  60

Tyr Leu Glu Glu Val Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

```
<210> SEQ ID NO 12
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 12
```

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30

Asn Pro Lys Leu Thr Arg Leu Leu Ser Phe Lys Phe Tyr Leu Pro Lys
        35                  40                  45

Lys Ala Thr Glu Leu Lys His Leu Gln Cys Leu Glu Glu Tyr Leu Lys
    50                  55                  60

Pro Leu Glu Glu Val Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 13
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 13

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30

Asn Pro Lys Leu Thr Arg Leu Leu Ser Phe Tyr Phe Tyr Leu Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

```
Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 14
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 14

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30

Asn Pro Lys Leu Thr Arg Leu Leu Ser Phe Lys Tyr Tyr Leu Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 15
<211> LENGTH: 133
<212> TYPE: PRT
<213> ORGANISM: Artificial Sequence
<220> FEATURE:
<223> OTHER INFORMATION: Description of Artificial Sequence: Synthetic
```

```
              polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 15

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
                20                  25                  30

Asn Pro Tyr Leu Thr Arg Leu Leu Ser Phe Lys Phe Tyr Leu Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 16
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
```

```
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 16

Ala Pro Thr Ser Ser Ser Thr Lys Lys Thr Gln Leu Gln Leu Glu Tyr
1               5                   10                  15

Leu Leu Leu Asp Leu Gln Leu Ile Leu Asn Gly Ile Asn Asn Tyr Lys
            20                  25                  30

Asn Pro Lys Leu Thr Arg Leu Leu Ser Phe Lys Phe Tyr Leu Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 17
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 17

Ala Pro Thr Ser Ser Ser Thr Lys Lys Thr Gln Leu Gln Leu Glu Tyr
1               5                   10                  15

Leu Leu Leu Asp Leu Gln Leu Ile Leu Asn Gly Ile Asn Asn Tyr Lys
            20                  25                  30
```

-continued

```
Asn Pro Lys Leu Thr Arg Leu Leu Ser Tyr Lys Phe Tyr Leu Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Ser Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Ser Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130
```

<210> SEQ ID NO 18
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 18

```
Ala Pro Thr Ser Ser Ser Thr Lys Lys Thr Gln Leu Gln Leu Glu His
 1               5                  10                  15

Leu Leu Leu Tyr Leu Gln Leu Ile Leu Asn Gly Ile Asn Asn Tyr Lys
             20                  25                  30

Asn Pro Lys Leu Thr Arg Leu Leu Ser Phe Lys Phe Tyr Leu Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Ser Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Ser Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125
```

```
Ile Ser Thr Leu Thr
        130

<210> SEQ ID NO 19
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 19

Ala Pro Thr Ser Ser Thr Lys Lys Thr Gln Leu Gln Leu Glu His
1               5                   10                  15

Leu Leu Leu Tyr Leu Gln Leu Ile Leu Asn Gly Ile Asn Asn Tyr Lys
                20                  25                  30

Asn Pro Lys Leu Thr Arg Leu Leu Ser Tyr Lys Phe Tyr Leu Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 20
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
```

<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 20

Ala Pro Thr Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30

Asn Pro Tyr Leu Thr Arg Leu Leu Ser Tyr Lys Phe Tyr Leu Pro Lys
        35                  40                  45

Lys Ala Thr Glu Leu Lys His Leu Gln Cys Leu Glu Glu Glu Leu Lys
50                  55                  60

Pro Leu Glu Glu Val Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 21
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES

```
<222> LOCATION: (104)..(104)
<223> OTHER INFORMATION: Hse

<400> SEQUENCE: 21

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30

Asn Pro Lys Leu Thr Arg Leu Leu Ser Tyr Lys Phe Tyr Leu Pro Lys
        35                  40                  45

Lys Ala Thr Glu Leu Lys His Leu Gln Cys Leu Glu Glu Tyr Leu Lys
    50                  55                  60

Pro Leu Glu Glu Val Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 22
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Leu Ile Leu Asn Gly Ile Asn Asn Tyr Lys
            20                  25                  30

Asn Pro Lys Leu Thr Arg Leu Leu Ser Tyr Lys Phe Tyr Leu Pro Lys
        35                  40                  45

Lys Ala Thr Glu Leu Lys His Leu Gln Cys Leu Glu Glu Tyr Leu Lys
    50                  55                  60
```

```
Tyr Leu Glu Glu Val Leu Ser Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 23
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (39)..(39)
<223> OTHER INFORMATION: Nle
<220> FEATURE:
<221> NAME/KEY: MOD_RES
<222> LOCATION: (41)..(41)
<223> OTHER INFORMATION: Hse
<220> FEATURE:
<221> NAME/KEY: MOD_RES
<222> LOCATION: (46)..(46)
<223> OTHER INFORMATION: Nle
<220> FEATURE:
<221> NAME/KEY: MOD_RES
<222> LOCATION: (71)..(71)
<223> OTHER INFORMATION: Hse
<220> FEATURE:
<221> NAME/KEY: MOD_RES
<222> LOCATION: (104)..(104)
<223> OTHER INFORMATION: Hse

<400> SEQUENCE: 23

```
Ala Pro Thr Ser Ser Ser Thr Lys Lys Thr Gln Leu Gln Leu Glu His
 1               5                  10                  15

Leu Leu Leu Asp Leu Gln Leu Ile Leu Asn Gly Ile Asn Asn Tyr Lys
                 20                  25                  30

Asn Pro Lys Leu Thr Arg Leu Leu Ser Phe Lys Phe Tyr Leu Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Ser Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Ser Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

MODIFIED IL-2 POLYPEPTIDES AND USES THEREOF

CROSS REFERENCE

This application claims the benefit of U.S. Provisional Application No. 62/959,382 filed Jan. 10, 2020, which application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 6, 2021, is named 56146-702_201_SL.txt and is 36,537 bytes in size.

BACKGROUND

Immunotherapies utilize the immune system of a subject to aid in the treatment of ailments. Immunotherapies can be designed to either activate or suppress the immune system depending on the nature of the disease being treated. The goal of various immunotherapies for the treatment of cancer is to stimulate the immune system so that it recognizes and destroys tumors or other cancerous tissue.

One method of activating the immune system to attack cancer cells in the body of a subject is cytokine therapy. Cytokines are proteins produced in the body that are important in cell signaling. Various cytokines have important roles in modulating the immune system. Some cytokine therapy utilizes these properties of the molecules in order to enhance the immune system of a subject in order to kill cancer cells.

Interleukin-2 (IL-2) is a cytokine signaling molecule important in regulating the immune system. IL-2 is implicated in helping the immune system differentiate between foreign and endogenous cell types, thereby preventing the immune system from attacking a subject's own cells. IL-2 accomplishes its activity through interactions with IL-2 receptors (IL-2R) expressed by lymphocytes. Through these binding interactions, IL-2 can modulate a subject's populations of T-effector ($T_{eff}$) cells, natural killer (NK) cells, and regulatory T-cells ($T_{reg}$).

For these reasons, IL-2 has been used in the treatment of certain cancers, both alone and in combination with other therapies. However, use of IL-2 as a treatment has been limited by toxicities, which include life threatening and sometimes fatal vascular leak syndrome, as well as by its short half-life, requiring dosing three times per day over eight days. There exists a need for improved IL-2 polypeptides with different selectivity for various IL-2 receptor subunits, for example, IL-2 receptor αβγ (IL-2Rα) and IL-2 receptor βγ (IL-2Rβ), to enhance therapeutic potential and minimize the risk of side effects of IL-2 therapies.

BRIEF SUMMARY

In one aspect, provided herein, is a modified interleukin-2 (IL-2) polypeptide, comprising a modified IL-2 polypeptide, wherein the modified IL-2 polypeptide comprises a first polymer covalently attached at residue F42Y, and wherein residue position numbering of the modified IL-2 polypeptide is based on SEQ ID NO: 1 as a reference sequence.

In another aspect, provided herein, is a modified interleukin-2 (IL-2) polypeptide, comprising a modified IL-2 polypeptide, wherein the modified IL-2 polypeptide comprises: (i) a tyrosine at residue 42, and (ii) a first polymer and a second polymer covalently attached to the modified IL-2 polypeptide, wherein at least one of the first polymer and the second polymer has a weight average molecular weight of higher than 5000 Daltons, and wherein residue position numbering of the modified IL-2 polypeptide is based on SEQ ID NO: 1 as a reference sequence.

In another aspect, provided herein, is a modified interleukin-2 (IL-2) polypeptide, comprising a modified IL-2 polypeptide, wherein a ratio of a half maximal effective concentration (EC50) value of the modified IL-2 polypeptide binding to IL-2 receptor βγ complex (IL-2Rβ) over an EC50 value of the modified IL-2 polypeptide binding to IL-2 receptor αβγ complex (IL-2Rα) is below 2:1, and wherein the EC50 value is measured in an agonist assay. In some embodiments, the ratio is determined by a ratio of Tregs/CD8+ according to levels of Tregs and CD8+ cells measured 1 hour after injection at a dose of 0.1 mg/kg in a mouse model.

In another aspect, provided herein, is a modified IL-2 polypeptide, comprising a modified IL-2 polypeptide, wherein a dissociation constant ($K_D$) of the modified IL-2 polypeptide/IL-2 Receptor βγ complex (IL-2Rβ) is less than 300 nM, and wherein the modified IL-2 polypeptide exhibits a greater affinity for IL-2Rβ than IL-2 Receptor αβγ complex (IL-2Rα) as measured by $K_d$. In some embodiments, the $K_d$ is determined according to a binding assay to IL-2R monomer in surface plasmon resonance experiments.

In some embodiments, the modified IL-2 polypeptide comprises a first polymer covalently attached at residue F42Y, and wherein residue position numbering of the modified IL-2 polypeptide is based on SEQ ID NO:1 as a reference sequence. In some embodiments, wherein the first polymer comprises a water-soluble polymer. In some embodiments, the first polymer has a weight average molecular weight of at most about 50,000 Daltons, at most about 25,000 Daltons, at most about 10,000 Daltons, or at most about 6,000 Daltons. In some embodiments, the first polymer has a weight average molecular weight of at least about 120 Daltons, at least about 250 Daltons, at least about 300 Daltons, at least about 400 Daltons, or at least about 500 Daltons.

In some embodiments, the modified IL-2 polypeptide further comprises a second polymer covalently attached to the modified IL-2 polypeptide. In some embodiments, the second polymer is covalently attached at an amino acid residue region from residue 40 to residue 50. In some embodiments, the second polymer is covalently attached at residue Y45. In some embodiments, the second polymer is covalently attached to the N-terminus of the modified IL-2 polypeptide. In some embodiments, the second polymer has a weight average molecular weight of at most about 50,000 Daltons, at most about 25,000 Daltons, at most about 10,000 Daltons, or at most about 6,000 Daltons.

In some embodiments, the second polymer has a weight average molecular weight of at least about 120 Daltons, at least about 250 Daltons, at least about 300 Daltons, at least about 400 Daltons, at least about 500 Daltons, at least about 1000 Daltons, at least about 2000 Daltons, at least about 3000 Daltons, at least about 4000 Daltons, or at least about 5000 Daltons. In some embodiments, the second polymer comprises a water-soluble polymer.

In some embodiments, the modified IL-2 polypeptide further comprises a third polymer. In some embodiments, the third polymer comprises a water-soluble polymer. In some embodiments, the third polymer is covalently attached to the N-terminus of the modified IL-2 polypeptide. In some embodiments, the third polymer has a weight average molecular weight of at most about 50,000 Daltons, at most about 40,000 Daltons, at most about 20,000 Daltons, or at most about 6000 Daltons. In some embodiments, the third polymer has a weight average molecular weight of at least about 500 Daltons, at least about 1000 Daltons, at least about 2000 Daltons, at least about 3000 Daltons, at least about 4000 Daltons, or at least about 5000 Daltons.

In one aspect, provided herein, is a modified interleukin-2 (IL-2) polypeptide, comprising a modified IL-2 polypeptide, wherein the modified IL-2 polypeptide comprises a) a first polymer having a weight average molecular weight of from about 250 Daltons to about 50,000 Daltons covalently attached to residue F42Y; and b) a second polymer having a weight average molecular weight of from about 250 Daltons to about 50,000 Daltons covalently attached to Y45; wherein residue position numbering of the modified IL-2 polypeptide is based on SEQ ID NO:1 as a reference sequence. In some embodiments, the modified IL-2 polypeptide comprises a third polymer having a weight average molecular weight of from about 250 Daltons to about 50,000 Daltons covalently attached thereto. In some embodiments, each of the first polymer and the second polymer independently comprises a water-soluble polymer. In some embodiments, the first polymer has a weight average molecular weight of from about 250 Daltons to about 1000 Daltons and the second polymer has a weight average molecular weight of from about 5000 Daltons to about 40,000 Daltons. In some embodiments, the second polymer has a weight average molecular weight of from about 250 Daltons to about 1000 Daltons and the first polymer has a weight average molecular weight of from about 5000 Daltons to about 40,000 Daltons. In some embodiments, the water-soluble polymer comprises poly(alkylene oxide), polysaccharide, poly(vinyl pyrrolidone), poly(vinyl alcohol), polyoxazoline, poly(acryloylmorpholine), or a combination thereof. In some embodiments, the water-soluble polymer comprises poly(alkylene oxide). In some embodiments, the water-soluble polymer comprises polyethylene glycol. In some embodiments, the third polymer comprises from 1 to 10 polyethylene glycol chains. In some embodiments, the third polymer comprises 4 polyethylene glycol chains. In some embodiments, each of the polyethylene glycol chains independently comprises from about 5 to about 300, from about 10 to about 200, from about 20 to about 100, or from about 25 to about 50 ethylene glycol units. In some embodiments, each of the first polymer and the second polymer independently comprises from 1 to 5 polyethylene glycol chains. In some embodiments, each of the first polymer and the second polymer independently comprises one polyethylene glycol chain with 3 to 25 ethylene glycol units. In some embodiments, each of the polyethylene glycol chains is independently linear or branched. In some embodiments, each of the polyethylene glycol chains is a linear polyethylene glycol. In some embodiments, each of the polyethylene glycol chains is independently terminally capped with a hydroxy, an alkyl, an alkoxy, or an amino group. In some embodiments, the modified IL-2 polypeptide comprises from 1 to 10 covalently attached water-soluble polymers. In some embodiments, the modified IL-2 polypeptide comprises from 2 to 6 covalently attached water-soluble polymers. In some embodiments, the modified IL-2 polypeptide comprises one or more PEGylated tyrosine having a structure of formula (I)

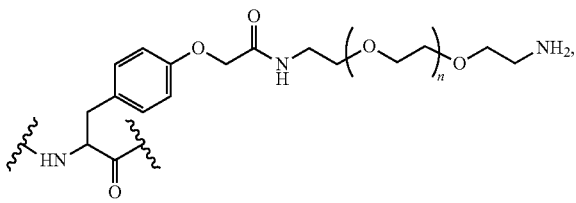

Formula (I)

wherein n is an integer selected from 4 to 30. In some embodiments, the modified IL-2 polypeptide comprises one or more PEGylated tyrosine having a structure of formula (I)

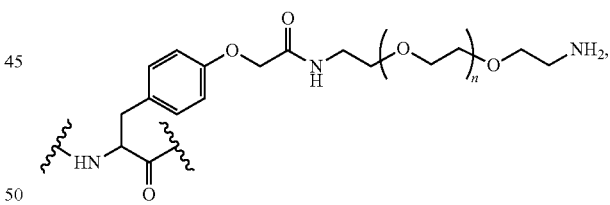

Formula (I)

wherein n is an integer selected from 4 to 30 and the PEG group is monodisperse.

In some embodiments, the one or more PEGylated tyrosine is located in an amino acid region from residue 35 to residue 45. In some embodiments, the one or more PEGylated tyrosine is located at residue 42, residue 45, or both. In some embodiments, the modified IL-2 polypeptide comprises two PEGylated tyrosine, each independently having a structure of Formula (I). In some embodiments, the modified IL-2 polypeptide comprises at least one polymer having a structure of Formula (II)

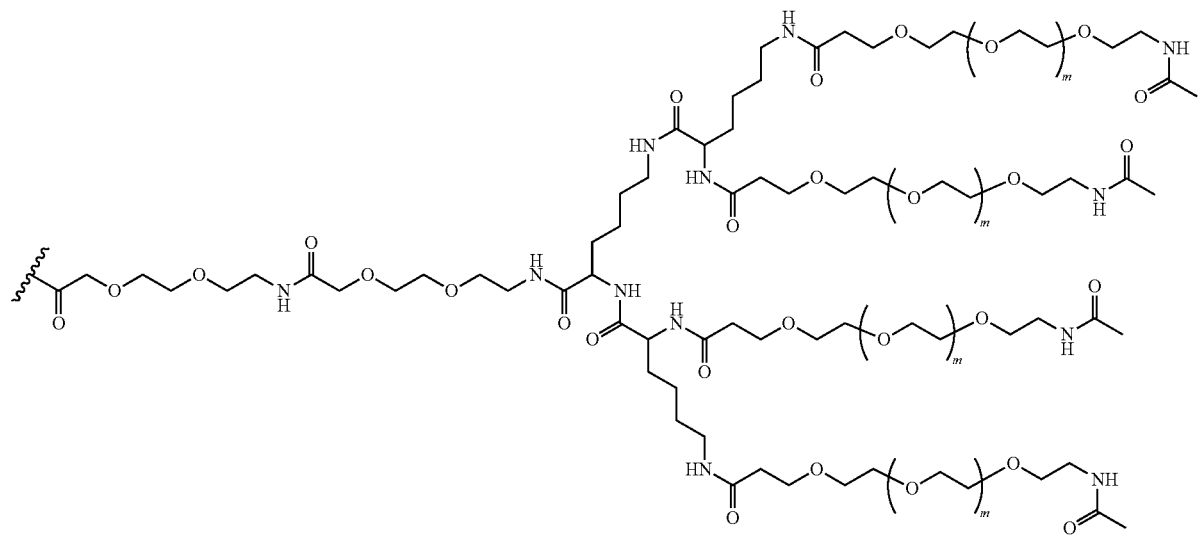

Formula (II)

wherein each m is independently an integer from 4-30. In some embodiments, each m is about 26.

In some embodiments, the modified IL-2 polypeptide comprises at least two amino acid substitutions, wherein the at least two amino acid substitutions are selected from a) a homoserine (Hse) residue located in any one of residues 35-45, b) a homoserine residue located in any one of residues 61-81, and c) a homoserine residue located in any one of residues 94-114. In some embodiments, the modified IL-2 polypeptide comprises Hse41, Hse71, Hse104, or a combination thereof. In some embodiments, the modified IL-2 polypeptide further comprises a norleucine (Nle) substitution. In some embodiments, the Nle substitution is located in any one of residues 20-60. In some embodiments, the modified IL-2 polypeptide comprises three Nle substitutions. In some embodiments, the modified IL-2 polypeptide comprises Nle23, Nle39, and Nle46. In some embodiments, the modified IL-2 polypeptide comprises SEQ ID NO: 3. In some embodiments, the modified IL-2 polypeptide comprises SEQ ID NO: 4. In some embodiments, the modified IL-2 polypeptide comprises at least three, at least 4, at least 5, at least 6, at least 7, or at least 9 amino acid substitutions.

In some embodiments, the modified IL-2 polypeptide exhibits a greater functional activity of IL-2Rβ than IL-2Rα as measured by half maximal effective concentration (EC50) in an agonist assay, and wherein a ratio of the EC50 value of the modified IL-2 polypeptide on IL-2Rβ over the EC50 value of the modified IL-2 polypeptide on IL-2Rα is below 2:1, below 1.75:1, below 1.5:1, below 1.25:1, below 1:1, below 0.75:1, or below 0.5:1. In some embodiments, the modified IL-2 polypeptide exhibits a greater affinity for IL-2Rβ than IL-2Rα as measured by dissociation constant ($K_d$), and wherein a $K_D$ of the modified IL-2 polypeptide/IL-2Rβ is less than 300 nM, less than 250 nM, less than 225 nM, less than 200 nM, less than 175 nM, or less than 150 nM. In some embodiments, binding between the modified IL-2 polypeptide and IL-2 Receptor α (IL-2Rα) is reduced by at least 30%, at least 40%, at least 50%, at least 60%, at least 70%, at least 80%, at least 90%, at least 95%, or at least 99% compared to the binding between a wild-type IL-2 polypeptide and IL-2Rα. In some embodiments, binding between the modified IL-2 polypeptide and IL-2 Receptor β (IL-2Rβ) is reduced by at most 0%, at most 1%, at most 2%, at most 5%, at most 10%, at most 15%, at most 20%, at most 25%, or at most 30% compared to the binding between a wild-type IL-2 polypeptide and IL-2Rβ. In some embodiments, binding between the modified IL-2 polypeptide and IL-2 Receptor β (IL-2Rβ) is increased by at least 0.1%, at least 1%, at least 2%, at least 5%, at least 10%, at least 15%, or at least 20% compared to the binding between a wild-type IL-2 polypeptide and IL-2Rβ. In some embodiments, the modified IL-2 polypeptide comprises at least about 80%, at least about 85%, at least about 90%, at least about 95%, at least about 96%, at least about 97%, at least about 98%, or at least about 99% sequence identity to SEQ ID NO: 1.

In some embodiments, the modified IL-2 polypeptide is capable of expanding CD4+ helper cell, CD8+ central memory cell, CD8+ effector memory cell, naïve CD8+ cell, Natural Killer (NK) cell, Natural killer T (NKT) cell populations, or a combination thereof. In some embodiments, the modified IL-2 polypeptide expands a cell population of regulatory T cells ($T_{reg}$ cells) by at least 1%, at least 2%, at least 5%, at least 10%, at least 15%, at least 20%, at least 30%, at least 40%, at least 50%, at least 100%, or at least 200% when the modified IL-2 polypeptide is in contact with the population. In some embodiments, the modified IL-2 polypeptide expands a cell population of regulatory T cells ($T_{reg}$ cells) by at most 5%, at most 10%, at most 20%, at most 30%, at most 40%, at most 50%, at most 75%, at most 100%, or at most 500% when the modified IL-2 polypeptide is in contact with the population. In some embodiments, the modified IL-2 polypeptide expands a cell population of effector T cells ($T_{eff}$ cells) by at least 1%, at least 2%, at least 5%, at least 10%, at least 15%, at least 20%, at least 30%, at least 40%, at least 50%, at least 100%, or at least 200% when the modified IL-2 polypeptide is in contact with the population. In some embodiments, the modified IL-2 polypeptide expands a cell population of effector T cells ($T_{eff}$ cells) by at most 5%, at most 10%, at most 20%, at most 30%, at most 40%, at most 50%, at most 75%, at most 100%, or at most 500% when the modified IL-2 polypeptide is in contact with the population. In some embodiments, a ratio of cell population expansion of $T_{eff}$ cells over cell population expansion of T$_{reg}$ cells expanded by the modified IL-2 polypeptide is from about 0.1 to about 15, from about 0.5 to about 10, from about 0.75 to about 5, or from about 1 to about 2. In some embodiments, the cell population is an in vitro cell population, an in vivo cell population, or an ex vivo cell population. In some embodiments, a plasma or serum half-life of the modified IL-2 polypeptide is at least 1.5-fold, 2-fold, 3-fold, 4-fold, 5-fold, 6-fold, 7-fold, 8-fold, 9-fold, or 10-fold longer compared to a plasma or serum half-life of a wild-type IL-2 polypeptide. In some embodiments, the modified IL-2 polypeptide is synthetic. In some embodiments, the modified IL-2 polypeptide is conjugated to an additional polypeptide.

In one aspect, provided herein, is a modified interleukin-2 (IL-2) polypeptide, comprising a polypeptide sequence having at least about 80%, 85%, or 90% sequence identity to SEQ ID NO: 3. In some embodiments, the sequence identity is measured by protein-protein BLAST algorithm using parameters of Matrix BLOSUM62, Gap Costs Existence: 11, Extension: 1, and Compositional Adjustments Conditional Compositional Score Matrix Adjustment. In some embodiments, the polypeptide sequence has at least 95%, 99%, or 100% sequence identity to SEQ ID NO:3. In some embodiments, the modified IL-2 polypeptide comprises a polypeptide sequence of SEQ ID NO: 3.

In one aspect, provided herein, is a polypeptide sequence having at least about 80%, 85%, or 90% sequence identity to any one of SEQ ID NOs: 4-22. In some embodiments, the sequence identity is measured by protein-protein BLAST algorithm using parameters of Matrix BLOSUM62, Gap Costs Existence: 11, Extension: 1, and Compositional Adjustments Conditional Compositional Score Matrix Adjustment. In some embodiments, the polypeptide sequence has at least 95%, 99%, or 100% sequence identity to any one of SEQ ID NO: 4-22. In some embodiments, the modified IL-2 polypeptide comprises a polypeptide sequence of any one of SEQ ID NO: 3-22.

In one aspect, provided herein, is a plurality of modified IL-2 polypeptides, wherein each of the modified IL-2 polypeptides comprises a first polymer covalently attached in the regions of residues 35 to 75, wherein residue position numbering of the modified IL-2 polypeptide is based on SEQ ID NOT as a reference sequence, and wherein at least 90% of the modified interleukin-2 (IL-2) polypeptides have a molecular weight that is within ±500 Da of the peak molecular weight of the plurality of the modified IL-2 polypeptides as determined by high resolution electrospray ionization mass spectrometry (ESI-HRMS. In some embodiments, wherein a ratio of weight average molecular weight over number average molecular weight for the population of modified IL-2 polypeptides is at most 1.5, at most 1.2, at most 1.1, or at most 1.05. In some embodiments, at least 80%, at least 85%, at least 90%, at least 95%, or at least 99% of the population of modified IL-2 polypeptides have a molecular weight that is within ±10% of the peak molecular weight as determined by mass spectrum. In some embodiments, at least 80%, at least 85%, at least 90%, at least 95%, or at least 99% of the population of modified IL-2 polypeptides have a molecular weight that is within ±5% of the peak molecular weight as determined by mass spectrum. In some embodiments, at least 80%, at least 85%, at least 90%, at least 95%, or at least 99% of the population of modified IL-2 polypeptides have a molecular weight that is within ±1% of the peak molecular weight as determined by mass spectrum. In some embodiments, at least at least 95% of the population of modified IL-2 polypeptides have a molecular weight that is within ±200 Daltons of the peak molecular weight as determined by mass spectrum. In some embodiments, at least at least 95% of the population of modified IL-2 polypeptides have a molecular weight that is within ±100 Daltons of the peak molecular weight as determined by mass spectrum. In some embodiments, at least at least 95% of the population of modified IL-2 polypeptides have a molecular weight that is within ±20 Daltons of the peak molecular weight as determined by mass spectrum. In some embodiments, at least 80%, at least 85%, at least 90%, or at least 95% of the population of modified IL-2 polypeptides have the same molecular weight as measured by mass spectrum.

In some embodiments, the first polymer is attached to amino acid residue 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 and wherein residue position numbering of the modified IL-2 polypeptide is based on SEQ ID NO:1 as a reference sequence. In some embodiments, the weight average molecular weight of the first polymers is at least about 3000 Da, at least about 6000 Da, at least about 12,000 Da, or at least about 24,000 Da. In some embodiments, each of the modified IL-2 polypeptides comprises a second polymer covalently attached thereto. In some embodiments, each of the modified IL-2 polypeptides comprises a third polymer covalently attached thereto. In some embodiments, the second polymer is covalently attached to residue 42 or 45, wherein residue position numbering of the modified IL-2 polypeptide is based on SEQ ID NO:1 as a reference sequence. In some embodiments, the second polymer is covalently attached to residue F42Y or Y45, wherein residue position numbering of the modified IL-2 polypeptide is based on SEQ ID NO: 1 as a reference sequence. In some embodiments, the second polymers and third polymers are covalently attached to residue 42 and 45, wherein residue position numbering of the modified IL-2 polypeptide is based on SEQ ID NO: 1 as a reference sequence. In some embodiments, the second polymers and third polymers are covalently attached to residue F42Y and Y45, wherein residue position numbering of the modified IL-2 polypeptide is based on SEQ ID NO:1 as a reference sequence. In some embodiments, the population comprises at least 100, at least 1000, or at least 1000 modified IL-2 polypeptides. In some embodiments, the population comprises at least 1 μg, at least 10 μg, or at least 1 mg of modified IL-2 polypeptides. In some embodiments, the plurality of modified IL-2 polypeptides comprise non-canonical amino acids. In some embodiments, the non-canonical amino acids are present in one or more residue positions selected from: 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 and 75.

In one aspect, provided herein is a modified interleukin-2 (IL-2) polypeptide population, comprising: a plurality of polymers, each polymer covalently attached to a modified IL-2 polypeptide at the N-terminus or in the region of residues 35 to 75, wherein residue position numbering of the modified IL-2 polypeptide is based on SEQ ID NO:1 as a reference sequence, and wherein at least 95% of the plurality of polymers have a molecular weight that is within ±10% of the peak molecular weight of the plurality of polymers as determined by mass spectrum.

In one aspect, provided herein, is a pharmaceutical composition comprising a modified IL-2 polypeptide or a population of modified IL-2 polypeptides provided herein; and a pharmaceutically acceptable carrier or excipient. In some embodiments, the pharmaceutical composition is formulated for parenteral or enteral administration. In some embodiments, the pharmaceutical composition is formulated for intravenous or subcutaneous administration. In some embodiments, the pharmaceutical composition is in a lyophilized form.

In one aspect, provided herein, is a method of treating cancer in a subject in need thereof, comprising administering to the subject an effective amount of a modified IL-2 polypeptide provided herein, population of modified IL-2 polypeptides provided herein, or a pharmaceutical composition provided herein. In some embodiments, the cancer is a solid cancer or a blood cancer. In some embodiments, the solid cancer is kidney cancer, skin cancer, bladder cancer, bone cancer, brain cancer, breast cancer, colorectal cancer, esophageal cancer, eye cancer, head and neck cancer, lung cancer, ovarian cancer, pancreatic cancer, or prostate cancer. In some embodiments, the solid cancer is metastatic renal cell carcinoma (metastatic RCC) or melanoma. In some embodiments, the blood cancer is leukemia, Non-Hodgkin's lymphoma, Hodgkin's lymphoma, or multiple myeloma. In some embodiments, the method comprises reconstituting a lyophilized form of the modified IL-2 polypeptide or the pharmaceutical composition.

In one aspect, provided herein is a method of making a modified IL-2 polypeptide provided herein, comprising a) synthesizing two or more fragments of the modified IL-2 polypeptide, b) ligating the fragments, and c) folding the ligated fragments. In some embodiments, the method further comprises attaching a water-soluble polymer to the folded, ligated fragments.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawing (also "figure" and "FIG." herein), of which:

DETAILED DESCRIPTION

Figure 1A:
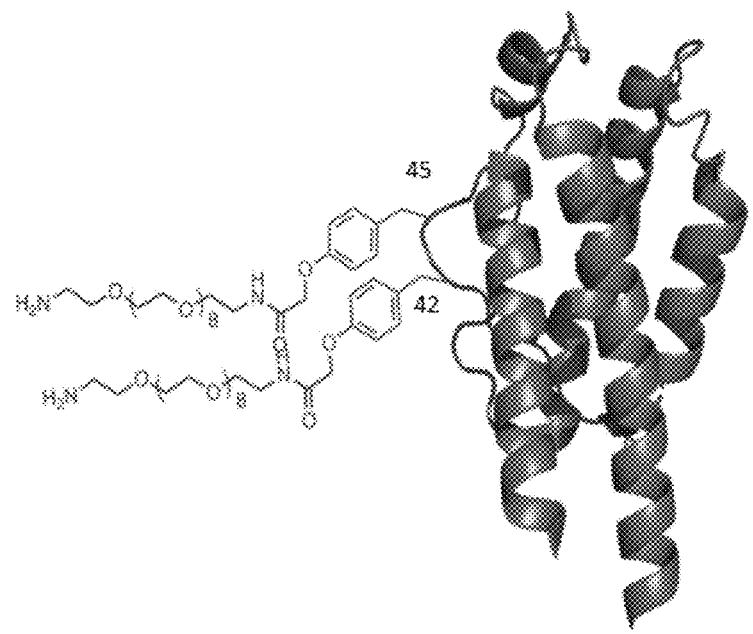
FIG. 1A shows an illustration of a modified IL-2 polypeptide (Composition A).
Figure 1B:
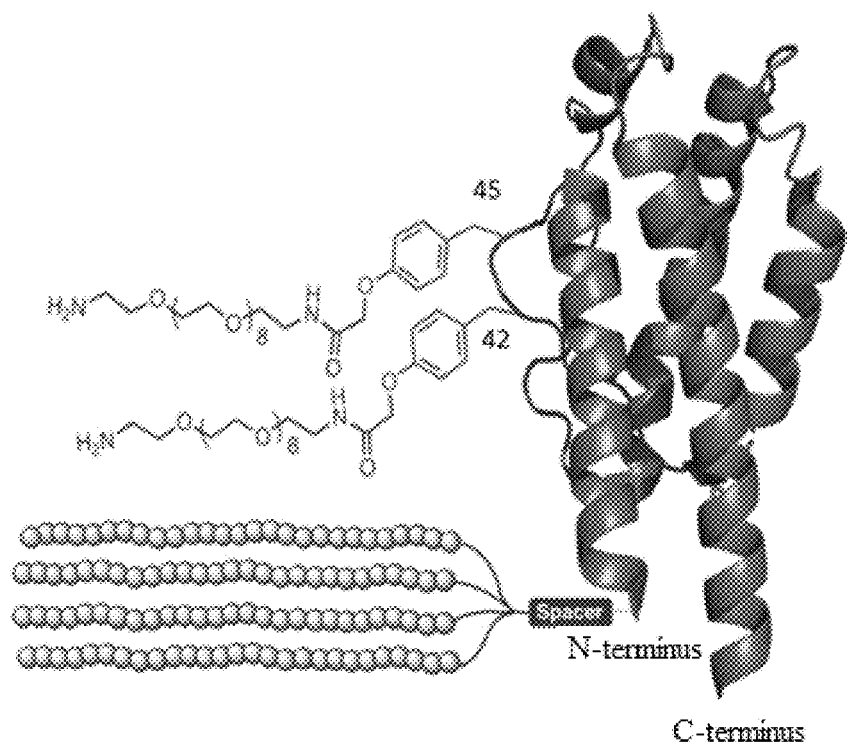
FIG. 1B shows an illustration of a modified IL-2 polypeptide (Composition B).
Figure 1C:
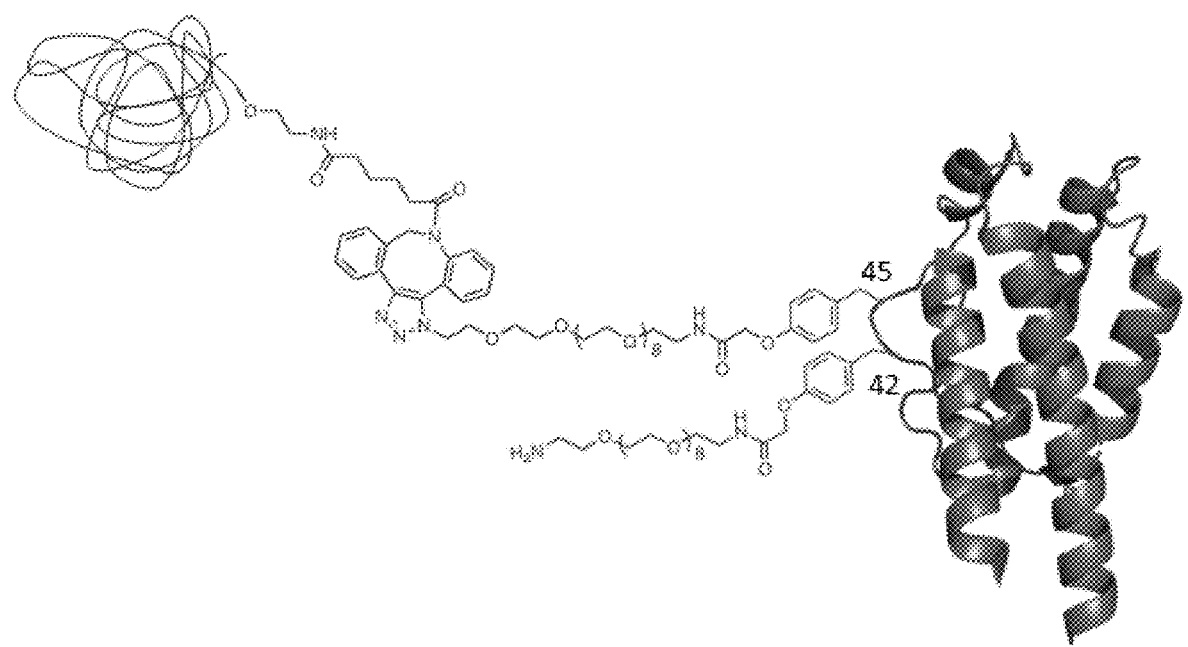
FIG. 1C shows an illustration of a modified IL-2 polypeptide (Composition C).
Figure 1D:
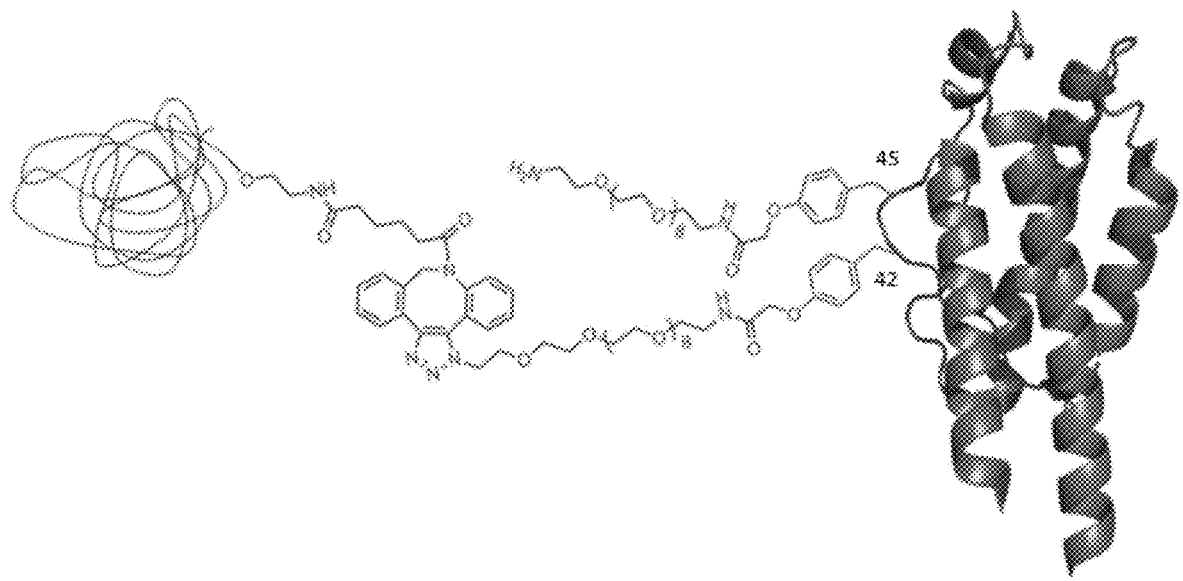
FIG. 1D shows an illustration of a modified IL-2 polypeptide (Composition D).
Figure 1E:
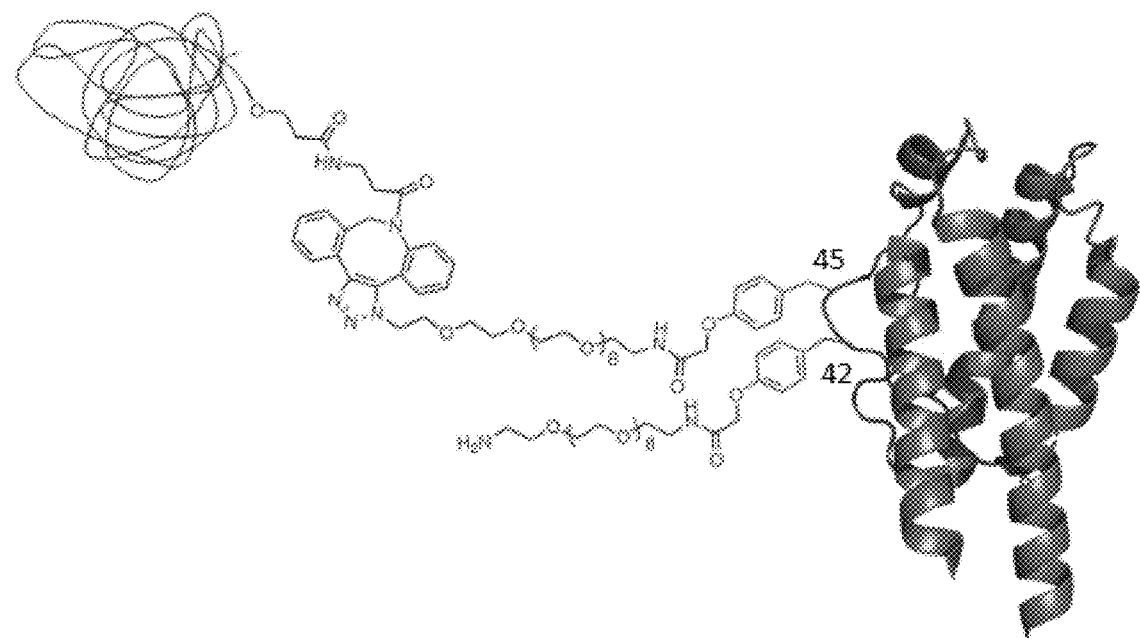
FIG. 1E shows an illustration of a modified IL-2 polypeptide (Composition C1).
Figure 1F:
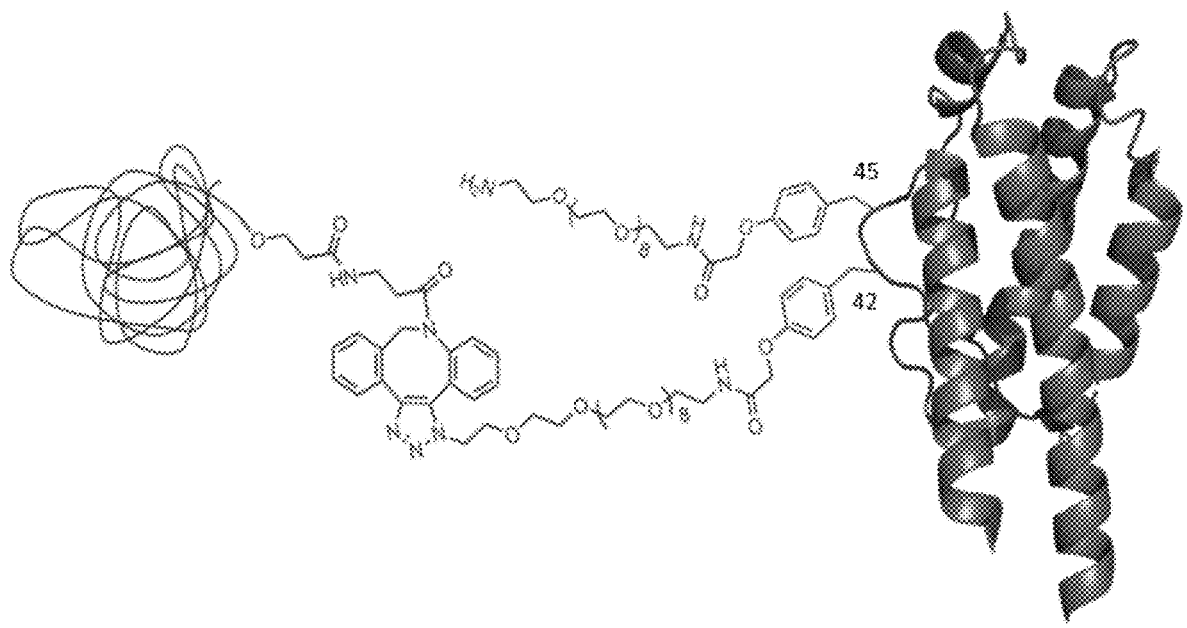
FIG. 1F shows an illustration of a modified IL-2 polypeptide (Composition D1).

The present disclosure relates to modified interleukin-2 (IL-2) polypeptides useful as therapeutic agents. Modified IL-2 polypeptides provided herein can be used as immunotherapies or as parts of other immunotherapy regimens. Such modified IL-2 polypeptides may display binding characteristics for the IL-2 receptor (IL-2R) that differ from wild-type IL-2. In one aspect, modified IL-2 polypeptides described herein have decreased affinity for the IL-2R αβγ complex (IL-2Rα). In some embodiments, the modified IL-2 polypeptides have an increased affinity for the IL-2R βγ complex (IL-2Rβ). In some embodiments, the binding affinity between the modified IL-2 polypeptides and IL-2Rβ is the same as or lower than the binding affinity between a wild-type IL-2 and IL-2Rβ.

In some embodiments, the modified IL-2 polypeptides described herein contain modified amino acid residues. Such modifications can take the form of mutations of a wild type IL-2 polypeptide such as the amino acid sequence of SEQ ID NO: 1, addition or deletion of amino acids from the sequence of SEQ ID NO: 1, or the addition of moieties to amino acid residues. In some embodiments, the modified IL-2 polypeptide described herein contains a deletion of the first amino acid from the sequence of SEQ ID NO: 1. In some embodiments, the modified IL-2 polypeptide described herein comprises a C125S mutation, using the sequence of SEQ ID NO: 1 as a reference sequence. Moieties which can be added to amino acid residues include, but are not limited to, polymers, linkers, spacers, and combinations thereof. When added to certain amino acid residues, these moieties can modulate the activity or other properties of the modified IL-2 polypeptide compared to wild-type IL-2. In some embodiments, the modified IL-2 polypeptides comprise two modifications in the range of amino acid residues 35-46. In some embodiments, the one modification is in the range of amino acid residues 40-43. In some embodiments, one modification is at amino acid residue 42. In some embodiments, one modification is in the range of amino acid residues 44-46. In some embodiments, one modification is at amino acid residue 45. In some embodiments, the modified IL-2 polypeptides described herein contain one or more polymers. For example, the addition of polymers to certain amino acid residues can have the effect of disrupting the binding interaction of the modified IL-2 polypeptide with IL-2R, particularly the αβγ complex. In some embodiments, residues to which polymers are added to disrupt this interaction include F42 and Y45. In some embodiments, the polymers are water-soluble polymers, such as polyethylene glycol (PEG) polymers. The F42 residue can be mutated to another residue to facilitate the addition of the PEG polymer, for example to a tyrosine residue. Polymers may be added to either one or both of residues F42 and Y45, or mutants thereof. Additionally, polymers may be added to modified IL-2 polypeptides in order to increase the half-life of the polypeptides. Such half-life extending polymers can be added to the N-terminus of the modified IL-2 polypeptides. The half-life extending polymers may be of any size, including up to about 6 kDa, up to about 25 kDa, or up to about 50 kDa. In some embodiments, the half-life extending polymers are PEG polymers. In some embodiments, a composition of the described modified IL-2 polypeptide is illustrated in FIGS. 1A-1D. In some embodiments, the modified IL-2 polypeptide comprises one or more amino acid mutations selected from Table 1.

TABLE 1

| WT IL-2 Residue Number* | WT IL-2 Residue | Mutations |
| --- | --- | --- |
| 35 | K | D, I, L, M, N, P, Q, T, Y |
| 36 | L | A, D, E, F, G, H, I, K, M, N, P, R, S, W, Y |
| 38 | R | A, D, G, K, N, P, S, Y |
| 40 | L | D, G, N, S, Y |
| 41 | T | E, G, Y |
| 42 | F | A, D, E, G, I, K, L, N, Q, R, S, T, V, Y |

TABLE 1-continued

| WT IL-2 Residue Number* | WT IL-2 Residue | Mutations |
|---|---|---|
| 43 | K | H, Y |
| 44 | F | K, Y |
| 45 | Y | A, D, E, G, K, L, N, Q, R, S, T, V |
| 46 | M | I, Y |
| 61 | E | K, M, R, Y |
| 62 | E | D, L, T, Y |
| 64 | K | D, E, G, L, Q, R, Y |
| 65 | P | D, E, F, G, H, I, K, L, N, Q, R, S, T, V, W, Y |
| 66 | L | A, F, Y |
| 67 | E | A, Y |
| 68 | E | V, Y |
| 72 | L | A, D, E, G, K, N, Q, R, S, T, Y |
| 125 | C | S |

*Residue position numbering based on SEQ ID NO: 1 as a reference sequence

In some embodiments, a modified IL-2 polypeptide provided herein comprises one or more amino acid mutations selected from Table 2.

TABLE 2

| WT IL-2 Residue Number* | WT IL-2 Residue | Mutations |
|---|---|---|
| 20 | D | T, Y |
| 35 | K | D, I, L, M, N, P, Q, T Y |
| 38 | R | A, D, G, K, N, P, S, Y |
| 42 | F | A, D, E, G, I, K, L, N, Q, R, S, T, V, Y |
| 43 | K | H, Y |
| 45 | Y | A, D, E, G, K, L, N, Q, R, S, T, V, Y |
| 62 | E | D, L, T, Y |
| 65 | P | D, E, F, G, H, I, K, L, N, Q, R, S, T, V, W, Y |
| 68 | E | V, Y |
| 72 | L | A, D, E, G, K, N, Q, R, S, T, Y |
| 125 | C | S |

*Residue position numbering based on SEQ ID NO: 1 as a reference sequence

In some embodiments, a modified IL-2 polypeptide provided herein comprises one or more polymers selected from Table 3.

TABLE 3

| Polymer Identifier | Polymer Structure | Approximate Molecular Weight |
|---|---|---|
| Formula A | 30 kDa PEG-O-... (DBCO-triazole-PEG8-phenoxyacetamide) | 30 kDa |
| Formula A' | | 30 kDa |
| Formula B | AcHN-PEG27-... trilysine branched structure with PEG27 arms and phenoxyacetamide terminus | 6 kDa |

TABLE 3-continued
| Polymer Identifier | Polymer Structure | Approximate Molecular Weight |
|---|---|---|
| Formula C |  | 32 kDa |
| Formula D |  | 500 Da |

In some embodiments, a modified IL-2 polypeptide provided herein comprises mutations and polymers as provided in Table 4.

TABLE 4

| Mutation* | Polymer Residue Location | Polymer |
|---|---|---|
| F42Y | 42, 45 | Formula D (Residues 42, 45) |
| F42Y | 42, 45 | Formula D (Residues 42), Formula A (Residues 45) |
| F42Y | 42, 45 | Formula D (Residues 45), Formula A (Residues 42) |
| F42Y | 42, 45 | Formula D (Residues 42), Formula A' (Residues 45) |
| F42Y | 42, 45 | Formula D (Residues 45), Formula A' (Residues 42) |
| F42Y | 42, 45 | Formula D (Residues 42), Formula C (Residues 45) |
| F42Y | 42, 45 | Formula D (Residues 45), Formula C (Residues 42) |
| F42Y | 1, 42, 45, | Formula A (Residue 1), Formula D (Residues 42, 45) |
| F42Y | 1, 42, 45, | Formula B (Residue 1), Formula D (Residues 42, 45) |
| F42Y | 1, 42, 45, | Formula C (Residue 1), Formula D (Residues 42, 45) |
| None | 45 | Formula D |
| F42A | 45 | Formula D |
| F42Y, L72G | 42, 45 | Formula D (Residues 42, 45) |
| F42Y, P65Y | 42, 65 | Formula D (Residues 42, 65) |
| F42Y, P65Y | 42, 45, 65 | Formula D (Residues 42, 45, 65) |
| R38Y, F42Y, E62Y, E68Y | 38, 42, 45, 62, 68 | Formula D (Residues 38, 42, 45, 62, 68) |
| F42Y, L72Y | 42, 45, 72 | Formula D (Residues 42, 45, 75) |
| F42Y, Y45K | 42 | Formula D |
| F42A | 45 | Formula A |
| F42A | 45 | Formula A' |
| F42A | 45 | Formula B |
| F42A | 45 | Formula C |
| F42A | 45 | Formula D |
| L72G | 45 | Formula A |
| L72G | 45 | Formula A' |
| L72G | 45 | Formula B |
| L72G | 45 | Formula C |
| L72G | 45 | Formula D |

*Residue position numbering based on SEQ ID NO: 1 as a reference sequence

The modified IL-2 polypeptides described herein may also be synthesized chemically rather than expressed as recombinant polypeptides. The modified IL-2 polypeptides can be made by synthesizing one or more fragments of the full-length modified IL-2 polypeptides, ligating the fragments together, and folding the ligated full-length polypeptide. In some embodiments, the modified IL-2 polypeptide comprises an F42Y mutation in the amino acid sequence, a first PEG polymer of about 500 Da covalently attached to residue F42Y, a second PEG polymer of about 500 Da covalently attached to residue Y45, and an optional third PEG polymer of about 6 kDa covalently attached to the N-terminus of the modified IL-2 polypeptide. Embodiments of a modified IL-2 polypeptide can be seen in FIGS. 1A-1D, which illustrate Compositions A, B, C, and D respectively.

In some embodiments, the modified IL-2 polypeptides enhance T-effector ($T_{eff}$) or natural killer (NK) cell proliferation when administered to a subject. In some embodiments, the modified IL-2 polypeptides enhance $T_{eff}$ or NK cell proliferation while sparing regulatory T-cells ($T_{reg}$) when administered to a subject. In some embodiments, the modified IL-2 polypeptides increase CD8+ T and NK cells without increasing CD4+ regulator T cells when administered to a subject. In some embodiments, the modified IL-2 polypeptides produce a $T_{eff}/T_{reg}$ ratio of close to 1 when administered to a subject.

The following description and examples illustrate embodiments of the present disclosure in detail. It is to be understood that this present disclosure is not limited to the particular embodiments described herein and as such can vary. Those of skill in the art will recognize that there are numerous variations and modifications of this present disclosure, which are encompassed within its scope.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment.

The section headings used herein are for organizational purposes only and are not to be construed as limiting the subject matter described.

All terms are intended to be understood as they would be understood by a person skilled in the art. Unless defined otherwise, all technical and scientific terms used herein have the same meaning as commonly understood by one of ordinary skill in the art to which the disclosure pertains.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only and is not intended to be limiting.

I. Definitions

The terminology used herein is for the purpose of describing particular cases only and is not intended to be limiting. In this application, the use of the singular includes the plural unless specifically stated otherwise. As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 15%, up to 10%, up to 5%, or up to 1% of a given value.

Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

The term "pharmaceutically acceptable" refers to approved or approvable by a regulatory agency of the Federal or a state government or listed in the U.S. Pharmacopeia or other generally recognized pharmacopeia for use in animals, including humans.

A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" suitable for the disclosure may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethyl sulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)n$-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts include those listed by Remington's Pharmaceutical Sciences, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

Certain formulas provided herein (e.g. Formulas A and A' and FIGS. 1C-1F) depict triazole reaction products resulting from azide-alkyne cycloaddition reactions. While such formulas generally depict only a single regioisomer of the resulting triazole formed in the reaction, it is intended that the formulas encompass both resulting regioisomers. Thus, while the formulas depict only a single regioisomer (e.g.

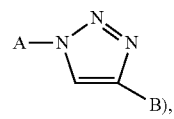

it is intended that the other regioisomer (e.g.

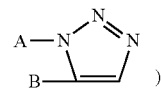

is also encompassed.

The term "optional" or "optionally" denotes that a subsequently described event or circumstance can but need not occur, and that the description includes instances where the event or circumstance occurs and instances in which it does not.

The term "moiety" refers to a specific segment or functional group of a molecule. Chemical moieties are often recognized chemical entities embedded in or appended to a molecule.

As used herein, the term "number average molecular weight" (Mn) means the statistical average molecular weight of all the individual units in a sample, and is defined by Formula (1):

$$Mn = \frac{\sum N_i M_i}{\sum N_i} \qquad \text{Formula (1)}$$

where $M_i$ is the molecular weight of a unit and $N_i$ is the number of units of that molecular weight.

As used herein, the term "weight average molecular weight" (Mw) means the number defined by Formula (2):

$$Mw = \frac{\sum N_i M_i^2}{\sum N_i M_i} \quad \text{Formula (2)}$$

where $M_i$ is the molecular weight of a unit and $N_i$ is the number of units of that molecular weight.

As used herein, "peak molecular weight" (Mp) means the molecular weight of the highest peak in a given analytical method (e.g. mass spectrometry, size exclusion chromatography, dynamic light scattering, analytical centrifugation, etc.).

The term "alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —$CH(CH_3)_2$ or —$C(CH_3)_3$. Unless stated otherwise specifically in the specification, an alkyl group may be optionally substituted. "Alkylene" or "alkylene chain" refers to a straight or branched divalent hydrocarbon chain linking the rest of the molecule to a radical group. In some embodiments, the alkylene is —$CH_2$—, —$CH_2CH_2$—, or —$CH_2CH_2CH_2$—. In some embodiments, the alkylene is —$CH_2$—. In some embodiments, the alkylene is —$CH_2CH_2$—. In some embodiments, the alkylene is —$CH_2CH_2CH_2$—. Unless stated otherwise specifically in the specification, an alkylene group may be optionally substituted.

The term "alkenylene" or "alkenylene chain" refers to a straight or branched divalent hydrocarbon chain in which at least one carbon-carbon double bond is present linking the rest of the molecule to a radical group. In some embodiments, the alkenylene is —CH=CH—, —$CH_2$CH=CH—, or —CH=$CHCH_2$—. In some embodiments, the alkenylene is —CH=CH—. In some embodiments, the alkenylene is —$CH_2$CH=CH—. In some embodiments, the alkenylene is —CH=$CHCH_2$—.

The term "alkynyl" refers to a type of alkyl group in which at least one carbon-carbon triple bond is present. In one embodiment, an alkenyl group has the formula —C≡C—$R^x$, wherein $R^x$ refers to the remaining portions of the alkynyl group. In some embodiments, $R^x$ is H or an alkyl. In some embodiments, an alkynyl is selected from ethynyl, propynyl, butynyl, pentynyl, hexynyl, and the like. Non-limiting examples of an alkynyl group include —C≡CH, —C≡$CCH_3$, —C≡$CCH_2CH_3$, and —$CH_2$C≡CH.

The term "aryl" refers to a radical comprising at least one aromatic ring wherein each of the atoms forming the ring is a carbon atom. Aryl groups can be optionally substituted. Examples of aryl groups include, but are not limited to, phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted. In some embodiments, an aryl group comprises a partially reduced cycloalkyl group defined herein (e.g., 1,2-dihydronaphthalene). In some embodiments, an aryl group comprises a fully reduced cycloalkyl group defined herein (e.g., 1,2,3,4-tetrahydronaphthalene). When aryl comprises a cycloalkyl group, the aryl is bonded to the rest of the molecule through an aromatic ring carbon atom. An aryl radical can be a monocyclic or polycyclic (e.g., bicyclic, tricyclic, or tetracyclic) ring system, which may include fused, spiro or bridged ring systems.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopentyl. In some embodiments, the monocyclic cycloalkyl is cyclopentenyl or cyclohexenyl. In some embodiments, the monocyclic cycloalkyl is cyclopentenyl. Polycyclic radicals include, for example, adamantyl, 1,2-dihydronaphthalenyl, 1,4-dihydronaphthalenyl, tetrainyl, decalinyl, 3,4-dihydronaphthalenyl-1(2H)-one, spiro[2.2]pentyl, norbornyl and bicycle[1.1.1]pentyl. Unless otherwise stated specifically in the specification, a cycloalkyl group may be optionally substituted.

The term "heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkylene groups include, but are not limited to —$CH_2$—O—$CH_2$—, —$CH_2$—N(alkyl)-$CH_2$—, —$CH_2$—N(aryl)-$CH_2$—, —$OCH_2CH_2O$—, —$OCH_2CH_2OCH_2CH_2O$—, or —$OCH_2CH_2OCH_2CH_2OCH_2CH_2O$—.

The term "heteocycloalkyl" refers to a cycloalkyl group that includes at least one heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 12 carbons in the ring. In some embodiments, heterocycloalkyls have from 2 to 10 carbons in the ring. In some embodiments, heterocycloalkyls have from 2 to 10 carbons in the ring and 1 or 2 N atoms. In some embodiments, heterocycloalkyls have from 2 to 10 carbons in the ring and 3 or 4 N atoms. In some embodiments, heterocycloalkyls have from 2 to 12 carbons, 0-2 N atoms, 0-2 O atoms, 0-2 P atoms, and 0-1 S atoms in the ring. In some embodiments, heterocycloalkyls have from 2 to 12 carbons, 1-3 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "heteroaryl" refers to an aryl group that includes one or more ring heteroatoms selected from nitrogen, oxygen, and sulfur. In some embodiments, heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-6 N atoms in the ring. In some embodiments, a heteroaryl contains 1-4 N atoms in the ring. In some embodiments, a heteroaryl contains 4-6 N atoms in the ring. In some embodiments, a heteroaryl contains 0-4 N atoms, 0-10 atoms, 0-1 P atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, a bicyclic heteroaryl is a $C_6$-$C_9$ heteroaryl. In some embodiments, a heteroaryl group comprises a partially reduced cycloalkyl or heterocycloalkyl group defined herein (e.g., 7,8-dihydroquinoline). In some embodiments, a heteroaryl group comprises a fully reduced cycloalkyl or heterocycloalkyl group defined herein (e.g., 5,6,7,8-tetrahydroquinoline). When heteroaryl comprises a cycloalkyl or heterocycloalkyl group, the heteroaryl is bonded to the rest of the molecule through a heteroaromatic ring carbon or hetero atom. A heteroaryl radical can be a monocyclic or polycyclic (e.g., bicyclic, tricyclic, or tetracyclic) ring system, which may include fused, spiro or bridged ring systems.

The term "optionally substituted" or "substituted" means that the referenced group is optionally substituted with one or more additional group(s) individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —NH(cyclopropyl), —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

II. Description

In one aspect, described herein is a modified polypeptide that comprises a modified interleukin-2 (IL-2) polypeptide, wherein the modified IL-2 polypeptide comprises a covalently attached first polymer. Described herein is a modified polypeptide comprising a modified interleukin-2 (IL-2) polypeptide, wherein the modified IL-2 polypeptide comprises a first polymer covalently attached at residue F42Y, and wherein residue position numbering of the modified IL-2 polypeptide is based on SEQ ID NO:1 as a reference sequence. In another aspect, described herein is a modified polypeptide, comprising: a modified interleukin-2 (IL-2) polypeptide, wherein the modified IL-2 polypeptide exhibits a greater functional activity of IL-2 Receptor β (IL-2Rβ) than IL-2 Receptor α (IL-2Rα) as measured by half maximal effective concentration (EC50) in an agonist assay, and wherein a ratio of the EC50 value of the modified IL-2 polypeptide on IL-2Rβ over the EC50 value of the modified IL-2 polypeptide on IL-2Rα is below 2:1. In certain embodiments is a modified polypeptide comprising a modified interleukin-2 (IL-2) polypeptide, wherein the modified IL-2 polypeptide exhibits a greater functional activity of IL-2 Receptor β (IL-2Rβ) than IL-2 Receptor α (IL-2Rα) as measured by half maximal effective concentration (EC50) in an agonist assay, and wherein a ratio of the EC50 value of the modified IL-2 polypeptide on IL-2Rβ over the EC50 value of the modified IL-2 polypeptide on IL-2Rα is below 1:1. In certain embodiments is a modified polypeptide comprising a modified interleukin-2 (IL-2) polypeptide, wherein the modified IL-2 polypeptide exhibits a greater functional activity of IL-2 Receptor β (IL-2Rβ) than IL-2 Receptor α (IL-2Rα) as measured by half maximal effective concentration (EC50) in an agonist assay, and wherein a ratio of the EC50 value of the modified IL-2 polypeptide on IL-2Rβ over the EC50 value of the modified IL-2 polypeptide on IL-2Rα is below 1:5. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

Binding Affinity

In one aspect, described herein is a modified IL-2 polypeptide that exhibits a greater affinity for IL-2 Receptor β (IL-2Rβ) than IL-2 Receptor α (IL-2Rα). In some embodiments, the affinity to IL-2Rβ, IL-2Rα, or both is measured by dissociation constant ($K_d$). As used herein, the phrase "the $K_d$ of the modified IL-2 polypeptide/IL-2Rβ" means the dissociation constant of the binding interaction of the modified IL-2 polypeptide and IL-2Rβ. Similarly, the phrase the $K_d$ of the modified IL-2 polypeptide/IL-2Rα" means the dissociation constant of the binding interaction of the modified IL-2 polypeptide and IL-2Rα. In some embodiments, the $K_d$ of the modified IL-2 polypeptide/IL-2Rβ is less than 300 nM. In some embodiments, the $K_d$ of the modified IL-2 polypeptide/IL-2Rβ is less than 1000 nM, less than 750 nM, less than 500 nM, less than 450, less than 400 nM, less than 350 nM, less than 300 nM, less than 250 nM, less than 200 nM, less than 150 nM, less than 140 nM, less than 130 nM, less than 125 nM, less than 120 nM, less than 100 nM. In some embodiments, the $K_d$ of the modified IL-2 polypeptide/IL-2Rβ is higher than 1000 nM, higher than 500 nM, higher than 450 nM, higher than 400 nM, higher than 350 nM, higher than 300 nM, higher than 250 nM, higher than 200 nM, higher than 150 nM, higher than 140 nM, higher than 130 nM, higher than 125 nM, higher than 120 nM, or higher than 100 nM. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, the $K_d$ of a modified IL-2 polypeptide described herein/IL-2Rβ is substantially the same as wild-type IL-2. In some embodiments, the $K_d$ of the modified IL-2 polypeptide/IL-2Rβ is lower compared to wild-type IL-2/IL-2Rβ. In some embodiments, the $K_d$ of the modified IL-2 polypeptide/IL-2Rβ is lower than the wild-type IL-2/IL-2Rβ. In some embodiments, the $K_d$ of the modified IL-2 polypeptide/IL-2Rβ is at least 10%, at least 20%, at least 30%, at least 40%, at least 50%, at least 60%, at least 70%, at least 80%, at least 85%, or at least 90% lower than the wild-type IL-2/IL-2Rβ. In some embodiments, the $K_d$ of the modified IL-2 polypeptide/IL-2Rβ is at least 20% lower than the wild-type IL-2/IL-2Rβ. In some embodiments, the $K_d$ of the modified IL-2 polypeptide/IL-2Rβ is at least 40% lower than the wild-type IL-2/IL-2Rβ. In some embodiments, the $K_d$ of the modified IL-2 polypeptide/IL-2Rβ is at least 60% lower than the wild-type IL-2/IL-2Rβ. In some embodiments, the $K_d$ of the modified IL-2 polypeptide/IL-2Rβ is at least 80% lower than the wild-type IL-2/IL-2Rβ.

In some embodiments, the $K_d$ of a modified IL-2 polypeptide described herein/IL-2Rα is at most 10%, at most 20%, at most 30%, at most 40%, or at most 50% higher compared to wild-type IL-2/IL-2Rα. In some embodiments, the $K_d$ of the modified IL-2 polypeptide/IL-2Rα is at most 10% higher compared to wild-type IL-2/IL-2Rα. In some embodiments, the $K_d$ of the modified IL-2 polypeptide/IL-2Rα is at most 20% higher compared to wild-type IL-2/IL-2Rα. In some embodiments, the $K_d$ of the modified IL-2 polypeptide/IL-2Rβ is at most 30% higher compared to wild-type IL-2/IL-2Rα. In some embodiments, the $K_d$ of the modified IL-2 polypeptide/IL-2Rα is at most 40% higher compared to wild-type IL-2/IL-2Rα. In some embodiments, the $K_d$ of the modified IL-2 polypeptide/IL-2Rα is at most 50% higher compared to wild-type IL-2/IL-2Rα.

In some embodiments, the $K_d$ of a modified IL-2 polypeptide described herein/IL-2Rα is at least 500 nM, at least 1000 nM, at least 1500 nM, at least 2000 nM, at least 2500 nM, or at least 5000 nM. In some embodiments, the $K_d$ of the modified IL-2 polypeptide/IL-2Rα is at least 500 nM. In some embodiments, the $K_d$ of the modified IL-2 polypeptide/IL-2Rα is at least 1000 nM. In some embodiments, the $K_d$ of the modified IL-2 polypeptide/IL-2Rα is at least 1500 nM. In some embodiments, the $K_d$ of the modified IL-2 polypeptide/IL-2Rα is at least 2500 nM. In some embodiments, the $K_d$ of the modified IL-2 polypeptide/IL-2Rα is at least 5000 nM.

In some embodiments, a modified IL-2 polypeptide described herein exhibits a greater affinity for IL-2 Receptor β (IL-2Rβ) than IL-2 Receptor α (IL-2Rα) as measured by dissociation constant ($K_d$), and wherein a $K_D$ of the modified IL-2 polypeptide/IL-2Rβ is less than 300 nM. In some embodiments, the modified IL-2 polypeptide exhibits a greater affinity for IL-2 Receptor β (IL-2Rβ) than IL-2 Receptor α (IL-2Rα) as measured by dissociation constant ($K_d$), and wherein a $K_d$ of the modified IL-2 polypeptide/IL-2Rβ is less than 500 nM. In some embodiments, the modified IL-2 polypeptide exhibits a greater affinity for IL-2 Receptor β (IL-2Rβ) than IL-2 Receptor α (IL-2Rα) as measured by dissociation constant ($K_d$), and wherein a $K_d$ of the modified IL-2 polypeptide/IL-2Rβ is less than 200 nM. In some embodiments, the modified IL-2 polypeptide exhibits a greater affinity for IL-2 Receptor β (IL-2Rβ) than IL-2 Receptor α (IL-2Rα) as measured by dissociation constant ($K_d$), and wherein a $K_d$ of the modified IL-2 polypeptide/IL-2Rβ is less than 100 nM. In some embodiments, the $K_d$ is determined by surface plasmon resonance. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, a modified IL-2 polypeptide described herein exhibits a greater functional activity for IL-2Rβ than IL-2Rα. In some embodiments, the functional activity is stimulation of immune cells through interactions of the modified IL-2 polypeptide and IL-2Rβ. In some embodiments, wherein the modified IL-2 polypeptide exhibits a greater functional activity of IL-2Rβ than IL-2Rα as measured by half maximal effective concentration (EC50) in an agonist assay. In some embodiments, wherein the modified IL-2 polypeptide exhibits a greater functional activity of IL-2Rβ than IL-2Rα as measured by half maximal effective concentration (EC50) in an agonist assay, and wherein a ratio of the EC50 value of the modified IL-2 polypeptide on IL-2Rβ over the EC50 value of the modified IL-2 polypeptide on IL-2Rα is below 2:1, below 1.75:1, below 1.5:1, or below 1.25:1. In some embodiments, a ratio of the EC50 value of the modified IL-2 polypeptide on IL-2Rβ over the EC50 value of the modified IL-2 polypeptide on IL-2Rα is below 2:1. In some embodiments, a ratio of the EC50 value of the modified IL-2 polypeptide on IL-2Rβ over the EC50 value of the modified IL-2 polypeptide on IL-2Rα is below 1.75:1. In some embodiments, a ratio of the EC50 value of the modified IL-2 polypeptide on IL-2Rβ over the EC50 value of the modified IL-2 polypeptide on IL-2Rα is below 1.5:1. In some embodiments, a ratio of the EC50 value of the modified IL-2 polypeptide on IL-2Rβ over the EC50 value of the modified IL-2 polypeptide on IL-2Rα is below 1.25:1. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, binding between a modified polypeptide described herein and IL-2 Receptor α (IL-2Rα) is reduced. In some embodiments, binding between the modified IL-2 polypeptide and IL-2 Receptor α (IL-2Rα) is reduced by at least 30%, at least 40%, at least 50%, at least 60%, at least 70%, at least 80%, at least 90%, at least 95%, or at least 99% compared to the binding between a wild-type IL-2 polypeptide and IL-2Rα. In some embodiments, binding between the modified IL-2 polypeptide and IL-2 Receptor α (IL-2Rα) is reduced by at least 70% compared to the binding between a wild-type IL-2 polypeptide and IL-2Rα. In some embodiments, binding between the modified IL-2 polypeptide and IL-2 Receptor α (IL-2Rα) is reduced by at least 80% compared to the binding between a wild-type IL-2 polypeptide and IL-2Rα. In some embodiments, binding between the modified IL-2 polypeptide and IL-2 Receptor α (IL-2Rα) is reduced by at least 90% compared to the binding between a wild-type IL-2 polypeptide and IL-2Rα. In some embodiments, binding between the modified IL-2 polypeptide and IL-2 Receptor α (IL-2Rα) is reduced by at least 95% compared to the binding between a wild-type IL-2 polypeptide and IL-2Rα. In some embodiments, binding between the modified IL-2 polypeptide and IL-2 Receptor α (IL-2Rα) is reduced by at least 99% compared to the binding between a wild-type IL-2 polypeptide and IL-2Rα. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, binding between a modified IL-2 polypeptide described herein and IL-2 Receptor β (IL-2Rβ) is reduced compared to the binding between a wild-type IL-2 polypeptide and IL-2Rβ. In some embodiments, binding between the modified IL-2 polypeptide and IL-2 Receptor β (IL-2Rβ) is reduced by at most 0%, at most 1%, at most 2%, at most 5%, at most 10%, at most 15%, at most 20%, at most 25%, or at most 30% compared to the binding between a wild-type IL-2 polypeptide and IL-2Rβ. In some embodiments, binding between the modified IL-2 polypeptide and IL-2Rβ is reduced by at most 10% compared to the binding between a wild-type IL-2 polypeptide and IL-2Rβ. In some embodiments, binding between the modified IL-2 polypeptide and IL-2Rβ is reduced by at most 15% compared to the binding between a wild-type IL-2 polypeptide and IL-2Rβ. In some embodiments, binding between the modified IL-2 polypeptide and IL-2Rβ is reduced by at most 20% compared to the binding between a wild-type IL-2 polypeptide and IL-2Rβ. In some embodiments, binding between the modified IL-2 polypeptide and IL-2Rβ is reduced by at most 25% compared to the binding between a wild-type IL-2 polypeptide and IL-2Rβ. In some embodiments, binding between the modified IL-2 polypeptide and IL-2Rβ is reduced by at most 30% compared to the binding between a wild-type IL-2 polypeptide and IL-2Rβ. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, binding between a modified IL-2 polypeptide described herein and IL-2 Receptor β (IL-2Rβ) is increased. In some embodiments, binding between the modified IL-2 polypeptide and IL-2 Receptor β (IL-2Rβ) is increased by at least 0.1%, at least 1%, at least 2%, at least 5%, at least 10%, at least 15%, or at least 20% compared to the binding between a wild-type IL-2 polypeptide and IL-2Rβ. In some embodiments, binding between the modified IL-2 polypeptide and IL-2Rβ is increased by at least 5% compared to the binding between a wild-type IL-2 polypeptide and IL-2Rβ. In some embodiments, binding between the modified IL-2 polypeptide and IL-2Rβ is increased by at least 10% compared to the binding between a wild-type IL-2 polypeptide and IL-2Rβ. In some embodiments, binding between the modified IL-2 polypeptide and IL-2Rβ is increased by at least 15% compared to the binding between a wild-type IL-2 polypeptide and IL-2Rβ. In some embodiments, binding between the modified IL-2 polypeptide and IL-2Rβ is increased by at least 20% compared to the binding between a wild-type IL-2 polypeptide and IL-2Rβ. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

Biological Activity

In some embodiments, a modified IL-2 polypeptide described herein is capable of expanding CD4+ helper cell, CD8+ central memory cell, CD8+ effector memory cell, naïve CD8+ cell, Natural Killer (NK) cell, Natural killer T (NKT) cell populations, or a combination thereof. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, a modified IL-2 described herein polypeptide expands a cell population of regulatory T cells ($T_{reg}$ cells). In some embodiments, the modified IL-2 polypeptide expands a cell population of $T_{reg}$ cells by at least 1%, at least 2%, at least 5%, at least 10%, at least 15%, at least 20%, at least 30%, at least 40%, at least 50%, at least 100%, or at least 200% when the modified IL-2 polypeptide is in contact with the population. In some embodiments, the modified IL-2 polypeptide expands a cell population of $T_{reg}$ cells by at least 20% when the modified IL-2 polypeptide is in contact with the population. In some embodiments, the modified IL-2 polypeptide expands a cell population of $T_{reg}$ cells by at least 30% when the modified IL-2 polypeptide is in contact with the population. In some embodiments, the modified IL-2 polypeptide expands a cell population of $T_{reg}$ cells by at least 40% when the modified IL-2 polypeptide is in contact with the population. In some embodiments, the modified IL-2 polypeptide expands a cell population of $T_{reg}$ cells by at least 50% when the modified IL-2 polypeptide is in contact with the population. In some embodiments, the modified IL-2 polypeptide expands a cell population of $T_{reg}$ cells by at least 100% when the modified IL-2 polypeptide is in contact with the population. In some embodiments, the modified IL-2 polypeptide expands a cell population of $T_{reg}$ cells by at least 200% when the modified IL-2 polypeptide is in contact with the population. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, the modified IL-2 polypeptide expands a cell population of regulatory T cells ($T_{reg}$ cells). In some embodiments, the modified IL-2 polypeptide expands a cell population Treg cells by at most 5%, at most 10%, at most 20%, at most 30%, at most 40%, at most 50%, at most 75%, at most 100%, or at most 500% when the modified IL-2 polypeptide is in contact with the population.

In some embodiments, a modified IL-2 polypeptide described herein expands a cell population of effector T cells ($T_{eff}$ cells). In some embodiments, the modified IL-2 polypeptide expands a cell population of $T_{eff}$ cells by at least 1%, at least 2%, at least 5%, at least 10%, at least 15%, at least 20%, at least 30%, at least 40%, at least 50%, at least 100%, or at least 200% when the modified IL-2 polypeptide is in contact with the population. In some embodiments, the modified IL-2 polypeptide expands a cell population of $T_{eff}$ cells by at least 20% when the modified IL-2 polypeptide is in contact with the population. In some embodiments, the modified IL-2 polypeptide expands a cell population of $T_{eff}$ cells by at least 30% when the modified IL-2 polypeptide is in contact with the population. In some embodiments, the modified IL-2 polypeptide expands a cell population of $T_{eff}$ cells by at least 40% when the modified IL-2 polypeptide is in contact with the population. In some embodiments, the modified IL-2 polypeptide expands a cell population of $T_{eff}$ cells by at least 50% when the modified IL-2 polypeptide is in contact with the population. In some embodiments, the modified IL-2 polypeptide expands a cell population of $T_{eff}$ cells by at least 100% when the modified IL-2 polypeptide is in contact with the population. In some embodiments, the modified IL-2 polypeptide expands a cell population of $T_{eff}$ cells by at least 200% when the modified IL-2 polypeptide is in contact with the population.

In some embodiments, a modified IL-2 polypeptide described herein expands a cell population of effector T cells ($T_{eff}$ cells). In some embodiments, the modified IL-2 polypeptide expands a cell population of $T_{eff}$ cells by at most 5%, at most 10%, at most 20%, at most 30%, at most 40%, at most 50%, at most 75%, at most 100%, or at most 500% when the modified IL-2 polypeptide is in contact with the population. In some embodiments, the modified IL-2 polypeptide expands a cell population of Teff cells by at most 5%, when the modified IL-2 polypeptide is in contact with the population. In some embodiments, the modified IL-2 polypeptide expands a cell population of $T_{eff}$ cells by at most 20%, when the modified IL-2 polypeptide is in contact with the population. In some embodiments, the modified IL-2 polypeptide expands a cell population of $T_{eff}$ cells by at most 50%, when the modified IL-2 polypeptide is in contact with the population. In some embodiments, the modified IL-2 polypeptide expands a cell population of $T_{eff}$ cells by at most 100%, when the modified IL-2 polypeptide is in contact with the population. In some embodiments, the modified IL-2 polypeptide expands a cell population of $T_{eff}$ cells by at most 500%, when the modified IL-2 polypeptide is in contact with the population.

In some embodiments, a ratio of cell population expansion of $T_{eff}$ cells over cell population expansion of $T_{reg}$ cells expanded by a modified IL-2 polypeptide described herein is from about 0.1 to about 15, from about 0.5 to about 10, from about 0.75 to about 5, or from about 1 to about 2. In some embodiments, a ratio of cell population expansion of $T_{eff}$ cells over cell population expansion of $T_{reg}$ cells expanded by the modified IL-2 polypeptide is 0.1 to 15. In some embodiments, a ratio of cell population expansion of $T_{eff}$ cells over cell population expansion of $T_{reg}$ cells expanded by the modified IL-2 polypeptide is 0.1 to 0.5, 0.1 to 0.75, 0.1 to 1, 0.1 to 2, 0.1 to 5, 0.1 to 10, 0.1 to 15, 0.5 to 0.75, 0.5 to 1, 0.5 to 2, 0.5 to 5, 0.5 to 10, 0.5 to 15, 0.75 to 1, 0.75 to 2, 0.75 to 5, 0.75 to 10, 0.75 to 15, 1 to 2, 1 to 5, 1 to 10, 1 to 15, 2 to 5, 2 to 10, 2 to 15, 5 to 10, 5 to 15, 10 to 15, or any numbers or ranges therebetween. In some embodiments, a ratio of cell population expansion of $T_{eff}$ cells over cell population expansion of $T_{reg}$ cells expanded by the modified IL-2 polypeptide is about 0.1, 0.5, 0.75, 1, 2, 5, 10, or 15. In some embodiments, a ratio of cell population expansion of $T_{eff}$ cells over cell population expansion of $T_{reg}$ cells expanded by the modified IL-2 polypeptide is at least 0.1, 0.5, 0.75, 1, 2, 5, or 10. In some embodiments, a ratio of cell population expansion of $T_{eff}$ cells over cell population expansion of $T_{reg}$ cells expanded by the modified IL-2 polypeptide is at most 0.5, 0.75, 1, 2, 5, 10, or 15.

In some embodiments, a cell population expanded by a modified IL-2 polypeptide provided herein is an in vitro cell population, an in vivo cell population, or an ex vivo cell population. In some embodiments, the cell population is an in vitro cell population. In some embodiments, the cell population is an in vivo cell population. In some embodiments, the cell population is an ex vivo cell population. The cell population may be a population of CD4+ helper cells, CD8+ central memory cells, CD8+ effector memory cells, naïve CD8+ cells, Natural Killer (NK) cells, Natural killer T (NKT) cells, or a combination thereof.

In some embodiments, the levels of cells are measured 1 hour after injection of the modified IL-2 polypeptide. In some embodiments, the levels of cells are measured 2 hours after injection of the modified IL-2 polypeptide. In some embodiments, the levels of cells are measured 4 hours after injection of the modified IL-2 polypeptide. In some embodiments, the levels of cells are measured 30 minutes after injection of the modified IL-2 polypeptide.

In some embodiments, a modified IL-2 polypeptide described herein comprises a covalently attached polymer for half-life extension. In some embodiments, the modified IL-2 polypeptide comprises a covalently attached polymer for plasma or serum half-life extension. In some embodiments, a plasma or serum half-life of the modified IL-2 polypeptide is at least 1.5-fold, 2-fold, 3-fold, 4-fold, 5-fold, 6-fold, 7-fold, 8-fold, 9-fold, or 10-fold longer compared to a plasma or serum half-life of a wild-type IL-2 polypeptide. In some embodiments, a plasma or serum half-life of the modified IL-2 polypeptide is 1.5-fold to 10-fold longer compared to a plasma or serum half-life of a wild-type IL-2 polypeptide. In some embodiments, a plasma or serum half-life of the modified IL-2 polypeptide is 1.5-fold to 2-fold, 1.5-fold to 4-fold, 1.5-fold to 6-fold, 1.5-fold to 8-fold, 1.5-fold to 10-fold, 2-fold to 4-fold, 2-fold to 6-fold, 2-fold to 8-fold, 2-fold to 10-fold, 4-fold to 6-fold, 4-fold to 8-fold, 4-fold to 10-fold, 6-fold to 8-fold, 6-fold to 10-fold, or 8-fold to 10-fold longer compared to a plasma or serum half-life of a wild-type IL-2 polypeptide. In some embodiments, a plasma or serum half-life of the modified IL-2 polypeptide is 1.5-fold, 2-fold, 4-fold, 6-fold, 8-fold, or 10-fold longer compared to a plasma or serum half-life of a wild-type IL-2 polypeptide. In some embodiments, a plasma or serum half-life of the modified IL-2 polypeptide is at least 1.5-fold, 2-fold, 4-fold, 6-fold, or 8-fold. In some embodiments, a plasma or serum half-life of the modified IL-2 polypeptide is at most 2-fold, 4-fold, 6-fold, 8-fold, or 10-fold longer compared to a plasma or serum half-life of a wild-type IL-2 polypeptide. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, a plasma or serum half-life of a modified IL-2 polypeptide described herein is at least 1.5-fold, 2-fold, 3-fold, 4-fold, 5-fold, 6-fold, 7-fold, 8-fold, 9-fold, or 10-fold longer compared to a plasma or serum half-life of the modified IL-2 polypeptide without the half-life extending polymer. In some embodiments, a plasma or serum half-life of the modified IL-2 polypeptide is 1.5-fold to 10-fold longer compared to a plasma or serum half-life of the modified IL-2 polypeptide without the half-life extending polymer. In some embodiments, a plasma or serum half-life of the modified IL-2 polypeptide is 1.5-fold to 2-fold, 1.5-fold to 4-fold, 1.5-fold to 6-fold, 1.5-fold to 8-fold, 1.5-fold to 10-fold, 2-fold to 4-fold, 2-fold to 6-fold, 2-fold to 8-fold, 2-fold to 10-fold, 4-fold to 6-fold, 4-fold to 8-fold, 4-fold to 10-fold, 6-fold to 8-fold, 6-fold to 10-fold, or 8-fold to 10-fold longer compared to a plasma or serum half-life of the modified IL-2 polypeptide without the half-life extending polymer. In some embodiments, a plasma or serum half-life of the modified IL-2 polypeptide is 1.5-fold, 2-fold, 4-fold, 6-fold, 8-fold, or 10-fold longer compared to a plasma or serum half-life of the modified IL-2 polypeptide without the half-life extending polymer. In some embodiments, a plasma or serum half-life of the modified IL-2 polypeptide is at least 1.5-fold, 2-fold, 4-fold, 6-fold, or 8-fold. In some embodiments, a plasma or serum half-life of the modified IL-2 polypeptide is at most 2-fold, 4-fold, 6-fold, 8-fold, or 10-fold longer compared to a plasma or serum half-life of the modified IL-2 polypeptide without the half-life extending polymer. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

Site-Specific Modification

In some embodiments, a modified IL-2 polypeptide described herein comprises one or more modifications at one or more amino acid residues. In some embodiments, the residue position numbering of the modified IL-2 polypeptide is based on SEQ ID NO:1 as a reference sequence. In some embodiments, the residue position numbering of the modified IL-2 polypeptide is based on a wild-type human IL-2 polypeptide as a reference sequence. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

Modifications to the polypeptides described herein encompass mutations, addition of various functionalities, deletion of amino acids, addition of amino acids, or any other alteration of the wild-type version of the protein or protein fragment. Functionalities which may be added to polypeptides include polymers, linkers, alkyl groups, detectable molecules such as chromophores or fluorophores, reactive functional groups, or any combination thereof. In some embodiments, functionalities are added to individual amino acids of the polypeptides. In some embodiments, functionalities are added site-specifically to the polypeptides.

In some embodiments, a modified IL-2 polypeptide described herein comprises a modification at an amino acid residue from the region of residues 35-46, wherein the residue numbering is based on SEQ ID NO:1. In some embodiments, the modification is at K35, L46, T37, R38, M39, L40, T41, F42, K43, F44, Y45, or M46. In some embodiments, the modification is at F42. In some embodiments, the modification is at Y45. In some embodiments, the modified IL-2 polypeptide comprises a modification at the N-terminal residue. In some embodiments, the modified IL-2 polypeptide comprises a C125S mutation. In some embodiments, the modified IL-2 polypeptide comprises an A1 deletion.

In some embodiments, a modified IL-2 polypeptide described herein comprises a first polymer covalently attached at residue in the region of residues 35-46, wherein residue position numbering of the modified IL-2 polypeptide is based on SEQ ID NO:1 as a reference sequence. In some embodiments, the modified IL-2 polypeptide comprises a first polymer covalently attached at residue in the region of residues 39-43. In some embodiments, the modified IL-2 polypeptide comprises a first polymer covalently attached at residue F42. In some embodiments, the modified IL-2 polypeptide comprises a first polymer covalently attached at residue F42Y. In some embodiments, the modified IL-2 polypeptide comprises a first polymer covalently attached at residue in the region of residues 44-46. In some embodiments, the modified IL-2 polypeptide comprises a first polymer covalently attached at residue Y45.

In some embodiments, a modified IL-2 polypeptide described herein comprises one or more PEGylated tyrosine located at an amino acid residue in the region from residue 35 to residue 45. In some embodiments, the one or more PEGylated tyrosine is located at residue 42, residue 45, or both.

In some embodiments, the one or more PEGylated tyrosine is located at residue 42. In some embodiments, the one or more PEGylated tyrosine is located at residue 45. In some embodiments, the one or more PEGylated tyrosine is located at both residue 42 and residue 45. In some embodiments, the modified IL-2 polypeptide comprises two PEGylated tyrosines, each independently having a structure of Formula (I).

In one aspect, disclosed herein is a modified IL-2 polypeptide comprising one or more amino acid substitutions. In some embodiments, the modified IL-2 polypeptide comprises F42Y and Y45. In some embodiments, the modified IL-2 polypeptide comprises a homoserine (Hse) residue located in any one of residues 35-45. In some embodiments, the modified IL-2 polypeptide comprises a Hse residue located in any one of residues 61-81. In some embodiments, the modified IL-2 polypeptide comprises a Hse residue located in any one of residues 94-114. In some embodiments, the modified IL-2 polypeptide comprises 1, 2, 3, or more Hse residues. In some embodiments, the modified IL-2 polypeptide comprises Hse41, Hse71, Hse104, or a combination thereof. In some embodiments, the modified IL-2 polypeptide comprises Hse41, Hse71, and Hse104. In some embodiments, the modified IL-2 polypeptide comprises at least two amino acid substitutions, wherein the at least two amino acid substitutions are selected from (a) a homoserine (Hse) residue located in any one of residues 35-45; (b) a homoserine residue located in any one of residues 61-81; and (c) a homoserine residue located in any one of residues 94-114. In some embodiments, the modified IL-2 polypeptide comprises Hse41 and Hse71. In some embodiments, the modified IL-2 polypeptide comprises Hse41 and Hse104. In some embodiments, the modified IL-2 polypeptide comprises Hse71 and Hse104. In some embodiments, the modified IL-2 polypeptide comprises Hse41. In some embodiments, the modified IL-2 polypeptide comprises Hse71. In some embodiments, the modified IL-2 polypeptide comprises Hse104. In some embodiments, the modified IL-2 polypeptide comprises 1, 2, 3, or more norleucine (Nle) residues. In some embodiments, the modified IL-2 polypeptide comprises a Nle residue located in any one of residues 18-28. In some embodiments, the modified IL-2 polypeptide comprises one or more Nle residues located in any one of residues 34-50. In some embodiments, the modified IL-2 polypeptide comprises a Nle residue located in any one of residues 20-60. In some embodiments, the modified IL-2 polypeptide comprises three Nle substitutions. In some embodiments, the modified IL-2 polypeptide comprises Nle23, Nle39, and Nle46. In some embodiments, the modified IL-2 polypeptide comprises SEQ ID NO: 3. In some embodiments, the modified IL-2 polypeptide comprises SEQ ID NO: 3 with an A1 deletion. In some embodiments, the modified IL-2 polypeptide comprises SEQ ID NO: 4. In some embodiments, the modified IL-2 polypeptide comprises an A1 deletion. In some embodiments, the modified IL-2 polypeptide comprises SEQ ID NO: 4 with an A1 deletion.

In some embodiments, a modified IL-2 polypeptide provided herein comprises an amino acid sequence of any one of SEQ ID NOs: 3-22 provided in Table 7. In some embodiments, the modified IL-2 polypeptide comprises an amino acid sequence at least 80%, 85%, 90%, 95%, 99, or 100% identical to the sequence of any one of SEQ ID NOs: 3-22. In some embodiments, the modified IL-2 polypeptide comprises an amino acid sequence of SEQ ID NO: 3. In some embodiments, the modified IL-2 polypeptide comprises an amino acid sequence at least 80%, 85%, 90%, 95%, 99, or 100% identical to the sequence of SEQ ID NO: 3. In some embodiments, the modified IL-2 polypeptide comprises an amino acid sequence of SEQ ID NO: 4. In some embodiments, the modified IL-2 polypeptide comprises an amino acid sequence at least 80%, 85%, 90%, 95%, 99, or 100% identical to the sequence of SEQ ID NO: 4. In some embodiments, the modified IL-2 polypeptide comprises an amino acid sequence of SEQ ID NO: 9. In some embodiments, the modified IL-2 polypeptide comprises an amino acid sequence at least 80%, 85%, 90%, 95%, 99, or 100% identical to the sequence of SEQ ID NO: 9.

In some embodiments, a modified IL-2 polypeptide described herein comprises at least 3, at least 4, at least 5, at least 6, at least 7, or at least 9 amino acid substitutions. In some embodiments, the modified IL-2 polypeptide comprises 3 to 9 amino acid substitutions. In some embodiments, the modified IL-2 polypeptide comprises 3 or 4 amino acid substitutions, 3 to 5 amino acid substitutions, 3 to 6 amino acid substitutions, 3 to 7 amino acid substitutions, 3 to 9 amino acid substitutions, 4 or 5 amino acid substitutions, 4 to 6 amino acid substitutions, 4 to 7 amino acid substitutions, 4 to 9 amino acid substitutions, 5 or 6 amino acid substitutions, 5 to 7 amino acid substitutions, 5 to 9 amino acid substitutions, 6 or 7 amino acid substitutions, 6 to 9 amino acid substitutions, or 7 to 9 amino acid substitutions. In some embodiments, the modified IL-2 polypeptide comprises 3 amino acid substitutions, 4 amino acid substitutions, 5 amino acid substitutions, 6 amino acid substitutions, 7 amino acid substitutions, or 9 amino acid substitutions. In some embodiments, the modified IL-2 polypeptide comprises at most 4 amino acid substitutions, 5 amino acid substitutions, 6 amino acid substitutions, 7 amino acid substitutions, or 9 amino acid substitutions. In some embodiments, one or more of the amino acid substitutions are selected from Table 1. In some embodiments, one or more of the amino acid substitutions are selected from Table 2. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, a modified IL-2 polypeptide described herein comprises a second modification. In some embodiments, the modified IL-2 polypeptide comprises a third modification. In some embodiments, the modified IL-2 polypeptide comprises a second and a third modification.

In some embodiments, a modified IL-2 polypeptide is linked with an additional polypeptide. In some embodiments, the modified IL-2 polypeptide and the additional polypeptide form a fusion polypeptide. In some embodiments, the modified IL-2 polypeptide and the additional polypeptide are conjugated together. In some embodiments, the additional polypeptide is part of a polypeptide complex. In some embodiments, the additional polypeptide comprises an antibody or binding fragment thereof. In some embodiments, the antibody comprises a humanized antibody, a murine antibody, a chimeric antibody, a bispecific antibody, any fragment thereof, or any combination thereof. In some embodiments, the antibody is a monoclonal antibody or any fragment thereof. In some embodiments, the modified IL-2 polypeptide is linked with at least one additional polypeptide. In some embodiments, the modified IL-2 polypeptide is linked with a plurality of additional polypeptides.

In some embodiments, a modified IL-2 polypeptide described herein comprises at least about 80%, at least about 85%, at least about 90%, at least about 95%, at least about 96%, at least about 97%, at least about 98%, at least about 99%, or 100% sequence identity to SEQ ID NO: 3. In some embodiments, the sequence identity is measured by protein-protein BLAST algorithm using parameters of Matrix BLOSUM62, Gap Costs Existence: 11, Extension: 1, and Compositional Adjustments Conditional Compositional Score Matrix Adjustment.

A modified IL-2 polypeptide as described herein can comprise one or more non-canonical amino acids. "Non-canonical" amino acids can refer to amino acid residues in D- or L-form that are not among the 20 canonical amino acids generally incorporated into naturally occurring proteins. For example, in some cases, Tyr 45 and/or Phe 42 are substituted with non-canonical amino acids. In some embodiments, one or more amino acids located at positions provided in Table 1 and/or Table 2 are substituted with one or more non-canonical amino acids. Non-canonical amino acids include, but are not limited to N-alpha-(9-Fluorenylmethyloxycarbonyl)-L-biphenylalanine (Fmoc-L-Bip-OH) and N-alpha-(9-Fluorenylmethyloxycarbonyl)-O-benzyl-L-tyrosine (Fmoc-L-Tyr(Bzl)-OH. Exemplary non-canonical amino acids include p-acetyl-L-phenylalanine, p-iodo-L-phenylalanine, p-methoxyphenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, p-Boronophenylalanine, O-propargyltyrosine, L-phosphoserine, phosphonoserine, phosphonotyrosine, p-bromophenylalanine, selenocysteine, p-amino-L-phenylalanine, isopropyl-L-phenylalanine, azido-lysine (AzK), an analogue of a tyrosine amino acid; an analogue of a glutamine amino acid; an analogue of a phenylalanine amino acid; an analogue of a serine amino acid; an analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, a β-amino acid; a cyclic amino acid other than proline or histidine; an aromatic amino acid other than phenylalanine, tyrosine or tryptophan; or a combination thereof. In some embodiments, the non-canonical amino acids are selected from β-amino acids, homoamino acids, cyclic amino acids and amino acids with derivatized side chains. In some embodiments, the non-canonical amino acids comprise β-alanine, β-aminopropionic acid, piperidinic acid, aminocaprioic acid, aminoheptanoic acid, aminopimelic acid, desmosine, diaminopimelic acid, $N^\alpha$-ethylglycine, $N^\alpha$-ethylaspargine, hydroxylysine, allo-hydroxylysine, isodesmosine, allo-isoleucine, ω-methylarginine, $N^\alpha$-methylglycine, $N^\alpha$-methylisoleucine, $N^\alpha$-methylvaline, γ-carboxyglutamate, ε-N,N,N-trimethyllysine, ε-N-acetyllysine, O-phosphoserine, $N^\alpha$-acetylserine, $N^\alpha$-formylmethionine, 3-methylhistidine, 5-hydroxylysine, and/or other similar amino acids. In some embodiments, Tyr 45 and/or Phe 42 are substituted with modified tyrosine residues. In some embodiments, the modified tyrosine residues comprise an amino, azide, alkyne allyl, ester, and/or amide functional groups. In some embodiments, the modified tyrosine residues at positions 42 and/or 45 have a structure built from precursors Structure 1, Structure 2, Structure 3, Structure 4, or Structure 5, wherein Structure 1 is

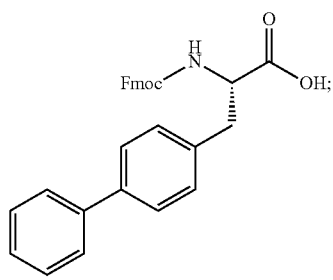

Structure 1

Structure 2 is

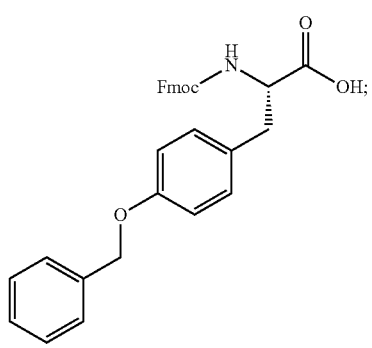

Structure 2

Structure 3 is

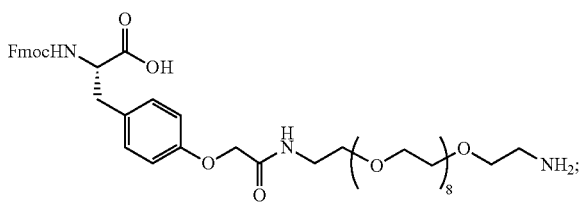

Structure 3

Structure 4 is

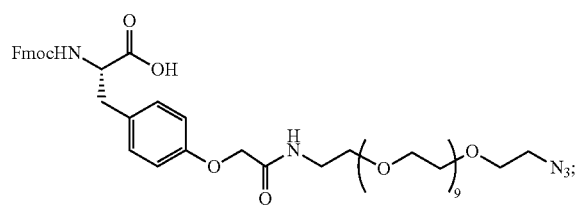

Structure 4 and Structure 5 is

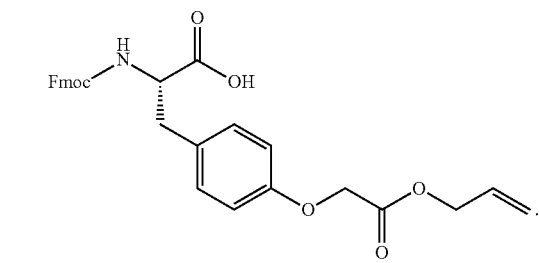

Structure 5

Polymers

In some embodiments, a herein described modified IL-2 polypeptide comprises one or more polymers covalently attached thereon. In some embodiments, the described modified IL-2 polypeptide comprises 1, 2, 3, 4, 5, 6, 7, 8, 9, 10, or more polymers covalently attached to the modified IL-2 polypeptide. In some embodiments, the described modified IL-2 polypeptide comprises a first polymer. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, the first polymer comprises a water-soluble polymer. In some embodiments, the water-soluble polymer comprises poly(alkylene oxide), polysaccharide, poly(vinyl pyrrolidone), poly(vinyl alcohol), polyoxazoline, poly(acryloylmorpholine), or a combination thereof.

In some embodiments, the water-soluble polymer is poly(alkylene oxide). In some embodiments, the water-soluble polymer is polysaccharide. In some embodiments, the water-soluble polymer is polyethylene oxide).

In some embodiments, a modified IL-2 polypeptide described herein comprises a first polymer covalently attached to the N-terminus of the IL-2 polypeptide. In some embodiments, the modified IL-2 polypeptide comprises a second polymer covalently attached thereto. In some embodiments, the modified IL-2 polypeptide comprises a second and a third polymer covalently attached thereto. In some embodiments, the second polymer is covalently attached to residue 42 or 45, wherein residue position numbering of the modified IL-2 polypeptide is based on SEQ ID NO:1 as a reference sequence. In some embodiments, the second polymer is covalently attached to residue F42Y or Y45, wherein the residue position numbering of the modified IL-2 polypeptide is based on SEQ ID NO:1 as a reference sequence. In some embodiments, the second and third polymers are covalently attached to residue 42 and 45, wherein residue position numbering of the modified IL-2 polypeptide is based on SEQ ID NO:1 as a reference sequence. In some embodiments, the second and third polymers are covalently attached to residue F42Y and Y45, wherein residue position numbering of the modified IL-2 polypeptide is based on SEQ ID NO:1 as a reference sequence.

In some embodiments, a modified IL-2 polypeptide described herein comprises (i) a tyrosine at residue 42, and (ii) a first polymer and a second polymer covalently attached thereto, wherein at least one of the first polymer and the second polymer has a weight average molecular weight of higher than 5000 Daltons, and wherein residue position numbering of the modified IL-2 polypeptide is based on SEQ ID NO:1 as a reference sequence.

In some embodiments, the attached polymer such as the first polymer has a weight average molecular weight of about 6,000 Daltons to about 50,000 Daltons. In some embodiments, the polymer has a weight average molecular weight of about 6,000 Daltons to about 10,000 Daltons, about 6,000 Daltons to about 25,000 Daltons, about 6,000 Daltons to about 50,000 Daltons, about 10,000 Daltons to about 25,000 Daltons, about 10,000 Daltons to about 50,000 Daltons, or about 25,000 Daltons to about 50,000 Daltons. In some embodiments, the polymer has a weight average molecular weight of about 6,000 Daltons, about 10,000 Daltons, about 25,000 Daltons, or about 50,000 Daltons. In some embodiments, the polymer has a weight average molecular weight of at least about 6,000 Daltons, about 10,000 Daltons, or about 25,000 Daltons. In some embodiments, the polymer has a weight average molecular weight of at most about 10,000 Daltons, about 25,000 Daltons, or about 50,000 Daltons.

In some embodiments, the attached polymer such as the first polymer has a weight average molecular weight of about 120 Daltons to about 1,000 Daltons. In some embodiments, the polymer has a weight average molecular weight of about 120 Daltons to about 250 Daltons, about 120 Daltons to about 300 Daltons, about 120 Daltons to about 400 Daltons, about 120 Daltons to about 500 Daltons, about 120 Daltons to about 1,000 Daltons, about 250 Daltons to about 300 Daltons, about 250 Daltons to about 400 Daltons, about 250 Daltons to about 500 Daltons, about 250 Daltons to about 1,000 Daltons, about 300 Daltons to about 400 Daltons, about 300 Daltons to about 500 Daltons, about 300 Daltons to about 1,000 Daltons, about 400 Daltons to about 500 Daltons, about 400 Daltons to about 1,000 Daltons, or about 500 Daltons to about 1,000 Daltons. In some embodiments, the polymer has a weight average molecular weight of about 120 Daltons, about 250 Daltons, about 300 Daltons, about 400 Daltons, about 500 Daltons, or about 1,000 Daltons. In some embodiments, the polymer has a weight average molecular weight of at least about 120 Daltons, about 250 Daltons, about 300 Daltons, about 400 Daltons, or about 500 Daltons. In some embodiments, the polymer has a weight average molecular weight of at most about 250 Daltons, about 300 Daltons, about 400 Daltons, about 500 Daltons, or about 1,000 Daltons.

In some embodiments, the attached polymer such as the first polymer comprises a water-soluble polymer. In some embodiments, the water-soluble polymer comprises poly (alkylene oxide), polysaccharide, poly(vinyl pyrrolidone), poly(vinyl alcohol), polyoxazoline, poly(acryloylmorpholine), or a combination thereof. In some embodiments, the water-soluble polymer is poly(alkylene oxide) such as polyethylene glycol (i.e., polyethylene oxide). In some embodiments, the water-soluble polymer is polyethylene glycol. In some embodiments, the water-soluble polymer comprises modified poly(alkylene oxide). In some embodiments, the modified poly(alkylene oxide) comprises one or more linker groups. In some embodiments, the one or more linker groups comprise bifunctional linkers such as an amide group, an ester group, an ether group, a thioether group, a carbonyl group and alike. In some embodiments, the one or more linker groups comprise an amide linker group. In some embodiments, the modified poly(alkylene oxide) comprises one or more spacer groups. In some embodiments, the spacer groups comprise a substituted or unsubstituted $C_1$-$C_6$ alkylene group. In some embodiments, the spacer groups comprise —$CH_2$—, —$CH_2CH_2$—, or —$CH_2CH_2CH_2$—. In some embodiments, the linker group is the product of a biorthogonal reaction (e.g., biocompatible and selective reactions). In some embodiments, the biorthogonal reaction is a Cu(I)-catalyzed or "copper-free" alkyne-azide triazole-forming reaction, the Staudinger ligation, inverse-electron-demand Diels-Alder (IEDDA) reaction, "photo-click" chemistry, or a metal-mediated process such as olefin metathesis and Suzuki-Miyaura or Sonogashira cross-coupling, in some embodiments, the first polymer is attached to the IL-2 polypeptide via click chemistry.

In some embodiments, a modified IL-2 polypeptide provided herein comprises a reaction group that facilitates the conjugation of the modified IL-2 polypeptide with a derivatized molecule or moiety such as an antibody and a polymer. In some embodiments, the reaction group comprises one or more of: carboxylic acid derived active esters, mixed anhydrides, acyl halides, acyl azides, alkyl halides, N-maleimides, imino esters, isocyanates, and isothiocyanates. In some embodiments, the reaction group comprises azides. In some embodiments, the reaction group comprises alkynes. In some embodiments, the reaction group is attached to the modified IL-2 polypeptide through a linker. In some embodiments, the modified IL-2 polypeptide comprises at least one reaction group. In some embodiments, the modified IL-2 polypeptide comprises a plurality of reaction groups. In some embodiments, the reaction group is attached at a residue selected from the residues indicated in Table 1 or Table 2. In some embodiments, the reaction group is attached at residue 42 or 45, wherein residue position numbering is based on SEQ ID NO: 1 as a reference sequence. In some embodiments, the reaction group is attached to the N-terminal residue of the modified IL-2 polypeptide. In some embodiments, the reaction group is attached to the C-terminal residue of the modified IL-2 polypeptide.

In some embodiments, a modified IL-2 polypeptide provided herein comprises a chemical reagent covalently attached to a residue. In some embodiments, the chemical reagent comprises a biorthogonal reagent. In some embodiments, the chemical reagent comprises an azide. In some embodiments, the chemical reagent comprises an alkyne. In some embodiments, the chemical reagent is covalently attached to a residue through a linker. In some embodiments, the chemical reagent is attached at a residue from 35-46, wherein the residue position numbering is based on SEQ ID NO: 1 as a reference sequence. In some embodiments, the chemical reagent is attached at a residue from 39-43, wherein the residue position numbering is based on SEQ ID NO: 1 as a reference sequence. In some embodiments, the chemical reagent is attached at residue 42, wherein the residue position numbering is based on SEQ ID NO:1 as a reference sequence. In some embodiments, the chemical reagent is attached at residue F42Y, wherein the residue position numbering is based on SEQ ID NO:1 as a reference sequence. In some embodiments, the chemical reagent is attached at a residue from 44-46, wherein the residue position numbering is based on SEQ ID NO:1 as a reference sequence. In some embodiments, the chemical reagent is attached at residue 45, wherein the residue position numbering is based on SEQ ID NO:1 as a reference sequence. In some embodiments, the chemical reagent is attached at any of the residues indicated in Table 1 or Table 2. In some embodiments, the chemical reagent is attached to the N-terminal residue of the modified IL-2 polypeptide.

In some embodiments, the water-soluble polymer comprises from 1 to 10 polyethylene glycol chains. In some embodiments, the first water-soluble polymer comprises 1 polyethylene glycol chains to 10 polyethylene glycol chains. In some embodiments, the first water-soluble polymer comprises 1 polyethylene glycol chains to 2 polyethylene glycol chains, 1 polyethylene glycol chains to 4 polyethylene glycol chains, 1 polyethylene glycol chains to 6 polyethylene glycol chains, 1 polyethylene glycol chains to 10 polyethylene glycol chains, 2 polyethylene glycol chains to 4 polyethylene glycol chains, 2 polyethylene glycol chains to 6 polyethylene glycol chains, 2 polyethylene glycol chains to 10 polyethylene glycol chains, 4 polyethylene glycol chains to 6 polyethylene glycol chains, 4 polyethylene glycol chains to 10 polyethylene glycol chains, or 6 polyethylene glycol chains to 10 polyethylene glycol chains. In some embodiments, the first water-soluble polymer comprises 1 polyethylene glycol chains, 2 polyethylene glycol chains, 4 polyethylene glycol chains, 6 polyethylene glycol chains, or 10 polyethylene glycol chains. In some embodiments, the first water-soluble polymer comprises at least 1 polyethylene glycol chains, 2 polyethylene glycol chains, 4 polyethylene glycol chains, or 6 polyethylene glycol chains. In some embodiments, the first water-soluble polymer comprises at most 2 polyethylene glycol chains, 4 polyethylene glycol chains, 6 polyethylene glycol chains, or 10 polyethylene glycol chains. In some embodiments, the first water-soluble polymer comprises 4 polyethylene glycol chains. In some embodiments, the first water-soluble polymer comprises a structure of Formula (II)

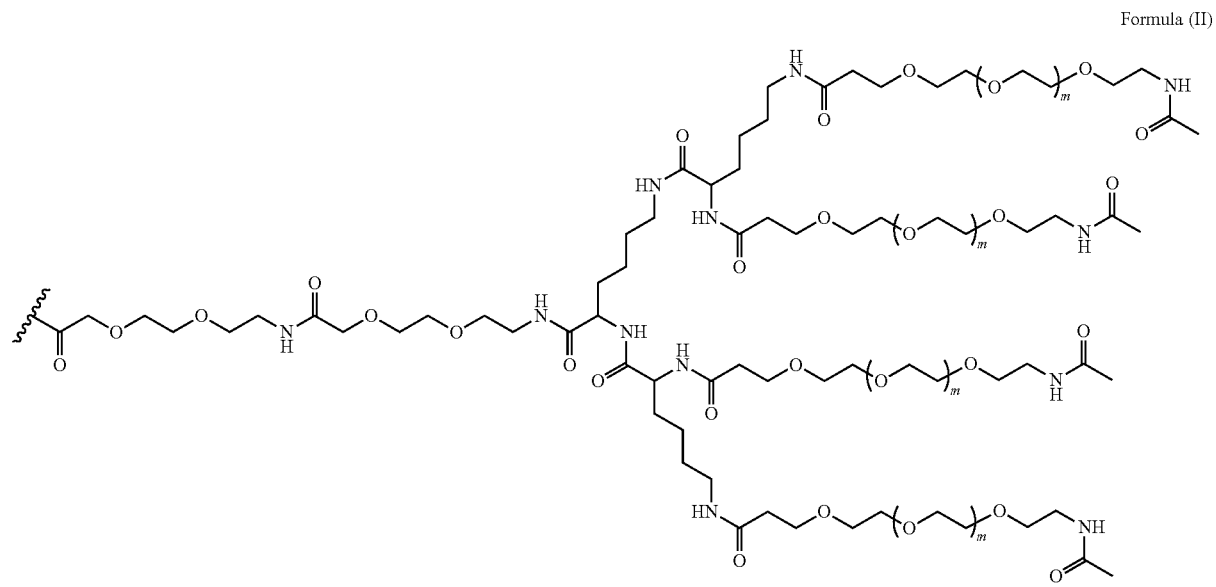

Formula (II)

wherein each m is independently an integer from 4-30. In some embodiments, at least one polyethylene glycol chain of the first water-soluble polymer comprises the structure of Formula (III)

Formula (III)

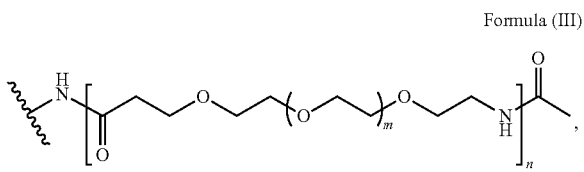

wherein each m is independently an integer from 4-30 and each n is independently an integer from 1-10. In some embodiments, each polyethylene glycol chain of the first water-soluble polymer comprises the structure of Formula (III). In some embodiments of Formula (III), m is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In some embodiments of Formula (III), n is 1, 2, 3, 4, 5, 6, 7, 8, 9, or 10.

In some embodiments, a modified IL-2 polypeptide described herein further comprises a second polymer covalently attached to the modified IL-2 polypeptide. In some embodiments, the second polymer is covalently attached at an amino acid residue region from residue 40 to residue 50.

In some embodiments, the second polymer is covalently attached at residue Y45. In some embodiments, the second polymer is covalently attached to the N-terminus of the modified IL-2 polypeptide.

In some embodiments, the second polymer has a weight average molecular weight of about 6,000 Daltons to about 50,000 Daltons. In some embodiments, the second polymer has a weight average molecular weight of about 6,000 Daltons to about 10,000 Daltons, about 6,000 Daltons to about 25,000 Daltons, about 6,000 Daltons to about 50,000 Daltons, about 10,000 Daltons to about 25.000 Daltons, about 10,000 Daltons to about 50,000 Daltons, or about 25,000 Daltons to about 50.000 Daltons. In some embodiments, the second polymer has a weight average molecular weight of about 6,000 Daltons, about 10,000 Daltons, about 25,000 Daltons, or about 50,000 Daltons. In some embodiments, the second polymer has a weight average molecular weight of at least about 6,000 Daltons, about 10,000 Daltons, or about 25,000 Daltons. In some embodiments, the second polymer has a weight average molecular weight of at most about 10,000 Daltons, about 25,000 Daltons, or about 50,000 Daltons.

In some embodiments, the second polymer has a weight average molecular weight of about 120 Daltons to about 1,000 Daltons. In some embodiments, the second polymer has a weight average molecular weight of about 120 Daltons to about 250 Daltons, about 120 Daltons to about 300 Daltons, about 120 Daltons to about 400 Daltons, about 120 Daltons to about 500 Daltons, about 120 Daltons to about 1,000 Daltons, about 250 Daltons to about 300 Daltons, about 250 Daltons to about 400 Daltons, about 250 Daltons to about 500 Daltons, about 250 Daltons to about 1,000 Daltons, about 300 Daltons to about 400 Daltons, about 300 Daltons to about 500 Daltons, about 300 Daltons to about 1.000 Daltons, about 400 Daltons to about 500 Daltons, about 400 Daltons to about 1,000 Daltons, or about 500 Daltons to about 1,000 Daltons. In some embodiments, the second polymer has a weight average molecular weight of about 120 Daltons, about 250 Daltons, about 300 Daltons, about 400 Daltons, about 500 Daltons, or about 1,000 Daltons. In some embodiments, the second polymer has a weight average molecular weight of at least about 120 Daltons, about 250 Daltons, about 300 Daltons, about 400 Daltons, or about 500 Daltons. In some embodiments, the second polymer has a weight average molecular weight of at most about 250 Daltons, about 300 Daltons, about 400 Daltons, about 500 Daltons, or about 1,000 Daltons.

In some embodiments, the second polymer comprises a water-soluble polymer. In some embodiments, the water-soluble polymer comprises poly(alkylene oxide), polysaccharide, poly(vinyl pyrrolidone), poly(vinyl alcohol), polyoxazoline, poly(acryloylmorpholine), or a combination thereof.

In some embodiments, the water-soluble polymer is poly (alkylene oxide). In some embodiments, the water-soluble polymer is polyethylene oxide). In some embodiments, the second polymer is attached to the IL-2 polypeptide via click chemistry.

In some embodiments, the second water-soluble polymer comprises from 1 to 10 polyethylene glycol chains. In some embodiments, the second water-soluble polymer comprises 1 polyethylene glycol chains to 10 polyethylene glycol chains. In some embodiments, the second water-soluble polymer comprises 1 polyethylene glycol chains to 2 polyethylene glycol chains, 1 polyethylene glycol chains to 4 polyethylene glycol chains, 1 polyethylene glycol chains to 6 polyethylene glycol chains, 1 polyethylene glycol chains to 10 polyethylene glycol chains, 2 polyethylene glycol chains to 4 polyethylene glycol chains, 2 polyethylene glycol chains to 6 polyethylene glycol chains, 2 polyethylene glycol chains to 10 polyethylene glycol chains, 4 polyethylene glycol chains to 6 polyethylene glycol chains, 4 polyethylene glycol chains to 10 polyethylene glycol chains, or 6 polyethylene glycol chains to 10 polyethylene glycol chains. In some embodiments, the second water-soluble polymer comprises 1 polyethylene glycol chains, 2 polyethylene glycol chains, 4 polyethylene glycol chains, 6 polyethylene glycol chains, or 10 polyethylene glycol chains. In some embodiments, the second water-soluble polymer comprises at least 1 polyethylene glycol chains, 2 polyethylene glycol chains, 4 polyethylene glycol chains, or 6 polyethylene glycol chains. In some embodiments, the second water-soluble polymer comprises at most 2 polyethylene glycol chains, 4 polyethylene glycol chains, 6 polyethylene glycol chains, or 10 polyethylene glycol chains. In some embodiments, the first water-soluble polymer comprises 4 polyethylene glycol chains. In some embodiments, the second water-soluble polymer comprises the structure of Formula (II)

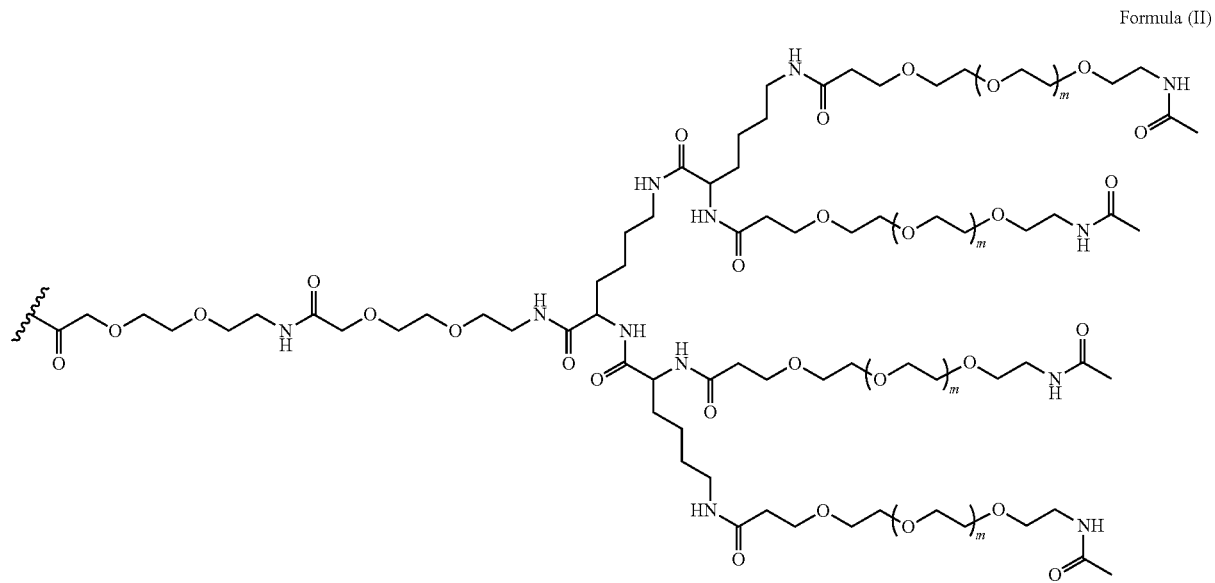

Formula (II)

wherein each m is independently an integer from 4-30. In some embodiments, at least one polyethylene glycol chain of the second water-soluble polymer comprises the structure of Formula

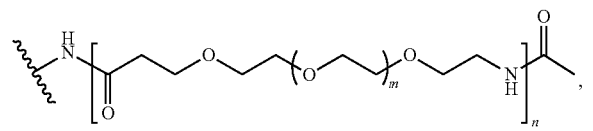

Formula (III)

wherein each m is independently an integer from 4-30 and each n is independently an integer from 1-10. In some embodiments, each polyethylene glycol chain of the second water-soluble polymer comprises the structure of Formula (III).

In some embodiments, a modified IL-2 polypeptide described herein further comprises a third polymer covalently attached to the modified IL-2 polypeptide. In some embodiments, the third polymer is covalently attached at an amino acid residue region from residue 40 to residue 50. In some embodiments, the third polymer is covalently attached at residue Y45. In some embodiments, the third polymer is covalently attached to the N-terminus of the modified IL-2 polypeptide.

In some embodiments, the third polymer has a weight average molecular weight of about 6,000 Daltons to about 50,000 Daltons. In some embodiments, the third polymer has a weight average molecular weight of about 6,000 Daltons to about 10,000 Daltons, about 6,000 Daltons to about 25,000 Daltons, about 6,000 Daltons to about 50,000 Daltons, about 10,000 Daltons to about 25,000 Daltons, about 10,000 Daltons to about 50,000 Daltons, or about 25,000 Daltons to about 50,000 Daltons. In some embodiments, the third polymer has a weight average molecular weight of about 6,000 Daltons, about 10,000 Daltons, about 25,000 Daltons, or about 50,000 Daltons. In some embodiments, the third polymer has a weight average molecular weight of at least about 6,000 Daltons, about 10,000 Daltons, or about 25,000 Daltons. In some embodiments, the third polymer has a weight average molecular weight of at most about 10,000 Daltons, about 25,000 Daltons, or about 50,000 Daltons.

In some embodiments, the third polymer has a weight average molecular weight of about 120 Daltons to about 1,000 Daltons. In some embodiments, the third polymer has a weight average molecular weight of about 120 Daltons to about 250 Daltons, about 120 Daltons to about 300 Daltons, about 120 Daltons to about 400 Daltons, about 120 Daltons to about 500 Daltons, about 120 Daltons to about 1,000 Daltons, about 250 Daltons to about 300 Daltons, about 250 Daltons to about 400 Daltons, about 250 Daltons to about 500 Daltons, about 250 Daltons to about 1,000 Daltons, about 300 Daltons to about 400 Daltons, about 300 Daltons to about 500 Daltons, about 300 Daltons to about 1,000 Daltons, about 400 Daltons to about 500 Daltons, about 400 Daltons to about 1,000 Daltons, or about 500 Daltons to about 1,000 Daltons. In some embodiments, the third polymer has a weight average molecular weight of about 120 Daltons, about 250 Daltons, about 300 Daltons, about 400 Daltons, about 500 Daltons, or about 1,000 Daltons. In some embodiments, the third polymer has a weight average molecular weight of at least about 120 Daltons, about 250 Daltons, about 300 Daltons, about 400 Daltons, or about 500 Daltons. In some embodiments, the third polymer has a weight average molecular weight of at most about 250 Daltons, about 300 Daltons, about 400 Daltons, about 500 Daltons, or about 1,000 Daltons.

In some embodiments, the modified IL-2 polypeptide comprises a third polymer having a weight average molecular weight of from about 250 Daltons to about 50,000 Daltons covalently attached thereto. In some embodiments, the modified IL-2 polypeptide comprises a third polymer having a weight average molecular weight of from about 500 Daltons to about 25,000 Daltons covalently attached thereto. In some embodiments, the modified IL-2 polypeptide comprises a third polymer having a weight average molecular weight of from about 1000 Daltons to about 10,000 Daltons covalently attached thereto.

In some embodiments, the third polymer comprises a water-soluble polymer. In some embodiments, the water-soluble polymer comprises poly(alkylene oxide), polysaccharide, poly(vinyl pyrrolidone), poly(vinyl alcohol), polyoxazoline, poly(acryloylmorpholine), or a combination thereof.

In some embodiments, the water-soluble polymer is poly(alkylene oxide). In some embodiments, the water-soluble polymer is polyethylene glycol. In some embodiments, the third polymer is attached to the IL-2 polypeptide via click chemistry.

In another aspect, described herein is a modified interleukin-2 (IL-2) polypeptide, comprising: a modified IL-2 polypeptide, wherein the modified IL-2 polypeptide comprises: (a) a first polymer having a weight average molecular weight of up to about 6000 Daltons covalently attached to residue F42Y; (b) a second polymer having a weight average molecular weight of up to about 6000 Daltons covalently attached to Y45; and wherein residue position numbering of the modified IL-2 polypeptide is based on SEQ ID NO:1 as a reference sequence. In one aspect, described herein is a modified interleukin-2 (IL-2) polypeptide, comprising: a modified IL-2 polypeptide, wherein the modified IL-2 polypeptide comprises: (a) a first polymer covalently attached to residue F42Y and (b) a second polymer covalently attached to Y45, wherein one of the first polymer and the second polymer has a weight average molecular weight within a range of from about 200 Da, 300 Da, or 400 Da to about 600 Da, 1000 Da, or 6000 Da and the other polymer has a weight average molecular weight within a range of from about 5000 Da, 10,000 Da, or 20,000 Da to about 30,000 Da, 40,000 Da, or 50,000 Da, and wherein residue position numbering of the modified IL-2 polypeptide is based on SEQ ID NO:1 as a reference sequence.

In another aspect, described herein is a modified interleukin-2 (IL-2) polypeptide, wherein the modified IL-2 polypeptide comprises: a. a first polymer having a weight average molecular weight of up to about 6000 Daltons covalently attached to residue F42Y; b. a second polymer having a weight average molecular weight of up to about 6000 Daltons covalently attached to Y45; and c. a covalently attached N-terminal third polymer having a weight average molecular weight of up to about 50,000 Daltons, and wherein residue position numbering of the modified IL-2 polypeptide is based on SEQ ID NO: 1 as a reference sequence. In some embodiments, each of the first polymer, the second polymer, and the third polymer independently comprises a water-soluble polymer.

In some embodiments, each polymer comprises a water-soluble polymer. In some embodiments, the water-soluble polymer comprises poly(alkylene oxide), polysaccharide, poly(vinyl pyrrolidone), poly(vinyl alcohol), polyoxazoline, poly(acryloylmorpholine), or a combination thereof.

In some embodiments, each water-soluble polymer is poly(alkylene oxide). In some embodiments, each water-soluble polymer is polyethylene glycol.

In some embodiments, each of the first polymer and the second polymer independently comprises from 1 to 5 polyethylene glycol chains. In some embodiments, each of the first polymer and the second polymer independently comprise single polyethylene glycol chains.

In some embodiments, each of the first polymer and the second polymer independently comprises one polyethylene glycol chain with 3 to 25 ethylene glycol units. In some embodiments, each of the first polymer and the second polymer independently comprises one polyethylene glycol chain with 3 ethylene glycol units to 25 ethylene glycol units. In some embodiments, each of the first polymer and the second polymer independently comprises one polyethylene glycol chain with 3 ethylene glycol units to 5 ethylene glycol units, 3 ethylene glycol units to 7 ethylene glycol units, 3 ethylene glycol units to 10 ethylene glycol units, 3 ethylene glycol units to 15 ethylene glycol units, 3 ethylene glycol units to 25 ethylene glycol units, 5 ethylene glycol units to 7 ethylene glycol units, 5 ethylene glycol units to 10 ethylene glycol units, 5 ethylene glycol units to 15 ethylene glycol units, 5 ethylene glycol units to 25 ethylene glycol units, 7 ethylene glycol units to 10 ethylene glycol units, 7 ethylene glycol units to 15 ethylene glycol units, 7 ethylene glycol units to 25 ethylene glycol units, 10 ethylene glycol units to 15 ethylene glycol units, 10 ethylene glycol units to 25 ethylene glycol units, or 15 ethylene glycol units to 25 ethylene glycol units. In some embodiments, each of the first polymer and the second polymer independently comprises one polyethylene glycol chain with 3 ethylene glycol units, 5 ethylene glycol units, 7 ethylene glycol units, 10 ethylene glycol units, 15 ethylene glycol units, or 25 ethylene glycol units. In some embodiments, each of the first polymer and the second polymer independently comprises one polyethylene glycol chain with at least 3 ethylene glycol units, 5 ethylene glycol units, 7 ethylene glycol units, 10 ethylene glycol units, or 15 ethylene glycol units. In some embodiments, each of the first polymer and the second polymer independently comprises one polyethylene glycol chain with at most 5 ethylene glycol units, 7 ethylene glycol units, 10 ethylene glycol units, 15 ethylene glycol units, or 25 ethylene glycol units.

In some embodiments, the third water-soluble polymer comprises from 1 to 10 polyethylene glycol chains. In some embodiments, the third water-soluble polymer comprises 1 polyethylene glycol chains to 10 polyethylene glycol chains. In some embodiments, the third water-soluble polymer comprises 1 polyethylene glycol chains to 2 polyethylene glycol chains, 1 polyethylene glycol chains to 4 polyethylene glycol chains, 1 polyethylene glycol chains to 6 polyethylene glycol chains, 1 polyethylene glycol chains to 10 polyethylene glycol chains, 2 polyethylene glycol chains to 4 polyethylene glycol chains, 2 polyethylene glycol chains to 6 polyethylene glycol chains, 2 polyethylene glycol chains to 10 polyethylene glycol chains, 4 polyethylene glycol chains to 6 polyethylene glycol chains, 4 polyethylene glycol chains to 10 polyethylene glycol chains, or 6 polyethylene glycol chains to 10 polyethylene glycol chains. In some embodiments, the third water-soluble polymer comprises 1 polyethylene glycol chains, 2 polyethylene glycol chains, 4 polyethylene glycol chains, 6 polyethylene glycol chains, or 10 polyethylene glycol chains. In some embodiments, the third water-soluble polymer comprises at least 1 polyethylene glycol chains, 2 polyethylene glycol chains, 4 polyethylene glycol chains, or 6 polyethylene glycol chains. In some embodiments, the third water-soluble polymer comprises at most 2 polyethylene glycol chains, 4 polyethylene glycol chains, 6 polyethylene glycol chains, or 10 polyethylene glycol chains. In some embodiments, the third water-soluble polymer comprises 4 polyethylene glycol chains. In some embodiments, the third water-soluble polymer comprises the structure of Formula (II)

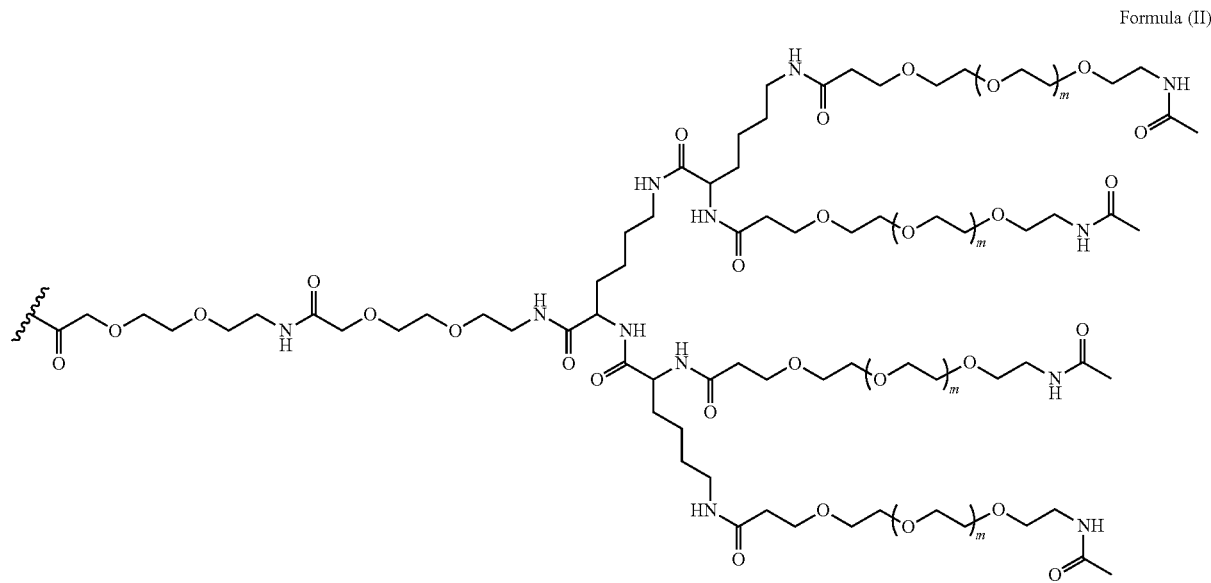

Formula (II)

wherein each m is independently an integer from 4-30. In some embodiments, each polyethylene glycol chain of the third water-soluble polymer comprises the structure of Formula (III)

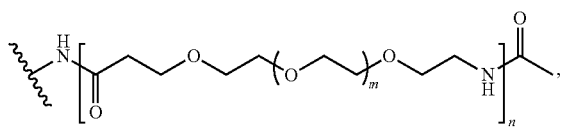

Formula (III)

wherein each m is independently an integer from 4-30 and each n is independently an integer from 1-10.

In some embodiments, each of the polyethylene glycol chains independently comprises from about 5 to about 300, from about 10 to about 200, from about 20 to about 100, or from about 25 to about 50 ethylene glycol units. In some embodiments, each of the polyethylene glycol chains independently comprises 5 ethylene glycol units to 300 ethylene glycol units. In some embodiments, each of the polyethylene glycol chains independently comprises 5 ethylene glycol units to 10 ethylene glycol units, 5 ethylene glycol units to 20 ethylene glycol units, 5 ethylene glycol units to 25 ethylene glycol units, 5 ethylene glycol units to 50 ethylene glycol units, 5 ethylene glycol units to 100 ethylene glycol units, 5 ethylene glycol units to 200 ethylene glycol units, 5 ethylene glycol units to 300 ethylene glycol units, 10 ethylene glycol units to 20 ethylene glycol units, 10 ethylene glycol units to 25 ethylene glycol units, 10 ethylene glycol units to 50 ethylene glycol units, 10 ethylene glycol units to 100 ethylene glycol units, 10 ethylene glycol units to 200 ethylene glycol units, 10 ethylene glycol units to 300 ethylene glycol units, 20 ethylene glycol units to 25 ethylene glycol units, 20 ethylene glycol units to 50 ethylene glycol units, 20 ethylene glycol units to 100 ethylene glycol units, 20 ethylene glycol units to 200 ethylene glycol units, 20 ethylene glycol units to 300 ethylene glycol units, 25 ethylene glycol units to 50 ethylene glycol units, 25 ethylene glycol units to 100 ethylene glycol units, 25 ethylene glycol units to 200 ethylene glycol units, 25 ethylene glycol units to 300 ethylene glycol units, 50 ethylene glycol units to 100 ethylene glycol units, 50 ethylene glycol units to 200 ethylene glycol units, 50 ethylene glycol units to 300 ethylene glycol units, 100 ethylene glycol units to 200 ethylene glycol units, 100 ethylene glycol units to 300 ethylene glycol units, or 200 ethylene glycol units to 300 ethylene glycol units. In some embodiments, each of the polyethylene glycol chains independently comprises 5 ethylene glycol units, 10 ethylene glycol units, 20 ethylene glycol units, 25 ethylene glycol units, 50 ethylene glycol units, 100 ethylene glycol units, 200 ethylene glycol units, or 300 ethylene glycol units. In some embodiments, each of the polyethylene glycol chains independently comprises at least 5 ethylene glycol units, 10 ethylene glycol units, 20 ethylene glycol units, 25 ethylene glycol units, 50 ethylene glycol units, 100 ethylene glycol units, or 200 ethylene glycol units. In some embodiments, each of the polyethylene glycol chains independently comprises at most 10 ethylene glycol units, 20 ethylene glycol units, 25 ethylene glycol units, 50 ethylene glycol units, 100 ethylene glycol units, 200 ethylene glycol units, or 300 ethylene glycol units.

In some embodiments, each of the polyethylene glycol chains is independently linear or branched. In some embodiments, each of the polyethylene glycol chains is a linear polyethylene glycol. In some embodiments, each of the polyethylene glycol chains is a branched polyethylene glycol. For example, in some embodiments, each of the first and the second polymers comprises a linear polyethylene glycol chain.

In some embodiments, each of the polyethylene glycol chains is independently terminally capped with a hydroxy, an alkyl, an alkoxy, an amido, or an amino group. In some embodiments, each of the polyethylene glycol chains is independently terminally capped with an amino group. In some embodiments, each of the polyethylene glycol chains is independently terminally capped with an amido group. In some embodiments, each of the polyethylene glycol chains is independently terminally capped with an alkoxy group. In some embodiments, each of the polyethylene glycol chains is independently terminally capped with an alkyl group. In some embodiments, each of the polyethylene glycol chains is independently terminally capped with a hydroxy group. In some embodiments, one or more of the polyethylene glycol chains independently has the structure

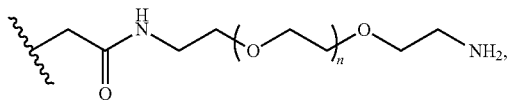

wherein n is an integer from 4-30. In some embodiments, one or more of the polyethylene glycol chains independently has the structure

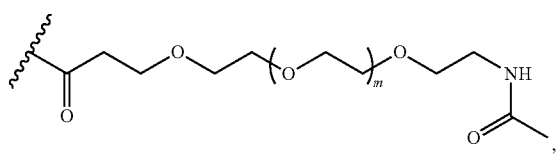

wherein m is an integer from 4-30.

In some embodiments, the modified IL-2 polypeptide comprises from 1 to 10 covalently attached water-soluble polymers. In some embodiments, the modified IL-2 polypeptide comprises 1 to 10 covalently attached water-soluble polymers. In some embodiments, the modified IL-2 polypeptide comprises 1 or 2 covalently attached water-soluble polymers, 1 to 3 covalently attached water-soluble polymers, 1 to 4 covalently attached water-soluble polymers, 1 to 6 covalently attached water-soluble polymers, 1 to 8 covalently attached water-soluble polymers, 1 to 10 covalently attached water-soluble polymers, 2 or 3 covalently attached water-soluble polymers, 2 to 4 covalently attached water-soluble polymers, 2 to 6 covalently attached water-soluble polymers, 2 to 8 covalently attached water-soluble polymers, 2 to 10 covalently attached water-soluble polymers, 3 or 4 covalently attached water-soluble polymers, 3 to 6 covalently attached water-soluble polymers, 3 to 8 covalently attached water-soluble polymers, 3 to 10 covalently attached water-soluble polymers, 4 to 6 covalently attached water-soluble polymers, 4 to 8 covalently attached water-soluble polymers, 4 to 10 covalently attached water-soluble polymers, 6 to 8 covalently attached water-soluble polymers, 6 to 10 covalently attached water-soluble polymers, or 8 to 10 covalently attached water-soluble polymers. In some embodiments, the modified IL-2 polypeptide comprises 1 covalently attached water-soluble polymer, 2 covalently attached water-soluble polymers, 3 covalently attached water-soluble polymers, 4 covalently attached water-soluble polymers, 6 covalently attached water-soluble polymers, 8 covalently attached water-soluble polymers, or 10 covalently attached water-soluble polymers. In some embodiments, the modified IL-2 polypeptide comprises at least 1 covalently attached water-soluble polymer, 2 covalently attached water-soluble polymers, 3 covalently attached water-soluble polymers, 4 covalently attached water-soluble polymers, 6 covalently attached water-soluble polymers, or 8 covalently attached water-soluble polymers. In some embodiments, the modified IL-2 polypeptide comprises at most 2 covalently attached water-soluble polymers, 3 covalently attached water-soluble polymers, 4 covalently attached water-soluble polymers, 6 covalently attached water-soluble polymers, 8 covalently attached water-soluble polymers, or 10 covalently attached water-soluble polymers. In some embodiments, the modified IL-2 polypeptide comprises from 2 to 6 covalently attached water-soluble polymers.

In some embodiments, one or more of the covalently attached polymers comprise a linker. In some embodiments, one or more of the covalently attached polymers, such as the third polymer, comprises one or more linkers. In some embodiments, the linker comprises one or more amino acids. In some embodiments, the linker comprises one or more lysines. In some embodiments, the linker comprises a spacer. In some embodiments, the linker comprises reactive functional groups or functional groups such as amide. In some embodiments, the linker has the structure of Formula (IV)

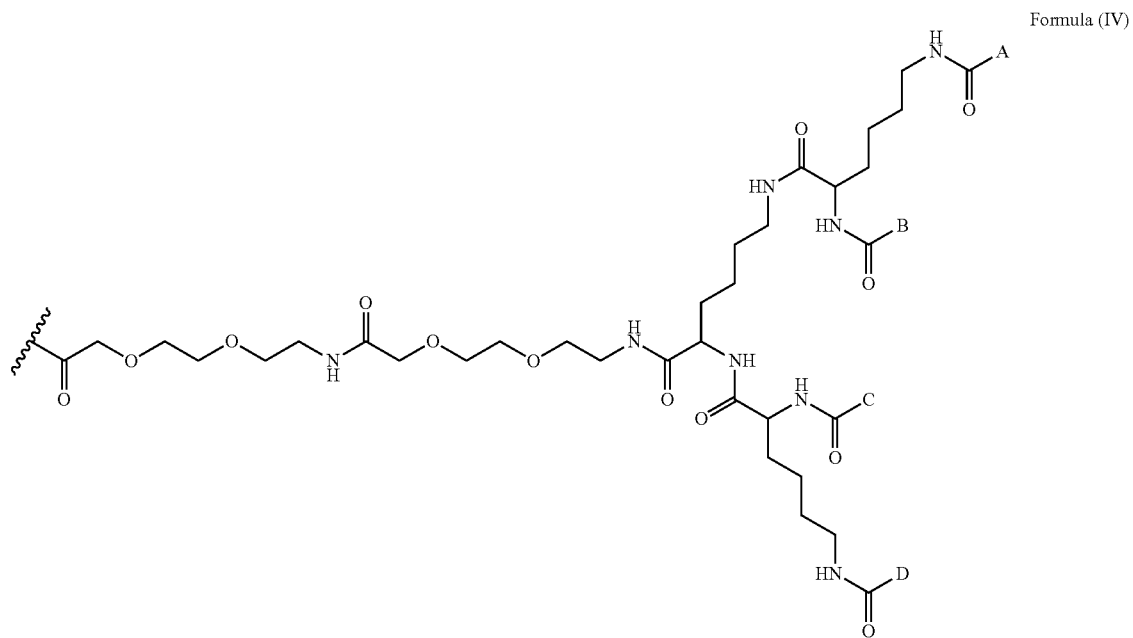

Formula (IV)

wherein A, B, C, and D are each independently polymers.

In some embodiments, the modified IL-2 polypeptide comprises one or more PEGylated tyrosine having a structure of formula (I) or Formula (F)

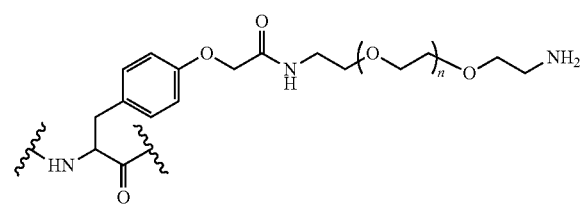

Formula (I)

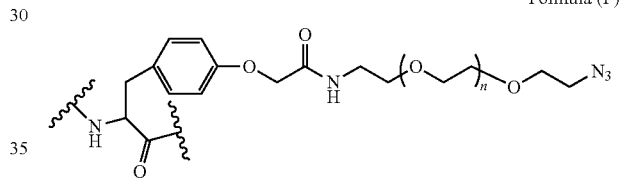

Formula (I')

wherein n is an integer selected from 4 to 30. In some embodiments, n is 4 to 6, 4 to 8, 4 to 10, 4 to 15, 4 to 20, 4 to 25, 4 to 30, 6 to 8, 6 to 10, 6 to 15, 6 to 20, 6 to 25, 6 to 30, 8 to 10, 8 to 15, 8 to 20, 8 to 25, 8 to 30, 10 to 15, 10 to 20, 10 to 25, 10 to 30, 15 to 20, 15 to 25, 15 to 30, 20 to 25, 20 to 30, or 25 to 30. In some embodiments, n is 4, 6, 8, 10, 15, 20, 25, or 30. In some embodiments, n is at least 4, 6, 8, 10, 15, 20, or 25. In some embodiments, n is at most 6, 8, 10, 15, 20, 25, or 30. In one aspect, a modified IL-2 polypeptide as described herein comprises one or two water-soluble polymers covalently attached at one or two amino acid residues. For example, in some embodiments, the modified IL-2 polypeptide comprises one or two water-soluble polymers having the characteristics and attachment sites as shown in Table.

TABLE 5

Exemplary Polypeptides Structures and Water-soluble Polymer Characteristics

| Exemplary Polypeptide structures | Characteristics of water-soluble polymer attached at residue 45 | Characteristics of water-soluble polymer attached at residue 42 |
|---|---|---|
| 1 | Linear; Mw: from about 15k to about 50k Da | Linear; Mw: from about 200 to about 1000 Da |
| 2 | Linear Mw: from about 200 to about 1000 Da | Linear; Mw: from about 15k to about 50k Da |
| 3 | Branched; Mw: from about 2k to about 10k Da | Linear; Mw: from about 200 to about 1000 Da |
| 4 | Linear; Mw: from about 200 to about 1000 Da | Branched; Mw: from about 2k to about 10k Da |

TABLE 5-continued

Exemplary Polypeptides Structures and Water-soluble Polymer Characteristics

| Exemplary Polypeptide structures | Characteristics of water-soluble polymer attached at residue 45 | Characteristics of water-soluble polymer attached at residue 42 |
|---|---|---|
| 5 | Linear; Mw: from about 15k to about 50k Da | Branched; Mw: from about 200 to about 1000 Da |
| 6 | Branched; Mw: from about 200 to about 1000 Da | Linear; Mw: from about 15k to about 50k Da |
| 7A | comprising polyethylene glycol of non-uniform size; Mw is from about 15k to about 50k Da | None |
| 7B | None | comprising polyethylene glycol of non-uniform size; Mw is from about 15k to about 50k Da |
| 8 | None | Linear; Mw: from about 15k to about 50k Da |
| 9 | Linear; Mw: from about 15k to about 50k Da | None |
| 10 | Branched; Mw: from about 2k to about 10k Da | None |
| 11 | None | Branched; Mw: from about 2k to about 10k Da |
| 12 | Branched; Mw: from about 15k to about 50k Da | None |
| 13 | None | Branched; Mw: from about 15k to about 50k Da |
| 14 | Branched; Mw: from about 2k to about 10k Da | Branched; Mw: from about 2k to about 10k Da |
| 15 | Linear; Mw: from about 2k to about 10k Da | Branched; Mw: from about 2k to about 10k Da |
| 16 | Linear; Mw: from about 200 to about 1000 Da | Linear; Mw: from about 200 to about 1000 Da |
| 17 | Linear; Mw: from about 200 to about 1000 Da | None |
| 18 | None | Linear; Mw: from about 200 to about 1000 Da |

In some embodiments, a water-soluble polymer that can be attached to a modified IL-2 polypeptide comprises a structure of Formula (A):

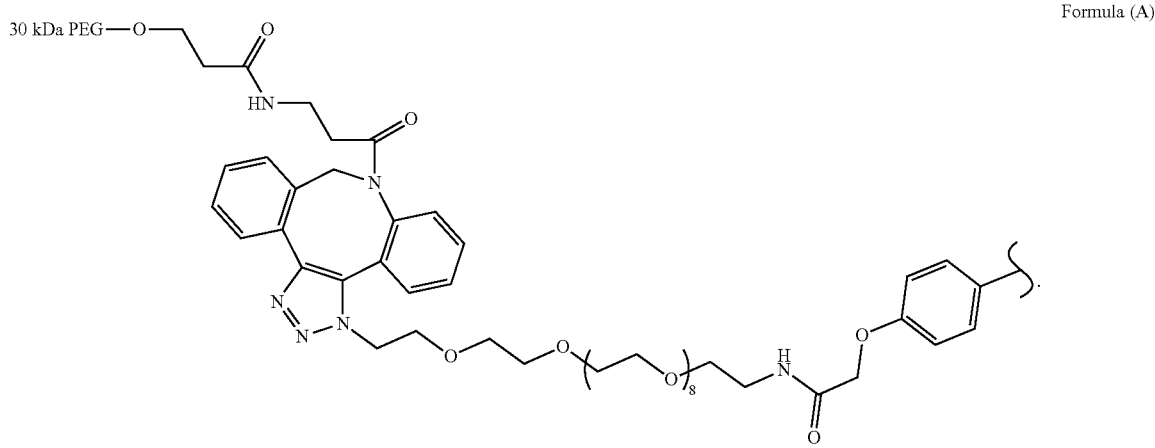

Formula (A)

In some embodiments, a water-soluble polymer that can be attached to a modified IL-2 polypeptide comprises a structure of Formula (A'):

Formula (A')

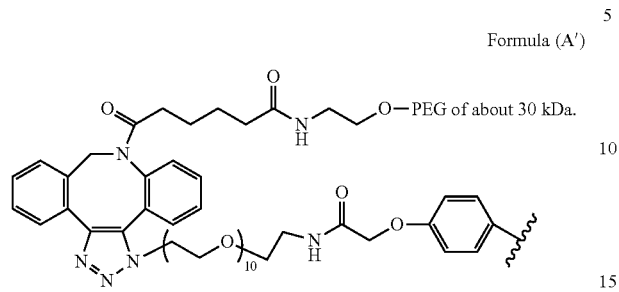

In some embodiments, a water-soluble polymer that can be attached to a modified IL-2 polypeptide comprises a structure of Formula (B):

Formula (B)

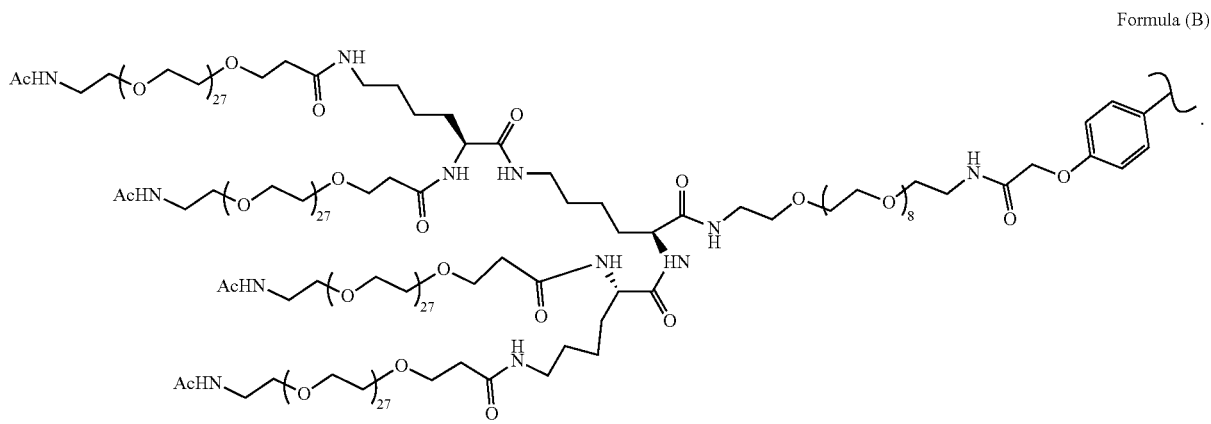

In some embodiments, a water-soluble polymer that can be attached to a modified IL-2 polypeptide comprises a structure of Formula (C):

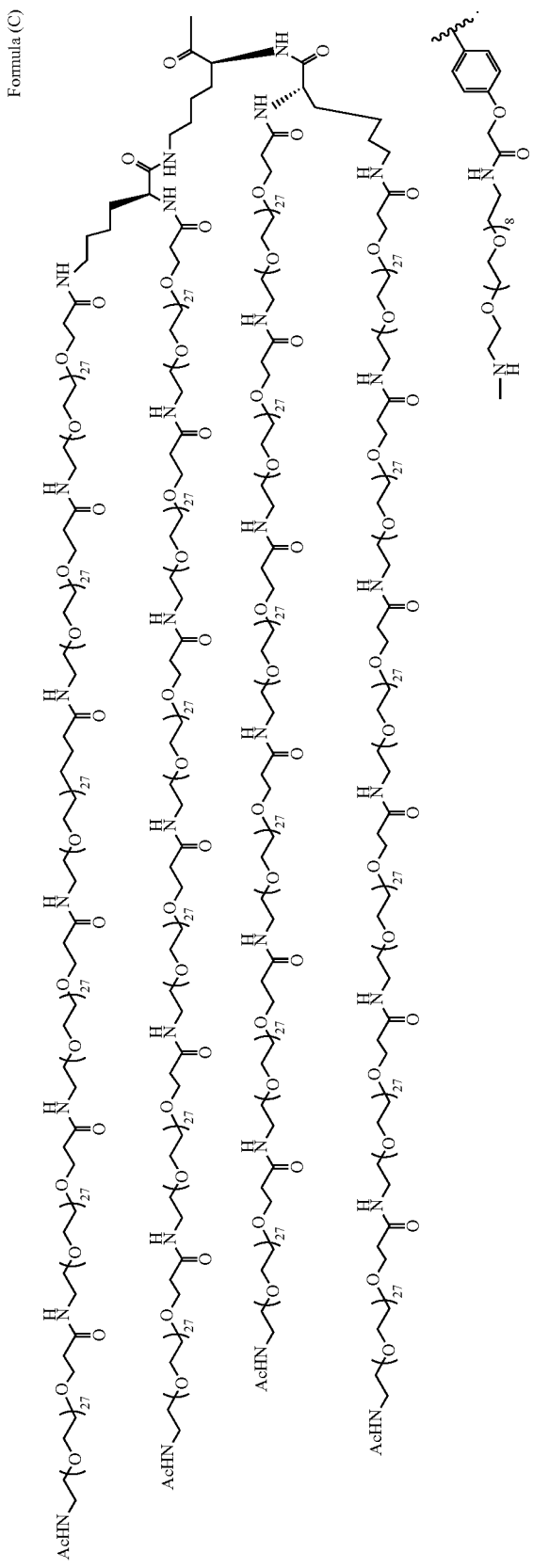
Formula (C)

In some embodiments, a water-soluble polymer that can be attached to a modified IL-2 polypeptide comprises a structure of Formula (D):

Formula (D)

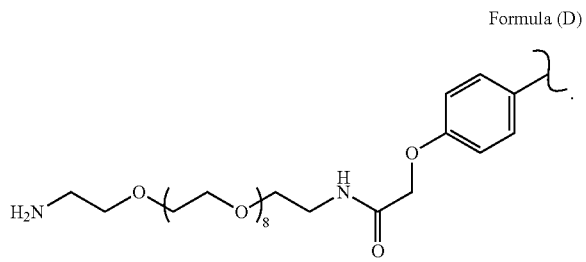

In some embodiments, the modified IL-2 polypeptide comprises one or two water-soluble polymers having the structures and attachment sites as shown in Table.

TABLE 6

Exemplary Polypeptides Structures and Water-soluble Polymer Structures

| Residue 42 Conjugate comprising a polymer that comprises a structure of Formula: | Residue 45 Conjugate comprising a polymer that comprises a structure of Formula: |
|---|---|
| Formula D | Formula A or A' |
| Formula A or A' | Formula D |
| Formula A or A' | Formula B |
| Formula B | Formula A or A' |
| Formula D | Formula C |
| Formula C | Formula D |
| None | Formula A or A' |
| Formula A or A' | None |
| None | Formula B |
| Formula B | None |
| None | Formula C |
| Formula C | None |
| Formula B | Formula D |
| Formula D | Formula B |
| Formula D | Formula D |
| Formula D | None |
| None | Formula D |

In some embodiments, the water-soluble polymer attached at residue 45 comprises one or more linkers and/or spacers. In some embodiments, the one or more linkers comprise one or more amide groups. In some embodiments, the one or more linkers comprise one or more lysine groups. In some embodiment, the water-soluble polymer attached at residue 45 comprises a structure of Formula (II), Formula (III), Formula (IV), or a combination thereof. In some embodiments, the water-soluble polymer attached at residue 45 comprises a structure of Formula (A), Formula (A'), Formula (B), Formula (C), Formula (D), or a combination thereof. In some embodiments, the water-soluble polymer attached at residue 45 comprises a structure of

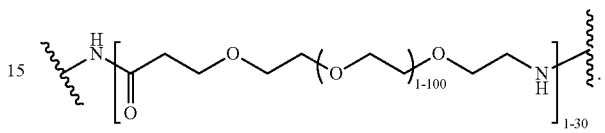

In some embodiments, the water-soluble polymer attached at residue 42 comprises one or more linkers and/or spacers. In some embodiments, the one or more linkers comprise one or more amide groups. In some embodiments, the one or more linkers comprise one or more lysine groups. In some embodiment, the water-soluble polymer attached at residue 42 comprises a structure of Formula (II), Formula (III), Formula (IV), or a combination thereof. In some embodiments, the water-soluble polymer attached at residue 42 comprises a structure of Formula (A), Formula (A'), Formula (B), Formula (C), Formula (D), or a combination thereof. In some embodiments, the water-soluble polymer attached at residue 42 comprises a structure of

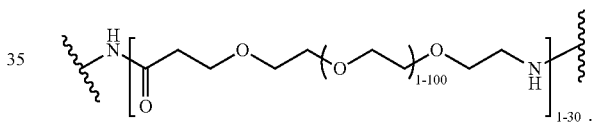

In some embodiments, the polymers are synthesized from suitable precursor materials. In some embodiments, the polymers are synthesized from the precursor materials of, Structure 6, Structure 7, Structure 8, or Structure 9, wherein Structure 6 is Structure 6

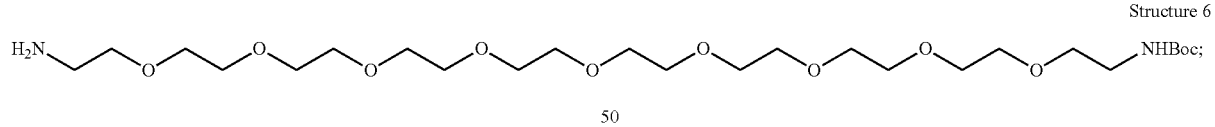

Structure 7 is

Structure 7

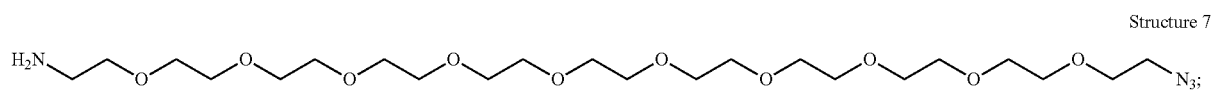 [SMILES: [N-]=[N+]=NCCOCCOCCOCCOCCOCCOCCOCCOCCOCCOCCN]

Structure 8 is

Structure 8

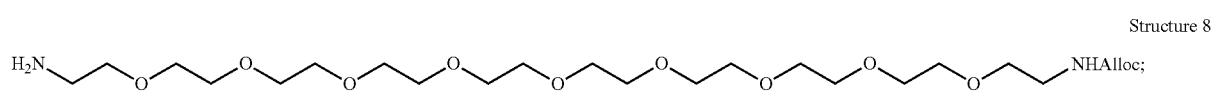

and Structure 9 is

Structure 9

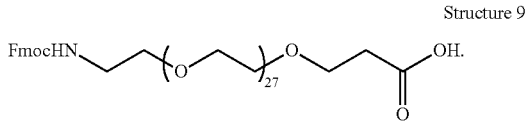

In some embodiments, a modified IL-2 polypeptide provided herein comprises a linker that covalently attaches a polymer (e.g., polyethylene glycol) to an amino acid residue of the IL-2 polypeptide. In some embodiments, the amino acid residue is a residue from 35-46, wherein the residue position numbering is based on SEQ ID NO:1 as a reference sequence. In some embodiments, the amino acid residue is residue 42. In some embodiments, the amino acid residue is residue 45. In some embodiments, the amino acid residue is a tyrosine such as F42Y or Y45. In some embodiments, a linker that covalently attaches a polymer (e.g., polyethylene glycol) to the IL-2 polypeptide comprises a structure of Formula (V), Formula (V)

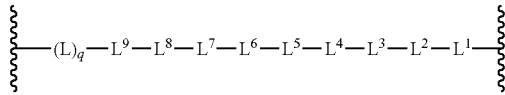

wherein each of L, $L^1$, $L^2$, $L^3$, $L^4$, $L^5$, $L^6$, $L^8$, and $L^9$ is independently —O—, —$NR^L$—, —$N(R^L)_2^+$—, —OP(=O)($OR^L$)O—, —S—, —S(=O)—, —S(=O)$_2$—, —C(=O)—, —C(=O)O—, —OC(=O)—, —OC(=O)O—, —C(=O)$NR^L$—, —$NR^L$C(=O)—, —OC(=O)$NR^L$—, —$NR^L$C(=O)O—, —$NR^L$C(=O)$NR^L$—, —$NR^L$C(=S)$NR^L$—, —$CR^L$=N—, —N=$CR^L$—, —$NR^L$S(=O)$_2$—, —S(=O)$_2NR^L$—, —C(=O)$NR^L$S(=O)$_2$—, —S(=O)$_2NR^L$C(=O)—, substituted or unsubstituted $C_1$-$C_6$ alkylene, substituted or unsubstituted $C_1$-$C_6$ heteroalkylene, substituted or unsubstituted $C_2$-$C_6$ alkenylene, substituted or unsubstituted $C_2$-$C_6$ alkynylene, —(CH$_2$—CH$_2$—O)$_{qa}$—, —(O—CH$_2$—CH$_2$)$_{qb}$—, —(CH$_2$—CH(CH$_3$)—O)$_{qc}$—, —(O—CH(CH$_3$)—CH$_2$)$_{qd}$—, or absent;

$L^7$ is —O—, —$NR^L$—, —$N(R^L)_2^+$—, —OP(=O)($OR^L$)O—, —S—, —S(=O)—, —S(=O)$_2$—, —C(=O)—, —C(=O)O—, —OC(=O)—, —OC(=O)O—, —C(=O)$NR^L$—, —$NR^L$C(=O)—, —OC(=O)$NR^L$—, —$NR^L$C(=O)O—, —$NR^L$C(=O)$NR^L$—, —$NR^L$C(=S)$NR^L$—, —$CR^L$=N—, —N=$CR^L$—, —$NR^L$S(=O)$_2$—, —S(=O)$_2NR^L$—, —C(=O)$NR^L$S(=O)$_2$—, —S(=O)$_2NR^L$C(=O)—, substituted or unsubstituted $C_1$-$C_6$ alkylene, substituted or unsubstituted $C_1$-$C_6$ heteroalkylene, substituted or unsubstituted $C_2$-$C_6$ alkenylene, substituted or unsubstituted $C_2$-$C_6$ alkynylene, —(CH$_2$—CH$_2$—O)$_{qa}$—, —(O—CH$_2$—CH$_2$)$_{qb}$—, —(CH$_2$—CH(CH$_3$)—O)$_{qc}$—, —(O—CH(CH$_3$)—CH$_2$)$_{qd}$—, a click chemistry residue, or absent;

each $R^L$ is independently hydrogen, substituted or unsubstituted $C_1$-$C_6$ alkyl, substituted or unsubstituted $C_1$-$C_6$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

q is 0, 1, 2, 3, 4, 5, or 6; and each of qa, qb, qc and qd is independently 1, 2, 3, 4, 5, 6, 7, 8, 9, 10, 11, 12, 13, 14, 15, 16, 17, 18, 19, 20, 21, 22, 23, 24, or 25.

In some embodiments, a modified IL-2 polypeptide described herein comprises one or more linkers that covalently attach the first polymer, the second polymer, or both to the remaining fragment of the modified IL-2 polypeptide, wherein each of the one or more linkers independently has a structure of Formula (V). In some embodiments, the linker of Formula (V) attaches to an amino acid residue of the IL-2 polypeptide through the $L^1$ end. In some embodiments, the linker of Formula (V) attaches to a polymer to the L end.

In some embodiments, a linker of Formula (V) has a structure of Formula (V-1),

Formula (V-1)

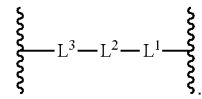

In some embodiments, a linker of Formula (V) has a structure of Formula (V-2),

Formula (V-1)

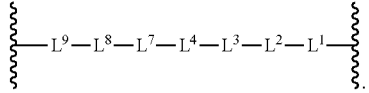

In some embodiments, a modified IL-2 polypeptide described herein comprises a linker of Formula (V-1) and a linker of Formula (V-2).

In some embodiments, $L^1$ is —O—, —$NR^L$—, —$N(R^L)_2^+$—, —S—, —S(=O)—, —S(=O)$_2$—, —C(=O)—, —C(=O)O—, —OC(=O)—, —OC(=O)O—, —C(=O)$NR^L$—, —$NR^L$C(=O)—, —OC(=O)$NR^L$—, —$NR^L$C(=O)O—, —$NR^L$C(=O)$NR^L$—, —$NR^L$C(=S)$NR^L$—, —$CR^L$=N—, —N=$CR^L$—, —$NR^L$S(=O)$_2$—, —S(=O)$_2NR^L$—, —C(=O)$NR^L$S(=O)$_2$—, —S(=O)$_2NR^L$C(=O)—, substituted or unsubstituted $C_1$-$C_6$ alkylene, substituted or unsubstituted $C_1$-$C_6$ heteroalkylene, —(CH$_2$—CH$_2$—O)$_{qa}$—, —(O—CH$_2$—CH$_2$)$_{qb}$—, —(CH$_2$—CH(CH$_3$)—O)$_{qc}$—, —(O—CH(CH$_3$)—CH$_2$)$_{qd}$—, or absent. In some embodiments, $L^1$ is substituted or unsubstituted $C_1$-$C_6$ alkylene. In some embodiments, $L^1$ is substituted or unsubstituted $C_1$-$C_3$ alkylene. In some embodiments, $L^1$ is —O—. In some embodiments, $L^1$ is —CH$_2$—. In some embodiments, $L^1$ is —CH$_2$CH$_2$—. In some embodiments, $L^1$ is —CH$_2$CH$_2$CH$_2$—. In some embodiments, $L^1$ is absent.

In some embodiments, $L^1$ is substituted or unsubstituted $C_1$-$C_3$ alkylene. In some embodiments, $L^1$ is unsubstituted $C_1$-$C_3$ alkylene. In some embodiments, $L^1$ is —CH$_2$—. In some embodiments, $L^1$ is —CH$_2$CH$_2$—. In some embodiments, $L^1$ is —CH$_2$CH$_2$CH$_2$—. In some embodiments, $L^1$ is absent.

In some embodiments, $L^2$ is —O—, —$NR^L$—, —$N(R^L)_2^+$—, —OP(=O)($OR^L$)O—, —S—, —S(=O)—, —S(=O)$_2$—, —C(=O)—, —C(=O)O—, —OC(=O)—, —OC(=O)O—, —C(=O)$NR^L$—, —$NR^L$C(=O)—, —OC(=O)$NR^L$—, —$NR^L$C(=O)O—, —$NR^L$C(=O)$NR^L$—, —$NR^L$C(=S)$NR^L$—, —$CR^L$=N—, —N=$CR^L$—, —$NR^L$S(=O)$_2$—, —S(=O)$_2NR^L$—, —C(=O)$NR^L$S(=O)$_2$—, —S(=O)$_2NR^L$C(=O)—, substituted or unsubstituted $C_1$-$C_6$ alkylene, substituted or unsubstituted $C_1$-$C_6$ heteroalkylene, —($CH_2$—$CH_2$—O)$_{qa}$—, —(O—$CH_2$—$CH_2$)$_{qb}$—, —($CH_2$—CH($CH_3$)—O)$_{qc}$—, —(O—CH($CH_3$)—$CH_2$)$_{qd}$—, or absent. In some embodiments, $L^2$ is —C(=O)O—, —OC(=O)—, —OC(=O)O—, —C(=O)NR$^L$—, —NR$^L$C(=O)—, —OC(=O)NR$^L$—, —NR$^L$C(=O)O—, —NR$^L$C(=O)NR$^L$—, or —NR$^L$C(=S)NR$^L$—. In some embodiments, $L^2$ is —C(=O)O—, —OC(=O)—, —C(=O)NR$^L$—, or —NR$^L$C(=O)—. In some embodiments, $L^2$ is —C(=O)NR$^L$—. In some embodiments, $L^2$ is —NR$^L$C(=O)—. In some embodiments, $L^2$ is —NH—C(=O)—. In some embodiments, $L^2$ is —C(=O)NH—. In some embodiments, $L^2$ is absent.

In some embodiments, $L^2$ is —C(=O)O—, —OC(=O)—, —C(=O)NR$^L$—, or —NR$^L$C(=O)—. In some embodiments, $L^2$ is —C(=O)NR$^L$—. In some embodiments, $L^2$ is —NR$^L$C(=O)—. In some embodiments, $L^2$ is —NH—C(=O)—. In some embodiments, $L^2$ is —C(=O)NH—.

In some embodiments, $L^3$ is —O—, —NR$^L$—, —N(R$^L$)$_2^+$—, —S—, —S(=O)—, —S(=O)$_2$—, —C(=O)—, —C(=O)O—, —OC(=O)—, —OC(=O)O—, —C(=O)NR$^L$—, —NR$^L$C(=O)—, —OC(=O)NR$^L$—, —NR$^L$C(=O)O—, —NR$^L$C(=O)NR$^L$—, —NR$^L$C(=S)NR$^L$—, —CR$^L$=N—, —N=CR$^L$—, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted $C_1$-$C_6$ alkylene, substituted or unsubstituted $C_1$-$C_6$ heteroalkylene, —($CH_2$—$CH_2$—O)$_{qa}$—, —(O—$CH_2$—$CH_2$)$_{qb}$—, —($CH_2$—CH($CH_3$)—O)$_{qc}$—, —(O—CH($CH_3$)—$CH_2$)$_{qd}$—, or absent. In some embodiments, $L^3$ is substituted or unsubstituted $C_1$-$C_6$ alkylene. In some embodiments, $L^3$ is substituted or unsubstituted $C_1$-$C_3$ alkylene. In some embodiments, $L^3$ is —O—. In some embodiments, $L^3$ is —$CH_2$—. In some embodiments, $L^3$ is —$CH_2CH_2$—. In some embodiments, $L^3$ is —$CH_2CH_2CH_2$—. In some embodiments, $L^3$ is absent.

In some embodiments, $L^3$ is substituted or unsubstituted $C_1$-$C_6$ alkylene. In some embodiments, $L^3$ is substituted or unsubstituted $C_1$-$C_3$ alkylene. In some embodiments, $L^3$ is —$CH_2$—. In some embodiments, $L^3$ is —$CH_2CH_2$—. In some embodiments, $L^3$ is —$CH_2CH_2CH_2$—.

In some embodiments, $L^4$ is —O—, —NR$^L$—, —N(R$^L$)$_2^+$—, —S—, —S(=O)—, —S(=O)$_2$—, —C(=O)—, —C(=O)O—, —OC(=O)—, —OC(=O)O—, —C(=O)NR$^L$—, —NR$^L$C(=O)—, —OC(=O)NR$^L$—, —NR$^L$C(=O)O—, —NR$^L$C(=O)NR$^L$—, —NR$^L$C(=S)NR$^L$—, —CR$^L$=N—, —N=CR$^L$—, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted $C_1$-$C_6$ alkylene, substituted or unsubstituted $C_1$-$C_6$ heteroalkylene, —($CH_2$—$CH_2$—O)$_{qa}$—, —(O—$CH_2$—$CH_2$)$_{qb}$—, —($CH_2$—CH($CH_3$)—O)$_{qc}$—, —(O—CH($CH_3$)—$CH_2$)$_{qd}$—, or absent. In some embodiments, $L^4$ is substituted or unsubstituted $C_1$-$C_6$ alkylene, substituted or unsubstituted $C_1$-$C_6$, heteroalkylene, —($CH_2$—$CH_2$—O)$_{qa}$—, —(O—$CH_2$—$CH_2$)$_{qb}$—, —($CH_2$—CH($CH_3$)—O)$_{qc}$—, or —(O—CH($CH_3$)—$CH_2$)$_{qd}$—. In some embodiments, $L^4$ is substituted or unsubstituted $C_1$-$C_6$, alkylene, substituted or unsubstituted $C_1$-$C_6$ heteroalkylene, —($CH_2$—$CH_2$—O)$_{qa}$—, or —(O—$CH_2$—$CH_2$)$_{qb}$—. In some embodiments, $L^4$ is —($CH_2$—$CH_2$—O)$_{qa}$—, or —(O—$CH_2$—$CH_2$)$_{qb}$—. In some embodiments, $L^4$ is absent.

In some embodiments, $L^5$ is —O—, —NR$^L$—, —N(R$^L$)$_2^+$—, —S—, —S(=O)—, —S(=O)$_2$—, —C(=O)—, —C(=O)O—, —OC(=O)—, —OC(=O)O—, —C(=O)NR$^L$—, —NR$^L$C(=O)—, —OC(=O)NR$^L$—, —NR$^L$C(=O)O—, —NR$^L$C(=O)NR$^L$—, —NR$^L$C(=S)NR$^L$—, —CR$^L$=N—, —N=CR$^L$—, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted $C_1$-$C_6$ alkylene, substituted or unsubstituted $C_1$-$C_6$ heteroalkylene, —($CH_2$—$CH_2$—O)$_{qa}$—, —(O—$CH_2$—$CH_2$)$_{qb}$—, —($CH_2$—CH($CH_3$)—O)$_{qc}$—, —(O—CH($CH_3$)—$CH_2$)$_{qd}$—, or absent. In some embodiments, $L^5$ is absent.

In some embodiments, $L^6$ is —O—, —NR$^L$—, —N(R$^L$)$_2^+$—, —S—, —S(=O)—, —S(=O)$_2$—, —C(=O)—, —C(=O)O—, —OC(=O)—, —OC(=O)O—, —C(=O)NR$^L$—, —NR$^L$C(=O)—, —OC(=O)NR$^L$—, —NR$^L$C(=O)O—, —NR$^L$C(=O)NR$^L$—, —NR$^L$C(=S)NR$^L$—, —CR$^L$=N—, —N=CR$^L$—, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted $C_1$-$C_6$ alkylene, substituted or unsubstituted $C_1$-$C_6$ heteroalkylene, —($CH_2$—$CH_2$—O)$_{qa}$—, —(O—$CH_2$—$CH_2$)$_{qb}$—, —($CH_2$—CH($CH_3$)—O)$_{qc}$—, —(O—CH($CH_3$)—$CH_2$)$_{qd}$—, or absent. In some embodiments, $L^6$ is absent.

In some embodiments, $L^8$ is —O—, —NR$^L$—, —N(R$^L$)$_2^+$—, —S—, —S(=O)—, —S(=O)$_2$—, —C(=O)—, —C(=O)O—, —OC(=O)—, —OC(=O)O—, —C(=O)NR$^L$—, —NR$^L$C(=O)—, —OC(=O)NR$^L$—, —NR$^L$C(=O)O—, —NR$^L$C(=O)NR$^L$—, —NR$^L$C(=S)NR$^L$—, —CR$^L$=N—, —N=CR$^L$—, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted $C_1$-$C_6$ alkylene, substituted or unsubstituted $C_1$-$C_6$ heteroalkylene, —($CH_2$—$CH_2$—O)$_{qa}$—, —(O—$CH_2$—$CH_2$)$_{qb}$—, —($CH_2$—CH($CH_3$)—O)$_{qc}$—, —(O—CH($CH_3$)—$CH_2$)$_{qd}$—, or absent. In some embodiments, $L^8$ is substituted or unsubstituted $C_1$-$C_6$, alkylene. In some embodiments, $L^8$ is substituted or unsubstituted $C_1$-$C_4$ alkylene. In some embodiments, $L^8$ is substituted or unsubstituted $C_3$-$C_4$ alkylene. In some embodiments, $L^8$ is —O—. In some embodiments, $L^8$ is —$CH_2$—. In some embodiments, $L^8$ is —$CH_2CH_2$—. In some embodiments, $L^8$ is —$CH_2CH_2CH_2$—. In some embodiments, $L^8$ is —$CH_2CH_2CH_2CH_2$—. In some embodiments, $L^8$ is absent.

In some embodiments, $L^9$ is —O—, —NR$^L$—, —N(R$^L$)$_2^+$—, —OP(=O)(OR$^L$)O—, —S—, —S(=O)—, —S(=O)$_2$—, —C(=O)—, —C(=O)O—, —OC(=O)—, —OC(=O)O—, —C(=O)NR$^L$—, —NR$^L$C(=O)—, —OC(=O)NR$^L$—, —NR$^L$C(=O)O—, —NR$^L$C(=O)NR$^L$—, —NR$^L$C(=S)NR$^L$—, —CR$^L$=N—, —N=CR$^L$—, —NR$^L$S(=O)$_2$—, —S(=O)$_2$NR$^L$—, —C(=O)NR$^L$S(=O)$_2$—, —S(=O)$_2$NR$^L$C(=O)—, substituted or unsubstituted $C_1$-$C_6$ alkylene, substituted or unsubstituted $C_1$-$C_6$ heteroalkylene, —($CH_2$—$CH_2$—O)$_{qa}$—, —(O—$CH_2$—$CH_2$)$_{qb}$—, —($CH_2$—CH($CH_3$)—O)$_{qc}$—, —(O—CH($CH_3$)—$CH_2$)$_{qd}$—, or absent. In some embodiments, $L^9$ is —C(=O)O—, —OC(=O)—, —OC(=O)O—, —C(=O)NR$^L$—, —NR$^L$C(=O)—, —OC(=O)NR$^L$—, —NR$^L$C(=O)O—, —NR$^L$C(=O)NR$^L$—, or —NR$^L$C(=S)NR$^L$—. In some embodiments, $L^9$ is —C(=O)O—, —OC(=O)—, —C(=O)NR$^L$—, or —NR$^L$C(=O)—. In some embodiments, $L^9$ is —C(=O)NR$^L$—. In some embodiments, $L^9$ is —NR$^L$C(=O)—. In some embodiments, $L^9$ is —NH—C(=O)—. In some embodiments, $L^9$ is —C(=O)NH—. In some embodiments, $L^9$ is absent.

In some embodiments, each $R^L$ is independently hydrogen, substituted or unsubstituted $C_1$-$C_4$ alkyl, substituted or unsubstituted $C_1$-$C_4$ heteroalkyl, or substituted or unsubstituted CVCx cycloalkyl.

In some embodiments, $R^L$ is hydrogen. In some embodiments, $R^L$ is substituted or unsubstituted $C_1$-$C_4$ alkyl. In some embodiments, $R^L$ is methyl. In some embodiments, $R^L$ is ethyl.

In some embodiments, qa is 1 to 20, 5 to 20, 5 to 15, 8 to 20 or 8 to 12. In some embodiments, qa is 5, 6, 7, 8, 9, 10, 11, 12, 13, 14, or 15. In some embodiments, qa is 9, 10, 11, or 12. In some embodiments, qa is about 10.

In some embodiments, qb is 1 to 20, 5 to 20, 5 to 15, 8 to 20 or 8 to 12. In some embodiments, qb is 5, 6, 7, 8, 9, 10, 11, 12, 13, 14, or 15. In some embodiments, qb is 9, 10, 11, or 12. In some embodiments, qb is about 10.

In some embodiments, qc is 1 to 20, 5 to 20, 5 to 15, 8 to 20 or 8 to 12. In some embodiments, qc is 5, 6, 7, 8, 9, 10, 11, 12, 13, 14, or 15. In some embodiments, qc is 9, 10, 11, or 12. In some embodiments, qc is about 10.

In some embodiments, qd is 1 to 20, 5 to 20, 5 to 15, 8 to 20 or 8 to 12. In some embodiments, qd is 5, 6, 7, 8, 9, 10, 11, 12, 13, 14, or 15. In some embodiments, qd is 9, 10, 11, or 12. In some embodiments, qd is about 10.

In some embodiments, q is 0. In some embodiments, q is 1. In some embodiments, q is 2. In some embodiments, q is 3. In some embodiments, q is 4. In some embodiments, q is 5. In some embodiments, q is 6.

In some embodiments, $L^7$ is —O—, —$NR^L$—, —$N(R^L)_2^+$—, —OP(=O)($OR^L$)O—, —S—, —S(=O)—, —S(=O)$_2$—, —C(=O)—, —C(=O)O—, —OC(=O)—, —OC(=O)O—, —C(=O)$NR^L$—, —$NR^L$C(=O)—, —OC(=O)$NR^L$—, —$NR^L$C(=O)O—, —$NR^L$C(=O)$NR^L$—, —$NR^L$C(=S)$NR^L$—, —$CR^L$=N—, —N=$CR^L$, —$NR^L$S(=O)$_2$—, —S(=O)$_2NR^L$—, —C(=O)$NR^L$S(=O)$_2$—, —S(=O)$_2NR^L$C(=O)—, a click chemistry residue, or absent. In some embodiments, $L^7$ is a click chemistry residue. In some embodiments, $L^7$ is a residue of copper-free click chemistry. In some embodiments, $L^7$ is a residue of nitrone dipole cycloaddition. In some embodiments, $L^7$ is a residue of tetrazine ligation. In some embodiments, $L^7$ is a residue of quadricyclane ligation. Exemplary groups of click chemistry residue are shown in Hein at al, "Click Chemistry, A Powerful Tool for Pharmaceutical Sciences," Pharmaceutical Research volume 25, pages 2216-2230 (2008); Thirumurugan et al, "Click Chemistry for Drug Development and Diverse Chemical-Biology Applications," Chem. Rev. 2013, 113, 7, 4905-4979; US20160107999A1; U.S. Ser. No. 10/266,502B2; and US20190204330A1, each of which is incorporated by reference in its entirety. In some embodiments, $L^7$ is

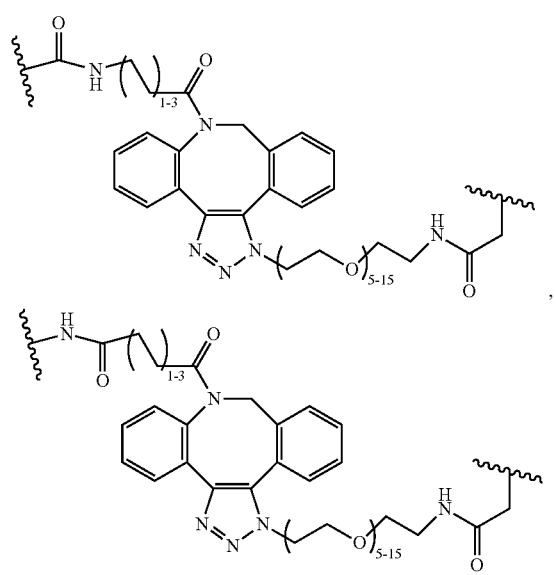

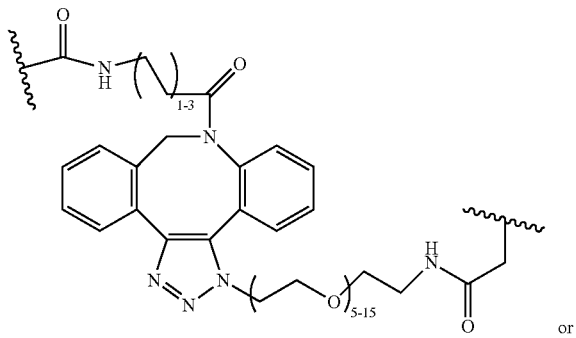

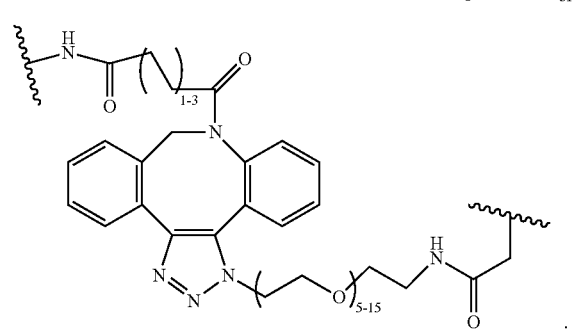

In some embodiments, $L^7$ is

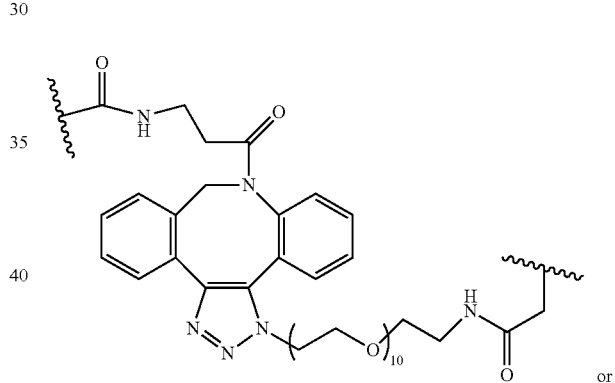

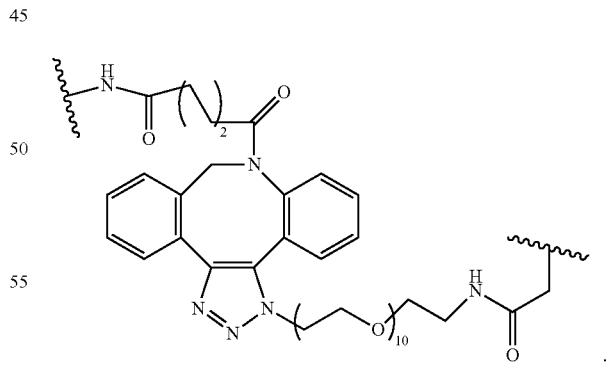

In some embodiments, provided herein a linker that comprises a click chemistry residue. In some embodiments, the linker comprises a structure of Formula (V) and $L^7$ is a click chemistry residue. In some embodiments, the click chemistry residue is a cyclooctynes-azide residue. For example, in some embodiments, the click chemistry residue is

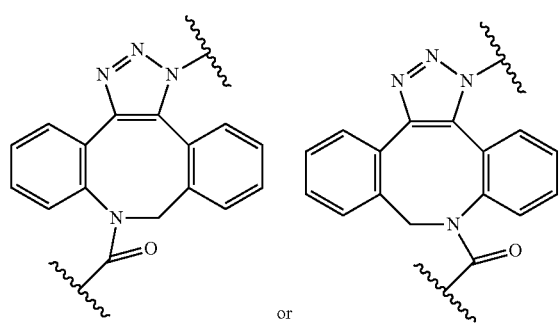

(DBCO-azide residue). In some embodiments, the click chemistry residue is

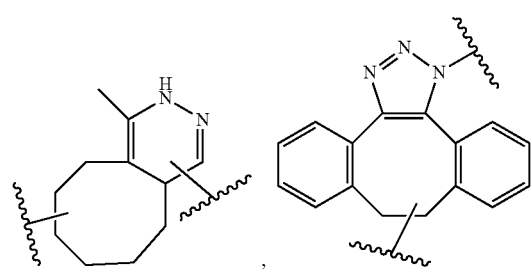

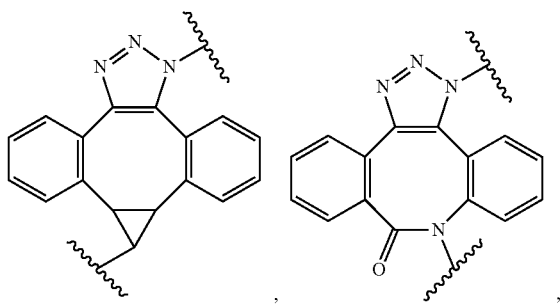

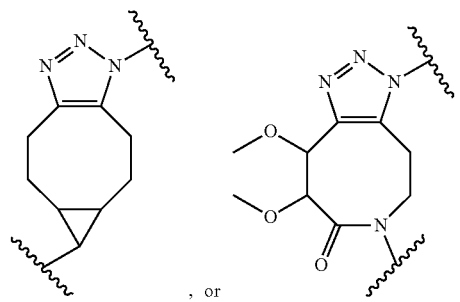

, or

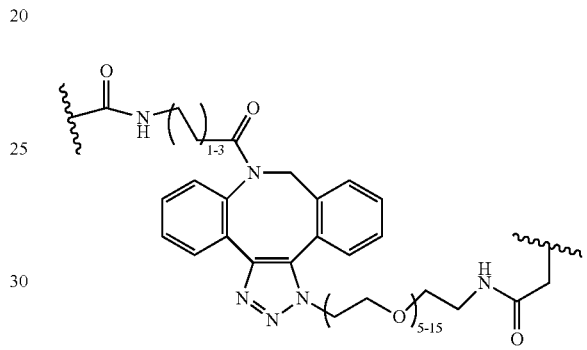

.

In some embodiments, the click chemistry residue is a DIBO-azide residue, BARAC-azide residue, DBCO-azide residue, DIFO-azide residue, COMBO-azide residue, BCN-azide residue, or DIMAC-azide residue. In some embodiments, the click chemistry residue comprises a triazole.

In some embodiments, provided herein a linker that comprises a structure of

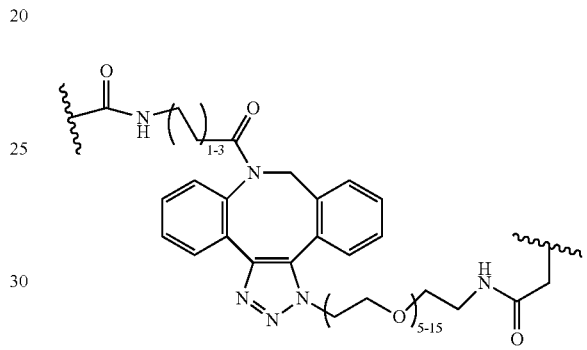

or

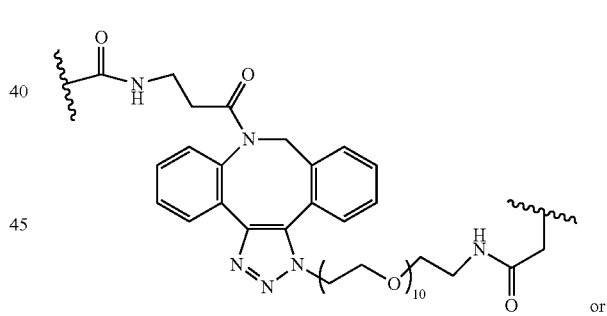

.

In some embodiments, the linker comprises a structure of

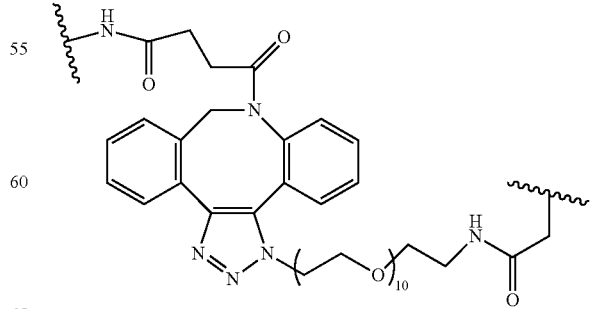

In some embodiments, provided herein a linker that comprises a structure of

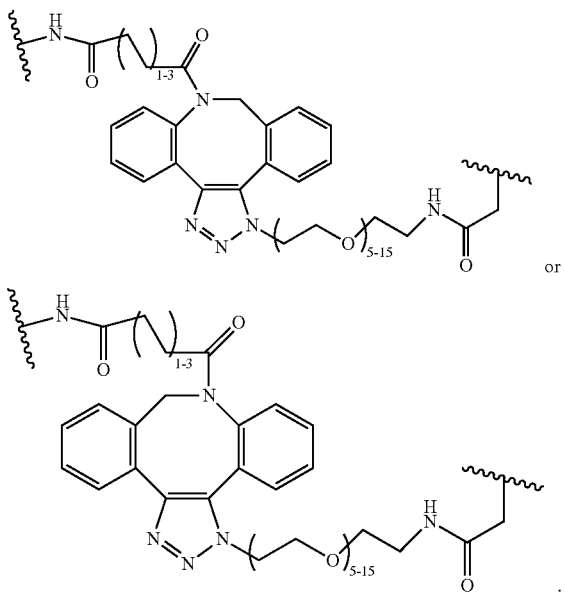

In some embodiments, the linker comprises a structure of

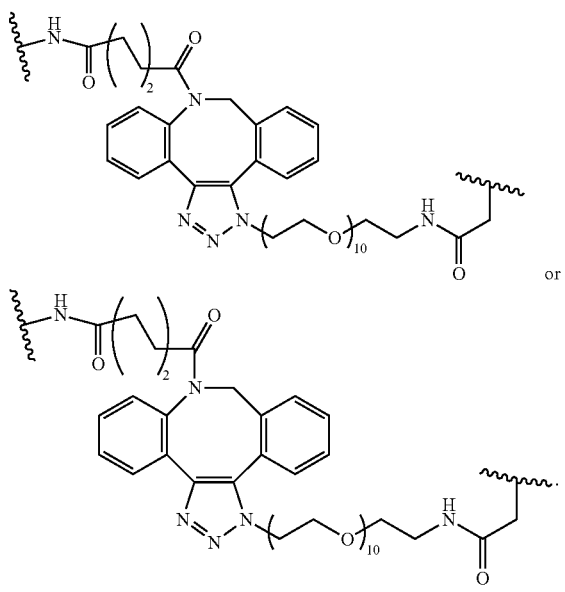

In some embodiments, the IL-2 polypeptide attaches to the linker through the azide side, and the polymer attaches to the linker through the cyclooctyne side. In some embodiments, the IL-2 polypeptide attaches to the linker through the cyclooctyne side, and the polymer attaches to the linker through the azide side.

Accordingly, also described herein is a method of making a modified IL-2 polypeptide that comprises a polymer, the method comprising conjugating an IL-2 polypeptide or fragment thereof that comprises a first linker with a polymer that comprises a second linker. In some embodiments, the first linker and the second linker can conjugate via biorthogonal chemistry, thereby making the modified IL-2 polypeptide that comprises a polymer. In some embodiments, the biorthogonal chemistry is a click chemistry. In some embodiments, the first linker comprises an azide moiety and the second linker comprises a cyclooctyne moiety. In some embodiments, the first linker comprises a cyclooctyne moiety and the second linker comprises an azide moiety.

Also described herein is a modified IL-2 polypeptide population comprising, a plurality of modified IL-2 polypeptides, wherein the plurality of modified IL-2 polypeptides comprise (i) a plurality of water-soluble polymers attached at residue 45, (ii) a plurality of water-soluble polymers attached at residue 42, and/or (iii) a plurality of water-soluble polymers attached at residue 42 and a plurality of water-soluble polymers attached at residue 45. In some embodiments, at least 75%, at least 80%, at least 85%, at least 90%, or at least 95% of the plurality of water-soluble polymers attached at residue 42 have a molecular weight that is within ±10% of the peak molecular weight of the plurality of water-soluble polymers attached at residue 42 as determined by matrix-assisted laser desorption/ionization mass spectroscopy (MALDI-MS). In some embodiments, at most 50%, at most 60%, at most 75%, at most 80%, at most 85%, at most 90%, or at most 95% of the plurality of water-soluble polymers attached at residue 42 have a molecular weight that is within ±10% of the peak molecular weight of the plurality of water-soluble polymers attached at residue 42 as determined by MALDI-MS. In some embodiments, a ratio of weight average molecular weight over number average molecular weight for the plurality of water-soluble polymers attached at residue 42 is from about 1.0 to about 1.5, from about 1.0 to about 1.1, from about 1.0 to about 1.2, from about 1.0 to about 1.3, from about 1.0 to about 1.25, from about 1.05 to about 1.1, from about 1.05 to about 1.2, from about 1.05 to about 1.5, from about 1.1 to about 1.2, from about 1.1 to about 1.5, or from about 1.2 to about 1.5, as determined by chromatography such as gel permeation chromatography (GPC) and high performance liquid chromatography (HPLC) or mass spectrometry such as MALDI-MS. In some embodiments, a ratio of weight average molecular weight over number average molecular weight for the plurality of water-soluble polymers attached at residue 42 is at least 1.1, at least 1.2, at least 1.3, at least 1.5, at least 1.6, at least 1.7, at least 1.8, at least 1.9, at least 2.0, at least 2.5, or at least 3.0 as determined by chromatography such as GPC and HPLC or mass spectrometry. In some embodiments, at least 75%, at least 80%, at least 85%, at least 90%, or at least 95% of the plurality of water-soluble polymers attached at residue 45 have a molecular weight that is within ±10% of the peak molecular weight of the plurality of water-soluble polymers attached at residue 45 as determined by MALDI-MS. In some embodiments, at most 50%, at most 60%, at most 75%, at most 80%, at most 85%, at most 90%, or at most 95% of the plurality of water-soluble polymers attached at residue 42 have a molecular weight that is within ±10% of the peak molecular weight of the plurality of water-soluble polymers attached at residue 45 as determined by MALDI-MS. In some embodiments, a ratio of weight average molecular weight over number average molecular weight for the plurality of water-soluble polymers attached at residue 45 is from about 1.0 to about 1.5, from about 1.0 to about 1.1, from about 1.0 to about 1.2, from about 1.0 to about 1.3, from about 1.0 to about 1.25, from about 1.05 to about 1.1, from about 1.05 to about 1.2, from about 1.05 to about 1.5, from about 1.1 to about 1.2, from about 1.1 to about 1.5, or from about 1.2 to about 1.5, as determined by chromatography such as GPC and HPLC or mass spectrometry. In some embodiments, a ratio of weight average molecular weight over number average molecular weight for the plurality of water-soluble polymers attached at residue 45 is at least 1.1, at least 1.2, at least 1.3, at least 1.5, at least 1.6, at least 1.7, at least 1.8, at least 1.9, at least 2.0, at least 2.5, or at least 3.0 as determined by chromatography such as GPC and HPLC or mass spectrometry.

Monodispersity

In one aspect, described herein is a population of modified IL-2 polypeptides. In some embodiments, a population of the modified IL-2 polypeptides described herein is monodispersed. In some embodiments, the population of modified IL-2 polypeptides comprises monodispersed polymers. In some embodiments, the monodispersed polymers are attached to the N-terminus, residue 42, and/or residue 45 of the modified IL-2 polypeptides. In some embodiments, the monodispersed polymers are attached to a residue position of the modified IL-2 polypeptide as described in Table 1 or Table 2. In some instances, the population of modified IL-2 polypeptides comprises a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, a population of modified IL-2 polypeptides described herein comprises a polymer covalently attached thereto. In some embodiments, each of the modified IL-2 polypeptides comprises a polymer covalently attached thereto. In some embodiments, the polymer is a monodisperse polymer. In some embodiments, the polymer is covalently attached to residue 42 or 45, wherein residue position numbering of the modified IL-2 polypeptide is based on SEQ ID NO:1 as a reference sequence. In some embodiments, the polymer is covalently attached to residue F42Y or Y45, wherein residue position numbering of the modified IL-2 polypeptide is based on SEQ ID NO: 1 as a reference sequence. In some embodiments, the polymer is covalently attached to the N-terminus of the modified IL-2 polypeptides.

In some embodiments, a population of modified IL-2 described herein comprises a second polymer covalently attached thereto. In some embodiments, each of the modified IL-2 polypeptides comprises a second polymer covalently attached thereto. In some embodiments, the second polymer is a monodisperse polymer. In some embodiments, the second polymer is covalently attached to residue 42 or 45, wherein residue position numbering of the modified IL-2 polypeptide is based on SEQ ID NO:1 as a reference sequence. In some embodiments, the second polymer is covalently attached to residue F42Y or Y45, wherein residue position numbering of the modified IL-2 polypeptide is based on SEQ ID NO: 1 as a reference sequence.

In some embodiments, a population of modified IL-2 polypeptides described herein comprises a third polymer covalently attached thereto, thereto. In some embodiments, each of the modified IL-2 polypeptides comprises a third polymer covalently attached thereto. In some embodiments, the third polymer is a monodisperse polymer. In some embodiments, the second polymer is covalently attached to residue F42Y or Y45, wherein residue position numbering of the modified IL-2 polypeptide is based on SEQ ID NO:1 as a reference sequence. In some embodiments, the second polymer and third polymers are covalently attached to residue F42Y and Y45, wherein residue position numbering of the modified IL-2 polypeptide is based on SEQ ID NO:1 as a reference sequence.

In some embodiments, a population of the modified IL-2 polypeptides described herein is monodispersed. In some embodiments, a ratio of weight average molecular weight over number average molecular weight for the population of the modified IL-2 polypeptide is at most 1.5, at most 1.2, at most 1.1, or at most 1.05. In some embodiments, the pharmaceutical composition comprises a population of the modified IL-2 polypeptides, and wherein a ratio of weight average molecular weight over number average molecular weight for the population of the modified IL-2 polypeptide is 1.05 to 1.5. In some embodiments, the pharmaceutical composition comprises a population of the modified IL-2 polypeptides, and wherein a ratio of weight average molecular weight over number average molecular weight for the population of the modified IL-2 polypeptide is from about 1.0 to about 1.5, from about 1.0 to about 1.1, from about 1.0 to about 1.2, from about 1.0 to about 1.3, from about 1.0 to about 1.4, from about 1.05 to about 1.1, from about 1.05 to about 1.2, from about 1.05 to about 1.5, from about 1.1 to about 1.2, from about 1.1 to about 1.5, or from about 1.2 to about 1.5. In some embodiments, the pharmaceutical composition comprises a population of the modified IL-2 polypeptides, and wherein a ratio of weight average molecular weight over number average molecular weight for the population of the modified IL-2 polypeptides is about 1.05, 1.1, about 1.2, or about 1.5.

In some embodiments, the pharmaceutical composition comprises a population of the modified IL-2 polypeptides, and wherein a ratio of weight average molecular weight over number average molecular weight for the population of the modified IL-2 polypeptide is at least 1.05, 1.1, or 1.2. In some embodiments, the pharmaceutical composition comprises a population of the modified IL-2 polypeptides, and wherein a ratio of weight average molecular weight over number average molecular weight for the population of the modified IL-2 polypeptide is at most 1.1, 1.2, or 1.5. In some embodiments, the ratio is determined by chromatography such as gel permeation chromatography (GPC) and high performance liquid chromatography (HPLC). In some embodiments, the ratio is determined by mass spectrum such as MALDI-MS and ESI-HRMS.

In some embodiments of a population of modified IL-2 polypeptides described herein, at least 80%, at least 85%, at least 90%, at least 95%, or at least 99% of the population of modified IL-2 polypeptides have a molecular weight that is within ±10% of the peak molecular weight as determined by mass spectrum. In some embodiments of the population of modified IL-2 polypeptides, at least 80% of the population of modified IL-2 polypeptides have a molecular weight that is within ±10% of the peak molecular weight as determined by mass spectrum. In some embodiments of the population of modified IL-2 polypeptides, at least 85% of the population of modified IL-2 polypeptides have a molecular weight that is within ±10% of the peak molecular weight as determined by mass spectrum. In some embodiments of the population of modified IL-2 polypeptides, at least 90% of the population of modified IL-2 polypeptides have a molecular weight that is within ±10% of the peak molecular weight as determined by mass spectrum. In some embodiments of the population of modified IL-2 polypeptides, at least 95% of the population of modified IL-2 polypeptides have a molecular weight that is within ±10% of the peak molecular weight as determined by mass spectrum. In some embodiments of the population of modified IL-2 polypeptides, at least 99% of the population of modified IL-2 polypeptides have a molecular weight that is within ±10% of the peak molecular weight as determined by mass spectrum. In some embodiments, the mass spectrum is a MALDI-mass spectrometry. In some embodiments, the mass spectrum is a high-resolution electrospray ionization mass spectrometry (ESI-MS or ESI-HRMS).

In some embodiments of a population of modified IL-2 polypeptides described herein, at least 80%, at least 85%, at least 90%, at least 95%, or at least 99% of the population of modified IL-2 polypeptides have a molecular weight that is within ±5% of the peak molecular weight as determined by mass spectrum. In some embodiments of the population of modified IL-2 polypeptides, at least 80% of the population of modified IL-2 polypeptides have a molecular weight that is within ±5% of the peak molecular weight as determined by mass spectrum. In some embodiments of the population of modified IL-2 polypeptides, at least 85% of the population of modified IL-2 polypeptides have a molecular weight that is within ±5% of the peak molecular weight as determined by mass spectrum. In some embodiments of the population of modified IL-2 polypeptides, at least 90% of the population of modified IL-2 polypeptides have a molecular weight that is within ±5% of the peak molecular weight as determined by mass spectrum. In some embodiments of the population of modified IL-2 polypeptides, at least 95% of the population of modified IL-2 polypeptides have a molecular weight that is within ±5% of the peak molecular weight as determined by mass spectrum. In some embodiments of the population of modified IL-2 polypeptides, at least 99% of the population of modified IL-2 polypeptides have a molecular weight that is within ±5% of the peak molecular weight as determined by mass spectrum.

In some embodiments of a population of modified IL-2 polypeptides described herein, at least 80%, at least 85%, at least 90%, at least 95%, or at least 99% of the population of modified IL-2 polypeptides have a molecular weight that is within ±2% of the peak molecular weight as determined by mass spectrum. In some embodiments of the population of modified IL-2 polypeptides, at least 80% of the population of modified IL-2 polypeptides have a molecular weight that is within ±2% of the peak molecular weight as determined by mass spectrum. In some embodiments of the population of modified IL-2 polypeptides, at least 85% of the population of modified IL-2 polypeptides have a molecular weight that is within ±2% of the peak molecular weight as determined by mass spectrum. In some embodiments of the population of modified IL-2 polypeptides, at least 90% of the population of modified IL-2 polypeptides have a molecular weight that is within ±2% of the peak molecular weight as determined by mass spectrum. In some embodiments of the population of modified IL-2 polypeptides, at least 95% of the population of modified IL-2 polypeptides have a molecular weight that is within ±2% of the peak molecular weight as determined by mass spectrum. In some embodiments of the population of modified IL-2 polypeptides, at least 99% of the population of modified IL-2 polypeptides have a molecular weight that is within ±2% of the peak molecular weight as determined by mass spectrum.

In some embodiments of a population of modified IL-2 polypeptides described herein, at least 80%, at least 85%, at least 90%, at least 95%, or at least 99% of the population of modified IL-2 polypeptides have a molecular weight that is within ±1% of the peak molecular weight as determined by mass spectrum. In some embodiments of the population of modified IL-2 polypeptides, at least 80% of the population of modified IL-2 polypeptides have a molecular weight that is within ±1% of the peak molecular weight as determined by mass spectrum. In some embodiments of the population of modified IL-2 polypeptides, at least 85% of the population of modified IL-2 polypeptides have a molecular weight that is within ±1% of the peak molecular weight as determined by mass spectrum. In some embodiments of the population of modified IL-2 polypeptides, at least 90% of the population of modified IL-2 polypeptides have a molecular weight that is within ±1% of the peak molecular weight as determined by mass spectrum. In some embodiments of the population of modified IL-2 polypeptides, at least 95% of the population of modified IL-2 polypeptides have a molecular weight that is within ±1% of the peak molecular weight as determined by mass spectrum. In some embodiments of the population of modified IL-2 polypeptides, at least 99% of the population of modified IL-2 polypeptides have a molecular weight that is within ±1% of the peak molecular weight as determined by mass spectrum.

In some embodiments of a population of modified IL-2 polypeptides described herein, at least 80%, at least 85%, at least 90%, at least 95%, or at least 99% of the population of modified IL-2 polypeptides have a molecular weight that is within ±1000 Daltons of the peak molecular weight as determined by mass spectrum. In some embodiments of the population of modified IL-2 polypeptides, at least 80% of the population of modified IL-2 polypeptides have a molecular weight that is within ±1000 Daltons of the peak molecular weight as determined by mass spectrum. In some embodiments of the population of modified IL-2 polypeptides, at least 85% of the population of modified IL-2 polypeptides have a molecular weight that is within ±1000 Daltons of the peak molecular weight as determined by mass spectrum. In some embodiments of the population of modified IL-2 polypeptides, at least 90% of the population of modified IL-2 polypeptides have a molecular weight that is within ±1000 Daltons of the peak molecular weight as determined by mass spectrum. In some embodiments of the population of modified IL-2 polypeptides, at least 95% of the population of modified IL-2 polypeptides have a molecular weight that is within ±1000 Daltons of the peak molecular weight as determined by mass spectrum. In some embodiments of the population of modified IL-2 polypeptides, at least 99% of the population of modified IL-2 polypeptides have a molecular weight that is within ±1000 Daltons of the peak molecular weight as determined by mass spectrum.

In some embodiments of a population of modified IL-2 polypeptides described herein, at least 80%, at least 85%, at least 90%, at least 95%, or at least 99% of the population of modified IL-2 polypeptides have a molecular weight that is within ±500 Daltons of the peak molecular weight as determined by mass spectrum. In some embodiments of the population of modified IL-2 polypeptides, at least 80% of the population of modified IL-2 polypeptides have a molecular weight that is within ±500 Daltons of the peak molecular weight as determined by mass spectrum. In some embodiments of the population of modified IL-2 polypeptides, at least 85% of the population of modified IL-2 polypeptides have a molecular weight that is within ±500 Daltons of the peak molecular weight as determined by mass spectrum. In some embodiments of the population of modified IL-2 polypeptides, at least 90% of the population of modified IL-2 polypeptides have a molecular weight that is within ±500 Daltons of the peak molecular weight as determined by mass spectrum. In some embodiments of the population of modified IL-2 polypeptides, at least 95% of the population of modified IL-2 polypeptides have a molecular weight that is within ±500 Daltons of the peak molecular weight as determined by mass spectrum. In some embodiments of the population of modified IL-2 polypeptides, at least 99% of the population of modified IL-2 polypeptides have a molecular weight that is within ±500 Daltons of the peak molecular weight as determined by mass spectrum.

In some embodiments of a population of modified IL-2 polypeptides described herein, at least 80%, at least 85%, at least 90%, at least 95%, or at least 99% of the population of modified IL-2 polypeptides have a molecular weight that is within ±100 Daltons of the peak molecular weight as determined by mass spectrum. In some embodiments of the population of modified IL-2 polypeptides, at least 80% of the population of modified IL-2 polypeptides have a molecular weight that is within ±100 Daltons of the peak molecular weight as determined by mass spectrum. In some embodiments of the population of modified IL-2 polypeptides, at least 85% of the population of modified IL-2 polypeptides have a molecular weight that is within ±100 Daltons of the peak molecular weight as determined by mass spectrum. In some embodiments of the population of modified IL-2 polypeptides, at least 90% of the population of modified IL-2 polypeptides have a molecular weight that is within ±100 Daltons of the peak molecular weight as determined by mass spectrum. In some embodiments of the population of modified IL-2 polypeptides, at least 95% of the population of modified IL-2 polypeptides have a molecular weight that is within ±100 Daltons of the peak molecular weight as determined by mass spectrum. In some embodiments of the population of modified IL-2 polypeptides, at least 99% of the population of modified IL-2 polypeptides have a molecular weight that is within ±100 Daltons of the peak molecular weight as determined by mass spectrum.

In some embodiments of the population of modified IL-2 polypeptides, at least 90% of the population of modified IL-2 polypeptides have a molecular weight that is within ±20 Da, ±10 Da, or ±5 Da of the peak molecular weight as determined by mass spectrum. In some embodiments of the population of modified IL-2 polypeptides, at least 95% of the population of modified IL-2 polypeptides have a molecular weight that is within ±20 Da, ±10 Da, or ±5 Da of the peak molecular weight as determined by mass spectrum. In some embodiments of the population of modified IL-2 polypeptides, at least 99% of the population of modified IL-2 polypeptides have a molecular weight that is within ±20 Da, ±10 Da, or ±5 Da of the peak molecular weight as determined by mass spectrum. In some embodiments, the mass spectrum is a MALDI-mass spectrometry. In some embodiments, the mass spectrum is ESI-HRMS.

In some embodiments of a population of modified IL-2 polypeptides described herein, at least 80%, at least 85%, at least 90%, or at least 95% of the population of modified IL-2 polypeptides have the same molecular weight as measured by mass spectrum. In some embodiments of the population of modified IL-2 polypeptides, at least 80% of the population of modified IL-2 polypeptides have the same molecular weight as measured by mass spectrum. In some embodiments of the population of modified IL-2 polypeptides, at least 85% of the population of modified IL-2 polypeptides have the same molecular weight as measured by mass spectrum. In some embodiments of the population of modified IL-2 polypeptides, at least 90% of the population of modified IL-2 polypeptides have the same molecular weight as measured by mass spectrum. In some embodiments of the population of modified IL-2 polypeptides, at least 95% of the population of modified IL-2 polypeptides have the same molecular weight as measured by mass spectrum.

In some embodiments, a population of modified IL-2 polypeptides described herein exists substantially in one apparent molecular weight form when assessed, for example, by size exclusion chromatography, dynamic light scattering, ESI-MS, MALDI-MS, or analytical ultracentrifugation. In some embodiments, the population of modified IL-2 polypeptides exists in at least about 80%, 85%, 90%, 91%, 92%, 93%, 94%, 95%, 96%, 97%, 98%, 99%, 99.5% or greater in one apparent molecular weight form when assessed, for example, by size exclusion chromatography, dynamic light scattering, ESI-MS, MALDI-MS, or analytical ultracentrifugation. In some embodiments, the population of modified IL-2 polypeptides exists substantially in one apparent molecular weight form when assessed by size exclusion chromatography. In some embodiments, the population of modified IL-2 polypeptides exists substantially in one apparent molecular weight form when assessed by dynamic light scattering. In some embodiments, the population of modified IL-2 polypeptides exists substantially in one apparent molecular weight form when assessed by MALDI-MS or ESI-MS. In some embodiments, the population of modified IL-2 polypeptides exist substantially in one apparent molecular weight form when assessed by analytical ultracentrifugation.

In one aspect, described herein is a modified interleukin-2 (IL-2) polypeptide population, comprising a plurality of modified IL-2 polypeptides, wherein the plurality of modified IL-2 polypeptides comprise a plurality of polymers (i.e., a plurality of first polymers), wherein each of the modified IL-2 polypeptides comprises one of the plurality of polymers covalently attached thereto. In some embodiments, at least 95% of the plurality of polymers have a molecular weight that is within ±10% of the peak molecular weight of the plurality of polymers as determined by mass spectrum. In some embodiments, at least 75%, at least 80%, at least 85%, at least 90%, or least 95% of the plurality of polymers have a molecular weight that is within ±10% of the peak molecular weight of the plurality of polymers as determined by mass spectrum. In some embodiments, at least 75%, at least 80%, at least 85%, at least 90%, or least 95% of the plurality of polymers have a molecular weight that is within ±5% of the peak molecular weight of the plurality of polymers as determined by MALDI-MS. In some embodiments, at most 50%, at most 60%, at most 75%, at most 80%, at most 85%, at most 90%, or most 95% of the plurality of polymers have a molecular weight that is within ±10% of the peak molecular weight of the plurality of polymers as determined by mass spectrum wherein at least 80%, at least 85%, at least 90%, at least 95%, or at least 99% of the population of modified IL-2 polypeptides have a molecular weight that is within ±10% of the peak molecular weight as determined by mass spectrum. In some embodiments, at most 50%, at most 60%, at most 75%, at most 80%, at most 85%, at most 90%, or most 95% of the plurality of polymers have a molecular weight that is within ±5% of the peak molecular weight of the plurality of polymers as determined by mass spectrum. In some embodiments, at least 80%, at least 85%, at least 90%, at least 95%, or at least 99% of the population of modified IL-2 polypeptides have a molecular weight that is within ±1% of the peak molecular weight as determined by mass spectrum, n some embodiments, at least 80%, at least 85%, at least 90%, at least 95%, or at least 99% of the population of modified IL-2 polypeptides have a molecular weight that is within ±0.5% of the peak molecular weight as determined by mass spectrum, n some embodiments, at least 80%, at least 85%, at least 90%, at least 95%, or at least 99% of the population of modified IL-2 polypeptides have a molecular weight that is within ±0.1% of the peak molecular weight as determined by mass spectrum. In some embodiments, a ratio of weight average molecular weight over number average molecular weight for the plurality of polymers is from about 1.0 to about 1.5, from about 1.0 to about 1.1, from about 1.0 to about 1.2, from about 1.0 to about 1.3, from about 1.0 to about 1.25, from about 1.05 to about 1.1, from about 1.05 to about 1.2, from about 1.05 to about 1.5, from about 1.1 to about 1.2, from about 1.1 to about 1.5, or from about 1.2 to about 1.5, as determined by chromatography such as GPC and HPLC or mass spectrometry such as MALDI-MS.

In some embodiments, a ratio of weight average molecular weight over number average molecular weight for the plurality of polymers is at least 1.1, at least 1.2, at least 1.3, at least 1.5, at least 1.6, at least 1.7, at least 1.8, at least 1.9, at least 2.0, at least 2.5, or at least 3.0 as determined by chromatography such as GPC and HPLC or mass spectrometry.

In some embodiments, the weight average molecular weight of the polymers is at least about 3000 Da, at least about 6000 Da, at least about 12,000 Da, or at least about 24,000 Da. In some embodiments, the weight average molecular weight of the polymers is at least about 3000 Da. In some embodiments, the weight average molecular weight of the polymers is at least about 6000 Da. In some embodiments, the weight average molecular weight of the polymers is at least about 12,000 Da. In some embodiments, the weight average molecular weight of the polymers is at least about 24,000 Da.

In some embodiments, a plurality of modified IL-2 polypeptides described herein comprise a plurality of second polymers, wherein each of the modified IL-2 polypeptides comprises one of the plurality of second polymers covalently attached thereto. In some embodiments, at least 75%, at least 80%, at least 85%, at least 90%, or least 95% of the plurality of second polymers have a molecular weight that is within ±10% of the peak molecular weight of the plurality of second polymers as determined by mass spectrum such as MALDI-MS and ESI-MS. In some embodiments, at least 75%, at least 80%, at least 85%, at least 90%, or least 95% of the plurality of second polymers have a molecular weight that is within ±5% of the peak molecular weight of the plurality of second polymers as determined by mass spectrum. In some embodiments, at most 50%, at most 60%, at most 75%, at most 80%, at most 85%, at most 90%, or most 95% of the plurality of second polymers have a molecular weight that is within ±10% of the peak molecular weight of the plurality of second polymers as determined by mass spectrum. In some embodiments, at most 50%, at most 60%, at most 75%, at most 80%, at most 85%, at most 90%, or most 95% of the plurality of second polymers have a molecular weight that is within ±5% of the peak molecular weight of the plurality of second polymers as determined by mass spectrum. In some embodiments, a ratio of weight average molecular weight over number average molecular weight for the plurality of second polymers is from about 1.0 to about 1.5, from about 1.0 to about 1.1, from about 1.0 to about 1.2, from about 1.0 to about 1.3, from about 1.0 to about 1.25, from about 1.05 to about 1.1, from about 1.05 to about 1.2, from about 1.05 to about 1.5, from about 1.1 to about 1.2, from about 1.1 to about 1.5, or from about 1.2 to about 1.5, as determined by chromatography such as GPC and HPLC or mass spectrometry such as mass spectrum. In some embodiments, a ratio of weight average molecular weight over number average molecular weight for the plurality of second polymers is at least 1.1, at least 1.2, at least 1.3, at least 1.5, at least 1.6, at least 1.7, at least 1.8, at least 1.9, at least 2.0, at least 2.5, or at least 3.0 as determined by chromatography such as GPC and HPLC or mass spectrometry.

In some embodiments, the weight average molecular weight of the second polymers is at least about 3000 Da, at least about 6000 Da, at least about 12,000 Da, or at least about 24,000 Da. In some embodiments, the weight average molecular weight of the second polymers is at least about 3000 Da. In some embodiments, the weight average molecular weight of the second polymers is at least about 6000 Da. In some embodiments, the weight average molecular weight of the second polymers is at least about 12,000 Da. In some embodiments, the weight average molecular weight of the second polymers is at least about 24,000 Da.

In some embodiments, the plurality comprises at least 100, at least 1000, at least 10000, at least 100000, at least 1000000, at least 10000000 of the modified IL-2 polypeptides. In some embodiments, the plurality comprises at least 100 of the modified IL-2 polypeptides. In some embodiments, the plurality comprises at least 1000 of the modified IL-2 polypeptides. In some embodiments, the plurality comprises at least 10000 of the modified IL-2 polypeptides. In some embodiments, the plurality comprises at least 100000 of the modified IL-2 polypeptides. In some embodiments, the plurality comprises at least 1000000 of the modified IL-2 polypeptides. In some embodiments, the plurality comprises at least 10000000 of the modified IL-2 polypeptides. In some embodiments, the plurality comprises at least 100000000 of the modified IL-2 polypeptides.

In some embodiments, the plurality comprises about 100, about 1000, about 10000, about 100000, about 1000000, about 10000000 of the modified IL-2 polypeptides. In some embodiments, the plurality comprises about 100 of the modified IL-2 polypeptides. In some embodiments, the plurality comprises about 1000 of the modified IL-2 polypeptides. In some embodiments, the plurality comprises about 10000 of the modified IL-2 polypeptides. In some embodiments, the plurality comprises about 100000 of the modified IL-2 polypeptides. In some embodiments, the plurality comprises about 1000000 of the modified IL-2 polypeptides. In some embodiments, the plurality comprises about 10000000 of the modified IL-2 polypeptides. In some embodiments, the plurality comprises about 100000000 of the modified IL-2 polypeptides.

In some embodiments, the plurality comprises at least 1 µg, at least 10 µg, at least 100 µg, at least 1 mg, at least 10 mg, or at least 100 mg of the modified IL-2 polypeptides. In some embodiments, the plurality comprises at least 1 µg of the modified IL-2 polypeptides. In some embodiments, the plurality comprises at least 10 µg of the modified IL-2 polypeptides. In some embodiments, the plurality comprises at least 100 µg of the modified IL-2 polypeptides. In some embodiments, the plurality comprises at least 1 mg of the modified IL-2 polypeptides. In some embodiments, the plurality comprises at least 10 mg of the modified IL-2 polypeptides.

In some embodiments, the plurality comprises about 100 mg of the modified IL-2 polypeptides. In some embodiments, the plurality comprises about 1 µg, about 10 µg, about 100 µg, about 1 mg, about 10 mg, or about 100 mg of the modified IL-2 polypeptides. In some embodiments, the plurality comprises about 1 µg of the modified IL-2 polypeptides. In some embodiments, the plurality comprises about 10 µg of the modified IL-2 polypeptides. In some embodiments, the plurality comprises about 100 µg of the modified IL-2 polypeptides. In some embodiments, the plurality comprises about 1 mg of the modified IL-2 polypeptides. In some embodiments, the plurality comprises about 10 mg of the modified IL-2 polypeptides. In some embodiments, the plurality comprises about 100 mg of the modified IL-2 polypeptides.

In some embodiments, a herein described modified IL-2 polypeptide is a linear polypeptide. In some embodiments, a herein described modified IL-2 polypeptide is folded. In some embodiments, the modified polypeptide comprises one or more disulfide bonds.

III. Compositions

In one aspect, described herein is a pharmaceutical composition comprising: a modified IL-2 polypeptide described herein; and a pharmaceutically acceptable carrier or excipient. In some embodiments, the pharmaceutical composition comprises a plurality of the modified IL-2 polypeptides. In some embodiments, the pharmaceutical compositions further comprises one or more excipient selected from a carbohydrate, an inorganic salt, an antioxidant, a surfactant, or a buffer. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, the pharmaceutical composition further comprises a carbohydrate. In certain embodiments, the carbohydrate is selected from the group consisting of fructose, maltose, galactose, glucose, D-mannose, sorbose, lactose, sucrose, trehalose, cellobiose raffinose, melezitose, maltodextrins, dextrans, starches, mannitol, xylitol, maltitol, lactitol, xylitol, sorbitol (glucitol), pyranosyl sorbitol, myo-inositol, cyclodextrins, and combinations thereof.

In some embodiments, the pharmaceutical composition comprises an inorganic salt. In certain embodiments, the inoragnic salt is selected from the group consisting of sodium chloride, potassium chloride, magnesium chloride, calcium chloride, sodium phosphate, potassium phosphate, sodium sulfate, or combinations thereof.

In certain embodiments, the pharmaceutical composition comprises an antioxidant. In certain embodiments, the antioxidant is selected from the group consisting of ascorbyl palmitate, butylated hydroxyanisole, butylated hydroxytoluene, potassium metabisulfite, propyl gallate, sodium metabisulfite, sodium thiosulfate, vitamin E, 3,4-dihydroxybenzoic acid, and combinations thereof.

In certain embodiments, the pharmaceutical composition comprises a surfactant. In certain embodiments, the surfactant is selected from the group consisting of polysorbates, sorbitan esters, lipids, phospholipids, phosphatidylethanolamines, fatty acids, fatty acid esters, steroids, EDTA, zinc, and combinations thereof.

In certain embodiments, the pharmaceutical composition comprises a buffer. In certain embodiments, the buffer is selected from the group consisting of citric acid, sodium phosphate, potassium phosphate, acetic acid, ethanolamine, histidine, amino acids, tartaric acid, succinic acid, fumaric acid, lactic acid, tris, HEPES, or combinations thereof.

In some embodiments, the pharmaceutical composition is formulated for parenteral or enteral administration. In some embodiments, the pharmaceutical composition is formulated for intravenous or subcutaneous administration. In some embodiments, the pharmaceutical composition is in a lyophilized form.

In one aspect, described herein is a liquid or lyophilized composition that comprises a described modified IL-2 polypeptide. In some embodiments, the modified IL-2 polypeptide is a lyophilized powder. In some embodiments, the lyophilized powder is resuspended in a buffer solution. In some embodiments, the buffer solution comprises a buffer, a sugar, a salt, a surfactant, or any combination thereof. In some embodiments, the buffer solution comprises a phosphate salt. In some embodiments, the phosphate salt is sodium $Na_2HPO_4$. In some embodiments, the salt is sodium chloride. In some embodiments, the buffer solution comprises phosphate buffered saline. In some embodiments, the buffer solution comprises mannitol. In some embodiments, the lyophilized powder is suspended in a solution comprising 10 mM Na2HPO4 buffer pH 7.5, 0.022% SDS and 50 mg/mL mannitol.

Dosage Forms

The modified IL-2 polypeptides described herein can be in a variety of dosage forms. In some embodiments, the modified IL-2 polypeptide is dosed as a lyophilized powder. In some embodiments, the modified IL-2 polypeptide is dosed as a suspension. In some embodiments, the modified IL-2 polypeptide is dosed as a solution. In some embodiments, the modified IL-2 polypeptide is dosed as an injectable solution. In some embodiments, the modified IL-2 polypeptides is dosed as an IV solution.

IV. Method of Treatment

In one aspect, described herein, is a method of treating cancer in a subject in need thereof, comprising: administering to the subject an effective amount of a modified IL-2 polypeptide or a pharmaceutical composition as described herein. In some embodiments, the cancer is a solid cancer.

In some embodiments, the solid cancer is a carcinoma or a sarcoma. In some embodiments, the solid cancer is kidney cancer, skin cancer, bladder cancer, bone cancer, brain cancer, breast cancer, colorectal cancer, esophageal cancer, eye cancer, head and neck cancer, lung cancer, ovarian cancer, pancreatic cancer, or prostate cancer. In some embodiments, the solid cancer is metastatic renal cell carcinoma (metastatic RCC) or melanoma. In some embodiments, the cancer is a blood cancer. In some embodiments, the blood cancer is the blood cancer is leukemia, Non-Hodgkin's lymphoma, Hodgkin's lymphoma, or multiple myeloma. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, the modified IL-2 polypeptide is administered in a single dose of the effective amount of the modified IL-2 polypeptide, including further embodiments in which (i) the modified IL-2 polypeptide is administered once a day; or (ii) the modified IL-2 polypeptide is administered to the subject multiple times over the span of one day. In some embodiments, the modified IL-2 polypeptide is administered daily, every other day, 3 times a week, once a week, every 2 weeks, every 3 weeks, every 4 weeks, every 5 weeks, every 3 days, every 4 days, every 5 days, every 6 days, bi-weekly, 3 times a week, 4 times a week, 5 times a week, 6 times a week, once a month, twice a month, 3 times a month, once every 2 months, once every 3 months, once every 4 months, once every 5 months, or once every 6 months. In some embodiments, the modified IL-2 polypeptide is administered daily. In some embodiments, the modified IL-2 polypeptide is administered every other day. In some embodiments, the modified IL-2 polypeptide is administered every other day. In some embodiments, the modified IL-2 polypeptide is administered 3 times a week. In some embodiments, the modified IL-2 polypeptide is administered once a week. In some embodiments, the modified IL-2 polypeptide is administered every 2 weeks. In some embodiments, the modified IL-2 polypeptide is administered every 3 weeks. In some embodiments, the modified IL-2 polypeptide is administered every 4 weeks. In some embodiments, the modified IL-2 polypeptide is administered every 5 weeks.

In some embodiments, the modified IL-2 polypeptide is administered every 3 days. In some embodiments, the modified IL-2 polypeptide is administered every 4 days. In some embodiments, the modified IL-2 polypeptide is administered every 5 days. In some embodiments, the modified IL-2 polypeptide is administered every 6 days. In some embodiments, the modified IL-2 polypeptide is administered bi-weekly. In some embodiments, the modified IL-2 polypeptide is administered 3 times a week. In some embodiments, the modified IL-2 polypeptide is administered 4 times a week. In some embodiments, the modified IL-2 polypeptide is administered 5 times a week. In some embodiments, the modified IL-2 polypeptide is administered 6 times a week. In some embodiments, the modified IL-2 polypeptide is administered once a month. In some embodiments, the modified IL-2 polypeptide is administered twice a month. In some embodiments, the modified IL-2 polypeptide is administered 3 times a month. In some embodiments, the modified IL-2 polypeptide is administered once every two months. In some embodiments, the modified IL-2 polypeptide is administered once every 3 months. In some embodiments, the modified IL-2 polypeptide is administered once every 4 months. In some embodiments, the modified IL-2 polypeptide is administered once every 5 months. In some embodiments, the modified IL-2 polypeptide is administered once every 6 months.

In some embodiments, the subject is 5 to 75 years old. In some embodiments, the subject is 5 to 10, 5 to 15, 5 to 18, 5 to 25, 5 to 35, 5 to 45, 5 to 55, 5 to 65, 5 to 75, 10 to 15, 10 to 18, 10 to 25, 10 to 35, 10 to 45, 10 to 55, 10 to 65, 10 to 75, 15 to 18, 15 to 25, 15 to 35, 15 to 45, 15 to 55, 15 to 65, 15 to 75, 18 to 25, 18 to 35, 18 to 45, 18 to 55, 18 to 65, 18 to 75, 25 to 35, 25 to 45, 25 to 55, 25 to 65, 25 to 75, 35 to 45, 35 to 55, 35 to 65, 35 to 75, 45 to 55, 45 to 65, 45 to 75, 55 to 65, 55 to 75, or 65 to 75 years old. In some embodiments, the subject is at least 5, 10, 15, 18, 25, 35, 45, 55, or 65 years old. In some embodiments, the subject is at most 10, 15, 18, 25, 35, 45, 55, 65, or 75 years old.

V. Methods of Manufacturing

In one aspect, described herein, is a method of making a modified IL-2 polypeptide. In another aspect, described herein, is a method of making a modified IL-2 polypeptide comprising synthesizing two or more fragments of the modified IL-2 polypeptide and ligating the fragments. In another aspect, described herein, is a method of making a modified IL-2 polypeptide comprising a. synthesizing two or more fragments of the modified IL-2 polypeptide, b. ligating the fragments; and c. folding the ligated fragments. In some instances, the modified IL-2 polypeptide is a modified IL-2 polypeptide described herein, a modified IL-2 polypeptide provided in Table 7 or Table 4, a modified IL-2 polypeptide having a mutation provided in Table 1 or Table 2, and/or a modified IL-2 polypeptide having a polymer provided in Table 3.

In some embodiments, the two or more fragments of the modified IL-2 polypeptide are synthesized chemically. In some embodiments, the two or more fragments of the modified IL-2 polypeptide are synthesized by solid phase peptide synthesis. In some embodiments, the two or more fragments of the modified IL-2 polypeptide are synthesized on an automated peptide synthesizer. In some embodiments, the modified IL-2 polypeptide is ligated from 2, 3, 4, 5, 6, 7, 8, 9, 10, or more peptide fragments. In some embodiments, the modified peptide is ligated from 2 peptide fragments. In some embodiments, the modified IL-2 polypeptide is ligated from 3 peptide fragments.

In some embodiments, the modified IL-2 polypeptide is ligated from 4 peptide fragments. In some embodiments, the modified IL-2 polypeptide is ligated from 2 to 10 peptide fragments.

In some embodiments, the two or more fragments of the modified IL-2 polypeptide are ligated together. In some embodiments, three or more fragments of the modified IL-2 polypeptide are ligated in a sequential fashion. In some embodiments, three or more fragments of the modified IL-2 polypeptide are ligated in a one-pot reaction.

In some embodiments, the modified IL-2 polypeptide is ligated from peptide fragments. In some embodiments, the peptide fragments are ligated such that a bond between at least one pair of residues selected from residues 40/41, residues 70/71, or residues 103/104 is formed in the ligation reaction. In some embodiments, the peptide fragments are ligates such that a bond between residues 103 and 104 is formed in the ligation reaction. In some embodiments, the modified IL-2 polypeptide is ligated from a fragment comprising residues 104-135 of the modified IL-2 polypeptide. In some embodiments, the modified IL-2 polypeptide comprises a first polymer covalently attached at residue F42Y.

In some embodiments, ligated fragments are folded. In some embodiments, folding comprises forming one or more disulfide bonds within the modified IL-2 polypeptide. In some embodiments, the ligated fragments are subjected to a folding process. In some embodiments, the ligated fragments are folding using methods well known in the art. In some embodiments, the ligated polypeptide or the folded polypeptide are further modified by attaching one or more polymers thereto. In some embodiments, the ligated polypeptide or the folded polypeptide are further modified by PEGylation.

In some embodiments, the modified IL-2 polypeptide is synthetic.

VI. SEQ IDs

TABLE 7

| SEQ ID NO | Sequence |
|---|---|
| 1 | APTSSSTKKTQLQLEHLLLDLQMILNGINNYKNPKLTRMLTFK FYMPKKATELKHLQCLEEELKPLEEVLNLAQSKNFHLRPRDLI SNINVIVLELKGSETTFMCEYADETATIVEFLNRWITFCQSII STLT |
| 2 | PTSSSTKKTQLQLEHLLLDLQMILNGINNYKNPKLTRMLTFKF YMPKKATELKHLQCLEEELKPLEEVLNLAQSKNFHLRPRDLIS NINVIVLELKGSETTFMCEYADETATIVEFLNRWITFSQSIIS TLT |
| 3 | APTSSSTKKTQLQLEHLLLDLQ(Nle)ILNGINNYKNPKLTR (Nle)L(Hse)YKFY(Nle)PKKATELKHLQCLEEELKPLEEV L(Hse)LAQSKNFHLRPRDLISNINVIVLELKGSETTF(Hse) CEYADETATIVEFLNRWITFSQSIISTLT |

TABLE 7-continued

| SEQ ID NO | Sequence |
|---|---|
| 4 | APTSSSTKKTQLQLEHLLLDLQ(Nle)ILNGINNYKNPKLTR (Nle)L(Hse)FKFY(Nle)PKKATELKHLQCLEEELKPLEEV L(Hse)LAQSKNFHLRPRDLISNINVIVLELKGSETTF(Hse) CEYADETATIVEFLNRWITFSQSIISTLT |
| 5 | APTSSSTKKTQLQLEHLLLDLQ(Nle)ILNGINNYKNPKLTR (Nle)L(Hse)YKFY(Nle)PKKATELKHLQCLEEELKPLEEV L(Hse)YAQSKNFHLRPRDLISNINVIVLELKGSETTF(Hse) CEYADETATIVEFLNRWITFSQSIISTLT |
| 6 | APTSSSTKKTQLQLEHLLLDLQ(Nle)ILNGINNYKNPKLTR (Nle)L(Hse)FKFY(Nle)PKKATELKHLQCLEEELKPLEEV L(Hse)YAQSKNFHLRPRDLISNINVIVLELKGSETTF(Hse) CEYADETATIVEFLNRWITFSQSIISTLT |
| 7 | APTSSSTKKTQLQLEHLLLDLQ(Nle)ILNGINNYKNPKLTR (Nle)L(Hse)YKFY(Nle)PKKATELKHLQCLEEELKPLEEV L(Hse)GAQSKNFHLRPRDLISNINVIVLELKGSETTF(Hse) CEYADETATIVEFLNRWITFSQSIISTLT |
| 8 | APTSSSTKKTQLQLEHLLLDLQ(Nle)ILNGINNYKNPKLTR (Nle)L(Hse)YKFY(Nle)PKKATELKHLQCLEEELKYLEEV L(Hse)LAQSKNFHLRPRDLISNINVIVLELKGSETTF(Hse) CEYADETATIVEFLNRWITFSQSIISTLT |
| 9 | APTSSSTKKTQLQLEHLLLDLQ(Nle)ILNGINNYKNPKLTR (Nle)L(Hse)FKFY(Nle)PKKATELKHLQCLEEELKYLEEV L(Hse)LAQSKNFHLRPRDLISNINVIVLELKGSETTF(Hse) CEYADETATIVEFLNRWITFSQSIISTLT |
| 10 | APTSSSTKKTQLQLEHLLLDLQ(Nle)ILNGINNYKNPKLTY (Nle)L(Hse)YKFY(Nle)PKKATELKHLQCLEEYLKYLEEV L(Hse)LAQSKNFHLRPRDLISNINVIVLELKGSETTF(Hse) CEYADETATIVEFLNRWITFSQSIISTLT |
| 11 | APTSSSTKKTQLQLEHLLLDLQ(Nle)ILNGINNYKNPKLTR (Nle)L(Hse)FKFY(Nle)PKKATELKHLQCLEEYLKYLEEV L(Hse)LAQSKNFHLRPRDLISNINVIVLELKGSETTF(Hse) CEYADETATIVEFLNRWITFSQSIISTLT |
| 12 | APTSSSTKKTQLQLEHLLLDLQ(Nle)ILNGINNYKNPKLTR (Nle)L(Hse)FKFY(Nle)PKKATELKHLQCLEEYLKPLEEV L(Hse)LAQSKNFHLRPRDLISNINVIVLELKGSETTF(Hse) CEYADETATIVEFLNRWITFSQSIISTLT |
| 13 | APTSSSTKKTQLQLEHLLLDLQ(Nle)ILNGINNYKNPKLTR (Nle)L(Hse)FYFY(Nle)PKKATELKHLQCLEEELKPLEEV L(Hse)LAQSKNFHLRPRDLISNINVIVLELKGSETTF(Hse) CEYADETATIVEFLNRWITFSQSIISTLT |
| 14 | APTSSSTKKTQLQLEHLLLDLQ(Nle)ILNGINNYKNPKLTR (Nle)L(Hse)FKYY(Nle)PKKATELKHLQCLEEELKPLEEV L(Hse)LAQSKNFHLRPRDLISNINVIVLELKGSETTF(Hse) CEYADETATIVEFLNRWITFSQSIISTLT |
| 15 | APTSSSTKKTQLQLEHLLLDLQ(Nle)ILNGINNYKNPYLTR (Nle)L(Hse)FKFY(Nle)PKKATELKHLQCLEEELKPLEEV L(Hse)LAQSKNFHLRPRDLISNINVIVLELKGSETTF(Hse) CEYADETATIVEFLNRWITFSQSIISTLT |
| 16 | APTSSSTKKTQLQLEYLLLDLQ(Nle)ILNGINNYKNPKLTR (Nle)L(Hse)FKFY(Nle)PKKATELKHLQCLEEELKPLEEV L(Hse)LAQSKNFHLRPRDLISNINVIVLELKGSETTF(Hse) CEYADETATIVEFLNRWITFS QSIISTLT |
| 17 | APTSSSTKKTQLQLEYLLLDLQ(Nle)ILNGINNYKNPKLTR (Nle)L(Hse)YKFY(Nle)PKKATELKHLQCLEEELKPLEEV L(Hse)LAQSKNFHLRPRDLISNINVIVLELKGSETTF(Hse) CEYADETATIVEFLNRWITFSQSIISTLT |
| 18 | APTSSSTKKTQLQLEHLLLYLQ(Nle)ILNGINNYKNPKLTR (Nle)L(Hse)FKFY(Nle)PKKATELKHLQCLEEELKPLEEV L(Hse)LAQSKNFHLRPRDLISNINVIVLELKGSETTF(Hse) CEYADETATIVEFLNRWITFSQSIISTLT |
| 19 | APTSSSTKKTQLQLEHLLLYLQ(Nle)ILNGINNYKNPKLTR (Nle)L(Hse)YKFY(Nle)PKKATELKHLQCLEEELKPLEEV L(Hse)LAQSKNFHLRPRDLISNINVIVLELKGSETTF(Hse) CEYADETATIVEFLNRWITFSQSIISTLT |
| 20 | APTSSSTKKTQLQLEHLLLDLQ(Nle)ILNGINNYKNPYLTR (Nle)L(Hse)YKFY(Nle)PKKATELKHLQCLEEELKPLEEV L(Hse)LAQSKNFHLRPRDLISNINVIVLELKGSETTF(Hse) CEYADETATIVEFLNRWITFSQSIISTLT |
| 21 | APTSSSTKKTQLQLEHLLLDLQ(Nle)ILNGINNYKNPKLTR (Nle)L(Hse)YKFY(Nle)PKKATELKHLQCLEEYLKPLEEV L(Hse)LAQSKNFHLRPRDLISNINVIVLELKGSETTF(Hse) CEYADETATIVEFLNRWITFSQSIISTLT |
| 22 | APTSSSTKKTQLQLEHLLLDLQ(Nle)ILNGINNYKNPKLTR (Nle)L(Hse)YKFY(Nle)PKKATELKHLQCLEEYLKYLEEV L(Hse)LAQSKNFHLRPRDLISNINVIVLELKGSETTF(Hse) CEYADETATIVEFLNRWITFSQSIISTLT |
| 23 | APTSSSTKKTQLQLEHLLLDLQ(Nle)ILNGINNYKNPKLTR (Nle)L(Hse)FKFY(Nle)PKKATELKHLQCLEEELKPLEEV L(Hse)LAQSKNFHLRPRDLISNINVIVLELKGSETTF(Hse) CEYADETATIVEFLNRWITFCQSIISTLT |

In Table 7 above, Nle is a norleucine residue and Hse is a homoserine residue.

Although the present disclosure and its advantages have been described in detail, it should be understood that various changes, substitutions and alterations can be made herein without departing from the spirit and scope of the disclosure as defined in the appended claims.

The present disclosure is further illustrated in the following Examples which are given for illustration purposes only and are not intended to limit the disclosure in any way.

EXAMPLES

Example 1—Synthesis of Modified IL-2 Polypeptides

Modified IL-2 polypeptide having an amino acid sequence of SEQ ID NO: 3, were synthesized by ligating individual peptides synthesized using solid phase peptide synthesis (SPPS). Individual peptides were synthesized on an automated peptide synthesizer using the methods described below.

Commercially available reagents were purchased from Sigma-Aldrich, Acros, Merck or TCI Europe and used without further purification. Fmoc amino acids with suitable side-chain protecting groups for solid phase peptide synthesis were purchased from Novabiochem, Christof Senn Laboratories AG or PeptART and they were used as supplied. The polyethylene glycol derivatives used for peptide synthesis were purchased by Polypure. HPLC grade $CH_3CN$ from Sigma Aldrich was used for analytical and preparative HPLC purification.

High resolution mass spectra (FTMS) for peptides and proteins were measured on a Bruker solariX (9.4T magnet) equipped with a dual ESI/MALDI-FTICR source using 4-hydroxy-α-cyanocinnamic acid (HCCA) as matrix. CD spectra were recorded with a Jasco J-715 spectrometer with a 1.0 mm path length cell. Spectra were collected at 25° C. in continuous scanning mode with standard sensitivity (100 mdeg), 0.5 nm data pitch, 50 nm/min scanning speed, 1 nm bandwidth and 5 accumulations.

Peptides and proteins fragments were analyzed and purified by reverse phase high performance liquid chromatography (RP-HPLC). The peptide analysis and reaction monitoring were performed on analytical Jasco instruments with dual pumps, mixer and in-line degasser, autosampler, a variable wavelength UV detector (simultaneous monitoring of the eluent at 220 nm and 254 nm) and an injector fitted with a 100 μl injection loop. The purification of the peptide fragments was performed on a Gilson preparative instrument with 20 mL injection loop. In both cases, the mobile phase was MilliQ-H$_2$O with 0.1% TFA (Buffer A) and HPLC grade CH$_3$CN with 0.1% TFA (Buffer B). Analytical HPLC was performed on bioZen™ Intact C4 column (3.6 μm, 150×4.6 mm) or Shiseido Capcell Pak MG III (5 μm, 150×4.6 mm) column with a flow rate of 1 mL/min. Preparative HPLC was performed on a Shiseido Capcell Pak UG80 C18 column (5 μm, 50 mm I.D.×250 mm) at a flow rate of 40 mL/min.

The peptide segments were synthesized on a Syro I or a CS Bio 136X peptide synthesizers using Fmoc SPPS chemistry. The following Fmoc amino acids with side-chain protection groups were used: Fmoc-Ala-OH, Fmoc-Arg(Pbf)-OH, Fmoc-Asn(Trt)-OH, Fmoc-Asp(OtBu)-OH, Fmoc-Cys(Acm), Fmoc-Gln(Trt)-OH, Fmoc-Glu(OtBu)-OH, Fmoc-Gly-OH, Fmoc-His(1-Trt)-OH, Fmoc-Ile-OH, Fmoc-Leu-OH, Fmoc-Lys(Boc)-OH, Fmoc-Nle-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH. Fmoc-pseudoproline dipeptides were incorporated in the synthesis where necessary. Fmoc deprotections were performed with 20% piperidine in DMF (2×8 min), and monitored by UV at 304 nm with a feedback loop to ensure complete Fmoc removal. Couplings were performed with Fmoc-amino acid (3.0-5.0 equiv to resin substitution), HCTU or HATU (2.9-4.9 equiv) as coupling reagents and DIPEA or NMM (6-10 equiv) in DMF at room temperature or at 50° C. After pre-activating for 3 min, the solution was transferred and allowed to react with the peptide on-resin for either 30 min or 2 h depending on the amino acid. In some cases, double couplings were required. After coupling, the resin was treated with 20% acetic anhydride in DMF for capping any unreacted free amine. LiCl washes were performed where required. The allylester deprotection was performed using phenylsilane (24 equiv) and Palladium(0) tetrakis (triphenylphosphine) (0.5 equiv) in anhydrous dichloromethane.

The synthesis of the peptide segments by SPPS was monitored by microcleavage and analysis of the corresponding resin. The peptides were cleaved from the resin using a mixture of 95:2.5:2.5 TFA:DODT:H$_2$O (α-ketoacid segments synthesized on α-ketoacid resins) or 95:2.5:2.5 TFA:TIPS:H$_2$O (peptide synthesized on 2-cholorotrityl polystyrene resin) for 2 h. The resin was filtered off and the filtrate was evaporated and treated with cold diethyl ether, triturated and centrifuged. Ether layer was carefully decanted and the residue was resuspended in diethyl ether, triturated and centrifuged. Ether washings were repeated twice.

1.1 Synthesis of Composition D Variant of IL-2

Synthesis of IL-2 (I-39)-Leu-α-Ketoacid

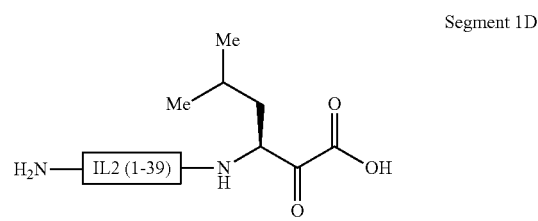

Segment 1D

IL2 (1-39)-Leu-α-ketoacid (See SEQ ID NO: 3) was synthesized on Rink-amide resin pre-loaded with protected Fmoc-α-Leu-ketoacid with a substitution capacity of 0.25 mmol/g. To do so, Fmoc-Rink Amide MBHA resin (4 g) was pre-swelled in DMF for 15 min and Fmoc-deprotection was performed. Fmoc-Leucine-protected-α-ketoacid (795 mg, 1 mmol, 1.00 equiv.) was dissolved in 40 mL DMF and pre-activated with HATU (361 mg, 0.95 mmol, 0.95 equiv.) and DIPEA (348 μL, 2 mmol, 2.00 equiv.). The coupling was allowed to proceed for 6 h at room temperature. Then, the resin was capped followed by Fmoc-deprotection. The synthesis of the segment was performed on 0.250 mmol scale up to Ala1 by automated Fmoc SPPS using the procedure described in the general methods section. The progress of the peptide synthesis was monitored by performing a microcleavage and analysis using a mixture of (95:2.5:2.5) TFA:DODT:H$_2$O for 1.5 h. HPLC analysis were performed on a C18 column at 60° C. The peptide was cleaved from the resin using a mixture of 95:2.5:2.5 TFA:DODT:H$_2$O (15 mL/g resin) for 2 h, following the procedure described in the general methods. Purification of crude IL2 (1-39) was performed by preparative HPLC using Shiseido capcell pak C18 column (50×250 mm) with a gradient of 30 to 80% CH$_3$CN with 0.1% TFA in 30 min. The pure product fractions were pooled and lyophilized to obtain 650 mg of the pure IL2 (1-39) 1-39)-Leu-α-ketoacid (69% yield for peptide synthesis, resin cleavage and purification steps). Analytical HPLC and ESI-HRMS were used to confirm the purity and exact mass of the product, m/z calculated for C$_{204}$H$_{346}$N$_{56}$O$_{61}$ [M]: 4556.5694; measured: 4556.5783.

Synthesis of Opr-IL2 (42-69) Photoprotected-Leu-α-Ketoacid of Composition D

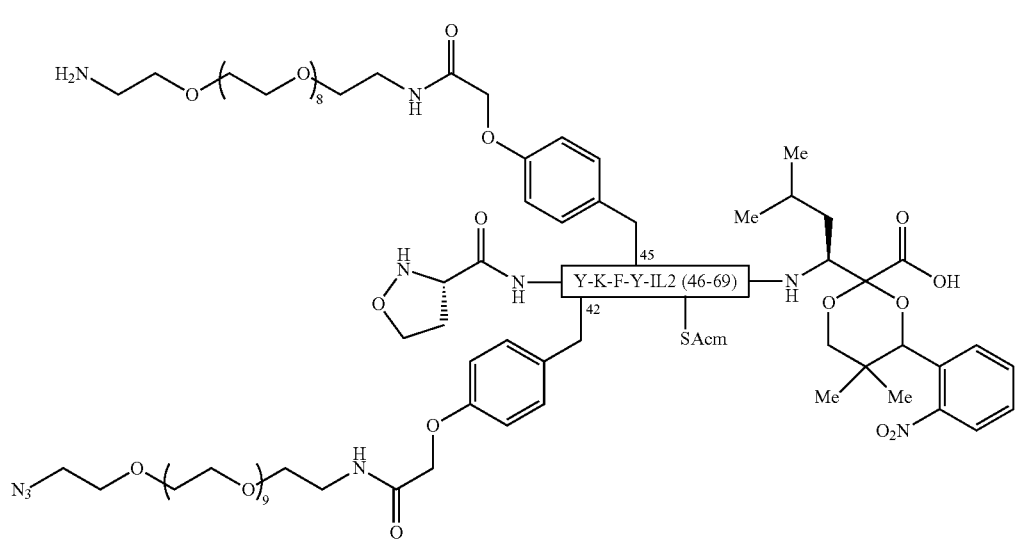

Segment 2D

Opr-IL2 (42-69) (See SEQ ID NO: 3) photoprotected-Leu-α-ketoacid segment was prepared on Rink Amide MBHA resin preloaded with Fmoc-Leucine-photoprotected-α-ketoacid with a substitution capacity of 0.25 mmol/g. To do so, 4 g of Fmoc-Rink Amide MBHA resin were swelled with DMF for 15 min and Fmoc-deprotection was performed. Fmoc-Leucine-photoprotected-α-ketoacid (795 mg, 1 mmol, 1.00 equiv.) was dissolved in 40 mL DMF and preactivated with HATU (361 mg, 0.95 mmol, 0.95 equiv.) and DIPEA (348 µL, 2 mmol, 2.00 equiv.). The reaction was stirred for 6 h at room temperature. Then, the resin was capped, followed by Fmoc-deprotection. The synthesis of the segment was performed up to Nle46 on 0.151 mmol scale by automated Fmoc SPPS using the procedure described in the general methods section. Cys (Acm)-OH (10 equiv relative to the resin) was used for the coupling of Cys58 by symmetric anhydride method using DIC (5 equiv relative to resin) for 2 h at rt. The preformed amino acid Fmoc-Tyr(Ac0.5 kDaPEG)-OH (3 equiv) was coupled in position 45 by single coupling using HATU (2.9 equiv) and DIPEA (6 equiv). Phe44 and Lys43 were coupled by automated SPPS, followed by the manual coupling of Fmoc Tyr-allylacetate (Structure 5) and Boc-5-(S)-Oxaproline in positions 42 and 41, respectively. The allyl ester deprotection was performed following established standard conditions using phenylsilane (449 µL, 3.6 mmol, 24 equiv) and Pd(Ph$_3$)$_4$ (87 mg, 0.075 mmol, 0.5 equiv) for 30 min at rt. After deprotection, O-(2-Aminoethyl)-O'-(2-azidoethyl) nonaethylene glycol (Structure 7) (237 mg, 0,450 mmol, 3 equiv) was coupled at 50° C. for 1.5 h. The progress of the peptide synthesis was monitored by performing a microcleavage and analysis using a mixture of (95:2.5:2.5) TFA:DODT:H$_2$O for 1.5 h. HPLC analysis were performed on a C18 column at 60° C. The peptide was cleaved from the resin using a mixture of 95:2.5:2.5 TFA:DODT:H$_2$O (15 mL/g resin) for 2 h, following the procedure described in the general methods. The cold ether:pentane mixture (1:1) was used to treat and wash the crude peptide. Purification of crude IL2 (42-69) was performed by preparative HPLC using Shiseido capcell pak C18 column (50×250 mm) with a two step gradient: firstly, 10 to 30% CH$_3$CN in MQ-H$_2$O with 0.1% TFA in 5 min, then 30 to 60% CH$_3$CN in MQ-H$_2$O with 0.1% TFA in 30 min. The pure product fractions were pooled and lyophilized to obtain 117.4 mg of the pure IL2 (42-69) (16% yield for peptide synthesis, resin cleavage and purification steps). Analytical HPLC and ESI-HRMS were used to confirm the purity and exact mass of the product, m/z calculated for C$_{230}$H$_{376}$N$_{46}$O$_{74}$S [M]: 4998.6794; measured 4998.6749.

Synthesis of Fmoc-Opr IL2 (72-102)-Phe-α-Ketoacid of Composition D

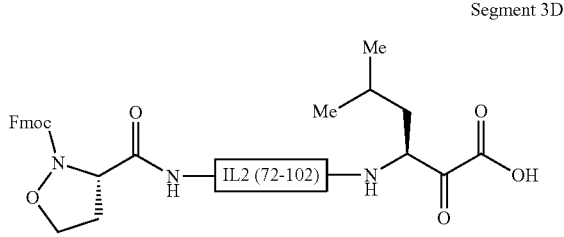

Segment 3D

Fmoc-Opr IL2 (72-102)-Phenylalanine-α-ketoacid was synthesized on Rink Amide ChemMatrix resin pre-loaded with Fmoc-Phe-protected-α-ketoacid with a substitution capacity of ~0.25 mmol/g. The synthesis was performed on 0.588 mmol scale by automated Fmoc SPPS up to Ala73 using HCTU as the coupling reagent. Coupling of residue 72, Fmoc-Leu was done with HATU as the coupling reagent. The coupling was repeated additional two times at 45° C. to ensure complete coupling. Fmoc-5-oxaproline (3.00 equiv to resin) was manually coupled to the free amine using HATU (2.95 equiv to resin) and NMM (6.00 equiv to resin) for 2 h at rt. The progress of the peptide synthesis was monitored by performing a microcleavage and analysis using a mixture of (95:2.5:2.5) TFA:DODT:H$_2$O for 2 h. HPLC analysis were performed on a C18 column at 60° C. The peptide was cleaved from resin using a mixture of 95:2.5:2.5 TFA:DODT:H$_2$O (15 mL/g resin) for 2.0 h. Purification of crude segment was performed by preparative HPLC using Shiseido Capcell Pak C18 column (50×250 mm) preheated at 60° C., with a gradient of 20 to 75% CH$_3$CN with 0.1% TFA in 30 min. The pure product fractions were pooled and lyophilized to obtain Fmoc-Opr IL2 (72-102)-Phe-α-ketoacid in >98% purity (147.9 mg, 6% yield for synthesis, cleavage and purification steps). Analytical HPLC and ESI-HRMS were used to confirm the purity and exact mass of the product, m/z calculated for C$_{184}$H$_{285}$N$_{47}$O$_{53}$ [M]: 4001.1051; measured 4001.1227.

Synthesis of Opr-IL2 (105-133)

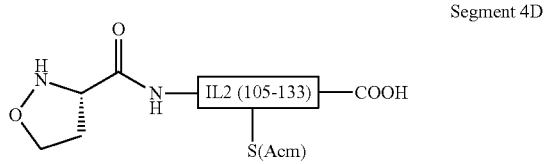

Segment 4D analysis were performed on a C18 column at 60° C. The peptide was cleaved from resin using a mixture of 95:2.5:2.5 TFA:TIPS:H$_2$O (15 mL/g resin) for 2.0 h. Purification of crude Opr-IL2(105-133) was performed by preparative HPLC using Shiseido Capcell Pak C4 column (50×250 mm) preheated at 60° C., with a gradient of 10 to 65% CH$_3$CN with 0.1% TFA in 10 min, then 65 to 95% CH$_3$CN with 0.1% TFA in 20 min. The pure product fractions were pooled and lyophilized to obtain Opr-IL2(105-133) in >98% purity (108.5 mg, 9% yield for synthesis, cleavage and purification steps). Analytical HPLC and ESI-HRMS were used to confirm the purity and exact mass of the product, m/z calculated for C$_{158}$H$_{242}$N$_{37}$O$_{52}$S [M+H]: 3521.7145; found 3521.7140.

Synthesis of IL2-Seg12 of Composition D by KAHA Ligation

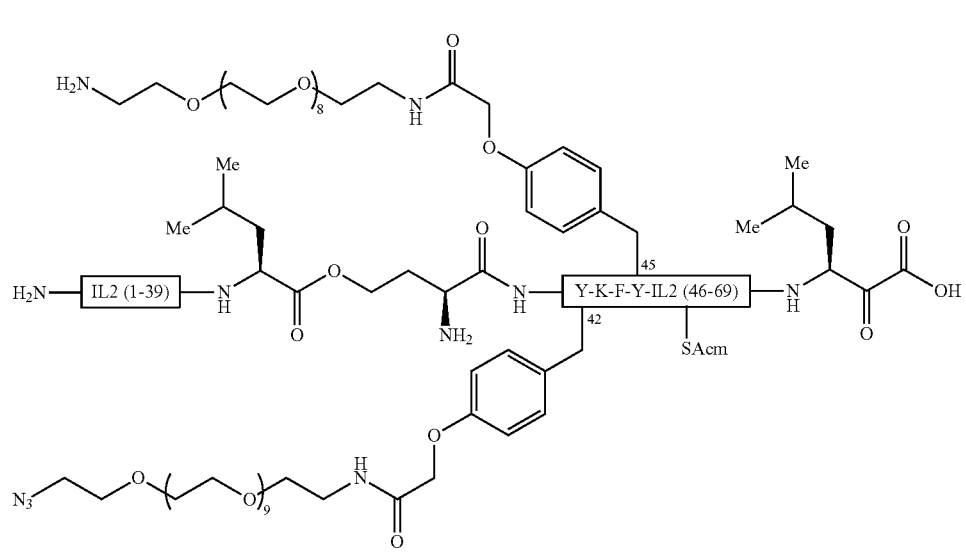

Segment 12D

Opr-IL2 (105-133) was synthesized on 2-Chlorotrityl-resin pre-loaded with Fmoc-Thr-OH with a substitution capacity of 0.25 mmol/g. After capping (diisopropylethylamine, methanol), the synthesis was performed on 0.34 mmol scale (1.5 g of resin) by automated Fmoc SPPS up to Glu106. Cys (Acm)-OH (10 equiv relative to the resin) was used for the coupling of Cys105 by symmetric anhydride method using DIC (5 equiv relative to resin) for 2 h at rt. Then, Boc-5-oxaproline (2.00 equiv to resin) was coupled to the free amine on-resin using HATU (1.95 equiv) and NMM (4 equiv). The progress of the peptide synthesis was monitored by performing a microcleavage and analysis using a mixture of (95:2.5:2.5) TFA:TIPS:H$_2$O for 1.5 h. HPLC KAHA ligation: Seg1 (44 mg, 9.6 µmol, 1.2 equiv) and Seg2 (40 mg, 8.0 µmol, 1 equiv) were dissolved in DMSO:H$_2$O (9:1) containing 0.1 M oxalic acid (400 µL, 20 mM) and allowed to react at 60° C. for 20 h. The ligation vial was protected from light by wrapping it in aluminum foil. The progress of the KAHA ligation was monitored by uHPLC using a Phenomenex C18 column (150×4.6 mm) at 60° C. with CH$_3$CN/H$_2$O containing 0.1% TFA as mobile phase, with a gradient of 5 to 95% CH$_3$CN in 7 min.

Photo-deprotection and purification: After completion of the ligation the mixture was diluted ~20 times (8 mL) with CH$_3$CN/H$_2$O (1:1) containing 0.1% TFA and irradiated at a wavelength of 365 nm for 1 h. The completion of photolysis reaction was confirmed by injecting a sample on uHPLC using previously described method. The photo-deprotected sample was purified by preparative HPLC using a Shiseido Capcell Pack UG80 C18 column (50×250 mm) kept at 60° C., with a 2-step gradient: double gradient of CH$_3$CN in water with 0.1% TFA: 10 to 35% in 5 min, then 35 to 65% in 35 min, with a flow of 40 mL/min with CH$_3$CN and MQ-H$_2$O containing 0.1% TFA as the eluents. The fractions containing the product were pooled and lyophilized to give pure Seg12 (25.4 mg, 40% yield for ligation and purification steps), m/z calculated for C$_{422}$H$_{709}$N$_{101}$O$_{130}$S [M]: 9304.1694; measured 9304.1639.

KAHA Ligation for the Preparation of IL2-Seg34 of Composition D by KAHA Ligation DMSO/H$_2$O (9:1) containing 0.1 M oxalic acid (423 µL. 15 mM) and the ligation was allowed to proceed for 24 h at 60° C. The progress of the KAHA ligation was monitored by analytical HPLC using a Shiseido Capcell Pak UG80 C18 column (250×4.6 mm) at 60° C. and CH$_3$CN/H$_2$O containing 0.1% TFA as mobile phase, with a gradient of 30 to 95% CH$_3$CN in 14 min.

Purification: After completion of ligation, the reaction mixture was diluted with 150 µL DMSO followed by further dilution with a mixture of (1:1) CH$_3$CN:H$_2$O containing 0.1% TFA (7 mL). The sample was purified by injecting on

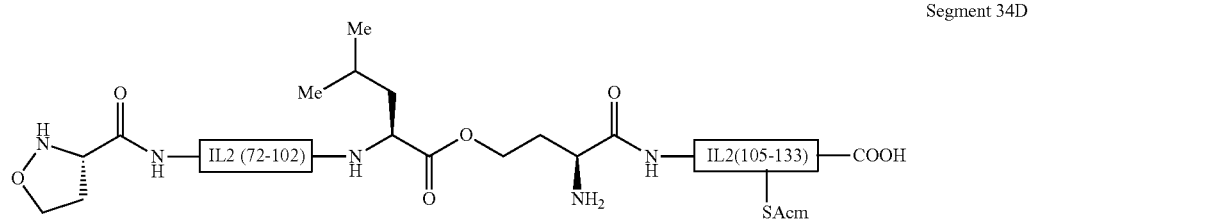

Segment 34D

Ligation: Seg3 (136 mg, 34 µmol, 1.2 equiv) and Seg4 (100 mg, 28.40 µmol, 1 equiv) were dissolved in DMSO/H$_2$O (9:1) containing 0.1 M oxalic acid (1.8 mL, 15 mM) and allowed to react for 16 h at 60° C. The progress of the KAHA ligation was monitored by uHPLC using a Phenomenex C18 column (150×4.56 mm) at 60° C. using CH$_3$CN/H$_2$O containing 0.1% TFA as mobile phase, with a gradient of 30 to 70% CH$_3$CN in 7 min.

Fmoc deprotection and purification: After completion of ligation, the reaction mixture was diluted with DMSO (6 mL), 5% of diethylamine (300 µL) was added and the reaction mixture was shaken for 7 min at room temperature. To prepare the sample for purification, it was diluted with DMSO (4 mL) containing TFA (300 µL).

The sample was purified by preparative HPLC on a Shiseido Capcell Pack UG80 C18 column (50×250 mm) kept at 60° C., using a gradient of 30 to 70% CH$_3$CN in water with 0.1% TFA in 35 min, with a flow of 40 mL/min. The fractions containing the product were pooled and lyophilized to give pure BPT-143-Seg34 (43.4 mg after ligation and purification, 21% yield). Analytical HPLC and ESI-HRMS were used to confirm the purity and exact mass of the product, m/z calculated for C$_{326}$H$_{516}$N$_{84}$O$_{101}$S [M]: 7255.7545; measured: 7255.7653.

Final KAHA Ligation for the Preparation of IL2 Linear Protein Composition D by KAHA Ligation Ligation: Seg12 (59.2 mg, 6.35 µmol, 1.2 equiv) and Seg34 (38.5 mg, 5.3 µmol, 1 equiv) were dissolved in a preparative HPLC using a Shiseido Capcell Pack UG80 C18 column (50×250 mm) preheated at 60° C., with a 2-step gradient: 10 to 40% in 5 min and 40 to 80% in 35 min, flow rate: 40 mL/min with CH$_3$CN and MQ-H$_2$O containing 0.1% TFA as the eluents. The fractions containing the product were pooled and lyophilized to give pure BPT-143 linear protein with Acm (42.3 mg, 48% yield for ligation and purification steps. Analytical HPLC and ESI-HRMS were used to confirm the purity and exact mass of the product, m/z calculated for C$_{747}$H$_{1225}$N$_{185}$O$_{229}$S$_2$ [M]: 16515.9340; measured 16515.9008.

Acm deprotection: The peptide IL2 linear protein with Acm (35.4 mg, 2.14 µmol) was dissolved in AcOH/H$_2$O (1:1) (8.6 mL, 0.25 mM) and 86 mg AgOAc (1% m/v) were added to the solution. The mixture was shaken for 2.5 h at 50° C. protected from light. After completion of reaction as ascertained by HPLC, the sample was diluted with CH$_3$CN:H$_2$O (1:1) containing 0.1% TFA, and purified by preparative HPLC using a Shiseido CapCell Pak UG80 C18 column (20×250 mm) kept at 60° C. A 2-step gradient was used for purification: 10 to 40% in 5 min and 40 to 95% in 30 min, flow rate: 10 mL/min, with CH$_3$CN and MQ-H$_2$O containing 0.1% TFA as the eluents. The fractions containing the product were pooled and lyophilized to give pure IL2 linear protein (26.1 mg, 74% yield for deprotection and purification steps), m/z calculated for C$_{741}$H$_{1215}$N$_{183}$O$_{227}$S$_2$ [M]: 16373.8597; measured: 16373.8253.

Synthesis of Folded IL-2 Composition D
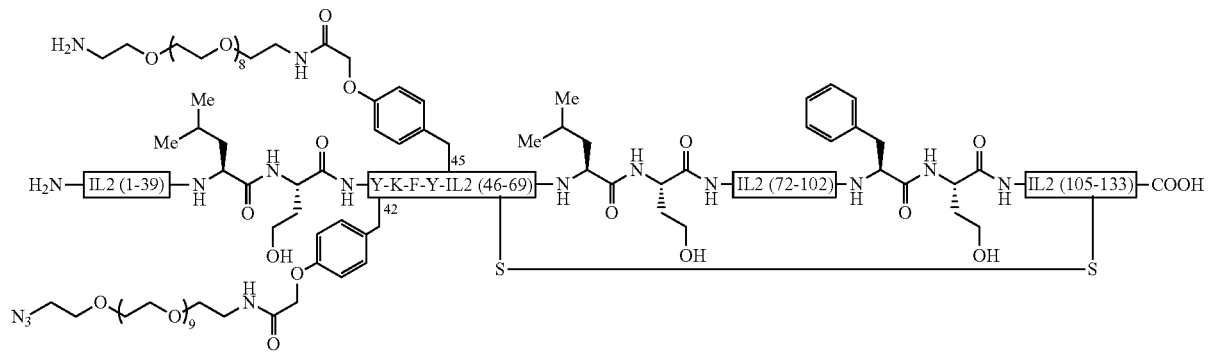
Composition D Precursor

Rearrangement of linear protein: the linear protein (20 mg, 1.221 μmol) was dissolved in aqueous 6M Gu.HCl containing 0.1 M Tris and 30 mM reduced glutathione (81 mL, 15 μM protein concentration), which was adjusted to pH 8.0 by solution of 6M aq. HCl. The mixture was gently shaken at 50° C. for 2 h and monitored by analytical reverse phase HPLC using a bioZen™ 3.6 μm Intact C4 column (150×4.6 mm) at 25° C., with a gradient of 30 to 95% $CH_3CN$ in MQ-$H_2O$ with 0.1% TFA in 18 min, flow rate: 1.0 mL/min.

Folding of the linear rearranged protein: the previous solution was cooled to room temperature and 3-fold diluted with a second buffer solution (240 mL) containing 0.1 M Tris and 1.5 mM oxidized glutathione at pH 8.0. the mixture was stored at room temperature and monitored by analytical HPLC using a bioZen™ 3.6 μm Intact C4 column (150×4.6 mm) at 25° C., with a gradient of 30 to 95% acetonitrile with 0.1% TFA in 18 min, flow rate: 1.0 mL/min. After 20 h, the folding solution was acidified with 10% aqueous TFA to pH 3 and purified on preparative HPLC, using a Shiseido Proteonavi C4 column (20×250 mm) with a two-step gradient of 5 to 40 to 95% acetonitrile with 0.1% TFA in 60 min, flow rate: 10.0 mL/min. The fractions containing the folded IL2 protein were pooled together and lyophilized. The Purity and identity of the pure folded protein (3.5 mg, 18% yield) was further confirmed by analytical RP-HPLC and high-resolution ESI mass spectrometry, m/z calculated for $C_{741}H_{1213}N_{183}O_{227}S_2$ [M]: 16371.8441; measured: 16371.8107.

PEGylation of Modification of the Folded Composition D Variant of IL2

The folded protein IL2 (3.5 mg) was further modified by reaction with a 30 kDa DBCO-polyethylene glycol polymer. The folded protein IL2 was dissolved in a $CH_3CN$:$H_2O$ solution (1:1) (50 μM protein concentration) and DBCO-$PEG_{30k}$ (20.1 mg, 3 equiv) were added. The reaction was gently mixed at 25° C. for 20 h, monitoring the progress using analytical HPLC with a bioZen™ 3.6 μm Intact C4 column (150×4.6 mm) at 25° C., using a gradient of 30 to 95% acetonitrile in water with 0.1% TFA in 18 min, flow rate: 1.0 mL/min. after 20 h, the reaction mixture was diluted with (1:1) $CH_3CN/H_2O$+0.1% TFA and purify on preparative HPLC, using a Shiseido Proteonavi C4 column (20×250 mm) with a two-step gradient of 5 to 40 to 95% acetonitrile with 0.1% TFA in 60 min, flow rate: 10.0 mL/min. The fractions containing the pegylated IL2 protein were pooled together and lyophilized overnight to obtain 5.2 mg of the pegylated IL2 protein (53% yield for pegylation and purification steps). The purity and identity of the pure folded protein was further confirmed by analytical RP-HPLC and MALDI-TOF. The final protein was further characterized by SEC-HPLC and CD. Purified Composition D was observed to elute from the RP-HPLC as a single peak with a retention time of about 8 min. See FIG. 12A, which shows absorbance on the Y-axis versus retention time of Composition D or unPEGylated precursor on the X-axis. Purified Composition D was also observed to have a molecular weight of approximately 47600 Da by MALDI-TOF. See FIG. 12B, which shows total ion count on the Y-axis versus molecular weight on the X-axis for purified PEGylated Composition D. The modified IL-2 polypeptide was also analyzed by circular dichroism. The resulting CD spectra shows the characteristic peaks of a well-folded interleukin-2 protein, which is indicative of Composition D being folded in a similar manner to wild-type IL-2. See FIG. 12C, which shows wavelength of polarized light (x-axis) versus absorbance (y-axis) of Composition A.

1.2 Synthesis of Composition a Variant of IL-2

For this variant, except segment 2, all the other segments are the same as the ones used for Composition Synthesis of Opr-IL2 (42-69) photoprotected-Leu-α-ketoacid of Composition A Segment 2A

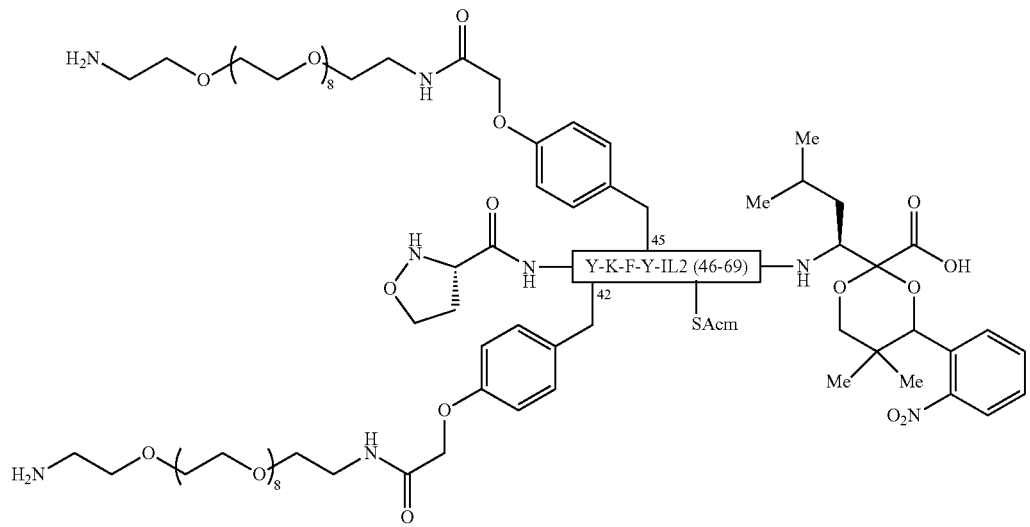

Opr-IL2 (42-69) photoprotected-Leu-α-ketoacid segment (See SEQ ID NO: 3) with modifications at position 42 and 45 was prepared on Rink Amide MBHA resin pre-loaded with Fmoc-Leucine-photoprotected-α-ketoacid with a substitution capacity of 0.25 mmol/g, following the procedure described in the corresponding step for the synthesis of Composition D. The synthesis of the segment was performed up to Nle46 on 0.129 mmol scale by automated Fmoc SPPS using the procedure described in the general methods section.

Modified Fmoc-Tyrosine derivative bearing an O-allyl ester functionality (Structure 5) (3 equiv) was coupled in positions 45 and 42 by single coupling using HATU (2.9 equiv) and DIPEA (6 equiv). Phe44 and Lys43 were coupled by automated SPPS, followed by the manual coupling of Boc-5-(S)-Oxaproline in position 41. The allyl ester deprotection was performed following established standard conditions described in the corresponding step for the synthesis of Composition D. After deprotection, O-(2-Aminoethyl)-O'-[2-(Boc-amino)ethyl]octaethylene glycol (Structure 6) (359 mg, 0.645 mmol, 5 equiv) was coupled at 50° C. for 1.5 h. The progress of the peptide synthesis was monitored by performing a microcleavage and analysis using a mixture of (95:2.5:2.5) TFA:DODT:H$_2$O for 1.5 h. HPLC analysis were performed on a C18 column at 60° C.

The peptide was cleaved from the resin using a mixture of 95:2.5:2.5 TFA:DODT:H$_2$O (15 mL/g resin) for 2 h, following the procedure described in the general methods. Purification of crude IL2 (42-69) was performed by preparative HPLC using Shiseido capcell pak C18 column (50×250 mm) with a gradient of 30% to 65% CH$_3$CN in MQ-H$_2$O with 0.1% TFA in 30 min. The pure product fractions were pooled and lyophilized to obtain 100.7 mg of the pure IL2 (42-69) (16% yield for peptide synthesis, resin cleavage and purification steps). Analytical HPLC and ESI-HRMS were used to confirm the purity and exact mass of the product, m/z calculated for C$_{228}$H$_{374}$N$_{44}$O$_{73}$S [M]: 4928.6627; measured 4928.6781.

Synthesis of IL2-Seg12 of Composition A by KAHA Ligation

Segment 12A

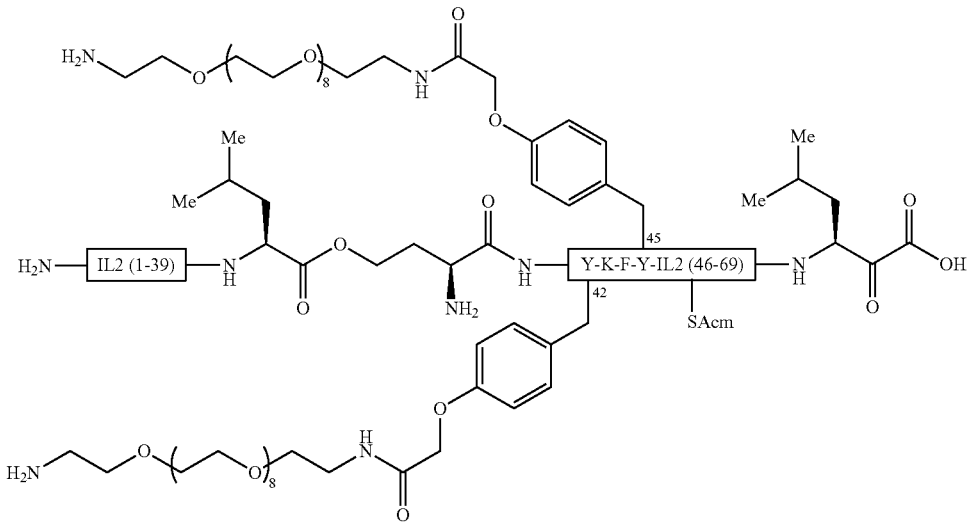

KAHA ligation: Seg1 (64.4 mg, 14.1 μmol, 1.2 equiv) and Seg2 with modified tyrosine at 42 and 45 (58.0 mg, 11.8 μmol, 1 equiv) were dissolved in DMSO:$H_2O$ (9:1) containing 0.1 M oxalic acid (587 μL, 20 mM) and allowed to react at 60° C. for 20 h. The ligation vial was protected from light by wrapping it in aluminum foil. The progress of the KAHA ligation was monitored by uHPLC using a Phenomenex C18 column (150×4.6 mm) at 60° C. with $CH_3CN/H_2O$ containing 0.1% TFA as mobile phase, with a gradient of 20 to 95% $CH_3CN$ in 7 min.

Photo-deprotection and purification: After completion of the ligation the mixture was diluted ~20 times (8 mL) with $CH_3CN/H_2O$ (1:1) containing 0.1% TFA and irradiated at a wavelength of 365 nm for 1 h. The completion of photolysis reaction was confirmed by injecting a sample on uHPLC using previously described method. The photo-deprotected sample is purified by preparative HPLC using a Shiseido Capcell Pack UG80 C18 column (50×250 mm) kept at 60° C., with a gradient of 30 to 70% $CH_3CN$ in water with 0.1% in 35 min, with a flow of 40 mL/min with $CH_3CN$ and MQ-$H_2O$ containing 0.1% TFA as the eluents. The fractions containing the product were pooled and lyophilized to give pure Seg12 of Composition A (57.4 mg, 53% yield for ligation and purification steps). Analytical HPLC and ESI-HRMS were used to confirm the purity and exact mass of the product, m/z calculated for $C_{420}H_{707}N_{99}O_{129}S$ [M]: 9234.1527; measured 9234.1734.

Final KAHA Ligation for the Preparation of IL2 Variant Composition a Linear Protein

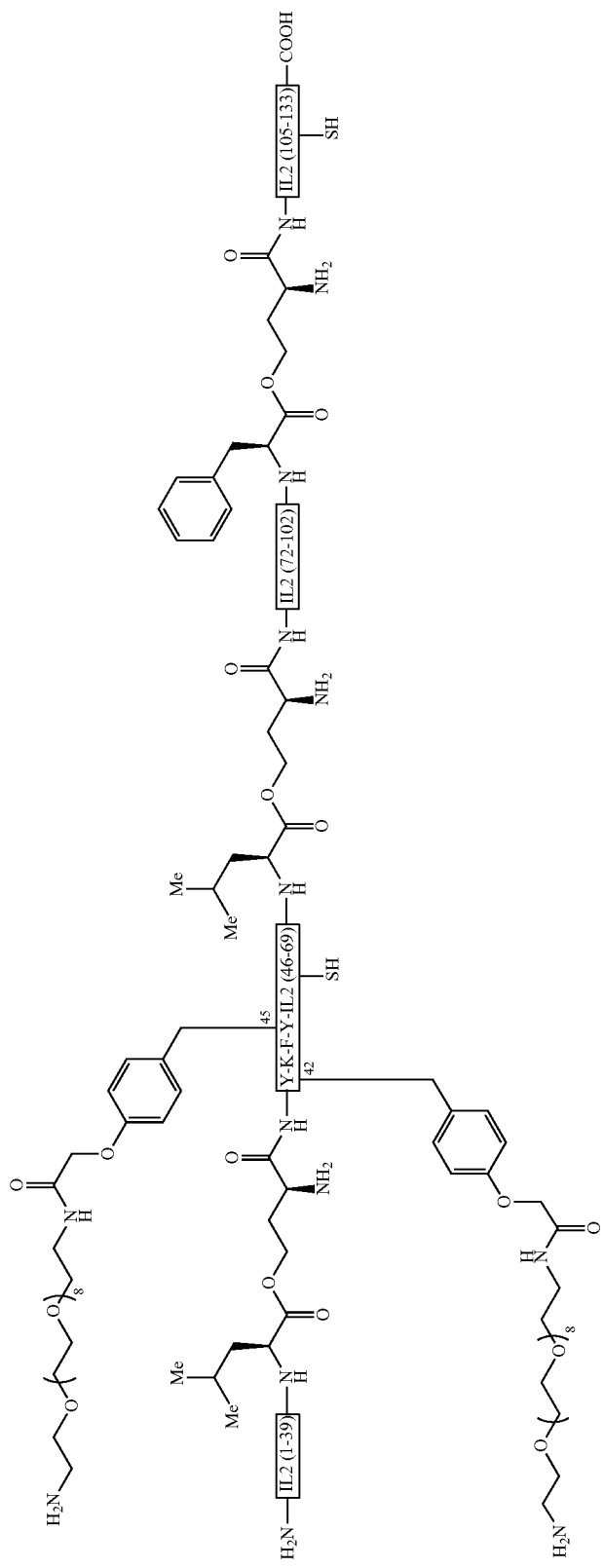

Ligation: Seg12 of Composition A (65.4 mg, 7.08 μmol, 1.2 equiv) and Seg34 (42.8 mg, 5.89 μmol, 1 equiv) were dissolved in DMSO/H$_2$O (9:1) containing 0.1 M oxalic acid (364 μL, 16 mM) and the ligation was allowed to proceed for 24 h at 60° C. The progress of the KAHA ligation was monitored by analytical HPLC using a Shiseido Capcell Pak UG80 C18 column (250×4.6 mm) at 60° C. and CH$_3$CN/H$_2$O containing 0.1% TFA as mobile phase, with a gradient of 30 to 95% CH$_3$CN in 14 min.

Purification: After completion of ligation, the reaction mixture was diluted with 300 μL DMSO followed by further dilution with a mixture of (1:1) CH$_3$CN:H$_2$O containing 0.1% TFA (9 mL). The sample was purified by injecting on a preparative HPLC using a Shiseido Capcell Pack UG80 C18 column (50×250 mm) preheated at 60° C., with a gradient of 30 to 85% CH$_3$CN in MQ-H$_2$O containing 0.1% TFA in 30 min, flow rate: 40 mL/min. The fractions containing the product were pooled and lyophilized to give pure linear protein with Acm (53.6 mg, 55% yield for ligation and purification steps). Analytical HPLC and ESI-HRMS were used to confirm the purity and exact mass of the product, m/z calculated for $C_{745}H_{1223}N_{183}O_{228}S_2$ [M]: 16454.9418; measured 16454.9604.

Acm deprotection: IL2 linear protein of Composition A with Acm (53.6 mg, 3.30 μmol) was dissolved in AcOH/H$_2$O (1:1) (13 mL, 0.25 mM) and 130 mg AgOAc (1% m/v) was added to the solution. The mixture was shaken for 2.5 h at 50° C. protected from light. After completion of reaction as ascertained by HPLC, the sample was diluted with CH$_3$CN: H$_2$O (1:1) containing 0.1% TFA, and purified by preparative HPLC using a Shiseido CapCell Pak UG80 C18 column (20×250 mm) kept at 60° C. A 2-step gradient was used for purification: 10 to 30% in 5 min and 30 to 85% in 20 min, flow rate: 10 mL/min, with CH$_3$CN and MQ-H$_2$O containing 0.1% TFA as the eluents. The fractions containing the product were pooled and lyophilized to give pure IL2 linear protein (22.8 mg, 52% yield for deprotection and purification steps). Analytical HPLC and ESI-HRMS were used to confirm the purity and exact mass of the product, m/z calculated for $C_{739}H_{1213}N_{181}O_{226}S_2$ [M+1]: 16312.8676; measured 16312.6032.

Preparation of Folded IL2-Variant Composition A

Rearrangement of linear protein: the linear protein (22.8 mg, 1.39 μmol) was dissolved in aqueous 6M Gnd.HCl containing 0.1 M Tris and 30 mM reduced glutathione (93.2 mL, 15 μM protein concentration), which was adjusted to pH 8.0 by solution of 6M aq. HCl. The mixture was gently shaken at 50° C. for 3 h and monitored by analytical reverse phase HPLC using a ProteonAvi C4 column (250×4.6 mm) at 25° C., with a gradient of 30 to 95% CH$_3$CN in MQ-H$_2$O with 0.1% TFA in 18 min, flow rate: 1.0 mL/min.

Figure 13:
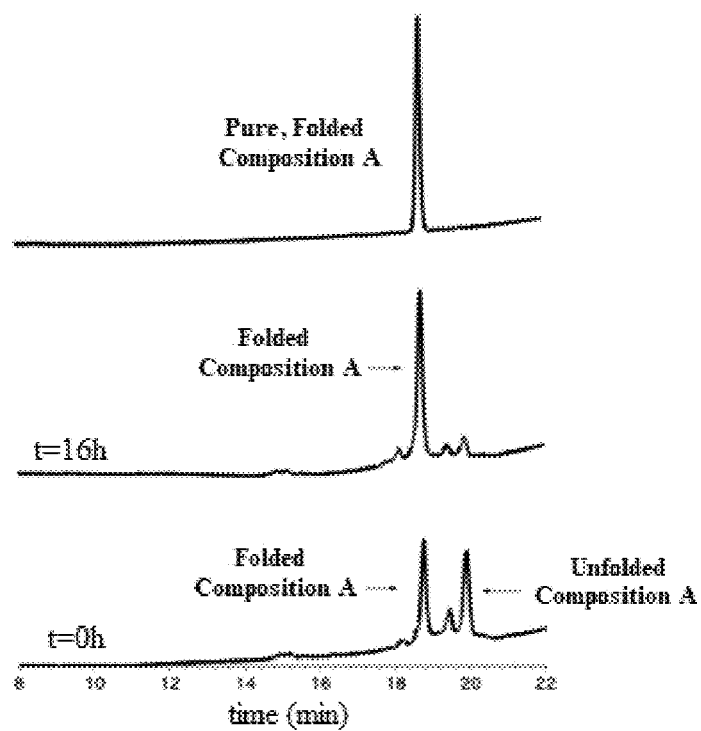
FIG. 13 shows an HPLC trace of purified, PEGylated Composition A, wherein the x-axis is retention time and the y-axis is absorbance.

Folding of the linear rearranged protein: the folding solution from above was cooled to room temperature and diluted 3-fold with a second buffer solution (186.4 mL) containing 0.1 M Tris and 1.5 mM oxidized glutathione at pH 8.0. the mixture was stored at room temperature and monitored by analytical HPLC using a ProteonAvi C4 column (250×4.6 mm) at 25° C., with a gradient of 30 to 95% acetonitrile with 0.1% TFA in 18 min, flow rate: 1.0 mL/min. After 20 h, the folding solution was acidified with 10% aqueous TFA to ~pH 3 and purified on preparative HPLC, using a Shiseido ProteonAvi C4 column (20×250 mm) with a two-step gradient of 5 to 40 to 95% acetonitrile with 0.1% TFA in 60 min, flow rate: 10.0 mL/min. The fractions containing the folded IL2 protein were pooled and lyophilized. The Purity and identity of the pure folded protein (5.7 mg, 25% yield) was further confirmed by analytical RP-HPLC and high-resolution ESI mass spectrometry, m/z calculated for $C_{739}H_{1211}N_{181}O_{226}S_2$: 16310.8519; measured 16310.8763. Purified Composition A was observed to elute from the RP-HPLC as a single peak with a retention time of about 19 min. See FIG. 13, which shows absorbance on the Y-axis versus retention time of Composition A or unfolded precursor on the X-axis. Purified Composition A was also observed to have a molecular weight of approximately 16300 Da with a tight molecular weight distribution by ESI-HRMS. See FIG. 2B, which shows total ion count on the Y-axis versus molecular weight on the X-axis for purified, folded Composition A.

1.3 Synthesis of Composition H Variant of IL-2

For this variant, except segment 1, all the other segments are the same as the ones used for Composition A.

Synthesis of IL2(I-39)-Leu-α-Ketoacid of Composition H

Composition A

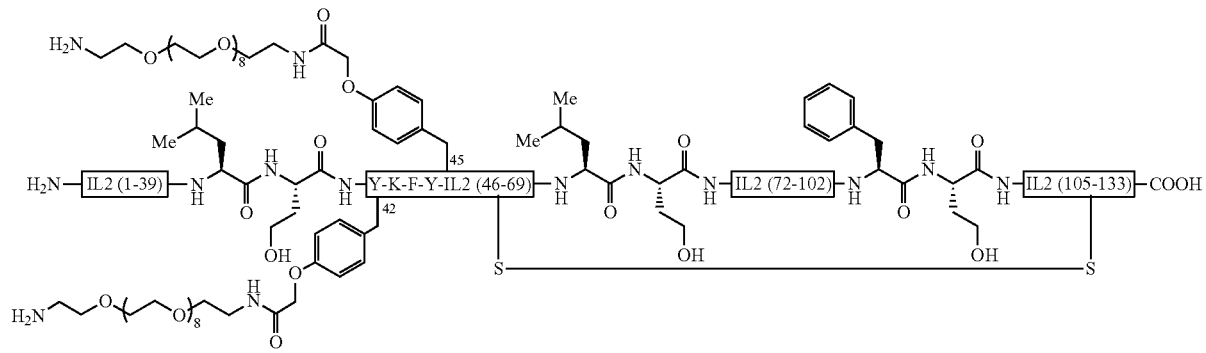

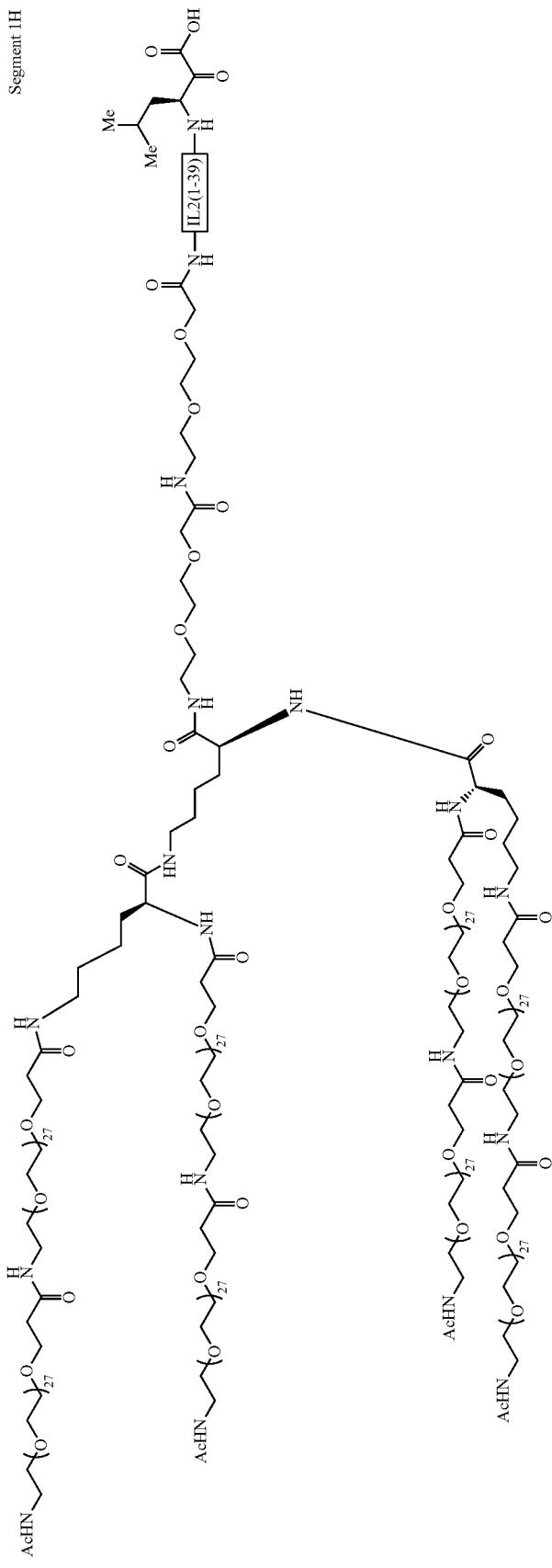

IL2 (1-39)-Leu-α-ketoacid (See SEQ ID NO: 3) was synthesized on Rink-amide resin pre-loaded with protected Fmoc-α-Leu-ketoacid with a substitution capacity of 0.25 mmol/g, following the procedure described in the corresponding step for Composition D. The synthesis of the segment was performed on 0.270 mmol scale up to Ala1 by automated Fmoc SPPS using the procedure described in the general methods section.

The N-terminus was extended by the sequential coupling of 2×Fmoc-amino-3,6 dioxaoctanoic acid, 3×Fmoc-Lys (Fmoc) and 8×Fmoc-NH-(PEG)$_{27}$-COOH. The progress of the couplings were monitored by performing a microcleavage and analysis using a mixture of (95:2.5:2.5) TFA:DODT:H$_2$O for 1.5 h. HPLC analysis were performed on a C18 column at 60° C.

Upon completion of the synthesis, the peptide was cleaved from the resin using a mixture of 95:2.5:2.5 TFA:DODT:H$_2$O (15 mL/g resin) for 2 h, following the procedure described in the general methods. Purification of crude IL2 (1-39) was performed by preparative HPLC using Shiseido capcell pak C18 column (50×250 mm) with a gradient of 20 to 80% CH$_3$CN with 0.1% TFA in 20 min. The pure product fractions were pooled and lyophilized to obtain 369 mg of the pure IL2 (1-39) Leu-α-ketoacid (9% yield for peptide synthesis, resin cleavage and purification steps). Analytical HPLC and ESI-HRMS were used to confirm the purity and exact mass of the product, m/z calculated for C$_{714}$H$_{1348}$N$_{72}$O$_{306}$: 15838.2412; measured 15838.2420.

Synthesis of IL2-Seg12 of Composition H by KAHA Ligation

KAHA ligation: Seg1 of Composition H (55.2 mg, 3.48 μmol, 1.2 equiv) and Seg2 (15.6 mg, 3.17 μmol, 1 equiv) were dissolved in DMSO:H$_2$O (9:1) containing 0.1 M oxalic acid (174 μL, 20 mM) and allowed to react at 60° C. for 20 h. The ligation vial was protected from light by wrapping it in aluminum foil. The progress of the KAHA ligation was monitored by uHPLC using a Phenomenex C18 column (150×4.6 mm) at 60° C. with CH$_3$CN/H$_2$O containing 0.1% TFA as mobile phase, with a gradient of 20 to 95% CH$_3$CN in 7 min.

Photo-deprotection and purification: After completion of the ligation the mixture was diluted ~20 times (8 mL) with CH$_3$CN/H$_2$O (1:1) containing 0.1% TFA and irradiated at a wavelength of 365 nm for 1 h. The completion of photolysis reaction was confirmed by injecting a sample on uHPLC using previously described method. The photo-deprotected sample was purified by preparative HPLC using a Shiseido Capcell Pack UG80 C18 column (50×250 mm) kept at 60° C., with a gradient of 30 to 75% CH$_3$CN in water with 0.1% in 30 min, with a flow of 40 mL/min with CH$_3$CN and MQ-H$_2$O containing 0.1% TFA as the eluents. The fractions containing the product were pooled and lyophilized to give pure Seg12 of Composition H (16.8 mg, 26% yield for ligation and purification steps). Analytical HPLC and ESI-HRMS were used to confirm the purity and exact mass of the product, m/z calculated for C$_{930}$H$_{1709}$N$_{115}$O$_{374}$S: 20518.8328; measured 20518.8115.

Final KAHA Ligation for the Preparation of IL2 Variant Composition H Linear Protein

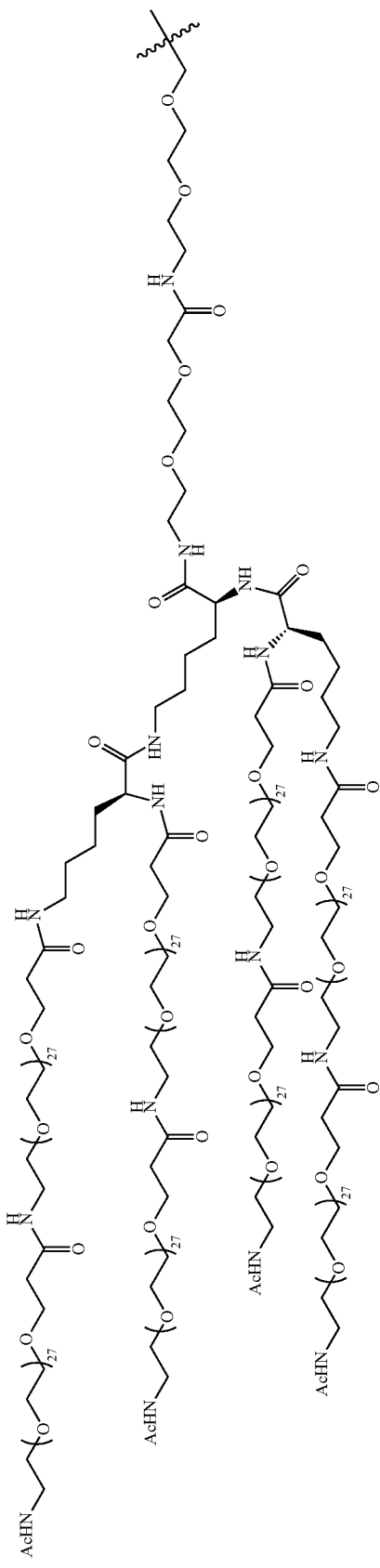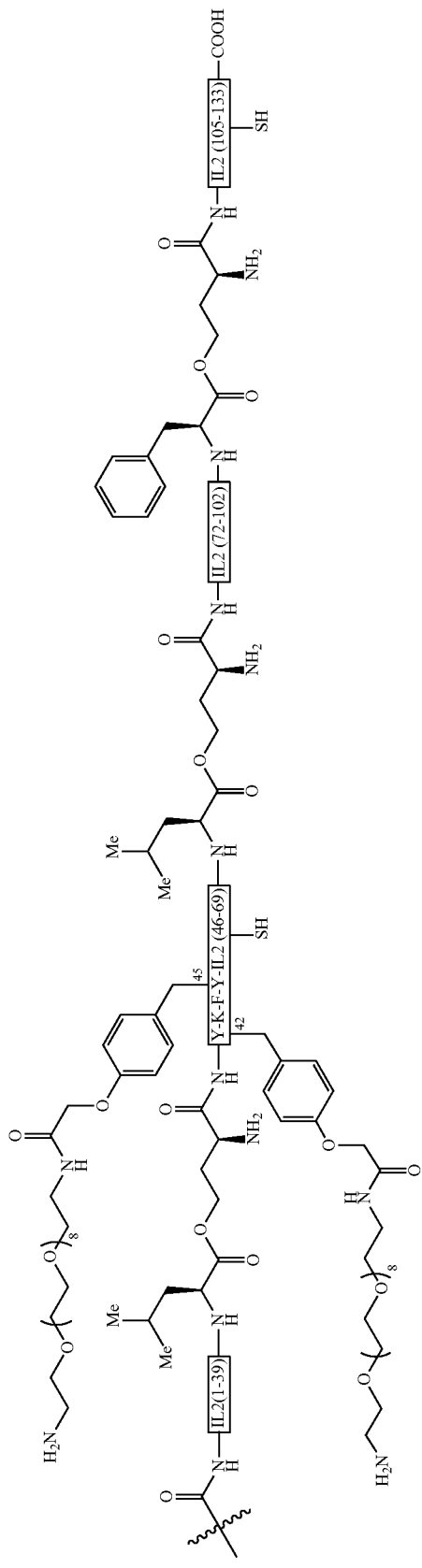

Ligation: Seg12 of Composition H (16.8 mg, 0.82 µmol, 1.2 equiv) and Seg34 (5.4 mg, 0.74 µmol, 1 equiv) were dissolved in DMSO/$H_2O$ (9:1) containing 0.1 M oxalic acid (54.6 µL, 15 mM) and the ligation was allowed to proceed for 24 h at 60° C. The progress of the KAHA ligation was monitored by analytical HPLC using a Shiseido Capcell Pak UG80 C18 column (250×4.6 mm) at 60° C. and $CH_3CN$/$H_2O$ containing 0.1% TFA as mobile phase, with a gradient of 30 to 95% $CH_3CN$ in 14 min.

Acm deprotection and purification: After completion of ligation, the reaction mixture was diluted with 55 µL DMSO followed by further dilution with a mixture of (1:1) AcOH:$H_2O$ (2 mL). 20.5 mg AgOAc (1% w/v) were added to the solution and the mixture was gently shaken for 2.5 h at 50° C. protected from the light. After completion of reaction as ascertained by HPLC, the sample was diluted with $CH_3CN$:$H_2O$ (1:1) containing 0.1% TFA, and purified by preparative HPLC using a Shiseido CapCell Pak UG80 C18 column (20×250 mm) kept at 60° C., with a gradient of 30 to 85% $CH_3CN$ in 28 min, flow rate: 10 mL/min, with $CH_3CN$ and MQ-$H_2O$ containing 0.1% TFA as the eluents. The fractions containing the product were pooled and lyophilized to give pure reduced IL2 linear protein of Composition H (3.5 mg, 17% yield for ligation, Acm deprotection and purification steps). Analytical HPLC and ESI-HRMS were used to confirm the purity and identity of the product, m/z calculated for $C_{1249}H_{2215}N_{197}O_{471}S2$: 27592.5341; measured 27592.2328

Synthesis of Folded Composition H IL-2 Variant

Composition H
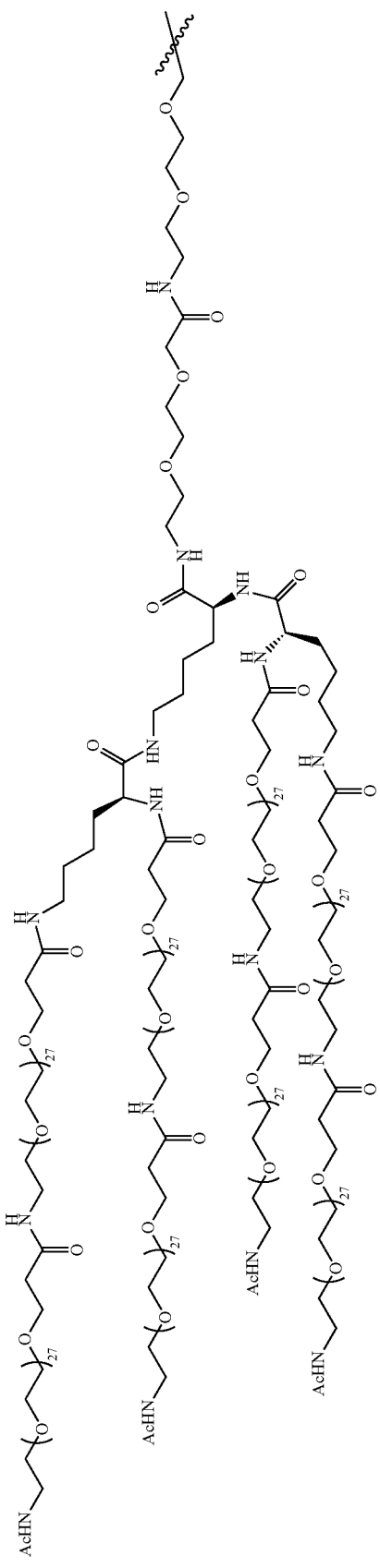
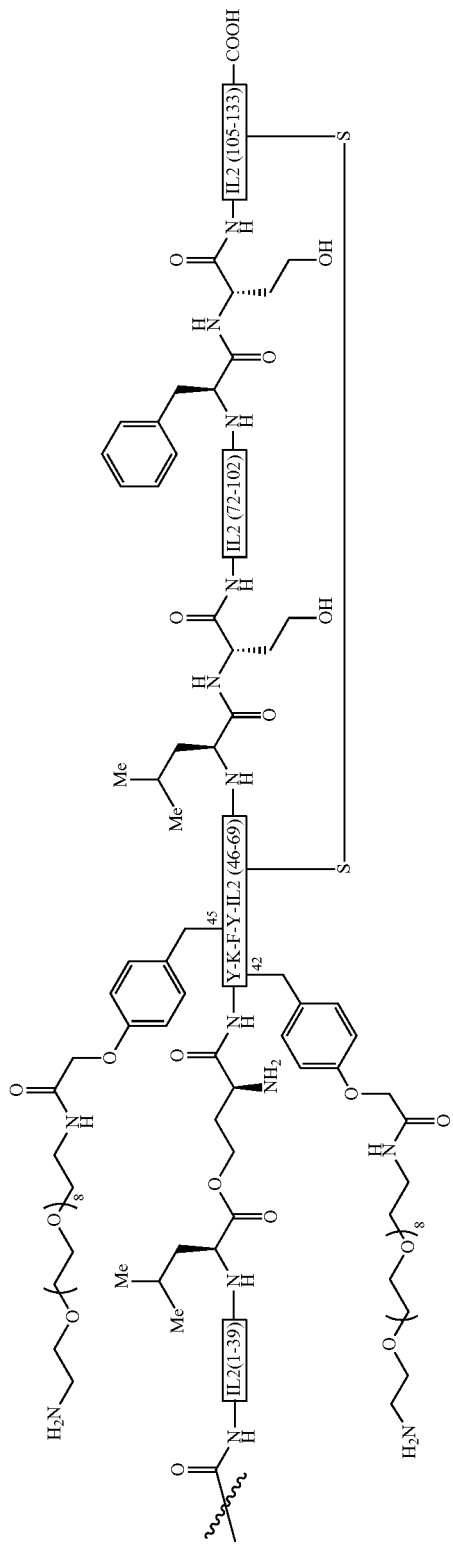

Rearrangement of linear protein: the linear protein (3.5 mg, 0.13 μmol) was dissolved in aqueous 6M Gu.HCl containing 0.1 M Tris and 30 mM reduced glutathione (8.4 mL, 15 μM protein concentration), which was adjusted to pH 8.0 by solution of 6M aq. HCl. The mixture was gently shaken at 50° C. for 2 h and monitored by analytical reverse phase HPLC using a bioZen™ 3.6 μm Intact C4 column (150×4.6 mm) at 25° C., with a gradient of 30 to 95% $CH_3CN$ in MQ-$H_2O$ with 0.1% TFA in 18 min, flow rate: 1.0 mL/min.

Figure 14A:
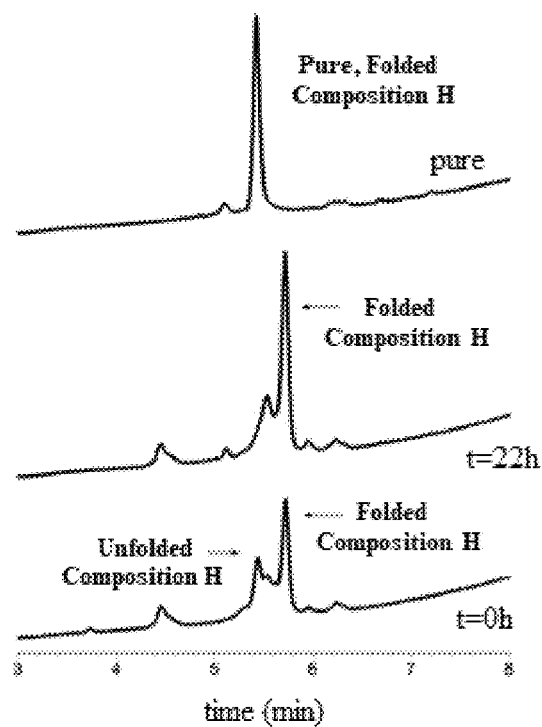
FIG. 14A shows an HPLC trace of folded, purified, PEGylated Composition H, wherein the x-axis is retention time and the y-axis is absorbance.
Figure 14B:
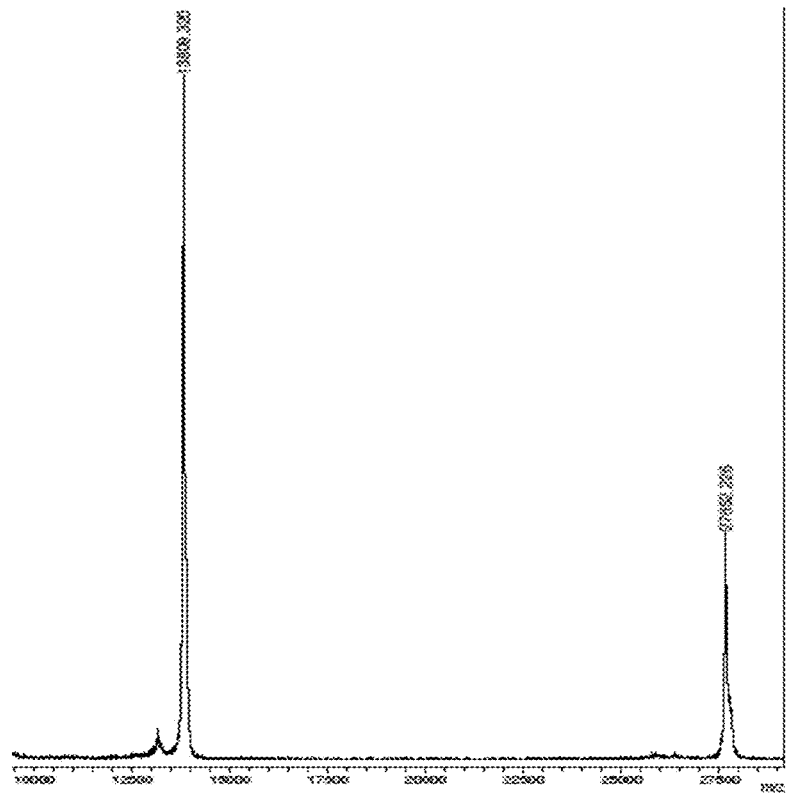
FIG. 14B shows a MALDI-TOF mass spectrum of purified, PEGylated Composition H, wherein the x-axis is mass to charge ratio and the y-axis represents relative abundance.

Folding of the linear rearranged protein: the folding solution from above was cooled to room temperature and diluted 3-fold with a second buffer solution (17 mL) containing 0.1 M Tris and 1.5 mM oxidized glutathione at pH 8.0. The mixture was stored at room temperature and monitored by analytical HPLC using a bioZen™ 3.6 μm Intact C4 column (150×4.6 mm) at 25° C., with a gradient of 30 to 95% acetonitrile with 0.1% TFA in 18 min, flow rate: 1.0 mL/min. After 20 h, the folding solution was acidified with 10% aqueous TFA to pH 3 and purified on preparative HPLC, using a Shiseido ProteonAvi C4 column (20×250 mm) with a two-step gradient of 5 to 40 to 95% acetonitrile with 0.1% TFA in 60 min, flow rate: 10.0 mL/min. The fractions containing the folded IL2 Composition H variant were pooled together and lyophilized. The Purity and identity of the pure folded protein (0.4 mg, 11% yield) was further confirmed by analytical RP-HPLC, MALDI-TOF mass spectrometry and CD spectroscopy among other methods. Purified Composition H was observed to elute from the RP-HPLC as a single peak with a retention time of about 5.5 min. See FIG. 14A, which shows absorbance on the Y-axis versus retention time of Composition H or unfolded precursor on the X-axis. Purified Composition H was also observed to have a molecular weight of approximately 27650 Da with a tight molecular weight distribution by MALDI-TOF. See FIG. 14B, which shows total ion count on the Y-axis versus molecular weight on the X-axis for purified, folded Composition H.

1.4 Synthesis of Composition M Variant of IL-2

For this variant, except segment 2, all the other segments are the same as the ones used for Composition D.

Synthesis of Opr-IL2 (42-69)
Photoprotected-Leu-α-Ketoacid, Segment 2 of Composition M

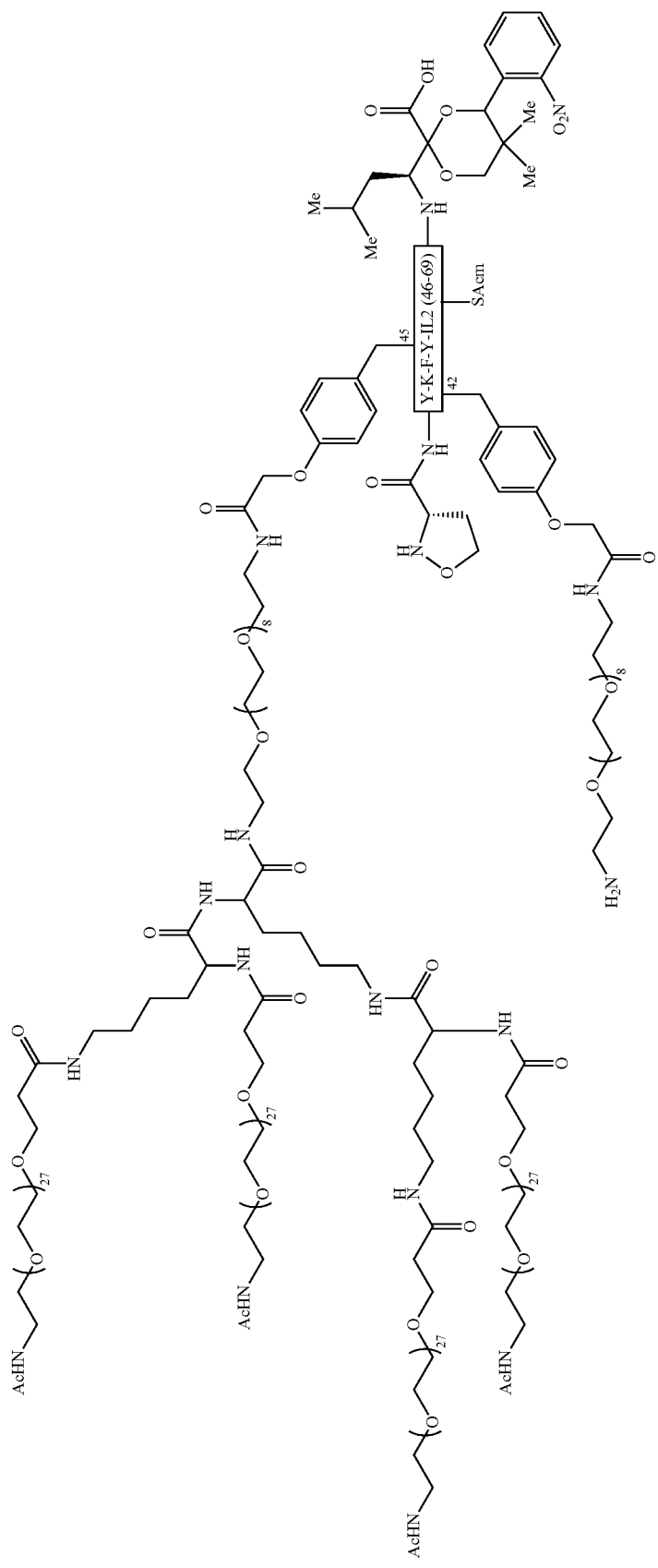

Opr-IL2 (42-69) photoprotected-Leu-α-ketoacid segment (See SEQ ID NO: 3) was prepared on Rink Amide MBHA resin pre-loaded with Fmoc-Leucine-photoprotected-α-ketoacid with a substitution capacity of 0.25 mmol/g following the procedure described in the corresponding step for the synthesis of Composition D. The synthesis of the segment was performed up to Nle46 on 0.2 mmol scale by automated Fmoc SPPS using the procedure described in the general methods section.

Fmoc-Tyrosine derivative bearing an O-allyl ester (Structure 5) was coupled in position 45 by single coupling using HATU (2.9 equiv) and DIPEA (6 equiv). Phe44 and Lys43 were coupled by automated SPPS, followed by manual coupling of Fmoc-Tyrosine derivative bearing the desired PEGs-amino functionality and Boc-5-(S)-Oxaproline in positions 42 and 41, respectively. The allyl ester deprotection was performed following the conditions described in the corresponding step for the synthesis of Composition D. After deprotection, O-[2-(alloc-amino)ethyl]-O-[2-aminoethyl]octaethylene glycol (Structure 8) (216.2 mg, 0,400 mmol, 2 equiv) was coupled at rt for 2 h. The allyl ester deprotection was then repeated, followed by sequential couplings of 3×Fmoc-Lys(Fmoc) and 4×Fmoc-NH-(PEG)$_{27}$-COOH. The progress of the peptide synthesis was monitored by performing a microcleavage and analysis using a mixture of (95:2.5:2.5) TFA:DODT:H$_2$O for 1.5 h. HPLC analysis were performed on a C18 column at 60° C. Upon confirmation of complete couplings, the Fmoc group was deprotected and acetylated.

The peptide was cleaved from the resin using a mixture of 95:2.5:2.5 TFA:DODT:H$_2$O (15 mL/g resin) for 2 h, following the procedure described in the general methods. Purification of crude IL2 (42-69) was performed by preparative HPLC using Shiseido capcell pak C18 column (50×250 mm) with a two-step gradient: starting with 10 to 40% CH$_3$CN in MQ-H$_2$O with 0.1% TFA in 10 min, then 40 to 60% CH$_3$CN in MQ-H$_2$O with 0.1% TFA in 30 min. The pure product fractions were pooled and lyophilized to obtain 110.6 mg of the pure IL2 (42-69) (5.2% yield for peptide synthesis, resin cleavage and purification steps). Analytical HPLC and ESI-HRMS were used to confirm the purity and exact mass of the product, m/z calculated for C$_{490}$H$_{886}$N$_{54}$O$_{196}$S: 10702.0925; measured 10702.0844

Synthesis of IL2-Seg12 of Composition M Variant by KAHA Ligation

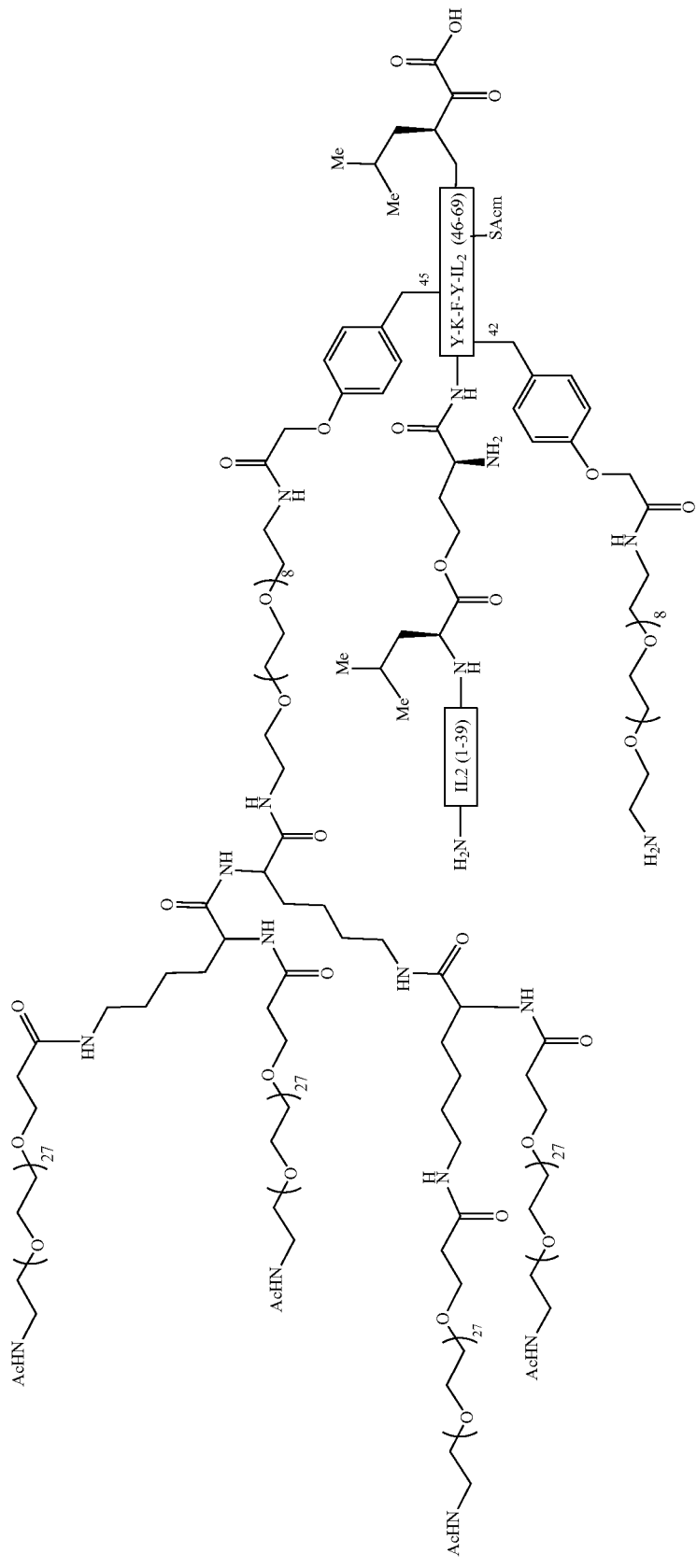

KAHA ligation: Seg1 (11.6 mg, 2.55 µmol, 1.2 equiv) and Seg2 of Composition M (22.7 mg, 2.12 µmol, 1 equiv) were dissolved in DMSO:H$_2$O (9:1) containing 0.1 M oxalic acid (128 µL, 20 mM) and allowed to react at 60° C. for 22 h. The ligation vial was protected from light by wrapping it in aluminum foil. The progress of the KAHA ligation was monitored by uHPLC using a Phenomenex C18 column (150×4.6 mm) at 60° C. with CH$_3$CN/H$_2$O containing 0.1% TFA as mobile phase, with a gradient of 30 to 70% CH$_3$CN in 7 min Photo-deprotection and purification: After completion of the ligation the mixture was diluted (8 mL) with CH$_3$CN/H$_2$O (1:1) containing 0.1% TFA and irradiated at a wavelength of 365 nm for 1 h. The completion of photolysis reaction was confirmed by injecting a sample on uHPLC using previously described method. The photo-deprotected sample is purified by preparative HPLC using a Shiseido Capcell Pack UG80 C18 column (50×250 mm) kept at 60° C., with a two-step gradient: firstly, 10 to 40% CH$_3$CN in MQ-H$_2$O with 0.1% TFA in 10 min, then 40 to 70% CH$_3$CN in MQ-H$_2$O with 0.1% TFA in 30 min. The fractions containing the product were pooled and lyophilized to give pure Seg12 of Composition M (10.7 mg, 34% yield for ligation and purification steps). Analytical HPLC and ESI-HRMS were used to confirm the purity and exact mass of the product, m/z calculated for C$_{682}$H$_{1219}$N$_{109}$O$_{252}$S: 15009.5881; measured 15009.9979.

Final KAHA Ligation for the Preparation of the IL2 Variant Composition M Linear Protein Ligation: Seg12 of Composition M (12.5 mg, 0.83 µmol, 1.1 equiv) and Seg34 (5.5 mg, 0.69 µmol, 1 equiv) were dissolved in DMSO/H$_2$O (9:1) containing 0.1 M oxalic acid (55.0 µL, 15 mM) and the ligation was allowed to proceed for 24 h at 60° C. The progress of the KAHA ligation was monitored by analytical HPLC using a Shiseido Capcell Pak UG80 C18 column (250×4.6 mm) at 60° C. and CH$_3$CN/H$_2$O containing 0.1% TFA as mobile phase, with a gradient of 30 to 95% CH$_3$CN in 7 min Acm deprotection and purification: After completion of ligation, the reaction mixture was diluted with 55 µL DMSO followed by further dilution with a mixture of (1:1) AcOH:H$_2$O (3.2 mL). 33 mg AgOAc (1% w/v) were added to the solution and the mixture was gently shaken for 2.5 h at 50° C. protected from the light. After completion of reaction as ascertained by HPLC, the sample was diluted with CH$_3$CN:H$_2$O (1:1) containing 0.1% TFA, and purified by preparative HPLC using a Shiseido CapCell Pak UG80 C18 column (20×250 mm) kept at 60° C., with a gradient of 30 to 85% CH$_3$CN in 28 min, flow rate: 10 mL/min, with CH$_3$CN and MQ-H$_2$O containing 0.1% TFA as the eluents. The fractions containing the product were pooled and lyophilized to give pure IL2 linear protein of Composition M (3.1 mg, 20% yield for ligation, deprotection and purification steps). Analytical HPLC and ESI-HRMS were used to confirm the purity and exact mass of the product, m/z calculated for C$_{1001}$H$_{1725}$N$_{191}$O$_{349}$S$_2$: 22084.2921; measured 22084.9738.

Preparation of Folded IL2 Variant Composition M

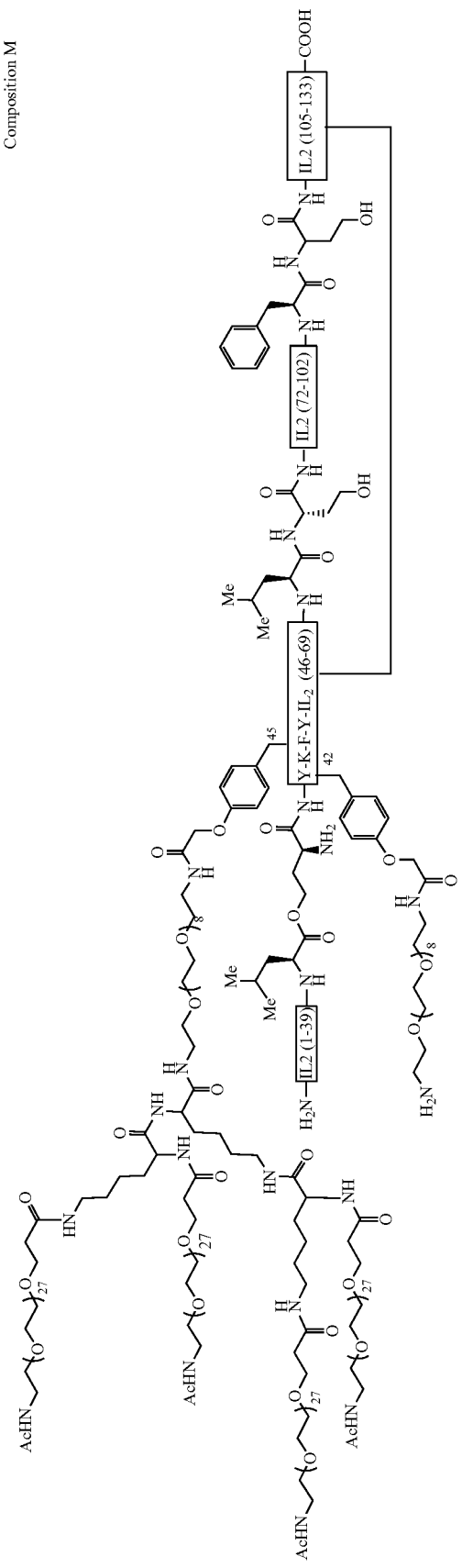
Composition M

Rearrangement of linear protein: the linear protein (3.1 mg, 0.14 μmol) was dissolved in aqueous 6M Gu.HCl containing 0.1 M Tris and 30 mM reduced glutathione (9.4 mL, 15 μM protein concentration), which was adjusted to pH 8.0 by solution of 6M aq. HCl. The mixture was gently shaken at 50° C. for 2 h and monitored by analytical reverse phase HPLC using a bioZen™ 3.6 μm Intact C4 column (150×4.6 mm) at 25° C., with a gradient of 30 to 95% $CH_3CN$ in MQ-$H_2O$ with 0.1% TFA in 18 min, flow rate: 1.0 mL/min.

Folding of the linear rearranged protein: the folding solution was cooled to room temperature and diluted 3-fold with a second buffer solution (18.7 mL) containing 0.1 M Tris and 1.5 mM oxidized glutathione at pH 8.0. the mixture was stored at room temperature and monitored by analytical HPLC using a bioZen™ 3.6 μm Intact C4 column (150×4.6 mm) at 25° C., with a gradient of 30 to 95% acetonitrile with 0.1% TFA in 18 min, flow rate: 1.0 mL/min. After 20 h, the folding solution was acidified with 10% aqueous TFA to ~pH 3 and purified on preparative HPLC, using a Shiseido Proteonavi C4 column (10×250 mm) with a gradient of 30 to 95% acetonitrile with 0.1% TFA in 40 min, flow rate: 5 mL/min. The fractions containing the folded IL2 protein were pooled together and lyophilized. The Purity and identity of the pure folded protein (0.87 mg, 28% yield) was further confirmed by analytical RP-HPLC and high-resolution ESI mass spectrometry, m/z calculated for $C_{1001}H_{1723}N_{191}O_{349}S_2$ [M]: 22082.2765; measured 22082.2618. The 3D-structure was ascertained using CD spectroscopy.

1.5 Synthesis of Composition N Variant of IL-2

For this variant, except segment 2, all the other segments are the same as the ones used for Composition D.

Synthesis of Opr-IL2 (42-69)
Photoprotected-Leu-α-Ketoacid of Composition N

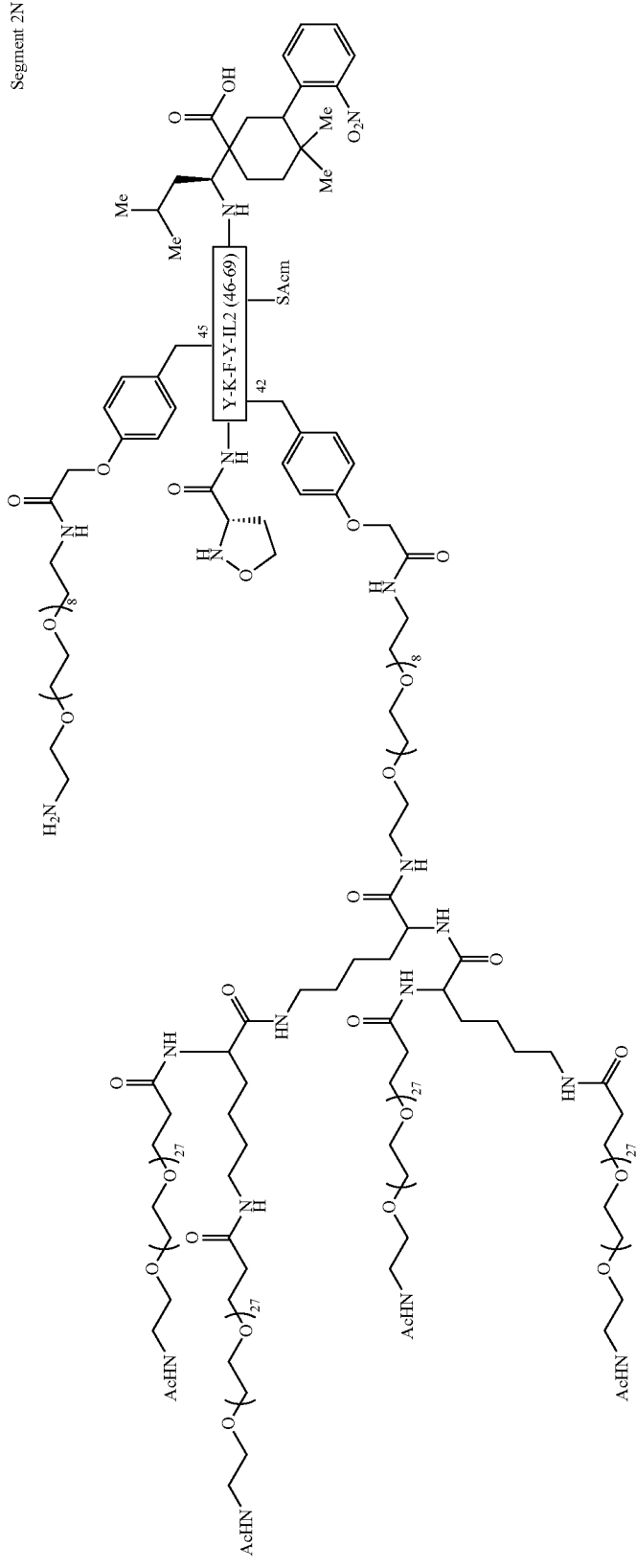

Opr-IL2 (42-69) photoprotected-Leu-α-ketoacid segment (See SEQ ID NO: 3) was prepared on Rink Amide MBHA resin preloaded with Fmoc-Leucine-photoprotected-α-ketoacid with a substitution capacity of 0.25 mmol/g, following the procedure described in the corresponding section for the synthesis of Composition D. The synthesis of the segment was performed up to Nle46 on 0.112 mmol scale by automated Fmoc SPPS using the procedure described in the general methods section.

Fmoc-Tyrosine derivative bearing the desired PEGs-amino group (2 equiv) was coupled in position 45 by single coupling using HATU (1.9 equiv) and DIPEA (4 equiv). Phe44 and Lys43 were coupled by automated SPPS, followed by the manual coupling of Fmoc-Tyr derivative bearing an O-allyl functionality (Structure 5) and Boc-5-(S)-Oxaproline in positions 42 and 41, respectively. The allyl ester deprotection was performed following the conditions described in the corresponding step for the synthesis of Composition D. After deprotection, 0-[2-(alloc-amino)ethyl]-O-[2-amino-ethyl]octaethylene glycol (Structure 8) (182 mg, 0.336 mmol, 2 equiv) was coupled at rt for 2 h. The allyl ester deprotection was then repeated, followed by sequential couplings of 3×Fmoc-Lys(Fmoc) and 4×Fmoc-NH-(PEG)$_{27}$-COOH. The progress of the peptide synthesis was monitored by performing a microcleavage and analysis using a mixture of (95:2.5:2.5) TFA:DODT:H$_2$O for 1.5 h. HPLC analysis were performed on a C18 column at 60° C. Upon confirmation of complete couplings, the Fmoc group was deprotected and acetylated The peptide was cleaved from the resin using a mixture of 95:2.5:2.5 TFA:DODT:H$_2$O (15 mL/g resin) for 2 h, following the procedure described in the general methods. Purification of crude IL2 (42-69) was performed by preparative HPLC using Shiseido capcell pak C18 column (50×250 mm) with a two-step gradient: firstly, 10 to 40% CH$_3$CN in MQ-H$_2$O with 0.1% TFA in 10 min, then 40 to 60% CH$_3$CN in MQ-H$_2$O with 0.1% TFA in 30 min. The pure product fractions were pooled and lyophilized to obtain 38.6 mg of the pure IL2 (42-69) (3.2% yield for peptide synthesis, resin cleavage and purification steps). Analytical HPLC and MALDI-TOF were used to confirm the purity and exact mass of the product, m/z calculated for C$_{490}$H$_{886}$N$_{54}$O$_{196}$S: 10702.7; measured 10702.8.

Synthesis of IL2 Seg12 of Composition N by KAHA Ligation

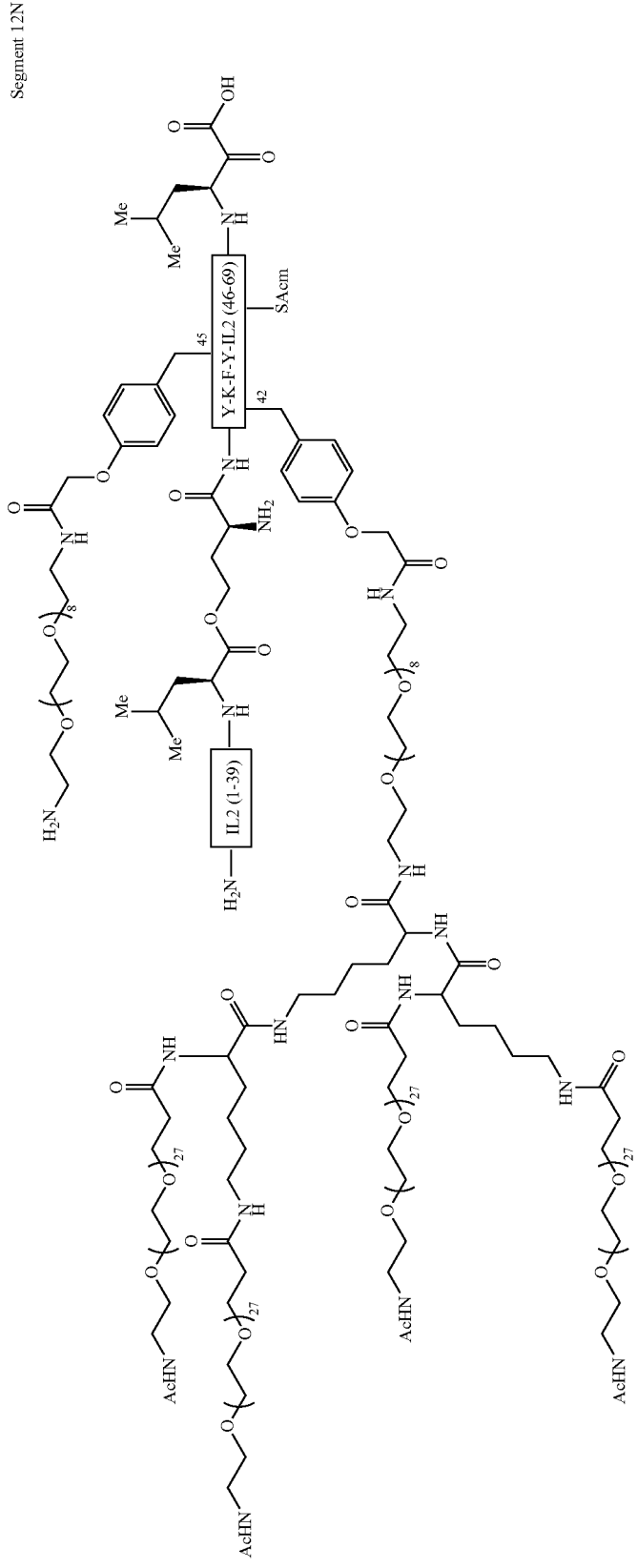

KAHA ligation: Seg1 (21.3 mg, 4.70 μmol, 1.3 equiv) and Seg2 of Composition N (38.6 mg, 3.61 μmol, 1 equiv) were dissolved in DMSO:$H_2O$ (9:1) containing 0.1 M oxalic acid (235 μL, 20 mM) and allowed to react at 60° C. for 22 h. The ligation vial was protected from light by wrapping it in aluminum foil. The progress of the KAHA ligation was monitored by uHPLC using a Phenomenex C18 column (150×4.6 mm) at 60° C. with $CH_3CN/H_2O$ containing 0.1% TFA as mobile phase, with a gradient of 30 to 70% $CH_3CN$ in 7 min Photo-deprotection and purification: After completion of the ligation the mixture was diluted ~20 times (8 mL) with $CH_3CN/H_2O$ (1:1) containing 0.1% TFA and irradiated at a wavelength of 365 nm for 1 h. The completion of photolysis reaction was confirmed by injecting a sample on uHPLC using previously described method. The photo-deprotected sample is purified by preparative HPLC using a Shiseido Capcell Pack UG80 C18 column (50×250 mm) kept at 60° C., with a two-step gradient: firstly, 10 to 40% $CH_3CN$ in MQ-$H_2O$ with 0.1% TFA in 7 min, then 40 to 70% $CH_3CN$ in MQ-$H_2O$ with 0.1% TFA in 30 min. The fractions containing the product were pooled and lyophilized to give pure Seg12 (13.4 mg, 25% yield for ligation and purification steps). Analytical HPLC and ESI-HRMS were used to confirm the purity and exact mass of the product, m/z calculated for $C_{682}H_{1219}N_{109}O_{252}S$: 15009.5881; measured 15009.5902

Final KAHA Ligation for the Preparation of the IL2 Variant Composition N Linear Protein

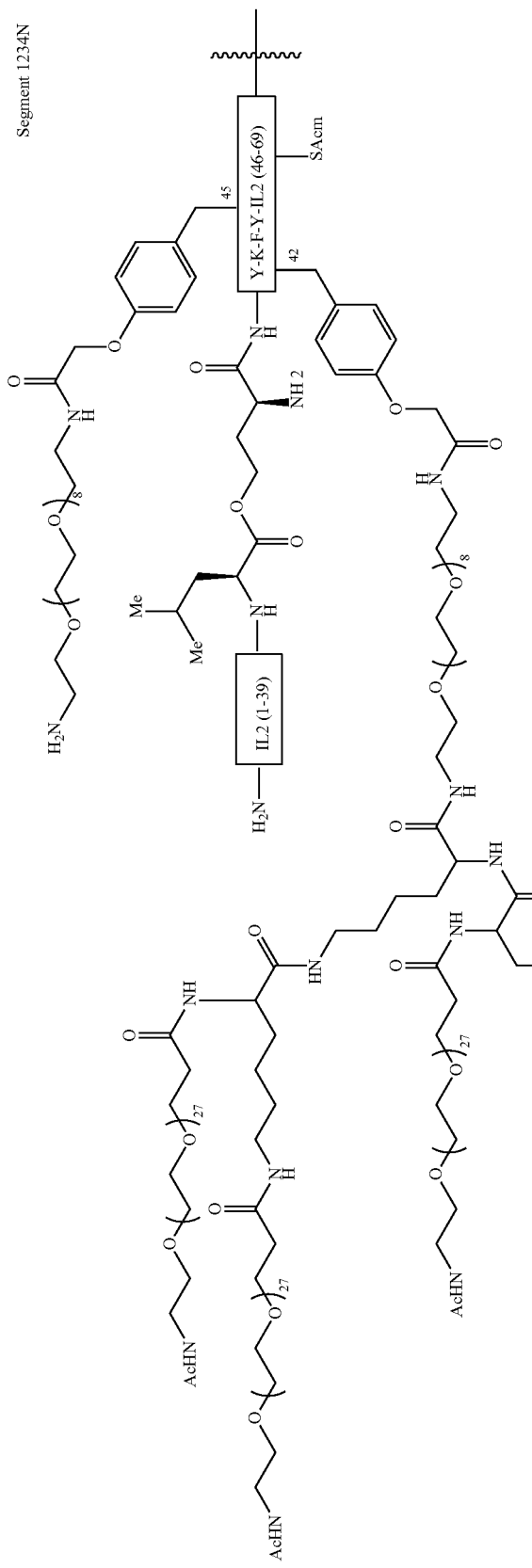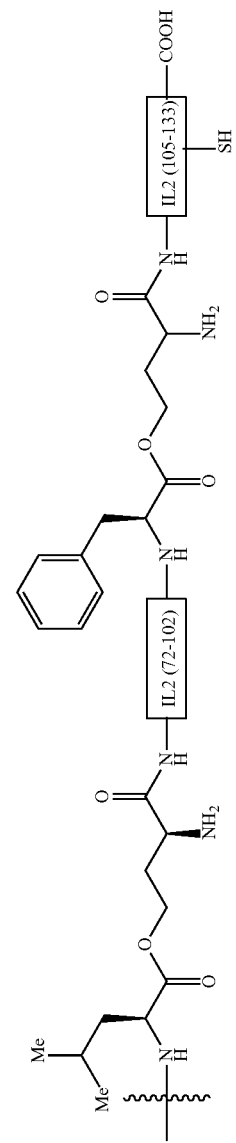

Ligation: Seg12 of Composition N (13.4 mg, 0.89 μmol, 1.1 equiv) and Seg34 (5.9 mg, 0.81 μmol, 1 equiv) were dissolved in DMSO/H$_2$O (9:1) containing 0.1 M oxalic acid (59.3 μL, 15 mM) and the ligation was allowed to proceed for 24 h at 60° C. The progress of the KAHA ligation was monitored by analytical HPLC using a Shiseido Capcell Pak UG80 C18 column (250×4.6 mm) at 60° C. and CH$_3$CN/H$_2$O containing 0.1% TFA as mobile phase, with a gradient of 30 to 95% CH$_3$CN in 7 min.

Acm deprotection and purification: After completion of ligation, the reaction mixture was diluted with 60 μL DMSO followed by further dilution with a mixture of (1:1) AcOH:H$_2$O (3.1 mL). 31 mg AgOAc (1% w/v) were added to the solution and the mixture was shacked for 2.5 h at 50° C. and protected from the light. After completion of reaction as ascertained by HPLC, the sample was diluted with CH$_3$CN:H$_2$O (1:1) containing 0.1% TFA, and purified by preparative HPLC using a Shiseido CapCell Pak UG80 C18 column (20×250 mm) kept at 60° C., with a two-step gradient: firstly, 10 to 40% CH$_3$CN in MQ-H$_2$O with 0.1% TFA in 5 min, then 40 to 85% CH$_3$CN in MQ-H$_2$O with 0.1% TFA in 30 min, flow rate: 10 mL/min, with CH$_3$CN and MQ-H$_2$O containing 0.1% TFA as the eluents. The fractions containing the product were pooled and lyophilized to give pure IL2 linear protein (4.4 mg, 25% yield for ligation, deprotection and purification steps). Analytical HPLC and ESI-HRMS were used to confirm the purity and exact mass of the product, m/z calculated for $C_{1001}H_{1725}N_{191}O_{349}S_2$: 22084.2921; measured 22084.3234.

Preparation of Folded IL2 Variant Composition N

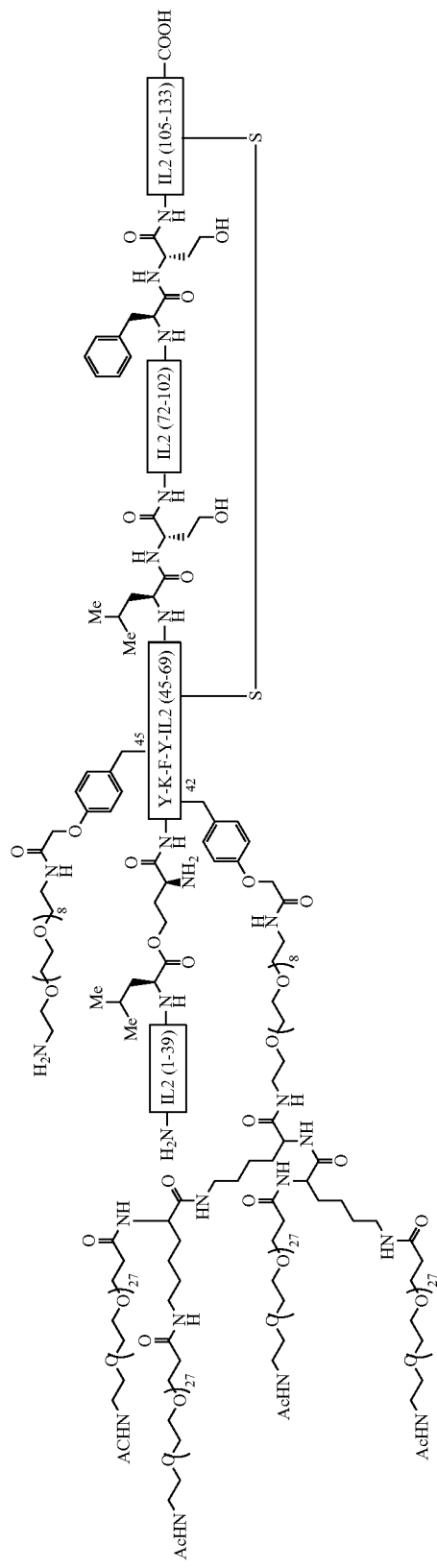

Rearrangement of linear protein: the linear protein (4.4 mg, 0.20 μmol) was dissolved in aqueous 6M Gu.HCl containing 0.1 M Tris and 30 mM reduced glutathione (13.3 mL, 15 μM protein concentration), which was adjusted to pH 8.0 by solution of 6M aq. HCl. The mixture was gently shaken at 50° C. for 2 h and monitored by analytical reverse phase HPLC using a bioZen™ 3.6 μm Intact C4 column (150×4.6 mm) at 25° C., with a gradient of 30 to 95% $CH_3CN$ in MQ-$H_2O$ with 0.1% TFA in 18 min, flow rate: 1.0 mL/min.

Folding of the linear rearranged protein: the previous solution was cooled to room temperature and diluted 3-fold with a second buffer solution (26.6 mL) containing 0.1 M Tris and 1.5 mM oxidized glutathione at pH 8.0. the mixture was stored at room temperature and monitored by analytical HPLC using a bioZen™ 3.6 μm Intact C4 column (150×4.6 mm) at 25° C., with a gradient of 30 to 95% acetonitrile with 0.1% TFA in 18 min, flow rate: 1.0 mL/min. After 20 h, the folding solution was acidified with 10% aqueous TFA to pH 3 and purified on preparative HPLC, using a Shiseido Proteonavi C4 column (10×250 mm) with a gradient of 30 to 95% acetonitrile with 0.1% TFA in 40 min, flow rate: 5 mL/min. The fractions containing the folded IL2 protein were pooled together and lyophilized. The Purity and identity of the pure folded protein (1.1 mg, 25% yield) was further confirmed by analytical RP-HPLC and high-resolution ESI mass spectrometry, m/z calculated for $C_{1001}H_{1723}N_{191}O_{34}9S_2$: 22082.2765; measured 22082.2603.

Example 2—Structure of Composition A, Composition B, Composition C, and Composition D Provided herein is an illustration of a modified IL-2 polypeptide (Composition A). See FIG. 1A. Composition A has an amino acid sequence of SEQ ID NO: 3. The secondary, tertiary, and quaternary structure of the modified IL-2 polypeptide is virtually identical to that of wild-type IL-2.

The modified IL-2 polypeptide of Composition A comprises multiple chemical modifications compared to wild-type IL-2. One modification of Composition A is a monodispersed PEG conjugated to the F42Y residue. In this example, the PEG conjugated to the F42Y residue is a monodispersed PEG having a molecular weight of ~500 Da. A second modification of the protein is a monodispersed PEG conjugated at the Y45 residues. This PEG is identical to that of the Y42 residue, also having a molecular weight of ~500 Da.

Also provided herein is the structure of another modified IL-2 polypeptide (Composition B). See FIG. 1B. Compared to Composition A, Composition B further comprises a modification at the N-terminus. This modification comprises a polymer having a structure of Formula (Ha) attached at the N terminus, and the Mw of this polymer is about 6 kDa. As illustrated in Formula (Ha), the attached polymer comprises four liner PEG chains, each comprising about 26 PEG units.

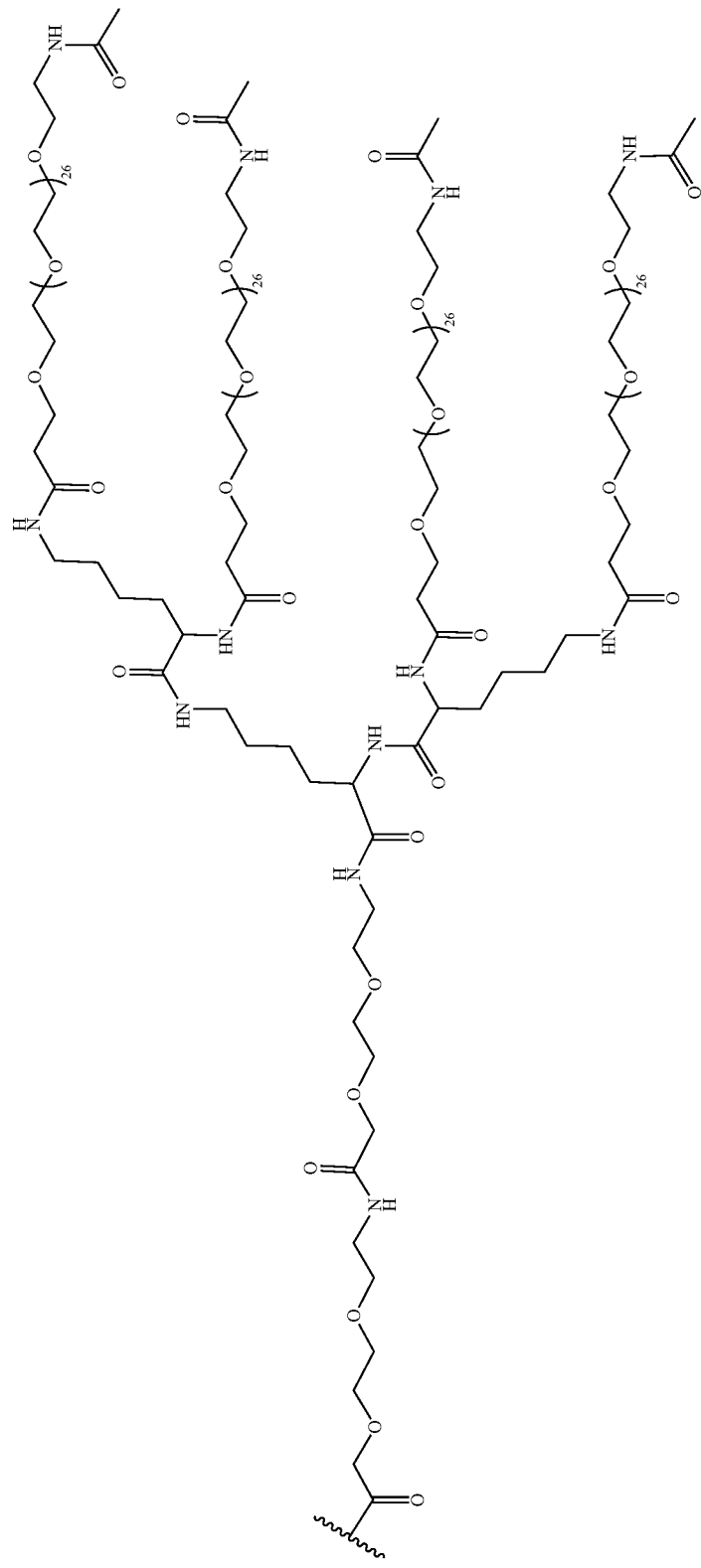
Formula (IIa)

Figure 1G:
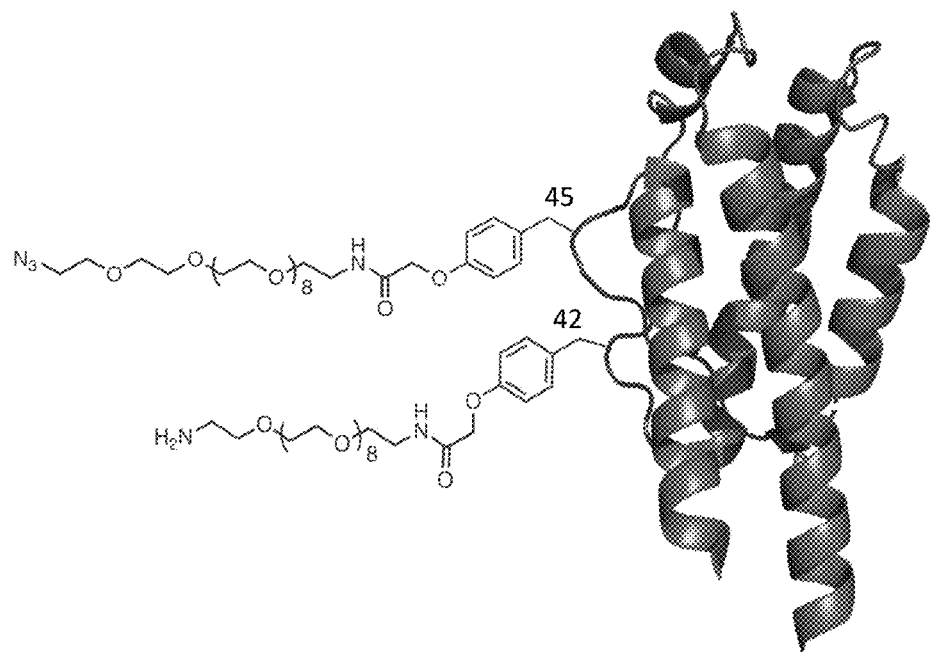
FIG. 1G shows an illustration of a modified IL-2 polypeptide (Composition A1).

Further provided herein is the structure of a modified IL-2 polypeptide Composition C. See FIG. 1C. Compared to Composition A, Composition C comprises a 30 kDa PEG functionality attached to residue 45 on the end of the short PEG polymer. Optionally, this 30 kDA PEG functionality is covalently attached to the short PEG polymer by means of a copper-free click chemical reaction. Also provided herein is a modified IL-2 with an alternative linker group attaching the copper-free click chemical reagent to the PEG group, so shown in FIG. 1E. Also provided herein is the structure of a modified IL-2 polypeptide shown having a reverse orientation of the CLICK chemistry reagents used to form the conjugate (e.g. Composition C with the azide functionality on the PEG polymer and the alkyne moiety attached to the IL-2 polypeptide moiety). Also provided herein is a modified IL-2 comprising an azide functionality at the terminal end of the PEG spacer attached to residue Y45, as shown in FIG. 1G.

Figure 1H:
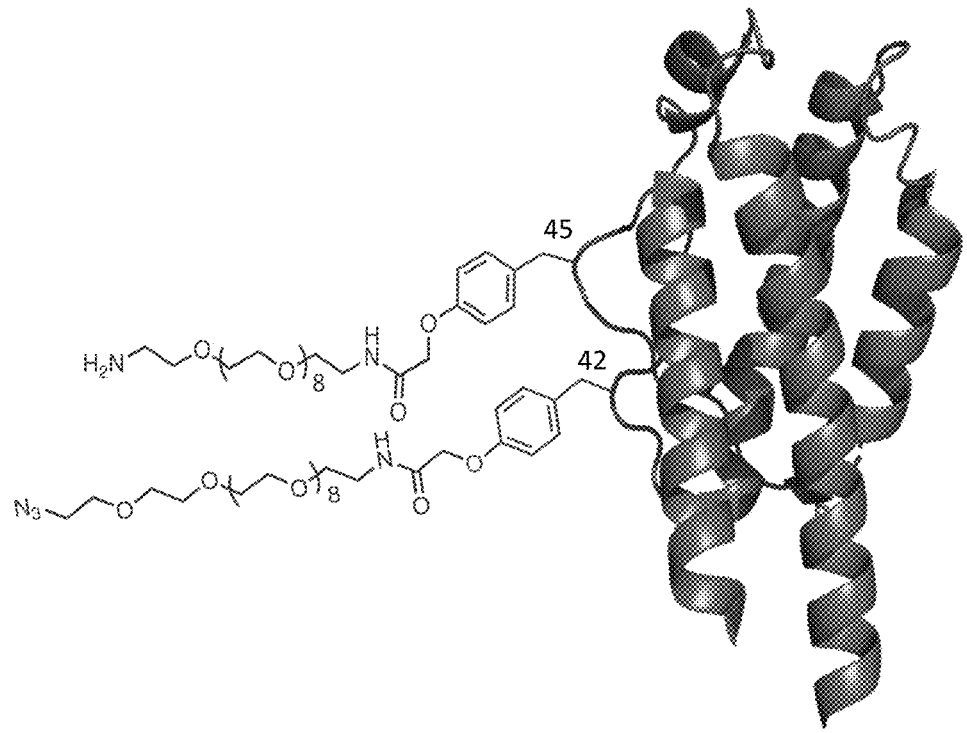
FIG. 1H shows an illustration of a modified IL-2 polypeptide (Composition A2).

Further provided herein is the structure of a modified IL-2 polypeptide Composition D. See FIG. 1D. Compared to Composition A, Composition D comprises a 30 kDa PEG functionality attached to residue Y42 on the end of the short PEG polymer. Optionally, this 30 kDA PEG functionality is covalently attached to the short PEG polymer by means of a copper-free click chemical reaction. Also provided herein is a modified IL-2 with an alternative linker group attaching the copper-free click chemical reagent to the PEG group, so shown in FIG. 1F. Also provided herein is the structure of a modified IL-2 polypeptide shown having a reverse orientation of the CLICK chemistry reagents used to form the conjugate (e.g. Composition D with the azide functionality on the PEG polymer and the alkyne moiety attached to the IL-2 polypeptide moiety). Also provided herein is a modified IL-2 comprising an azide functionality at the terminal end of the PEG spacer attached to residue F42Y, as shown in FIG. 1H.

Figure 1I:
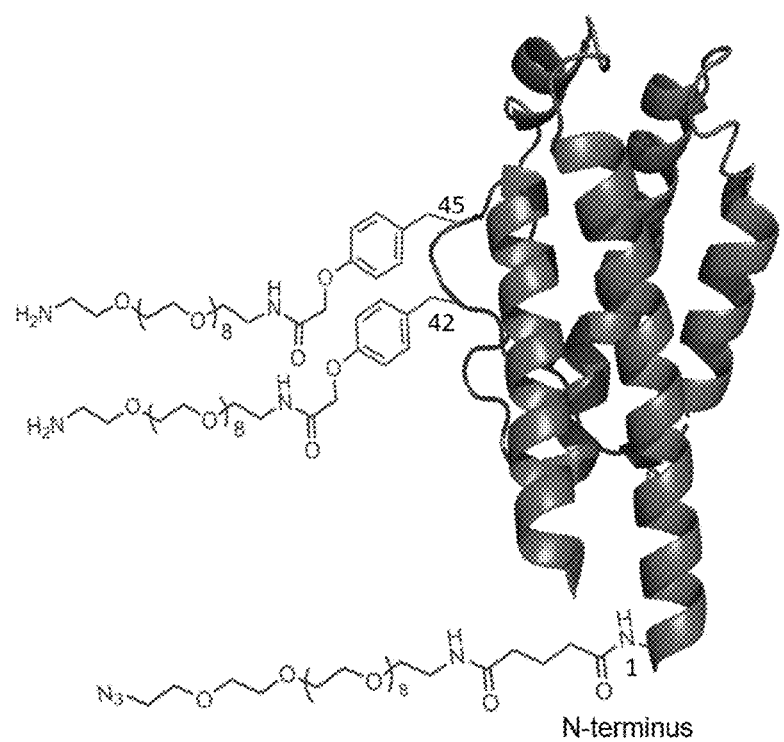
FIG. 1I shows an illustration of a modified IL-2 polypeptide (Composition Z).

Further provided herein is the structure of a modified IL-2 polypeptide Composition Z. See FIG. 1I. Compared to Composition A, Composition Z further comprises an azide functionality linked to the N-terminal residue through a short linker.

Example 3—Characterization of Composition A

Figure 2A:
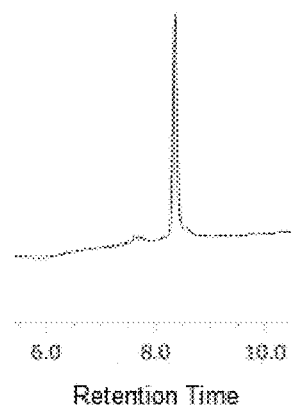
FIG. 2A shows an HPLC trace of a purified modified IL-2 polypeptide, wherein the x-axis shows retention time and the y-axis shows absorbance. The sample in this figure is Composition A.
Figure 2B:
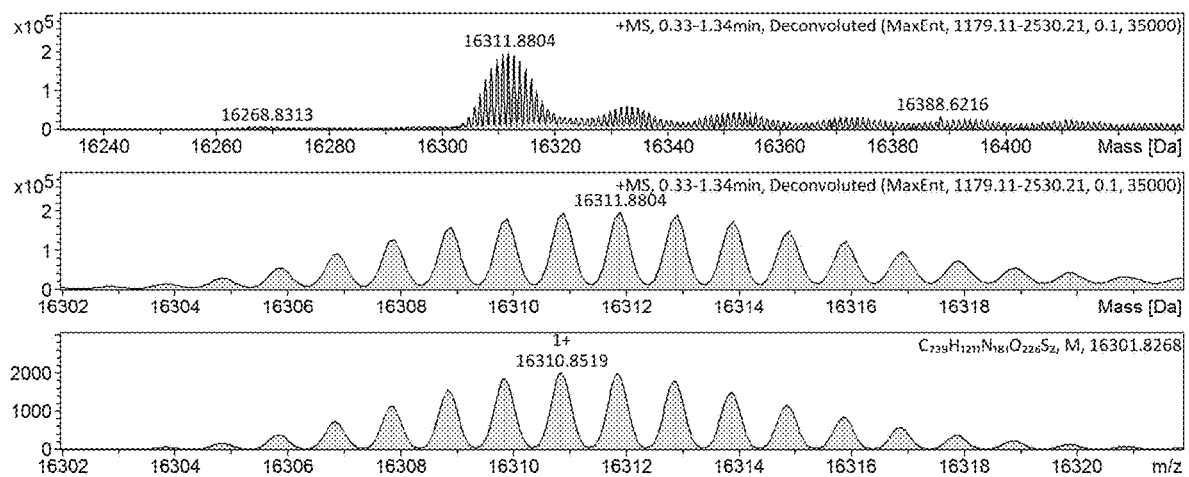
FIG. 2B shows a plot measuring the mass/charge ratio of a modified IL-2 polypeptide, where the x-axis is the mass to charge ratio and the y-axis is intensity of the signal (Top—Measured, middle—measured zoomed, bottom—calculated spectra). The sample shown in this plot is the modified IL-2 polypeptide Composition A provided herein.
Figure 2C:
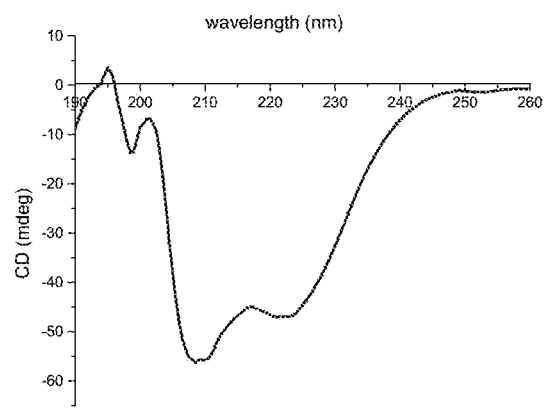
FIG. 2C shows a plot measuring the absorbance of polarized light of a modified IL-2 polypeptide, where the x-axis is wavelength of polarized light and the y-axis is absorbance. The sample shown in this plot is the modified IL-2 polypeptide Composition A provided herein.

Composition A was subject to a series of analytical experiments to characterize it. The results of these experiments are shown in FIG. 2A, FIG. 2B, and FIG. 2C. Details of these experiments are described below.

The modified IL-2 polypeptide was analyzed by HPLC. Composition A eluted as a single, narrow peak, indicative of a high degree of uniformity in the sample. The resulting HPLC trace is shown in FIG. 2A, which shows absorbance (y-axis) as a function of retention time on the column (x-axis).

The modified IL-2 polypeptide was further analyzed by ESI-HRMS (Electrospray ionization high resolution mass spectrometry). As shown in FIG. 2B, the isotopic distribution pattern of calculated and measured high-resolution mass spectrum closely matches confirming high purity and homogeneity of Composition A. In FIG. 2B, the x-axis denotes molecular weight and the y-axis denotes intensity of signal.

The modified IL-2 polypeptide was also analyzed by circular dichroism. The resulting CD spectra shows the characteristic peaks of a well-folded interleukin-2 protein, which is indicative of Composition A being folded in a similar manner to wild-type IL-2. See FIG. 2C, which shows wavelength of polarized light (x-axis) versus absorbance (y-axis) of Composition A.

Figure 2D:
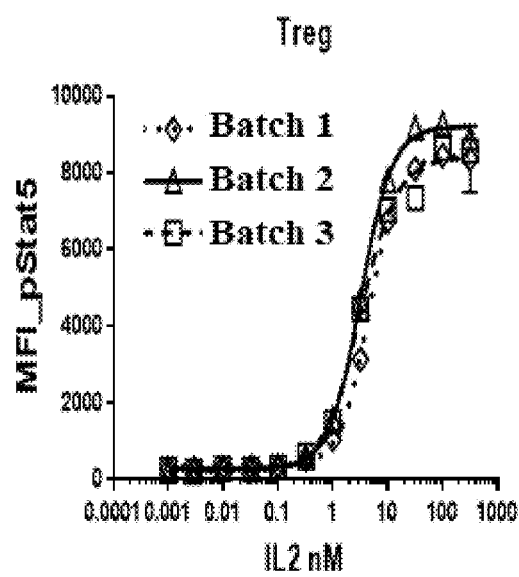
FIG. 2D shows the batch-to-batch variability of the bioactivity of a modified IL-2 polypeptide on the inducement of Treg cells in an in vitro sample of human T-cells, with the figure showing mean fluorescence intensity for phosphorylated signal transducer and activator of transcription 5 (pSTAT5) on the y-axis and dosage of wild type IL-2 or a modified IL-2 polypeptide on the x-axis. The sample shown in this plot is the modified IL-2 polypeptide Composition D provided herein.

The modified IL-2s produced by the methods provided herein display significant consistency from lot to lot of IL-2 polypeptide. FIG. 2D shows the in vitro efficacy of three different batches of a modified IL-2 polypeptide as all being substantially identical. FIG. 2D shows the batch-to-batch variability of the bioactivity of a modified IL-2 polypeptide on the inducement of Treg cells in an in vitro sample of human T-cells, with the figure showing mean fluorescence intensity for phosphorylated signal transducer and activator of transcription 5 (pSTAT5) on the y-axis and dosage of wild type IL-2 or a modified IL-2 polypeptide on the x-axis. The sample shown in this plot is the modified IL-2 polypeptide Composition D provided herein.

Example 4—Formulation of Modified IL-2 Polypeptides

A lyophilized modified IL-2 polypeptide is prepared using the process described in Example 1. The lyophilized, folded composition A is dissolved in 0.05 M $Na_2HPO_4$ buffer (pH7.5) containing 1% SDS by gently shaking to aid complete solubilization. The target concentration as measured by bicinchoninic acid (BCA) assay is approximately 0.4 mg/mL. The sample is then dialyzed using a Slide-A-Lyzer™ dialysis cassette against 0.05 M $Na_2HPO_4$ buffer (pH 7.5) containing 0.1% SDS and 50 mg/mL mannitol. The buffer is exchanged twice after two three-hour periods, and the sample is then left overnight in the buffer. The dialysis cassette is then transferred to a vessel containing the final formulation buffer of 10 mM $Na_2HPO_4$, pH 7.5 containing 0.022% SDS and 50 mg/mL of mannitol and the sample dialyzed with three buffer exchanges (2×4 hours, 1× overnight). The sample is then removed from the dialysis cassette and assessed again by BCA assay. Samples are then aliquoted and stored at −80° C.

Example 5—IL-2 Receptor Binding Activity of Composition A and Other IL-2 Polypeptides Surface plasmon resonance experiments were performed on wild type IL-2, aldesleukin (SEQ ID NO: 2), Composition A, Composition B, and selected other modified IL-2 polypeptides to determine their binding characteristics on IL-2R monomer subunits. The interaction of the IL-2 polypeptides with human IL-2 receptor subunits were measured with Surface Plasmon Resonance (SPR) technology at Crelux, a Wuxi AppTec company, Martinsried, GER. For these studies, anti-His antibodies were bound by amine coupling onto a CM5 chip to capture 42 nM of His tagged human IL2 receptor alpha (Abcam, Ab221397) or of His tagged human IL2 receptor beta (Abcam, Abl74003). In other settings, 42 nM of alpha and beta IL2 receptors were mixed and pre-incubated for 30 min before capture of the alpha/beta heterodimer IL2 receptor.

The kinetic binding of the IL2 analytes were measured with a Biacore 8K instrument (GE Healthcare) in a two-fold serial dilutions starting at 2.5 uM down to 2.4 nM. Regeneration of the surface back to amine coupled anti His antibody was done after every concentration of analyte. To measure the protein association to the receptors, the samples were injected with a flow rate of 50 ul/min for 30 s, followed by 180 s buffer only to detect the dissociation. The used running buffer was 1×PBS with 0.05% Tween20. The relative response units (RU, Y-axis) are plotted against time (s, X-axis) and analyzed in a kinetic 1:1 binding model for the monomer receptor binding and with a kinetic heterogenous ligand fit model for the alpha/beta heterodimer binding.

Compositions A, B, C, and D displayed no binding with IL-2Rα, each having an observed $K_d$ of >2500 nM. See FIG. 3, which shows relative response (y-axis) versus time (x-axis) for surface plasmon resonance experiment measuring binding interactions of various IL-2 polypeptides and IL-2 receptor subunits. Comparatively, aldesleukin bound to IL-2Rα with a $K_d$ of 23 nM (Table 8). Compositions A and B thus display substantially less binding to the alpha subunit of the IL-2 receptor.

Figure 3:
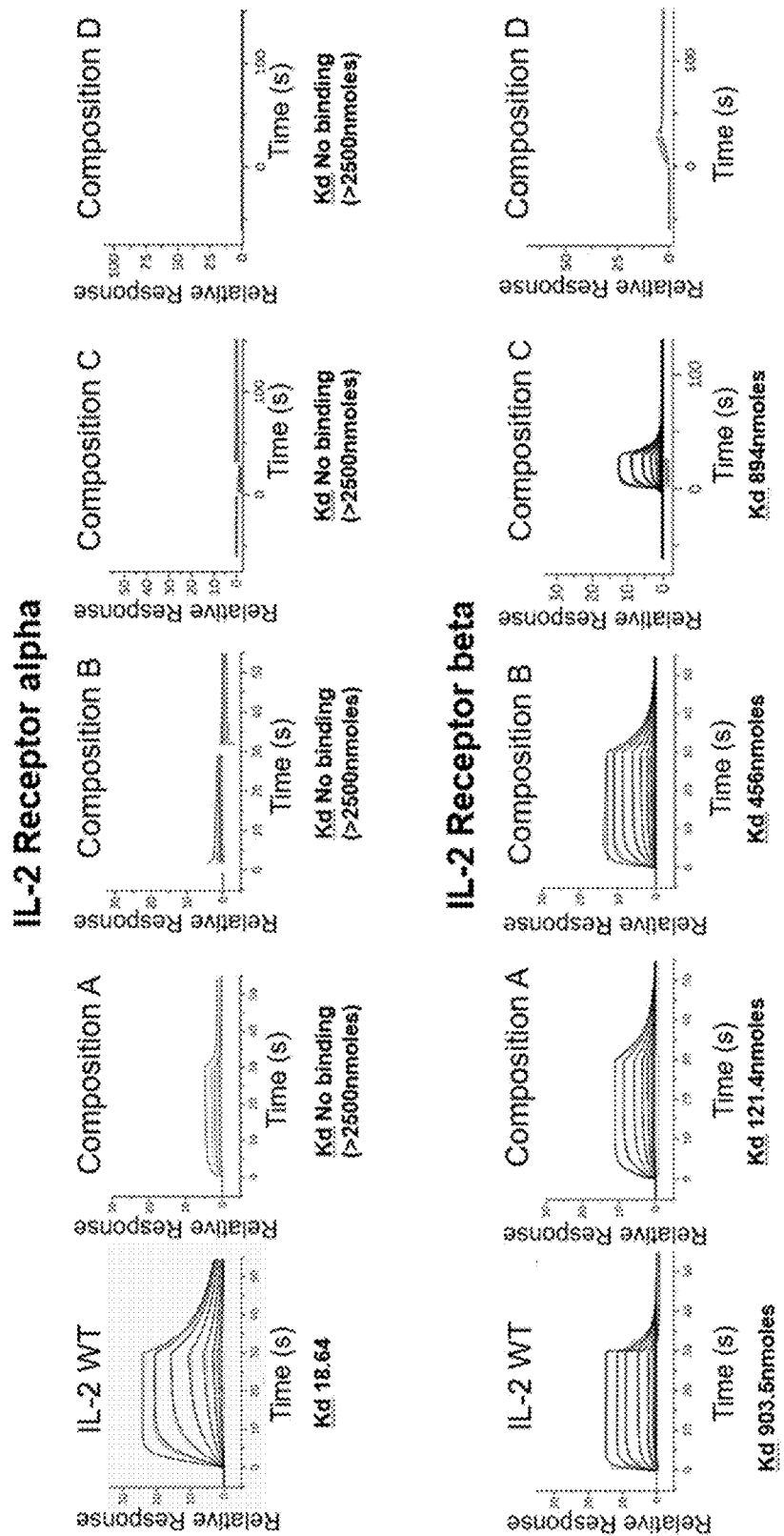
FIG. 3 shows plots measuring the binding activity of wild type IL-2 and of modified IL-2 polypeptides to IL-2 receptor a and IL-2 receptor b in surface plasmon resonance experiments, where the x-axis is time and the y-axis is relative response. The modified IL-2 polypeptides tested in these experiments were Composition A, Composition B, Composition C, and Composition D.

Conversely, Compositions A and B exhibited increased binding to the β subunit of the IL-2 receptor, with a $K_d$ of 133 nM and 456 nM respectively (FIG. 3). This marks an approximately 7-fold increase in binding for Composition A and 2-fold increase in binding for Composition B to the β subunit compared to aldesleukin (Table 9) or wild type IL-2 (FIG. 3), both which exhibited a $K_d$ of about 900 nM.

Table 8 below shows the results of the same surface plasmon resonance experiment performed with additional modified IL-2 polypeptides to measure binding to IL-2Rα (CD25). All of the tested modified IL-2 polypeptides displayed minimal binding to IL-2Rα. NT indicates the IL-2 polypeptide as not tested.

TABLE 8

| Assay | Composition | Side chain modifications | Ka (1/Ms) | Kd (1/s) | KD (nM) |
|---|---|---|---|---|---|
| Alpha (CD25) | Aldesleukin | None | 6.74e+06 | 1.54e−01 | 23.6 |
| | K | 5 kDaPEG on Y45 | — | — | >2500 |
| | L | 0.5 kDaPEG on Y45 | — | — | >1000 |
| | E | 1 kDaPEG on Y45 | — | — | >2500 |
| | A | 0.5 kDaPEG on Y42 & Y45 | — | — | >2500 |
| | B | 0.5 kDaPEG on Y42 & Y45 6 kDa PEG on N-term | — | — | >2500 |
| | H | 0.5 kDaPEG on Y42 & Y45 11 kDa PEG on N-term | NT | NT | NT |
| | I | 0.5 kDaPEG on Y42 & Y45 3xPEG- Cys handle on N-term | NT | NT | NT |
| | J | 0.5 kDaPEG on Y42 & Y45 3xPEG+ 40 kDa on N-term | NT | NT | NT |
| | M | 0.5 kDaPEG on Y42 0.5 kDa + 6 kDa PEG Y45 | — | — | >2500 |
| | N | 0.5 kDa + 6 kDa PEG on Y42 0.5 kDa PEG Y45 | — | — | >2500 |
| | C | 0.5 kDaPEG on Y42 0.5 kDa + 30 kDa PEG Y45 | — | — | >2500 |
| | D | 0.5 kDa + 30 kDa PEG on Y42 0.5 kDa PEG Y45 | — | — | >2500 |
| | O | 0.5 kDa + 32 kDa monoPEG on Y42 0.5 kDa PEG Y45 | NT | NT | NT |

Table 9 shows the results of the same surface plasmon resonance experiment performed with additional modified IL-2 polypeptides to measure binding to IL-2Rβ (CD122). All of the tested modified IL-2 polypeptides displayed comparable binding to IL-2Rβ or better binding as compared to aldesleukin. NT indicates the IL-2 polypeptide was not tested.

TABLE 9

| Assay | Composition | Side chain modifications | Ka (1/Ms) | Kd (1/s) | KD (nM) |
|---|---|---|---|---|---|
| Beta (CD122) | Aldesleukin | None | 3.19e+05 | 2.89e−01 | 918.3 |
| | K | 5 kDaPEG on Y45 | 1.89e+05 | 2.38e−01 | 1260 |
| | L | 0.5 kDaPEG on Y45 | 1.95e+06 | 1.90e−01 | 97.5 |
| | E | 1 kDaPEG on Y45 | 1.24e+06 | 1.81e−01 | 146 |
| | A | 0.5 kDaPEG on Y42 & Y45 | 1.455e+06 | 1.66e−01 | 48.4 |

TABLE 9-continued

| Assay | Composition | Side chain modifications | Ka (1/Ms) | Kd (1/s) | KD (nM) |
|---|---|---|---|---|---|
| | B | 0.5 kDaPEG on Y42 & Y45 6 kDa PEG on N-term | 3.96e+05 | 1.81e−01 | 456 |
| | H | 0.5 kDaPEG on Y42 & Y45 11 kDa PEG on N-term | NT | NT | NT |
| | I | 0.5 kDaPEG on Y42 & Y45 3xPEG− Cys handle on N-term | NT | NT | NT |
| | J | 0.5 kDaPEG on Y42 & Y45 3xPEG+ 40 kDa on N-term | NT | NT | NT |
| | M | 0.5 kDaPEG on Y42 0.5 kDa + 6 kDa PEG Y45 | 5.93e+05 | 1.79e−01 | 302 |
| | N | 0.5 kDa + 6 kDa PEG on Y42 0.5 kDaPEG Y45 | 3.13e+05 | 1.68e−01 | 537 |
| | C | 0.5 kDaPEG on Y42 0.5 kDa + 30 kDa PEG Y45 | 1.60e+05 | 0.142e−01 | 896 |
| | D | 0.5 kDa + 30 kDa PEG on Y42 0.5 kDa PEG Y45 | 1.38e+05 | 0.148e−01 | 1098 |
| | O | 0.5 kDa + 32 kDa monoPEG on Y42 0.5 kDa PEG Y45 | NT | NT | NT |

Additional surface plasmon resonance experiments were performed to determine the binding characteristics of the modified IL-2 polypeptides with IL2R alpha/beta heterodimers. The experiments were performed as indicated above, but the monomeric subunits were replaced with the IL2R heterodimers. The results for the primary interaction are shown below in Table 10. Notably, the modified IL-2 polypeptides all displayed substantially reduced affinity for the primary interaction. In the table below, NT indicates the composition was not tested.

TABLE 10

| Composition | Side chain modifications | Ka (1/Ms) | Kd (1/s) | KD (nM) |
|---|---|---|---|---|
| Aldesleukin | None | 8.01e+06 | 1.75e−03 | 0.25 |
| K | 5 kDaPEG on Y45 | — | — | >2500 |
| L | 0.5 kDaPEG on Y45 | — | — | >1000 |
| E | 1 kDaPEG on Y45 | — | — | >2500 |
| A | 0.5 kDaPEG on Y42 & Y45 | Too small components to trust kinetic | Too small components to trust kinetic | >2500 |
| B | 0.5 kDaPEG on Y42 & Y45 6 kDa PEG on N-term | Too small components to trust kinetic | Too small components to trust kinetic | >2500 |
| H | 0.5 kDaPEG on Y42 & Y45 11 kDa PEG on N-term | NT | NT | NT |
| I | 0.5 kDaPEG on Y42 & Y45 3xPEG− Cys handle on N-term | NT |

TABLE 10-continued

| Composition | Side chain modifications | Ka (1/Ms) | Kd (1/s) | KD (nM) |
|---|---|---|---|---|
| C | 0.5 kDaPEG on Y42 0.5 kDa + 30 kDa PEG Y45 | Too small components to trust kinetic | Too small components to trust kinetic | >2500 |
| D | 0.5 kDa + 30 kDa PEG on Y42 0.5 kDa PEG Y45 | Too small components to trust kinetic | Too small components to trust kinetic | >2500 |
| O | 0.5 kDa + 32 kDa monoPEG on Y42 0.5 kDa PEG Y45 | NT | NT | NT |

The secondary interactions between IL-2R heterodimers and the modified IL-2 polypeptides were also measured. The results of this experiment are shown below in Table 11. Nearly all of the modified IL-2 polypeptides retained at least some affinity for the secondary interaction. In particular, Composition A displayed a KD of less than 10-fold greater than aldesleukin for this secondary interaction. In the table below, NT indicates the composition was not tested.

TABLE 11

| Composition | Side chain modifications | Ka (1/Ms) | Kd (1/s) | KD (nM) |
|---|---|---|---|---|
| Aldesleukin | | 5.13e+06 | 9.56 − 02 | 28.77 |
| K | 5 kDaPEG on Y45 | 1.89e+05 | 2.38e−01 | 1260 |
| L | 0.5 kDaPEG on Y45 | 1.95e+06 | 1.90e−01 | 97.5 |
| E | 1 kDaPEG on Y45 | 1.24e+06 | 1.81e−01 | 146 |
| A | 0.5 kDaPEG on Y42 & Y45 | 1.24e+06 | 1.95e−01 | 164 |
| B | 0.5 kDaPEG on Y42 & Y45 6 kDa PEG on N-term | 2.42e+05 | 2.02e−01 | 837 |
| H | 0.5 kDaPEG on Y42 & Y45 11 kDa PEG on N-term | NT | NT | NT |
| I | 0.5 kDaPEG on Y42 & Y45 3xPEG− Cys handle on N-term | NT | NT | NT |
| J | 0.5 kDaPEG on Y42 & Y45 3xPEG+ 40 kDa on N-term | NT | NT | NT |
| M | 0.5 kDaPEG on Y42 0.5 kDa + 6 kDa PEG Y45 | Too small components to trust kinetic | Too small components to trust kinetic | — |
| N | 0.5 kDa + 6 kDa PEG on Y42 0.5 kDa PEG Y45 | 4.74e+05 | 2.08e−01 | 439 |
| C | 0.5 kDaPEG on Y42 0.5 kDa + 30 kDa PEG Y45 | 1.33e+05 | 1.42e−01 | 1057 |
| D | 0.5 kDa + 30 kDa PEG on Y42 0.5 kDa PEG Y45 | 1.31e+03 | 1.47e−01 | 1152 |
| O | 0.5 kDa + 32 kDa monoPEG on Y42 0.5 kDa PEG Y45 | NT | NT | NT |

Example 6—Cell Based In Vitro Characterization of Composition A

An experiment was performed to determine the effect of various IL-2 polypeptides on human T-cell populations. Primary pan T-cells (CD4+, CD8+ and Tregs T cells) were obtained from healthy donor buffy coat by peripheral blood mononuclear cell (PBMC) purification using ficoll gradient centrifugation followed by negative selection with magnetic beads and then cryopreserved until use. Pan T-cells were thawed, allowed to recover overnight in T-cell medium (RPMI 10% FCS, 1% Glutamin, 1% NEAA, 25 µM bMeoH, 1% NaPyrovate), and after two washing steps with PBS cells were resuspended in PBS. Cells were then distributed at 200'000 cells per well and stimulated with 3.16-fold serial dilutions of aldesleukin or of modified IL-2 polypeptides with a starting concentration of 316 nM down to 3 µM, for 20 min to 40 min at 37° C./5% $CO_2$. After incubation, cells were fixed and permeabilized using the Transcription Factor Phospho Buffer kit followed by a surface and intracellular immunostaining for CD4, CD8, CD25, FoxP3, CD45RA and pStat5 to enable cell subset identification and measurement of Stat5 (signal transducer and activator of transcription 5) phosphorylation levels. The FACS (fluorescence activated cell sorting) measurement was done either with a NovoCyte or a Quanteon Flow Cytometer from Acea.

pStat5 MFI (medium fluorescence intensity) signals for the T-cell subsets shown in Table 12 were plotted against concentrations of aldesleukin or of modified IL-2 polypeptides. Half maximal effective concentration ($EC_{50}$) was calculated based on a variable slope, four parameter analysis using GraphPad PRISM software.

TABLE 12

Figure 4:
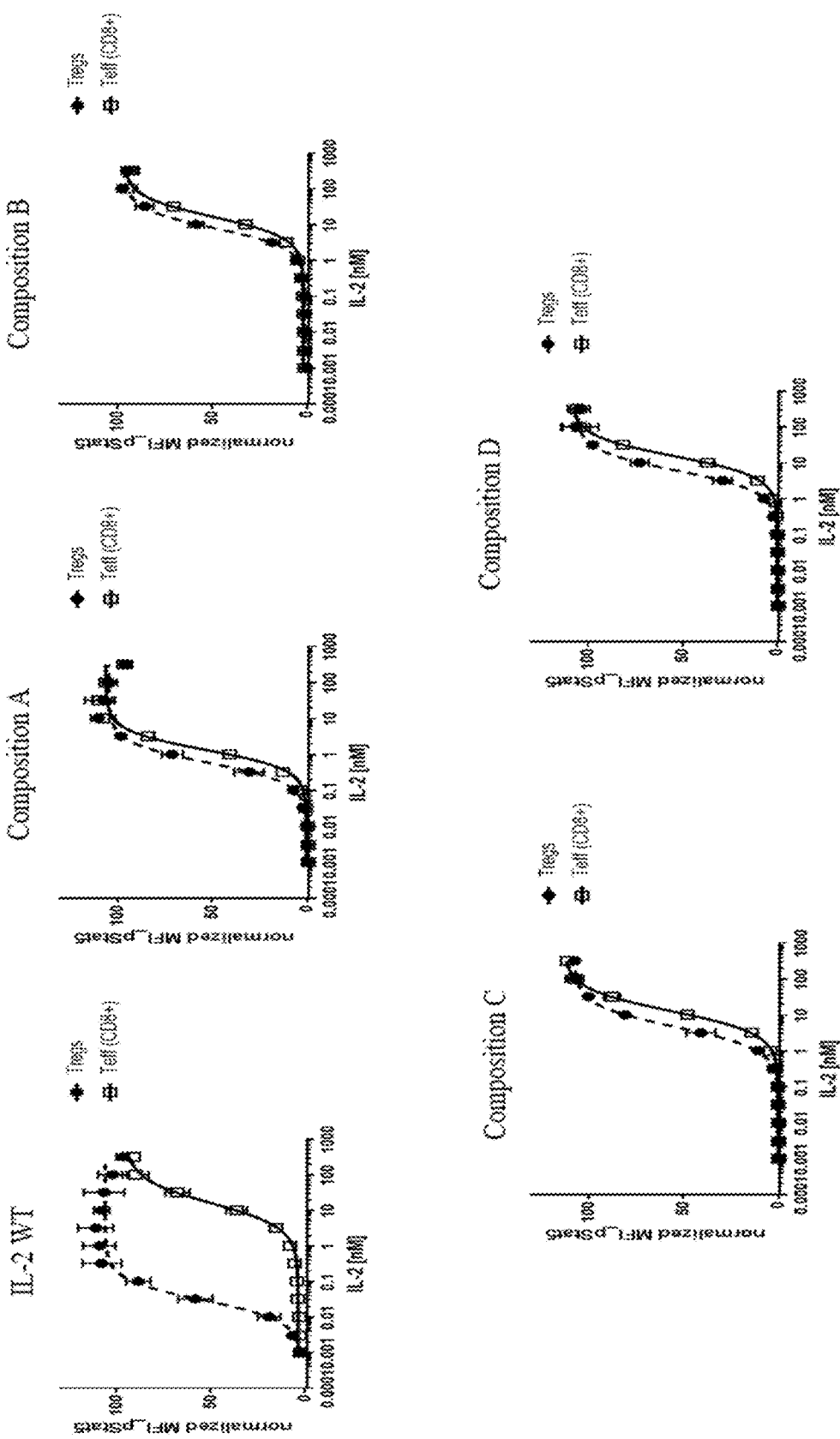
FIG. 4 shows plots measuring the effect of a wild type and of modified IL-2 polypeptides on the inducement of $T_{eff}$ and $T_{reg}$ cells in an in vitro sample of human T-cells, with the figure showing mean fluorescence intensity for phosphorylated signal transducer and activator of transcription 5 (pSTAT5) on the y-axis and dosage of wild type IL-2 or a modified IL-2 polypeptide on the x-axis. The modified IL-2 polypeptides tested in this figure are Composition A, Composition B, Composition C, and Composition D.

| Gating Strategy for T-cell Subset Identification | |
|---|---|
| T-Reg | CD4+, $CD25^{Hi}$, FoxP3+ |
| CD8 Teff | CD8+ |
| Naïve CD8 Teff | CD8+, CD45RA+ |
| CD4 conv | CD4+, FoxP3− | tative results are shown in FIG. 4 depicting the mean fluorescence intensity (MFI) for pStat5 (y-axis) as a function of dosage of either wild type IL-2, Composition A, Composition B, Composition C, or Composition D (x-axis).

Additional results of this experiment are shown below in Table 13. Notably, Composition A showed increased potency in inducing CD8+ cells compared to aldesleukin, whereas Composition B displayed only a modest reduction in potency. Compositions C and D similarly showed only modest reductions in potency in inducing CD8+ cells compared to aldesleukin. Additionally, all modified IL-2 polypeptides bearing a polymer group on residue 42 or 45 displayed substantial reduction in the CD8+/$T_{reg}$ half maximal effective concentration ($EC_{50}$) ratio compared to aldesleukin. In the table below, NT indicates the composition was not tested.

TABLE 13

| Composition | Side chain modifications | Tregs $EC_{50}$ | CD8+ $EC_{50}$ | CD8/ Tregs | Potency loss Syntein/PL |
|---|---|---|---|---|---|
| Aldesleukin | None | 0.019 | 9.069 | 477 | — |
| F | Y45 Obn | 0.168 | 27.646 | 165 | 3.0x |
| G | F42 Bip | 0.05 | 14.149 | 283 | 1.6x |
| K | 5 kDaPEG on Y45 | 3.016 | 24.68 | 8.18 | 2.7x |
| L | 0.5 kDaPEG on Y45 | 0.527 | 2.396 | 4.55 | 0.3x |
| E | 1 kDaPEG on Y45 | 0.796 | 3.628 | 4.56 | 0.4x |
| A | 0.5 kDaPEG on Y42 & Y45 | 0.709 | 1.521 | 2.15 | 0.2x |
| B | 0.5 kDaPEG on Y42 & Y45 6 kDa PEG on N-term | 9.267 | 16.534 | 1.78 | 1.8x |
| H | 0.5 kDaPEG on Y42 & Y45 11 kDa PEG on N-term | 37.156 | 77.458 | 2.08 | 8.5x |
| I | 0.5 kDaPEG on Y42 & Y45 3xPEG− Cys handle on N-term | 5.219 | 9.359 | 1.79 | 1x |
| J | 0.5 kDaPEG on Y42 & Y45 3xPEG+ 40 kDa on N-term | 57.115 | 153.836 | 2.69 | 17x |
| M | 0.5 kDaPEG on Y42 0.5 kDa + 6 kDa PEG Y45 | 1.468 | 3.397 | 2.31 | 0.4x |
| N | 0.5 kDa + 6 kDa PEG on Y42 0.5 kDa PEG Y45 | 2.252 | 5.317 | 2.36 | 0.6x |
| C | 0.5 kDaPEG on Y42 0.5 kDa + 30 kDa PEG Y45 | 4.598 | 12.939 | 2.81 | 1.4x |
| D | 0.5 kDa + 30 kDa PEG on Y42 0.5 kDa PEG Y45 | 4.396 | 14.075 | 3.2 | 1.6x |
| O | 0.5 kDa + 32 kDa monoPEG on Y42 0.5 kDa PEG Y45 | NT | NT | NT | NT |

Dose response curves for the inducement of $T_{eff}$ (CD8+) cells and $T_{reg}$ cells show that aldesleukin was substantially more potent in inducing $T_{reg}$ cells than Teff cells. Conversely, Compositions A-D each exhibited comparable potency in the induction of $T_{eff}$ cells and $T_{reg}$ cells. Compositions A-D all displayed a similar ability to induce $T_{eff}$ cells compared to aldesleukin or wild type IL-2, but substantially diminished ability to induce $T_{reg}$ cells. Represen- Example 7—Pharmacokinetic/Pharmacodynamic Studies A single-dose pharmacokinetic/pharmacodynamic experiment was performed in mice. Naïve, 6-8 weeks old, C57Bl/6 mice (Shanghai SLAC Laboratory Animal Co., LTD, Shanghai, China) received a single bolus intravenous (i.v.) injection of 52 nmoles/kg wild type or of modified IL-2 polypeptides. Study included 14 time points (5 min, 15 min, 1 h, 2 h, 4 h, 6 h, 12 h, 24 h, 36 h, 48 h, 72 h, 120 h, 168 h, 240 h) with 3 mice sampled per time point. At indicated time points, blood samples were collected in the presence of EDTA either via tail vein sampling or via cardiac puncture (end-point).

Blood samples were immediately processed by centrifugation. Plasma samples were cryopreserved at −80° C. until bioanalysis.

Bioanalysis of plasma samples was performed using a qualified human IL-2 LegendPlex bead assay (Biolegend, #740717, #740368, #740758). Concentrations of wild type and of modified IL-2 polypeptides and the internal standard in samples derived from plasma were determined using human IL-2 LegendPlex bead assay. PK data were subjected to a non-compartmental pharmacokinetic analysis by using the Phoenix WinNonlin software (version 6.3, Pharsight, Mountain View, Calif.). The linear/log trapezoidal rule was applied in obtaining the PK parameters.

Cell pellets were treated with 1×Lyse/Fix buffer (BD Bioscience, 558050) during 10 min. After washing, cells were stained with anti CD3, anti CD335, and anti CD25

TABLE 14-continued

| Eosinophils | Siglec-F+, SSC-A$^{high}$ |
|---|---|
| T | Siglec-F−, CD3+, CD335− |
| NK | Sielec-F−, CD3−, CD335+ |

Figure 5:
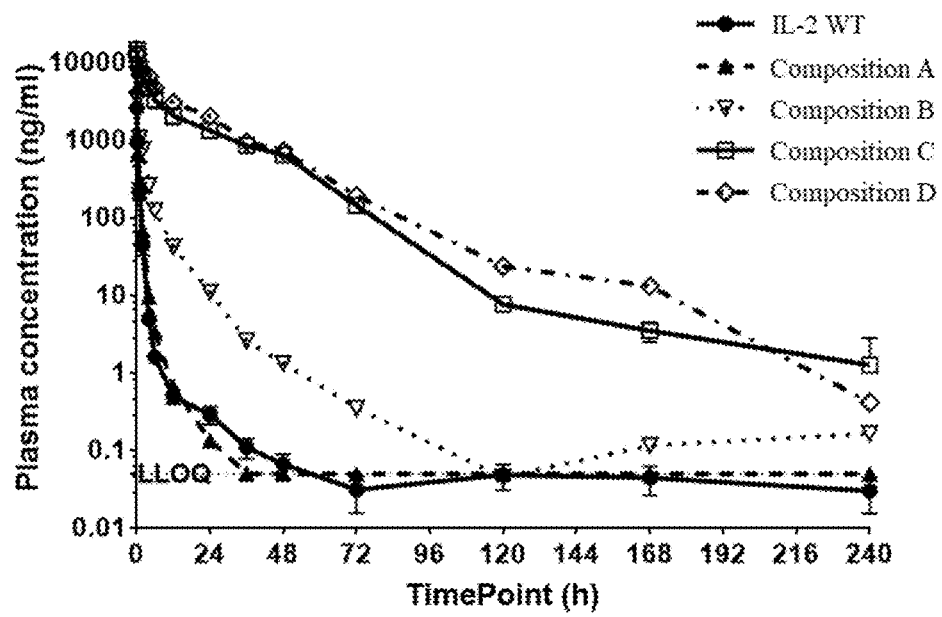
FIG. 5 shows plots measuring the effect of pegylation of modified IL-2 polypeptide on half-life extension, with the figure showing plasma concentration of modified IL-2 polypeptides on the y-axis and time on the x-axis. The modified IL-2 polypeptide tested in this figure are Composition A, Composition B, Composition C, and Composition D all tested at 52 nmoles/kg.

The resulting plasma concentrations of modified IL-2 polypeptide at various time points post dosing is shown in FIG. 5. Wild type IL-2 and Composition D were tested concurrently in the same study and monitored for 14 days while Composition A, Composition B, and Composition C were followed over 10 days in different studies performed under identical conditions. Compositions C and D showed substantially longer half-lives than the other compositions tested, indicating the beneficial effect of the large PEG group. Table 15 below shows additional PK parameters measured during this experiment. The PK parameters were determined by means of non-compartmental analysis (NCA) using R package "PK". The area under plasma concentration-time curves (AUC0-last) were calculated using the linear trapezoidal rule on the arithmetic means at the different time points while the extrapolation necessary for the AUC0-inf and AUMC 0-Inf was achieved assuming an exponential decay on the last 3 time points.

TABLE 15

| Composition | Side chain modifications | Dose (mg/kg) | AUC$_{0-last}$ (ng/mL*h) | AUCD (ng/mL*h)* (mg/kg) | MRT$_{last}$ (h) | T$_{1/2}$ (h) | C$_l$ (mL/min/kg) | Vss (L/kg) |
|---|---|---|---|---|---|---|---|---|
| Aldesleukin | — | .8 | 1227 | 1534 | 0.61 | .347 | 10.85 | 0.40 |
| A | 0.5 kDaPEG on Y42 & Y45 | .8 | 1741 | 2176 | 0.40 | .16 | 7.65 | 0.18 |
| B | 0.5 kDaPEG on Y42 & Y45 6 kDa PEG on N-term | .8 | 6767 | 68459 | 2.6 | 12.5 | 1.97 | 0.31 |
| C | 0.5 kDaPEG on Y42 0.5 kDa + 30 kDa PEG Y45 | .8 | 110095 | 137619 | 19 | 21 | 0.12 | 0.14 |
| D | 0.5 kDa + 30 kDa PEG on Y42 0.5 kDa PEG Y45 | 0.8 | 141462 | 176828 | 20 | 19 | 0.09 | 0.11 |
| O | 0.5 kDa + 32 kDa monoPEG on Y42 0.5 kDa PEG Y45 | 0.8 | NT | NT | NT | NT | NT | NT | antibodies for 30 min at 4° C. Cells were then permeabilized using cold BD Perm Buffer III and stained with antibodies against either Ki67, Siglec-F, CD4, CD8, FoxP3, CD62L, CD44 or pSTAT5. The FACS (fluorescence activated cell sorting) measurement was done with a Fortessa X-20 Flow Cytometer from BD.

For each cell subset indicated below in Table 14, the percentage of pSTAT5 positive cells, and percentage of Ki67 positive cells, cell counts, and cell frequency was determined.

TABLE 14

| T-Reg | Siglec-F−, CD3+, CD4+, CD25$^{Hi}$, FoxP3+ |
|---|---|
| CD8 Teff | Siglec-F−, CD3+, CD8+, CD4− |
| Naïve CD8 Teff | Siglec-F−, CD3+, CD8+, CD4−, CD62L$^{Hi}$, CD44$^{low}$ |
| CD8+ Central Memory (TCM) | Siglec-F−, CD3+, CD8+, CD4−, CD62L$^{Hi}$, CD44$^{Hi}$ |
| CD8+ Effector Memory (TEM) | Siglec-F−, CD3+, CD8+, CD4−, CD62L$^{low}$, CD44$^{Hi}$ |
| CD4 Teff | Siglec-F−, CD3+, CD4+, CD8− |
| Naïve CD4 Teff | Siglec-F−, CD3+, CD4+, CD8−, CD62L$^{Hi}$, CD44$^{low}$ |
| CD4+ Central Memory (TCM) | Siglec-F−, CD3+, CD4+, CD8−, CD62L$^{Hi}$, CD44$^{Hi}$ |
| CD4+ Effector Memory (TEM) | Siglec-F−, CD3+, CD4+, CD8−, CD62L$^{low}$, CD44$^{Hi}$ |

Figure 6A:
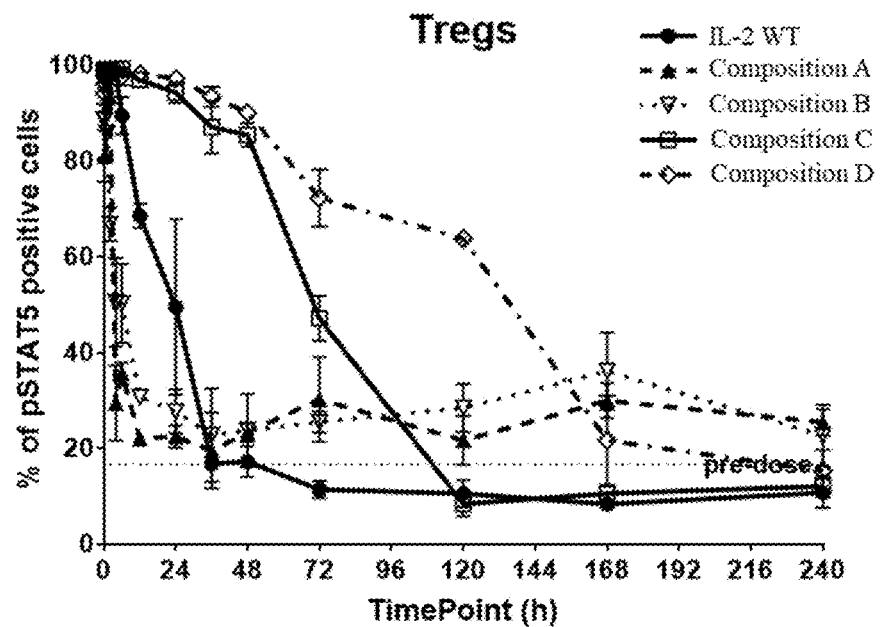
FIG. 6A shows plots measuring the effect of wild type and modified IL-2 polypeptides on the inducement of IL-2 signaling in Tregs in C57BL/6 mice, with the figure showing percentage of regulatory CD4+ T-cells (CD4+, FoxP3+, $CD25^{Hi}$) with phosphorylated signal transducer and activator of transcription 5 (pSTAT5) on the y-axis and time on the x-axis. The modified IL-2 polypeptide tested in this figure are Composition A, Composition B, Composition C, and Composition D all tested at 52 nmoles/kg.
Figure 6B:
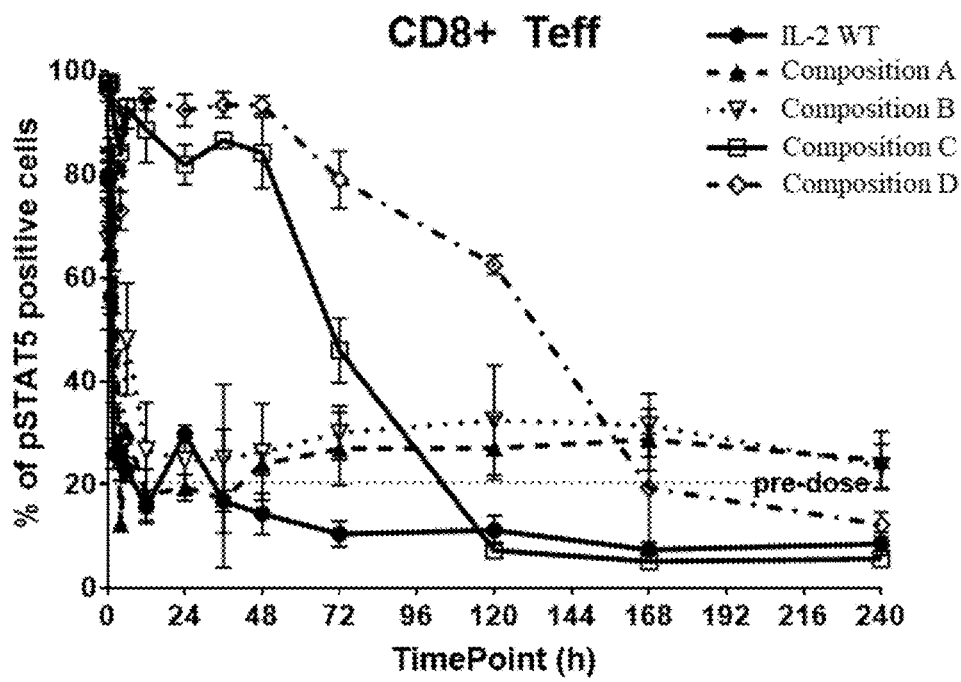
FIG. 6B shows plots measuring the effect of wild type and modified IL-2 polypeptides on the inducement of IL-2 signaling in CD8+ Teff in C57BL/6 mice, with the figure showing percentage of CD8+ Teff (CD3+, CD8+) with phosphorylated signal transducer and activator of transcription 5 (pSTAT5) on the y-axis and time on the x-axis. The modified IL-2 polypeptide tested in this figure are Composition A, Composition B, Composition C, and Composition D all tested at 52 nmoles/kg.

In addition to the concentration of the modified IL-2 polypeptide at each time point, inducement of proliferation of various immune cell types at each time point was also measured. Wild type IL-2 and Composition D were tested concurrently in the same study and monitored for 14 days while Composition A, Composition B, and Composition C were followed over 10 days in different studies performed under identical conditions. FIG. 6A shows plots measuring the effect of wild type and modified IL-2 polypeptides on the inducement of IL-2 signaling in Tregs with the figure showing percentage of regulatory CD4+ T-cells (CD4+, FoxP3+, CD25$^{Hi}$) with phosphorylated signal transducer and activator of transcription 5 (pSTAT5) on the y-axis and time on the x-axis. Composition D was shown to effectuate the response over the longest period of time. Similarly, FIG. 6B shows plots measuring the effect of wild type and modified IL-2 polypeptides on the inducement of IL-2 signaling in CD8+ Teff in C57BL/6 mice, with the figure showing percentage of CD8+ Teff (CD3+, CD8+) with phosphorylated signal transducer and activator of transcription 5 (pSTAT5) on the y-axis and time on the x-axis, with Composition D showing the highest duration of response. Additionally, percentages of pSTAT5 positive cells at peak levels (1 h after injection of IL-2 polypeptide) were measured for various dosage levels of different IL-2 polypeptides. The results are shown below in Table 16.

TABLE 16

| Composition | Side chain modifications | Dose (mg/kg) | Tregs % of pSTAT5 positive cells | CD8+ % of pSTAT5 positive cells | Ratio Tregs/CD8+ |
|---|---|---|---|---|---|
| Aldesleukin | None | 0.01 | 81.0 ± 5.8 | 21.3 ± 6.7 | 3.8 |
| | | 0.03 | 86.9 ± 5.2 | 31.3 ± 6.2 | 2.8 |
| | | 0.1 | 91.1 ± 2.9 | 29.6 ± 4.4 | 3.1 |
| | | 0.3 | 96.2 ± 1.3 | 63.2 ± 9.0 | 1.5 |
| | | 0.8 | 93.3 ± 3.8 | 74.1 ± 11 | 1.3 |
| A | 0.5 kDaPEG on Y42 & Y45 | 0.01 | 24.1 ± 4.8 | 36.2 ± 7.1 | 0.7 |
| | | 0.03 | 19.2 ± 8.4 | 37.2 ± 9.4 | 0.5 |
| | | 0.1 | 73.2 ± 4.0 | 74.0 ± 7.7 | 1 |
| | | 0.3 | 80.9 ± 6.0 | 77.7 ± 5.4 | 1 |
| | | 0.8 | 96 ± 1.0 | 80.5 ± 6.6 | 1.2 |
| B | 0.5 kDaPEG on Y42 & Y45 6 kDa PEG on N-term | 0.8 | 85.9 ± 5.9 | 68.5 ± 3.3 | 1.3 |
| C | 0.5 kDaPEG on Y42 0.5 kDa + 30 kDa PEG Y45 | 0.8 | 98.5 ± 0.5 | 97.7 ± 0.6 | 1.0 |
| D | 0.5 kDa + 30 kDa PEG on Y42 0.5 kDa PEG Y45 | 0.8 | 98.6 ± 0.1 | 97.2 ± 0.8 | 1.0 |
| O | 0.5 kDa + 32 kDa monoPEG on Y42 0.5 kDa PEG Y45 | 0.8 | NT | NT | NT |

Figure 7A:
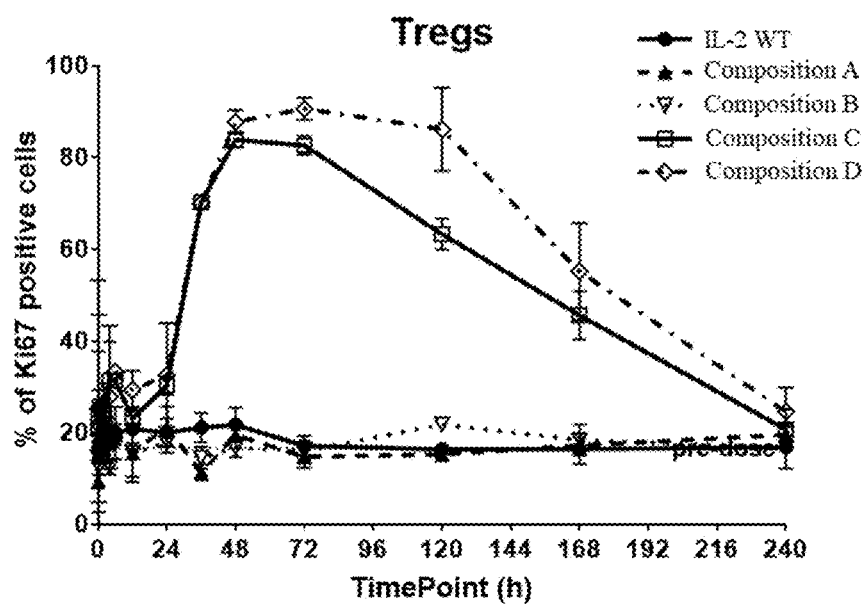
FIG. 7A shows plots measuring the effect of wild type and modified IL-2 polypeptides on the inducement of Tregs proliferation in C57BL/6 mice, with the figure showing percentage of regulatory CD4+ T-cells (CD4+, FoxP3+, $CD25^{Hi}$) positive for marker of proliferation Ki67 on the y-axis and time on the x-axis. The modified IL-2 polypeptide tested in this figure are Composition A, Composition B, Composition C, and Composition D all tested at 52 nmoles/kg.
Figure 7B:
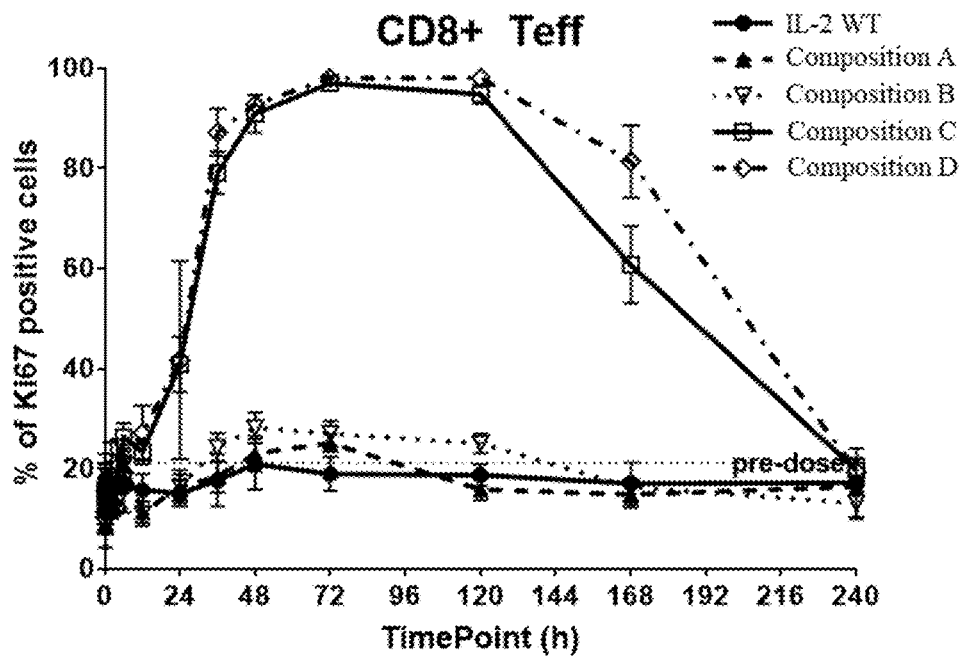
FIG. 7B shows plots measuring the effect of wild type and modified IL-2 polypeptides on the proliferation of CD8+ Teff in C57BL/6 mice, with the figure showing percentage of CD8+ Teff (CD3+, CD8+) positive for marker of proliferation Ki67 on the y-axis and time on the x-axis. The modified IL-2 polypeptide tested in this figure are Composition A, Composition B, Composition C, and Composition D all tested at 52 nmoles/kg.

Additionally, immune cells positive for the marker of proliferation Ki67 were also measured at these time points. Wild type IL-2 and Composition D were tested concurrently in the same study and monitored for 14 days while Composition A, Composition B, and Composition C were followed over 10 days in different studies performed under identical conditions. FIG. 7A shows plots measuring the effect of wild type and modified IL-2 polypeptides on the inducement of Treg proliferation in C57BL/6 mice, with the figure showing percentage of regulatory CD4+ T-cells (CD4+, FoxP3+, CD25$^{Hi}$) positive for marker of proliferation Ki67 on the y-axis and time on the x-axis. FIG. 7B shows plots measuring the effect of wild type and modified IL-2 polypeptides on the proliferation of CD8+ Teff in C57BL/6 mice, with the figure showing percentage of CD8+ Teff (CD3+, CD8+) positive for marker of proliferation Ki67 on the y-axis and time on the x-axis. Both FIG. 7A and FIG. 7B show that compositions C and D exhibit a greater ability to induce proliferation of Treg and CD8+ cells over timer Table 17 shows additional pharmacodynamic data for the peak time point of Ki67 positive cells for the various modified IL-2 polypeptides tested in the study.

TABLE 17

| Composition | Side chain modifications | Dose (mg/kg) | Tregs % of Ki67+ positive cells | Timepoint at Peak Tregs | CD8+ % of Ki67+ positive cells | Timepoint at Peak Teff |
|---|---|---|---|---|---|---|
| Aldesleukin | None | 0.8 | 28.3 ± 3.7 | 20 h | 19.6 ± 3 | 48 h |
| A | 0.5 kDaPEG on Y42 & Y45 | 0.8 | 21.3 ± 4.4 | 20 h | 23 ± 3.5 | 48 h |
| B | 0.5 kDaPEG on Y42 & Y45 6 kDa PEG on N-term | 0.8 | 17.8 ± 2.2 | 20 h | 28.2 ± 3.1 | 48 h |
| C | 0.5 kDaPEG on Y42 0.5 kDa + 30 kDa PEG Y45 | 0.8 | 83.9 ± 1.7 | 48 h | 97 ± 1.2 | 72 h |
| D | 0.5 kDa + 30 kDa PEG on Y42 0.5 kDa PEG Y45 | 0.8 | 90.7 ± 2.4 | 72 h | 98.1 ± 0.5 | 120 h |
| O | 0.5 kDa + 32 kDa monoPEG on Y42 0.5 kDa PEG Y45 | 0.8 | NT | NT | NT | NT |

Figure 8A:
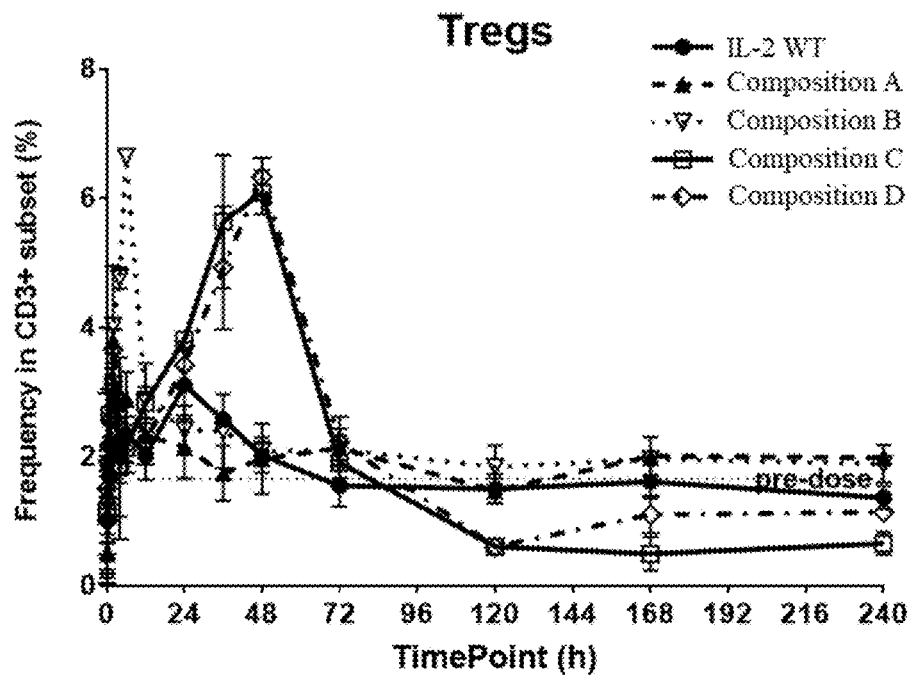
FIG. 8A shows plots measuring the effect of wild type and modified IL-2 polypeptides on the expansion of Tregs in C57BL/6 mice, with the figure showing percentage of regulatory CD4+ T-cells (CD4+, FoxP3+, $CD25^{Hi}$) within the lymphocyte compartment (CD3+) on the y-axis and time on the x-axis. The modified IL-2 polypeptide tested in this figure are Composition A, Composition B, Composition C, and Composition D all tested at 52 nmoles/kg.
Figure 8B:
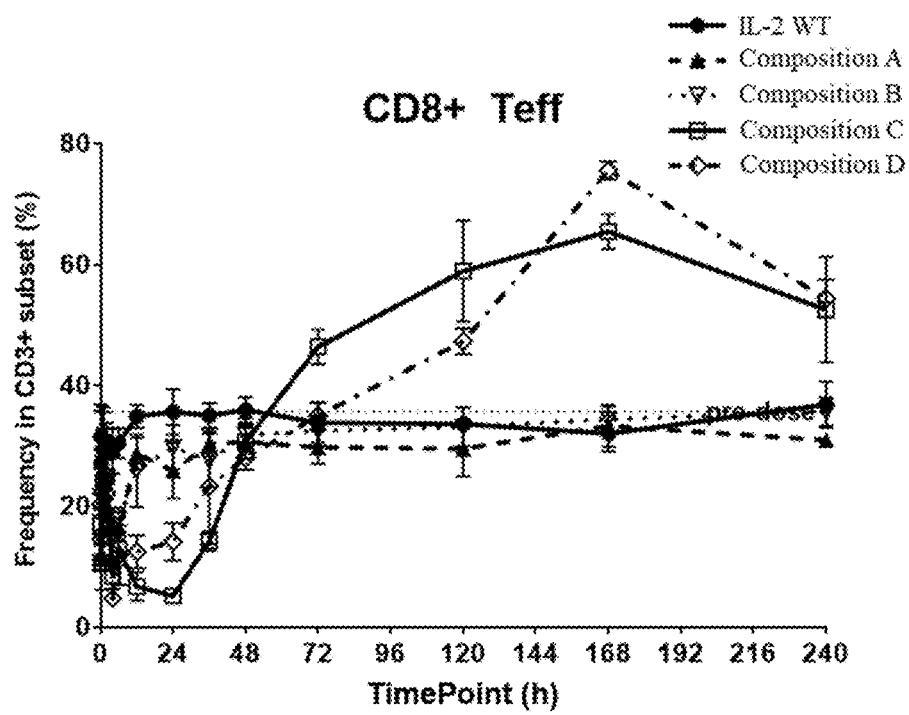
FIG. 8B shows plots measuring the effect of wild type and modified IL-2 polypeptides on the expansion of circulating CD8+ Teff in C57BL/6 mice, with the figure showing percentage of CD8+ Teff (CD3+, CD8+) within the lymphocyte compartment (CD3+) on the y-axis and time on the x-axis. The modified IL-2 polypeptide tested in this figure are Composition A, Composition B, Composition C, and Composition D all tested at 52 nmoles/kg.
Figure 9:
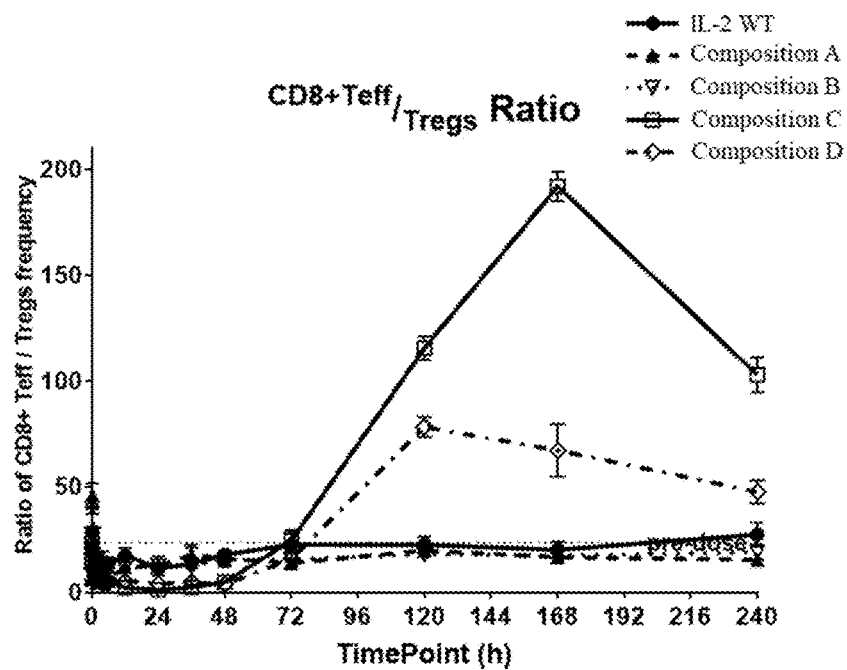
FIG. 9 shows plots measuring the effect of wild type and modified IL-2 polypeptides on the ratio of circulating CD8+ Teff and regulatory CD4+ T-cells in C57BL/6 mice, with the figure showing ratio of frequencies CD8+ Teff (CD3+, CD8+) and regulatory CD4+ T-cells (CD4+, FoxP3+, $CD25^{Hi}$) within the lymphocyte compartment (CD3+) on the y-axis and time on the x-axis. The modified IL-2 polypeptide tested in this figure are Composition A, Composition B, and Composition C, and Composition D all tested at 52 nmoles/kg.

FIG. 8A shows plots measuring the effect of wild type and modified IL-2 polypeptides on the expansion of Tregs in C57BL/6 mice, with the figure showing percentage of regulatory CD4+ T-cells (CD4±, FoxP3±, CD25$^{Hi}$) within the lymphocyte compartment (CD3±) on the y-axis and time on the x-axis. FIG. 8B shows plots measuring the effect of wild type and modified IL-2 polypeptides on the expansion of circulating CD8±Teff in C57BL/6 mice, with the figure showing percentage of CD8±Teff (CD3±, CD8±) within the lymphocyte compartment (CD3±) on the y-axis and time on the x-axis. FIG. 9 shows plots measuring the effect of wild type and modified IL-2 polypeptides on the ratio of circulating CD8+ Teff and regulatory CD4+ T-cells in C57BL/6 mice, with the figure showing ratio of frequencies CD8+ Teff (CD3+, CD8+) and regulatory CD4+ T-cells (CD4+, FoxP3+, CD25$^{Hi}$) within the lymphocyte compartment (CD3+) on the y-axis and time on the x-axis. The modified IL-2 polypeptides tested and depicted in these figures were Composition A, Composition B, Composition C, and Composition D, all tested at 52 nmoles/kg. Table 18 shows additional pharmacodynamic data for the peak time point of cells within the lymphocyte compartment positive cells for the various modified IL-2 polypeptides tested in the study. For each of FIGS. 8A, 8B, and 9, wild type IL-2 and Composition D were tested concurrently in the same study and monitored for 14 days while Composition A, Composition B, and Composition C were followed over 10 days in different studies performed under identical conditions.

TABLE 18

| Composition | Side chain modifications | Dose (mg/kg) | Tregs % of Tregs within CD3+ | Timepoint at Peak Tregs | CD8+ % of CD8+ within CD3+ | Timepoint at Peak Teff |
|---|---|---|---|---|---|---|
| Aldesleukin | None | 0.8 | 3.52 ± 0.4 | 20 h | 32.1 ± 3 | 36 h |
| A | 0.5 kDaPEG on Y42 & Y45 | 0.8 | 3.8 ± 0.2 | 2 h | 33.3 ± 3.5 | 168 h |
| B | 0.5 kDaPEG on Y42 & Y45 6 kDa PEG on N-term | 0.8 | 6.6 ± 0 | 6 h | 35.7 ± 2.4 | 240 h |
| C | 0.5 kDaPEG on Y42 0.5 kDa + 30 kDa PEG Y45 | 0.8 | 6.1 ± 0.3 | 48 h | 65.5 ± 2.9 | 168 h |
| D | 0.5 kDa + 30 kDa PEG on Y42 0.5 kDa PEG Y45 | 0.8 | 6.3 ± 0.3 | 48 h | 75.7 ± 1.5 | 168 h |
| O | 0.5 kDa + 32 kDa monoPEG on Y42 0.5 kDa PEG Y45 | 0.8 | NT | NT | NT | NT |

Figure 10A:
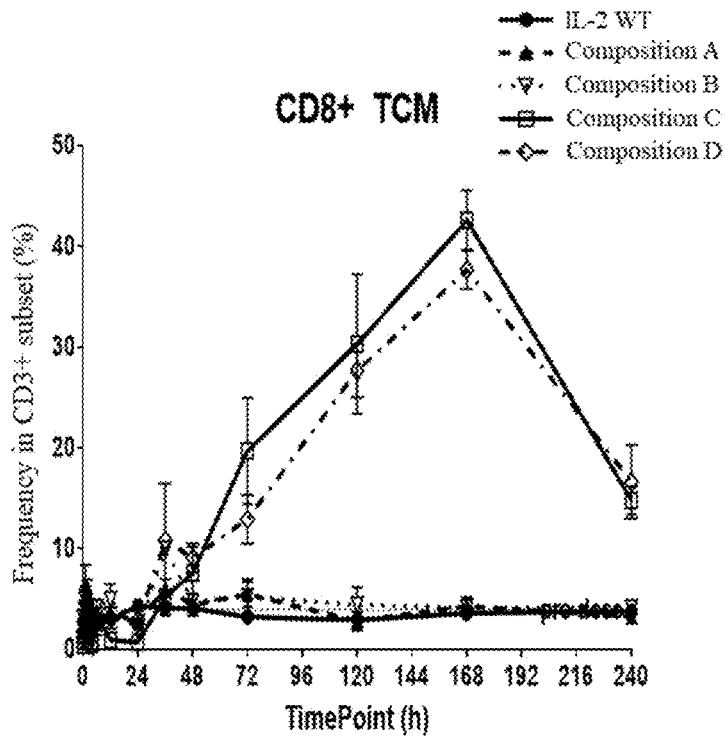
FIG. 10A shows plots measuring the effect of wild type and modified IL-2 polypeptides on the expansion of circulating Central Memory CD8+ Teff in C57BL/6 mice, with the figure showing percentage of CD8+ Central Memory T-cells (CD3+, CD8+, $CD62L^{hi}$. $CD44^{hi}$) within the lymphocyte compartment (CD3+) on the y-axis and time on the x-axis. The modified IL-2 polypeptide tested in this figure are Composition A, Composition B, and Composition C, and Composition D all tested at 52 nmoles/kg.
Figure 10B:
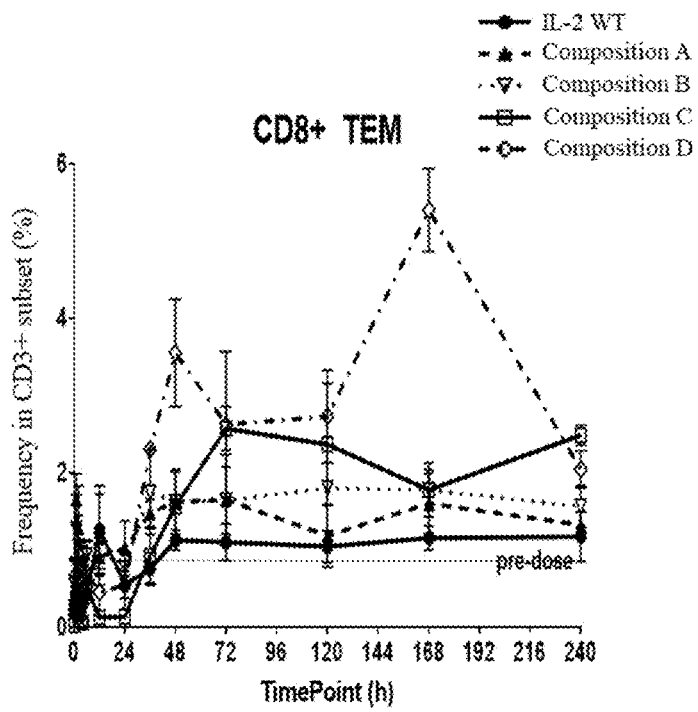
FIG. 10B shows plots measuring the effect of wild type and modified IL-2 polypeptides on the expansion of circulating Effector Memory CD8+ Teff in C57BL/6 mice, with the figure showing percentage of CD8+ Effector Memory T-cells (CD3+, CD8+, $CD62L^{low}$, $CD44^{hi}$) within the lymphocyte compartment (CD3+) on the y-axis and time on the x-axis. The modified IL-2 polypeptide tested in this figure are Composition A, Composition B, and Composition C, and Composition D all tested at 52 nmoles/kg.
Figure 10C:
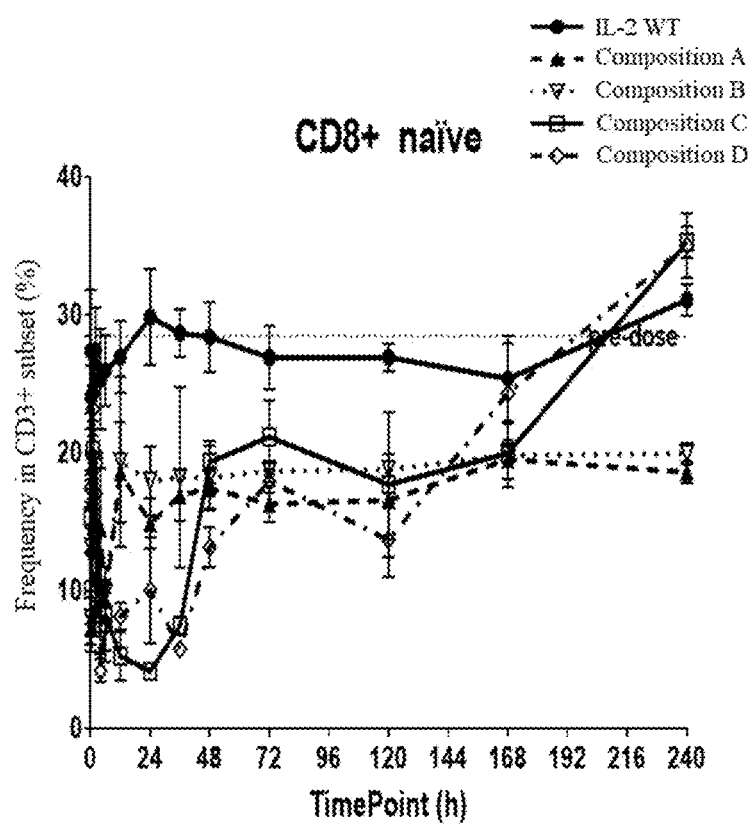
FIG. 10C shows plots measuring the effect of wild type and modified IL-2 polypeptides on the expansion of naïve CD8+ Teff in C57BL/6 mice, with the figure showing percentage of CD8+ naïve T-cells (CD3+, CD8+, $CD62L^{Hi}$, $CD44^{low}$) within the lymphocyte compartment (CD3+) on the y-axis and time on the x-axis. The modified IL-2 polypeptide tested in this figure are Composition A, Composition B, and Composition C, and Composition D all tested at 52 nmoles/kg.
Figure 15A:
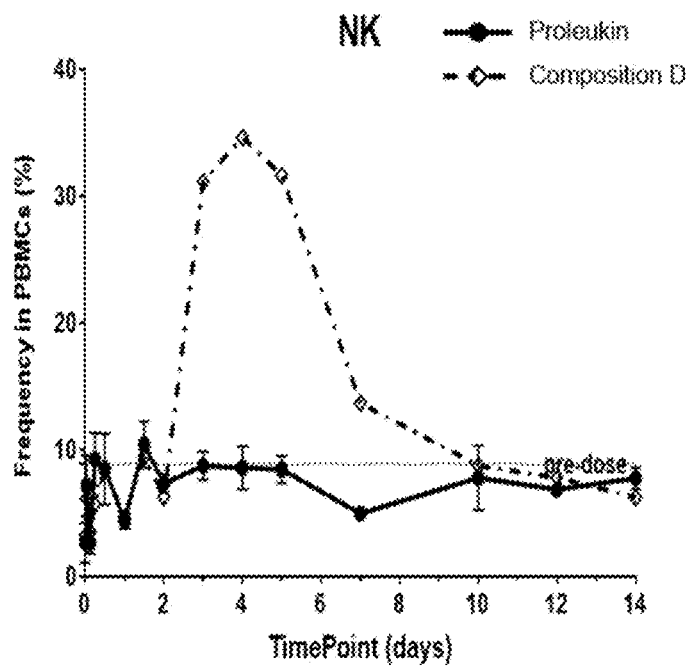
FIG. 15A shows plots measuring the effect of wild type and modified IL-2 polypeptide on the expansion of circulating Natural Killer cells in C57BL/6 mice, with the figure showing percentage of Natural Killer cells (CD3−, $CD49b^+$) within the leukocyte compartment on the y-axis and time on the x-axis. The modified IL-2 polypeptide tested in this figure is Composition D, tested at 52 nmoles/kg.
Figure 15B:
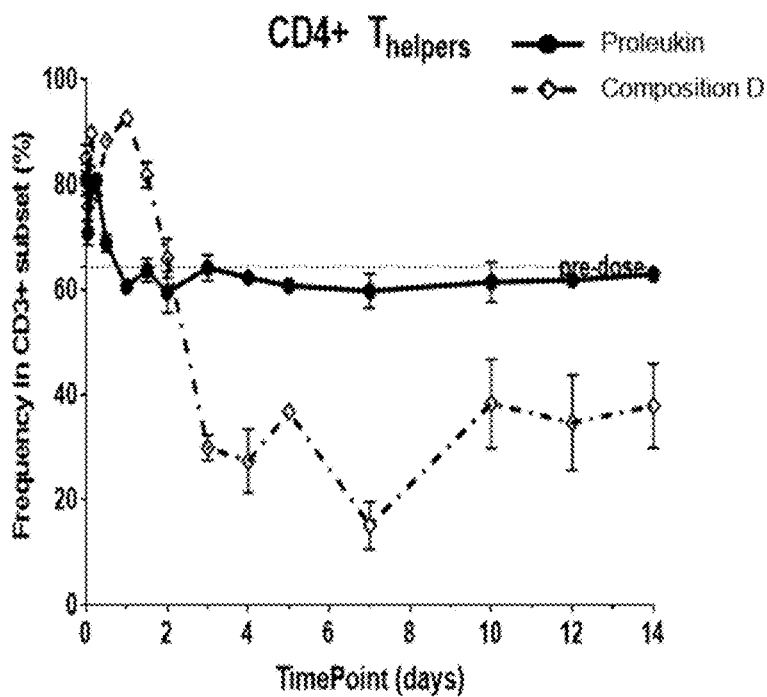
FIG. 15B shows plots measuring the effect of wild type and modified IL-2 polypeptides on the expansion of circulating CD4+ $T_{helpers}$ cells in C57BL/6 mice, with the figure showing percentage of CD4+ $T_{helpers}$ cells (CD3+, CD4+, $CD25^{low}$) within the lymphocyte compartment (CD3+) on the y-axis and time on the x-axis. The modified IL-2 polypeptide tested in this figure is Composition D, tested at 52 nmoles/kg.
Figure 15C:
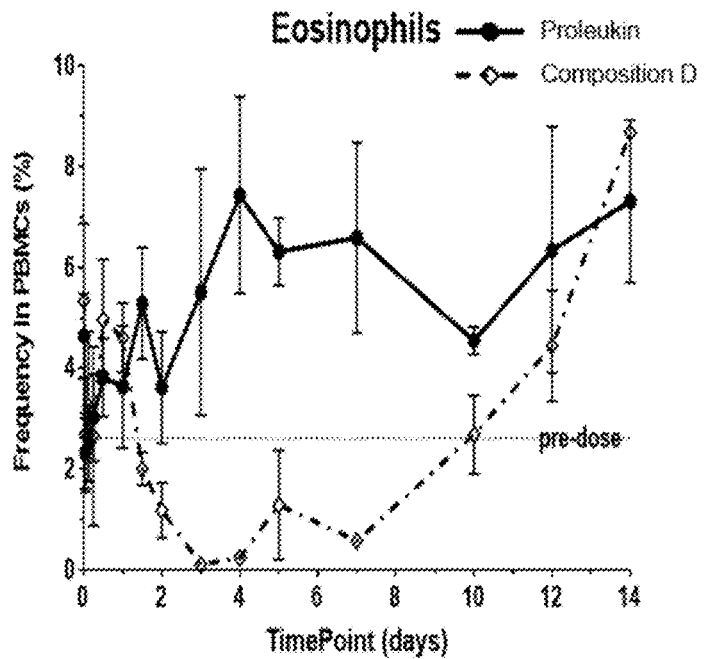
FIG. 15C shows plots measuring the effect of wild type and modified IL-2 polypeptides on the expansion of eosinophils in C57BL/6 mice, with the figure showing percentage of eosinophils ($SSC^{Hi}$, $Siglec-F^{Hi}$) within the lymphocyte leukocyte on the y-axis and time on the x-axis. The modified IL-2 polypeptide tested in this figure is Composition D, tested at 52 nmoles/kg.

FIG. 10A shows plots measuring the effect of wild type and modified IL-2 polypeptides on the expansion of circulating Central Memory CD8±Teff in C57BL/6 mice, with the figure showing percentage of CD8±Central Memory T-cells (CD3±, CD8±, $CD62L^{hi}$, $CD44^{hi}$) within the lymphocyte compartment (CD3±) on the y-axis and time on the x-axis. FIG. 10B shows plots measuring the effect of wild type and modified IL-2 polypeptides on the expansion of circulating Effector Memory CD8±Teff in C57BL/6 mice, with the figure showing percentage of CD8±Effector Memory T-cells (CD3±, CD8±, $CD62L^{low}$, $CD44^{hi}$) within the lymphocyte compartment (CD3±) on the y-axis and time on the x-axis. FIG. 10C shows plots measuring the effect of wild type and modified IL-2 polypeptides on the expansion of naïve CD8+ Teff in C57BL/6 mice, with the figure showing percentage of CD8+ naïve T-cells (CD3+, CD8+, $CD62L^{Hi}$, $CD44^{low}$) within the lymphocyte compartment (CD3+) on the y-axis and time on the x-axis. The modified IL-2 polypeptides tested and depicted in these figures were Composition A, Composition B, and Composition C, and Composition D all tested at 52 nmoles/kg. For each of FIGS. 10A-C, wild type IL-2 and Composition D were tested concurrently in the same study and monitored for 14 days while Composition A, Composition B, and Composition C were followed over 10 days in different studies performed under identical conditions. FIG. 15A shows plots measuring the effect of wild type and modified IL-2 polypeptides on the expansion of circulating Natural Killer cells in C57BL/6 mice, with the figure showing percentage of Natural Killer cells (CD3−, $CD49b^{+}$) within the leukocyte compartment on the y-axis and time on the x-axis. The modified IL-2 polypeptide tested in this figure was Composition D, tested at 52 nmoles/kg. FIG. 15B shows plots measuring the effect of wild type and modified IL-2 polypeptides on the expansion of circulating $CD4+T_{helpers}$ cells in C57BL/6 mice, with the figure showing percentage of CD4+ $T_{helpers}$ cells (CD3+, CD4+, $CD25^{low}$) within the lymphocyte compartment (CD3+) on the y-axis and time on the x-axis. The modified IL-2 polypeptide tested in this figure was Composition D, tested at 52 nmoles/kg. FIG. 15C shows plots measuring the effect of wild type and modified IL-2 polypeptides on the expansion of eosinophils in C57BL/6 mice, with the figure showing percentage of eosinophils ($SSC^{Hi}$, $Siglec\text{-}F^{Hi}$) within the lymphocyte leukocyte on the y-axis and time on the x-axis. The modified IL-2 polypeptide tested in this figure was Composition D, tested at 52 nmoles/kg.

Example 8—Pharmacokinetic/Pharmacodynamic Studies

Figure 16A:
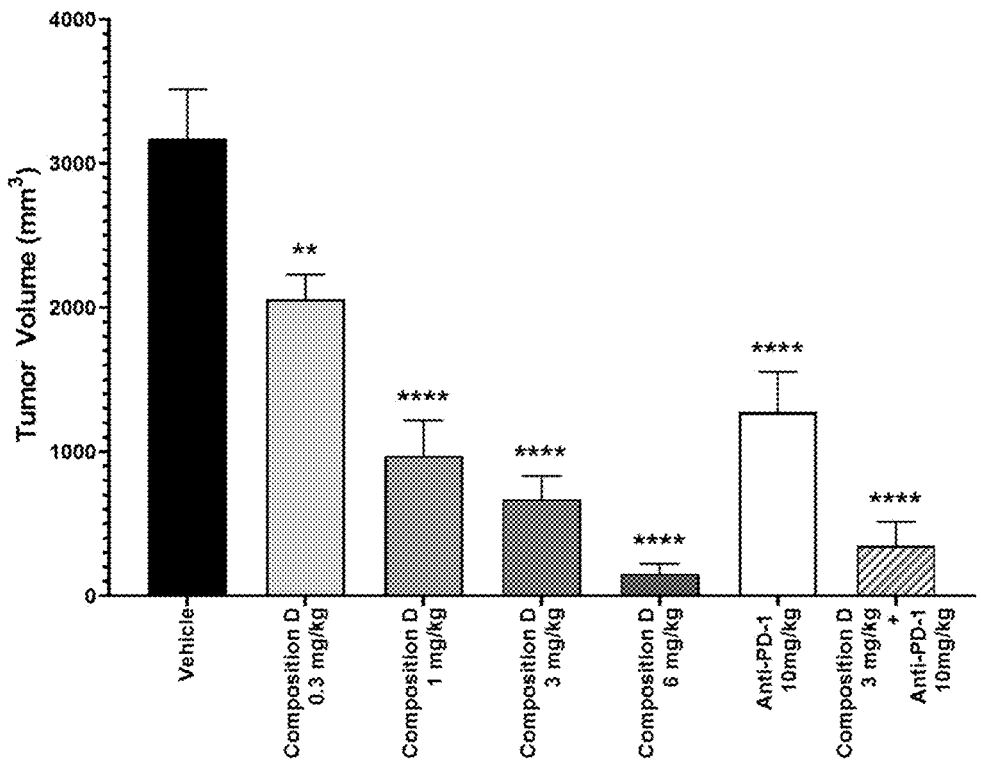
FIG. 16A shows a bar chart measuring the effect of anti-PD1 antibody and modified IL-2 polypeptide on the size of CT26 syngeneic colon carcinoma tumors in BALB/c mice after three weeks of treatment. The modified IL-2 polypeptide tested in this figure is Composition D tested as a single agent at 0.3, 1, 3, and 6 mg/kg (18, 61, 184, and 368 nmoles/kg, respectively). Composition D was also tested at 3 mg/kg in combination with anti-PD1 antibody at 10 mg/kg. (n=9 animals; mean±SEM).
Figure 16B:
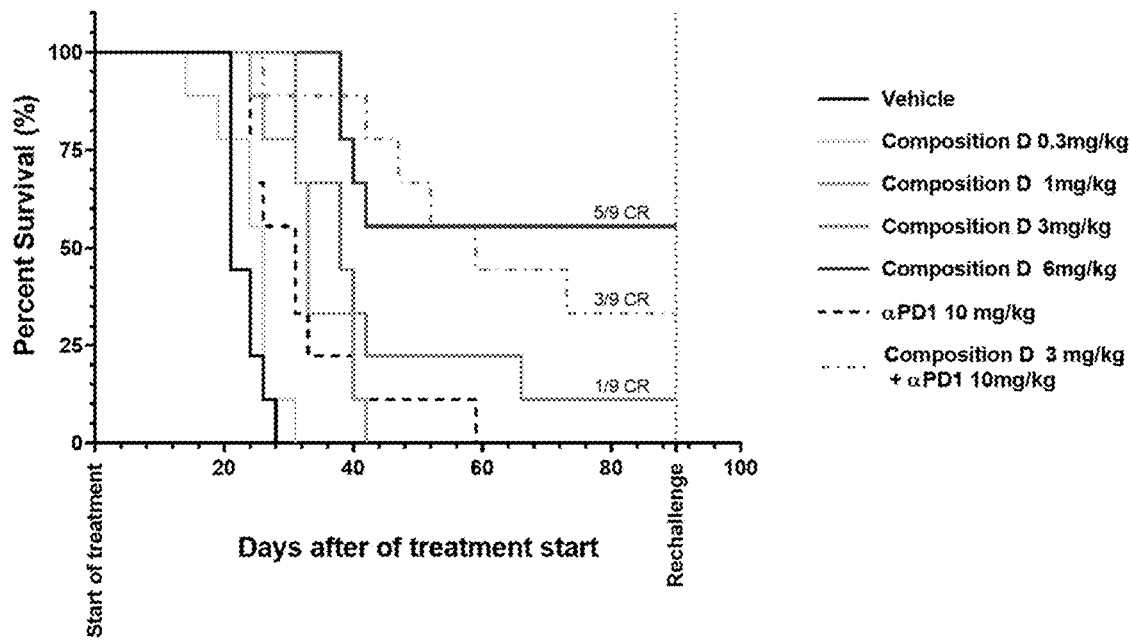
FIG. 16B shows plot measuring the effect of anti-PD1 antibody and modified IL-2 polypeptide on the survival of BALB/c mice engrafted with CT26 syngeneic colon carcinoma tumor cells. The modified IL-2 polypeptide tested in this figure is Composition D tested as a single agent at 0.3, 1, 3, and 6 mg/kg (18, 61, 184, and 368 nmoles/kg, respectively). Composition D was also tested at 3 mg/kg in combination with anti-PD1 antibody at 10 mg/kg. (n=9 animals; CR=Complete Regression).

An in vivo efficacy study was performed in mice. Naïve, 6-8 weeks old, BALB/c female mice (Shanghai SLAC Laboratory Animal Co., LTD, Shanghai, China) were inoculated subcutaneously at the right lower flank with CT26 tumor cells ($3\times10^5$) in 0.1 mL of PBS for tumor development. The animals were randomized (using an Excel-based randomization software performing stratified randomization based upon tumor volumes), and treatment started when the average tumor volume reached approximately 65 $mm^3$. Animals treated with composition D receiving two to three 10 mL/kg bolus intravenous (i.v.) injections of 0.3, 1, 3, and 6 mg/kg (18, 61, 184, and 368 nmoles/kg respectively) of modified IL-2 polypeptides. Animals treated with anti-PD-1 antibody received 10 mL/kg bolus intraperitoneal (i.p.) injections of 10 mg/kg of InVivoMAb anti-mouse PD-1/CD279 (Clone RMP1-14; BioXcell; Cat #BE0146) twice per week over three weeks. Finally, animals treated with a combination of composition D and anti-PD-1 antibody received a single 10 mL/kg bolus intravenous (i.v.) injection of 3 mg/kg (184 nmoles/kg) of modified IL-2 polypeptides on day 0, 7, and 14 and 10 ml/kg bolus intraperitoneal (i.p.) injections of 10 mg/kg of InVivoMAb anti-mouse PD-1/CD279 (Clone RMP1-14; BioXcell; Cat #BE0146) twice per week over three weeks. After inoculation, the animals were checked daily for morbidity and mortality. At the time, animals were checked for effects on tumor growth and normal behavior such as mobility, food and water consumption, body weight gain/loss (body weights were measured twice weekly), eye/hair matting and any other abnormal effect. The major endpoints were delayed tumor growth or complete tumor regression. Tumor sizes were measured twice a week in two dimensions using a caliper, and the volume was expressed in $mm^3$ using the formula: V=0.5 a×b² where a and b are the long and short diameters of the tumor, respectively. Death and observed clinical signs were recorded on the basis of the numbers of animals within each subset. FIG. 16A shows a bar chart describing the effect of anti-PD1 antibody and modified IL-2 polypeptide on the size of CT26 syngeneic colon carcinoma tumors in BALB/c mice after three weeks of treatment. The modified IL-2 polypeptide tested in this figure is Composition D tested as a single agent at 0.3, 1, 3, and 6 mg/kg (18, 61, 184, and 368 nmoles/kg respectively). Composition D was also tested at 3 mg/kg in combination with anti-PD1 antibody at 10 mg/kg. (n=9 animals; mean±SEM). FIG. 16B shows a plot describing the effect of anti-PD1 antibody and modified IL-2 polypeptide on the survival of BALB/c mice engrafted with CT26 syngeneic colon carcinoma tumors cells. The modified IL-2 polypeptide tested in this figure is Composition D tested as a single agent at 0.3, 1, 3, and 6 mg/kg (18, 61, 184, and 368 nmoles/kg respectively). Composition D was also tested at 3 mg/kg in combination with anti-PD1 antibody at 10 mg/kg. (n=9 animals; CR=Complete Regression).

Figure 17:
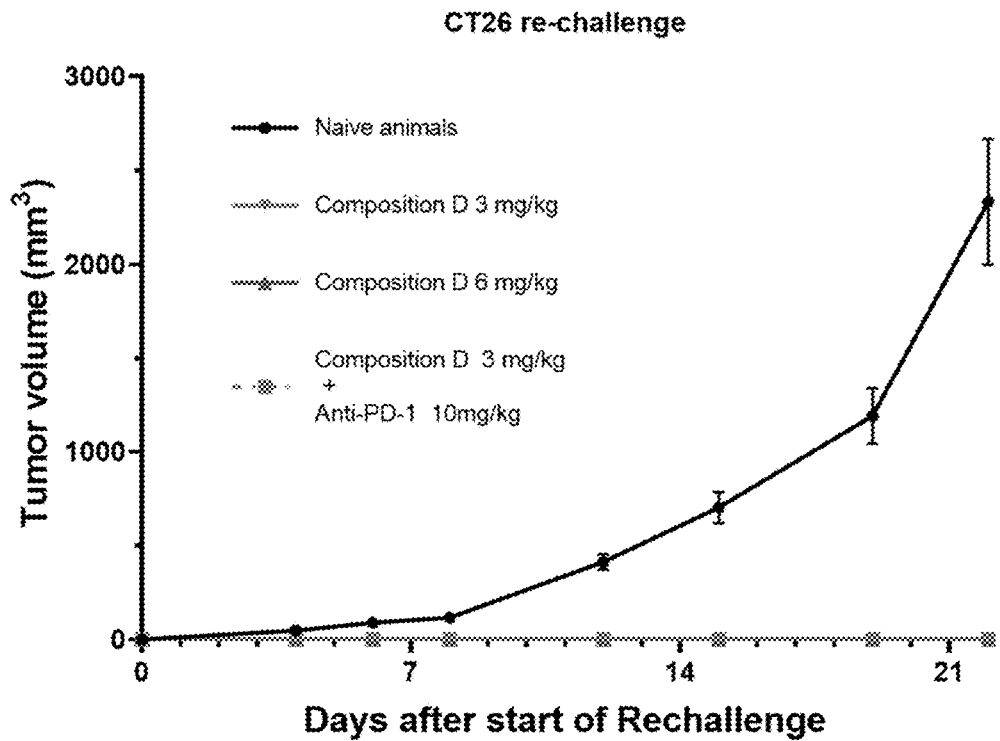
FIG. 17 shows a plot measuring the effect of anti-PD1 antibody and modified IL-2 polypeptide pre-treatment on the engraftment and growth of CT26 syngeneic colon carcinoma tumors inoculated in naïve BALB/c mice vs in pre-treated animals. Ninety days after first treatment initiation (69 days after end of treatment) ten naïve animals and nine experienced animals that showed complete tumor rejection were rechallenged with $3 \times 10^5$ CT26 cells s.c in the opposite flank. Experienced animals were the following: 1 animal treated with composition D at 3 mg/kg, 5 animals treated with composition D at 6 mg/kg, and 3 animals treated with Composition D at 3 mg/kg in combination with anti-PD1 antibody at 10 mg/kg. Figure shows tumor volume ($mm^3$) on the y-axis and time on the x-axis. (naïve group: n=10 animals; mean±SEM).

A re-challenge study was performed on tumor-free animals. Three months after start of treatment, animals that showed complete tumor regression were enrolled in a re-challenge study to probe the establishment of a long-lasting immunological memory response. Briefly, ten naïve non-treated control animals, one animal previously treated with composition D at 3 mg/kg, five animals previously treated with composition D at 6 mg/kg, and three animals previously treated with Composition D at 3 mg/kg in combination with anti-PD1 antibody at 10 mg/kg were inoculated subcutaneously at the left lower flank with CT26 tumor cells (3×10⁵) in 0.1 mL of PBS. At the time of routine monitoring, animals were checked for effects on tumor growth and normal behavior such as mobility, food and water consumption, body weight gain/loss (body weights were measured twice weekly), eye/hair matting and any other abnormal effect. The major endpoints were delayed tumor growth or tumor graft rejection. Tumor sizes were measured twice a week in two dimensions using a caliper, and the volume was expressed in mm³ using the formula: V=0.5 a×b² where a and b are the long and short diameters of the tumor, respectively. Death and observed clinical signs were recorded on the basis of the numbers of animals within each subset. FIG. 17 shows a plot depicting the effect of anti-PD1 antibody and modified IL-2 polypeptide pre-treatment on the engraftment and growth of CT26 syngeneic colon carcinoma tumors inoculated in naïve BALB/c mice vs in pre-treated animals. Ninety days after first treatment initiation (69 days after end of treatment) ten naïve animals and nine experienced animal that showed completed tumor rejection were rechallenged with 3×10⁵ CT26 cells s.c in the opposite flank. Experienced animals were the following: one animal treated with composition D at 3 mg/kg, five animals treated with composition D at 6 mg/kg, and three animals treated with Composition D at 3 mg/kg in combination with anti-PD 1 antibody at 10 mg/kg. FIG. 17 shows tumor volume (mm³) on the y-axis and time on the x-axis. (naïve group: n=10 animals; mean±SEM).

Example 9—Pharmacokinetic/Pharmacodynamic Studies in Non-Human Primates

A pharmacokinetic/pharmacodynamic experiment was performed in cynomolgus monkeys following single intravenous administration. Cynomolgus monkeys of Mauritius origin at least 24-months old were acclimated for 14 days and allocated to 3 groups (1 Male/1 Female per group) and dosed via a 15-minute intravenous infusion of composition D at doses of 0.01, 0.03 and 0.1 mg/kg of modified IL-2 polypeptides (0.61, 1.83 and 6.1 nmoles/kg respectively) formulated in 10 mM sodium acetate buffer, 8.4% w/v sucrose, 0.02% w/v, polysorbate 80 at pH 5.0. Animals were sampled for blood at various timepoints for pharmacokinetics and immunophenotyping assessment. Blood samples for pharmacokinetics (500 µL) were collected from the appropriate vein (femoral artery/vein when possible) into a tube containing K2EDTA and placed on wet ice pending centrifugation (10 min, 3500 rpm, +4° C.). Resulting plasma was stored at −80° C. until bioanalysis. Bioanalysis of plasma samples was performed using a sandwich Meso Scale Discovery (MSD) electrochemiluminescence (ECL) assay built on anti-IL-2 (R&D Systems, cat. no. MAB2021) and biotinylated anti-PEG (GenScript, cat. no. A01796-100) antibodies as capture and detection reagents, respectively. PK evaluation was subjected to a non-compartmental pharmacokinetic analysis by using the Phoenix software (version 8.2.0, Certara). The linear/log trapezoidal rule was applied in obtaining the PK parameters.

Blood samples for immunophenotyping (150 µL) were collected and transferred into a 96-well V-bottom plate then fixed and permeabilized with precooled 1×TFP Fix/Perm buffer (Transcription Factor Phospho Buffer Set, BD Biosciences, #563239) during 50-60 minutes at 4° C. Cells were then washed twice with 200 µl of 1×TFP Perm/Wash buffer (Transcription Factor Phospho Buffer Set, BD Biosciences, #563239) at 4° C.). Cells were then permeabilized on ice for 20-22 minutes using 200 µl BD Phosflow Perm Buffer III (BD Biosciences, #558050) precooled at −20° C. After permeabilization, cells were washed three times with 200 µl of 1×TFP Perm/Wash buffer at 4° C. and then stained with the antibody mix during 60-65 min at 4° C. Finally, cells were washed (500 g, 5 min at 4° C. twice), resuspended in 250 µL of flow buffer (stored at 5° C. if needed), and analyzed on the MACSquant flow cytometer and analyzed with the MACSQuantify software (Miltenyi Biotec).

A dedicated immunophenotyping panel based on the combination of 13 specific markers was performed for the white blood cell subsets and markers indicated on table 19:

TABLE 19

| Cell subsets | Main markers |
| --- | --- |
| NK cells | CD159a⁺ |
| NK cells | CD20⁻, CD3⁺, CD159a⁺ |
| T Lymphocytes | CD20⁻, CD3⁺, CD159a⁻ |
| CD8+ T Effector Cells | CD20⁻, CD3⁺, CD159a⁻, CD8⁺ |
| CD4+ Helper T Cells | CD20⁻, CD3⁺, CD159a⁻, CD4⁺, CD25$^{low}$, FoxP3⁻ |
| CD4+ Regulatory T Cells | CD20⁻, CD3⁺, CD4⁺, CD25$^{Hi}$, FoxP3⁺ |
| CD8+ Central Memory T cells | CD20⁻, CD3⁺, CD159a⁻, CD8⁺, CD28⁺, CD95⁺ |
| CD8+ Effector Memory T cells | CD20⁻, CD3⁺, CD159a⁻, CD8⁺, CD28⁻, CD95⁺ |
| CD8+ Naïve T cells | CD20⁻, CD3⁺, CD159a⁻, CD8⁺, CD28⁺, CD95⁻ |
| CD4+ Central Memory T cells | CD20⁻, CD3⁺, CD159a⁻, CD4⁺, CD25$^{low}$, FoxP3⁻, CD28⁺, CD95⁺ |
| CD4+ Effector Memory T cells | CD20⁻, CD3⁺, CD159a⁻, CD4⁺, CD25$^{low}$, FoxP3⁻, CD28⁻, CD95⁺ |
| CD4+ Naïve T cells | CD20⁻, CD3⁺, CD159a⁻, CD4⁺, CD25$^{low}$, FoxP3⁻, CD28⁺, CD95⁻ |
| B cells | CD20⁺, CD3⁻, |
| Eosinophils | SSC$^{Hi}$, CD49d⁺ |
| Monocytes | CD14⁺ |
| Phosphorylated STAT5 | pSTAT5 |
| Proliferation Ki67 | Ki67 |

Figure 18:
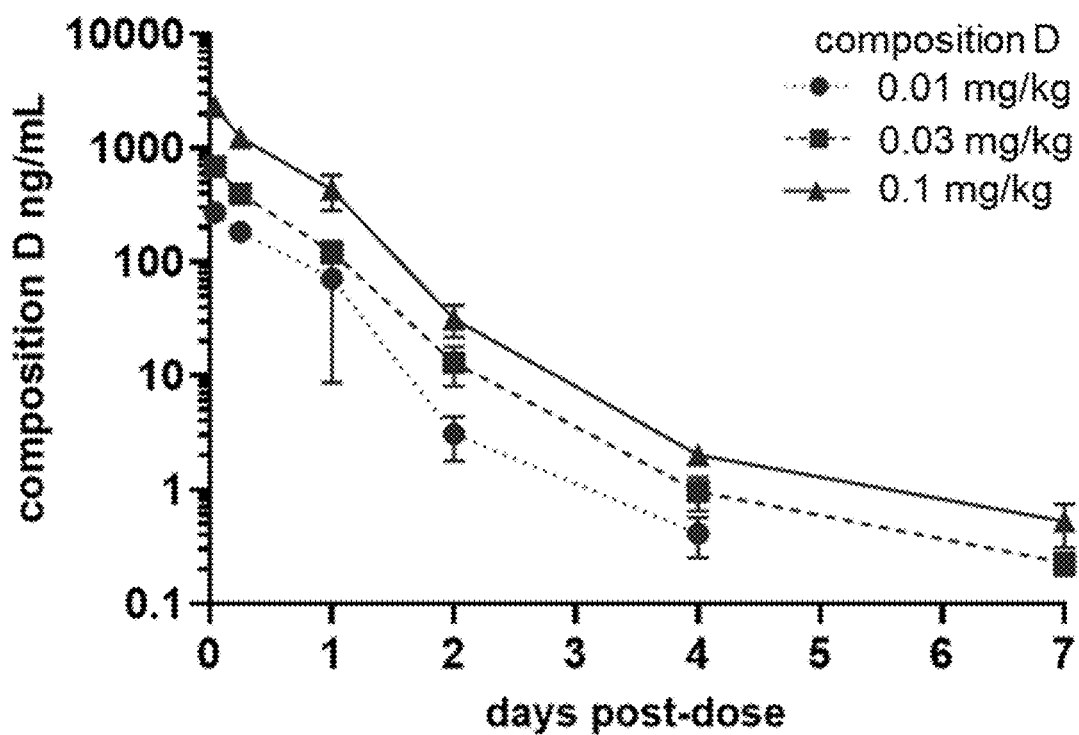
FIG. 18 depicts the pharmacokinetic profile of composition D injected intravenously to cynomolgus monkeys at three different doses. Concentration in plasma of composition D expressed as IL-2 mass equivalents is indicated on the y-axis and time on the x-axis.

In addition, hematological parameters were determined using the ADVIA 120 Hematology analyzer, including among others counts of erythrocytes, thrombocytes and various leucocyte types. The pharmacokinetic profile of composition D is shown in FIG. 18, along with the estimated PK parameters listed in Table 20. Composition D exhibited a sustained half-life (t½) and mean residence time (MRT-last).

TABLE 20

|  |  | Group | | |
| --- | --- | --- | --- | --- |
|  |  | 1 | 2 | 3 |
| Dose | µg/kg | 10 | 30 | 100 |
| CL | mL/h/kg | 2.73 | 3.52 | 3.65 |
| Vss | mL/kg | 33.7 | 48.6 | 47.8 |
| t½ | h | 10.0 | 10.2 | 9.5 |
| MRTlast | h | 12.7 | 13.8 | 13.1 |
| Cmax | ng/mL | 272 | 687 | 2315 |
| AUC(0-last) | h*ng/mL | 3896 | 8598 | 27607 |
| AUC(0-inf) | h*ng/mL | 3902 | 8601 | 27614 |
| AUC(0-inf)/Dose | h*ng/ml/(µg/kg) | 390 | 287 | 276 |
| AUC_% extrapolated | % | 0.15 | 0.04 | 0.03 |

Figure 19:
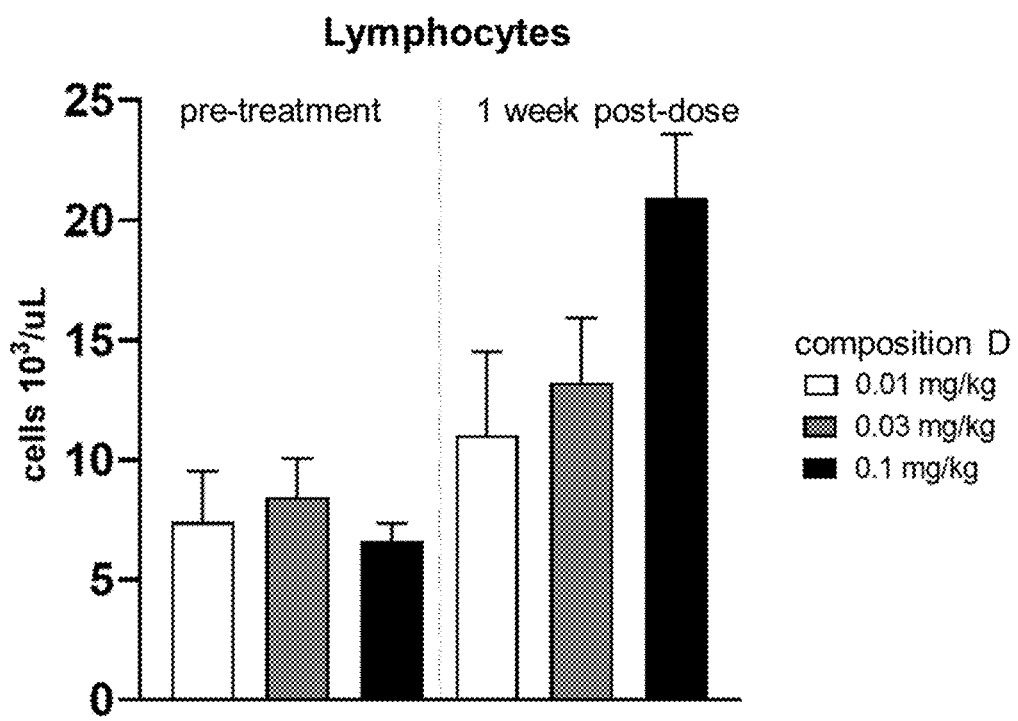
FIG. 19 shows bars indicating the effect of composition D on the cell counts of circulating lymphocytes in cynomolgus monkeys. Blood lymphocyte counts are indicated on the y-axis and x-axis is arranged by pretreatment (left) vs 1 week post-dose (right) at increasing doses.
Figure 20A:
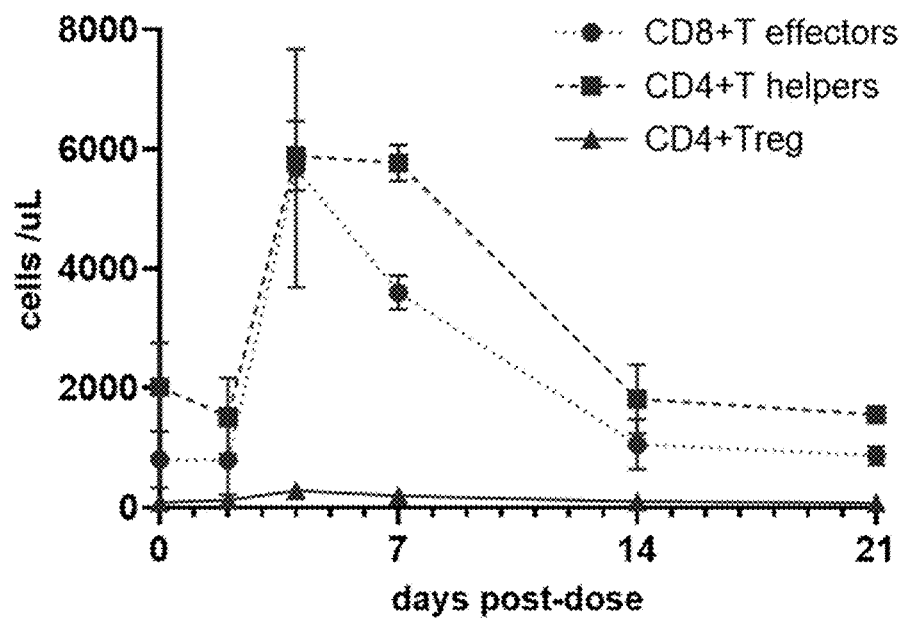
FIG. 20A shows the kinetic cell count profiles upon treatment with composition D for the two main T cell populations CD8+ T effectors (CD3+, CD8+) and CD4+ T helpers (CD3+, CD4+) as well as regulatory T cells (Treg; CD4+, FoxP3+, CD25Hi) expressed as number of cells per microliter of blood on the y-axis and time on the x-axis.
Figure 20B:
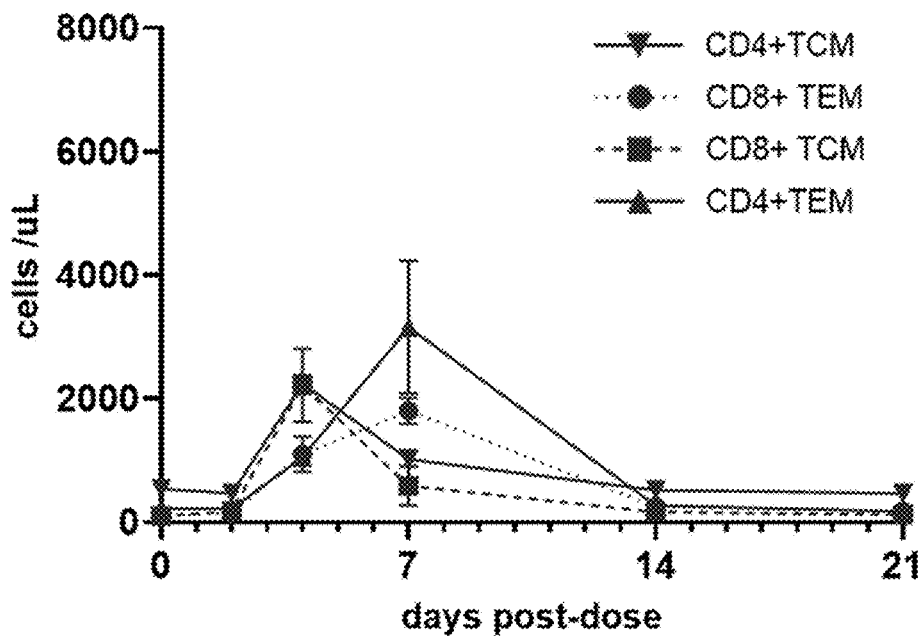
FIG. 20B shows the kinetic cell count profiles upon treatment with composition D for the effector memory (TEM, CD28−/CD95+) and central memory (TCM, CD28+/CD95+) subpopulations of both CD4+ and CD8+ T cells expressed as number of cells per microliter of blood on the y-axis and time on the x-axis.
Figure 20C:
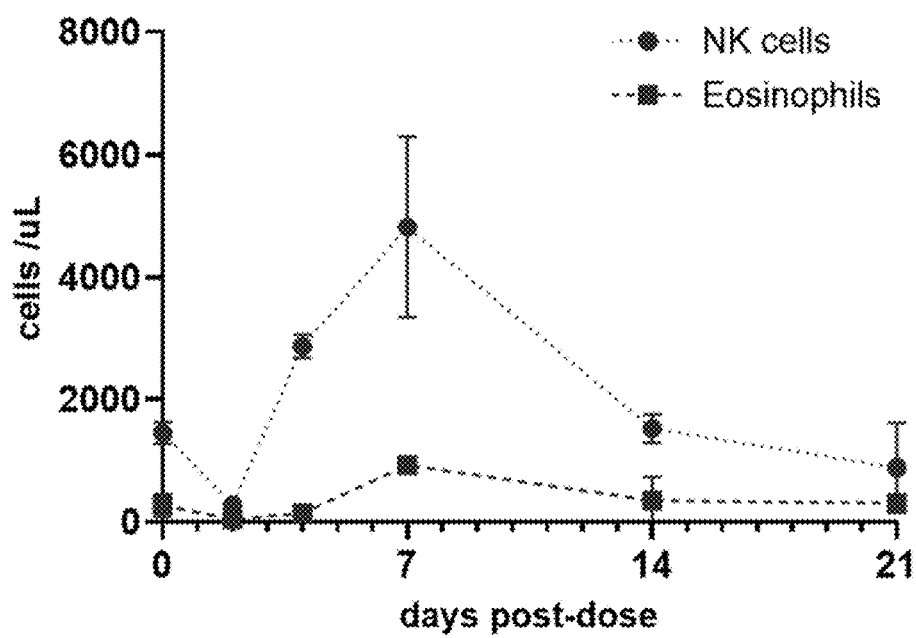
FIG. 20C shows cell count kinetic profiles upon treatment of cynomolgus monkeys with composition D for NK cells and eosinophils. Values are expressed as number of cells per microliter of blood on the y-axis and time on the x-axis.

Effects of composition D on different immune cell populations in blood were monitored. As shown in FIG. 19, composition D had a pronounced and dose-dependent effect on the expansion of lymphocytes one week post-dose. FIG. 20A depicts kinetic cell count profiles upon treatment with composition D for the two main T cell populations CD8+ T effectors (CD3+, CD8+) and CD4+ T helpers (CD3+, CD4+) as well as regulatory T cells (Treg; CD4+, FoxP3+, CD25Hi), showing a large expansion of T effectors and Theirs with limited effect on Tregs. FIG. 20B shows the treatment effect on the corresponding subpopulations of effector memory (TEM, CD20−, CD3+, CD159a−, CD28−, CD95+) and central memory (TCM, CD20−, CD3+, CD159a−, CD28+, CD95+) of both CD4+ and CD8+ T cells. All memory subpopulations showed a significant expansion compared to baseline. FIG. 20C shows how the treatment with composition D also led to an expansion of NK cells with limited effect on eosinophils.

Example 10—General Protocol for Synthesis of Modified IL-2 Polypeptides

A modified IL-2 polypeptide as described herein, such as a modified IL-2 polypeptide having an amino acid sequence of, for example, SEQ ID NO: 3, or any of SEQ ID NOs: 4-22, or a modified IL-2 polypeptide described in Tables 4-6, can be synthesized by ligating individual peptides synthesized using solid phase peptide synthesis (SPPS). Individual peptides are synthesized on an automated peptide synthesizer using the methods described below.

Commercially available reagents can be purchased from Sigma-Aldrich, Acros, Merck or TCI Europe, or any other suitable manufacturer, and can be used without further purification. Fmoc amino acids with suitable side-chain protecting groups for solid phase peptide synthesis can be purchased from Novabiochem, Christof Senn Laboratories AG or PeptART and they can be used as supplied. The polyethylene glycol derivatives used for peptide synthesis can be purchased by Polypure. HPLC grade $CH_3CN$ from Sigma Aldrich can be used for analytical and preparative HPLC purification.

High resolution mass spectra (FTMS) for peptides and proteins are measured on a Bruker solariX (9.4T magnet) equipped with a dual ESI/MALDI-FTICR source using 4-hydroxy-α-cyanocinnamic acid (HCCA) as matrix. CD spectra are recorded with a Jasco J-715 spectrometer with a 1.0 mm path length cell. Spectra are collected at 25° C. in continuous scanning mode with standard sensitivity (100 mdeg), 0.5 nm data pitch, 50 nm/min scanning speed, 1 nm bandwidth and 5 accumulations.

Peptides and proteins fragments are analyzed and purified by reverse phase high performance liquid chromatography (RP-HPLC). The peptide analysis and reaction monitoring are performed on analytical Jasco instruments with dual pumps, mixer and in-line degasser, autosampler, a variable wavelength UV detector (simultaneous monitoring of the eluent at 220 nm and 254 nm) and an injector fitted with a 100 µl injection loop. The purification of the peptide fragments is performed on a Gilson preparative instrument with 20 mL injection loop. In both cases, the mobile phase is MilliQ-$H_2O$ with 0.1% TFA (Buffer A) and HPLC grade $CH_3CN$ with 0.1% TFA (Buffer B). Analytical HPLC is performed on bioZen™ Intact C4 column (3.6 µm, 150×4.6 mm) or Shiseido Capcell Pak MG III (5 µm, 150×4.6 mm) column with a flow rate of 1 mL/min. Preparative HPLC is performed on a Shiseido Capcell Pak UG80 C18 column (5 µm, 50 mm I.D.×250 mm) at a flow rate of 40 mL/min.

The peptide segments are synthesized on a Syro I or a CS Bio 136X peptide synthesizers using Fmoc SPPS chemistry. The following Fmoc amino acids with side-chain protection groups are used: Fmoc-Ala-OH, Fmoc-Arg(Pbf)-OH, Fmoc-Asn(Trt)-OH, Fmoc-Asp(OtBu)-OH, Fmoc-Cys(Acm), Fmoc-Gln(Trt)-OH, Fmoc-Glu(OtBu)-OH, Fmoc-Gly-OH, Fmoc-His(l-Trt)-OH, Fmoc-Ile-OH, Fmoc-Leu-OH, Fmoc-Lys(Boc)-OH, Fmoc-Nle-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH. Fmoc-pseudoproline dipeptides are incorporated in the synthesis where necessary. Fmoc deprotections are performed with 20% piperidine in DMF (2×8 min), and monitored by UV at 304 nm with a feedback loop to ensure complete Fmoc removal. Couplings are performed with Fmoc-amino acid (3.0-5.0 equiv to resin substitution), HCTU or HATU (2.9-4.9 equiv) as coupling reagents and DIPEA or NMM (6-10 equiv) in DMF at room temperature or at 50° C. After pre-activating for 3 min, the solution is transferred and allowed to react with the peptide on-resin for either 30 min or 2 h depending on the amino acid. In some cases, double couplings are required. After coupling, the resin is treated with 20% acetic anhydride in DMF for capping any unreacted free amine. LiCl washes are performed where required. The allylester deprotection is performed using phenylsilane (24 equiv) and Palladium(0) tetrakis (triphenylphosphine) (0.5 equiv) in anhydrous dichloromethane.

The synthesis of the peptide segments by SPPS is monitored by microcleavage and analysis of the corresponding resin. The peptides are cleaved from the resin using a mixture of 95:2.5:2.5 TFA:DODT:$H_2O$ (α-ketoacid segments synthesized on α-ketoacid resins) or 95:2.5:2.5 TFA:TIPS:$H_2O$ (peptide synthesized on 2-cholorotrityl polystyrene resin) for 2 h. The resin is filtered off and the filtrate is evaporated and treated with cold diethyl ether, triturated and centrifuged. Ether layer is carefully decanted and the residue is resuspended in diethyl ether, triturated and centrifuged. Ether washings are repeated twice.

Figure 11:
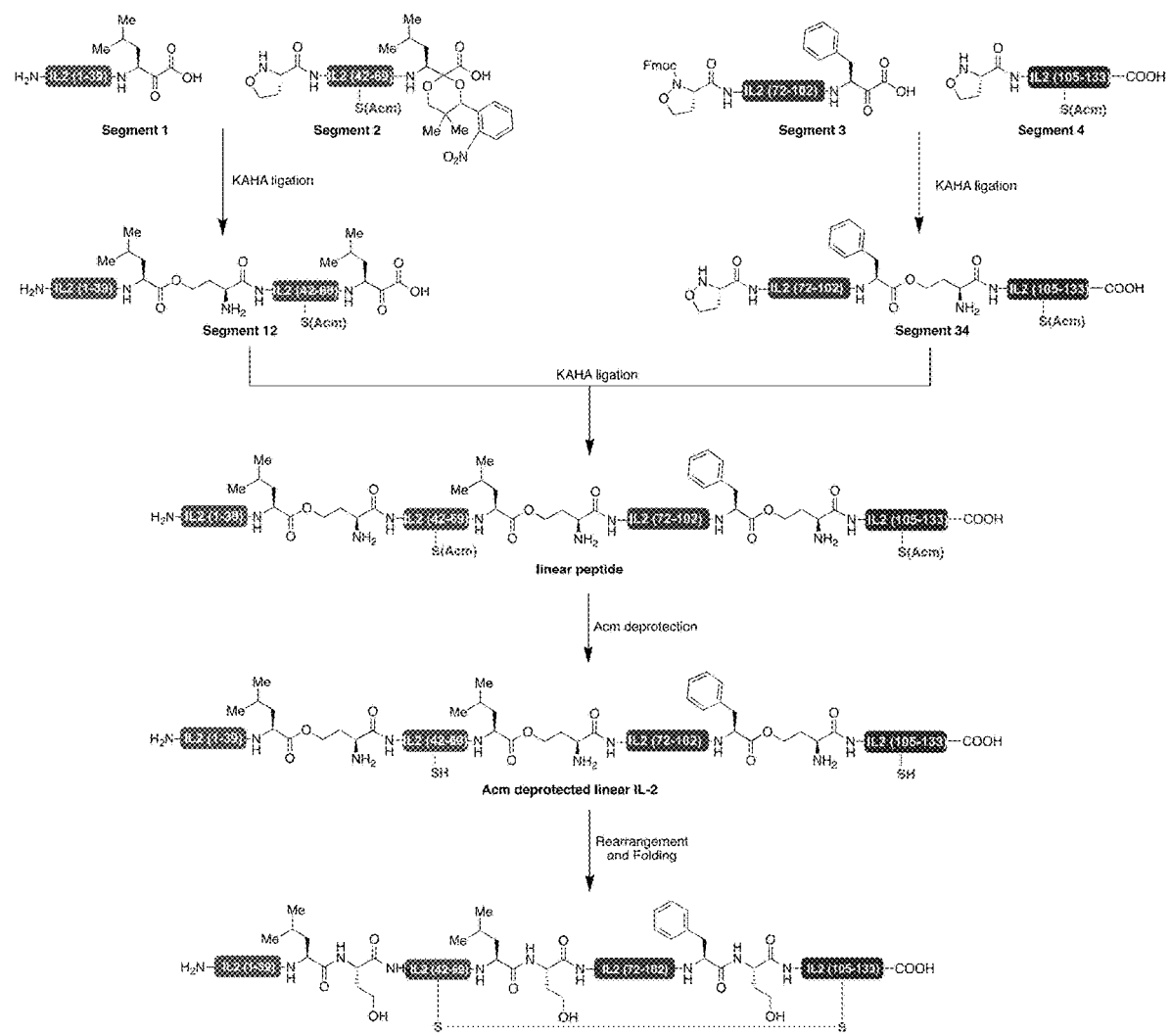
FIG. 11 shows a general synthetic scheme for preparing exemplary modified IL-2 polypeptides provided herein.
Figure 12A:
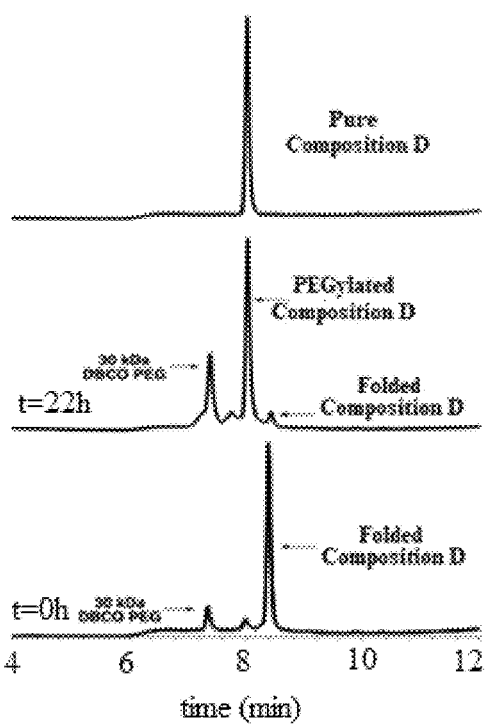
FIG. 12A shows an HPLC trace of purified, PEGylated Composition D, wherein the x-axis is retention time and the y-axis is absorbance.
Figure 12B:
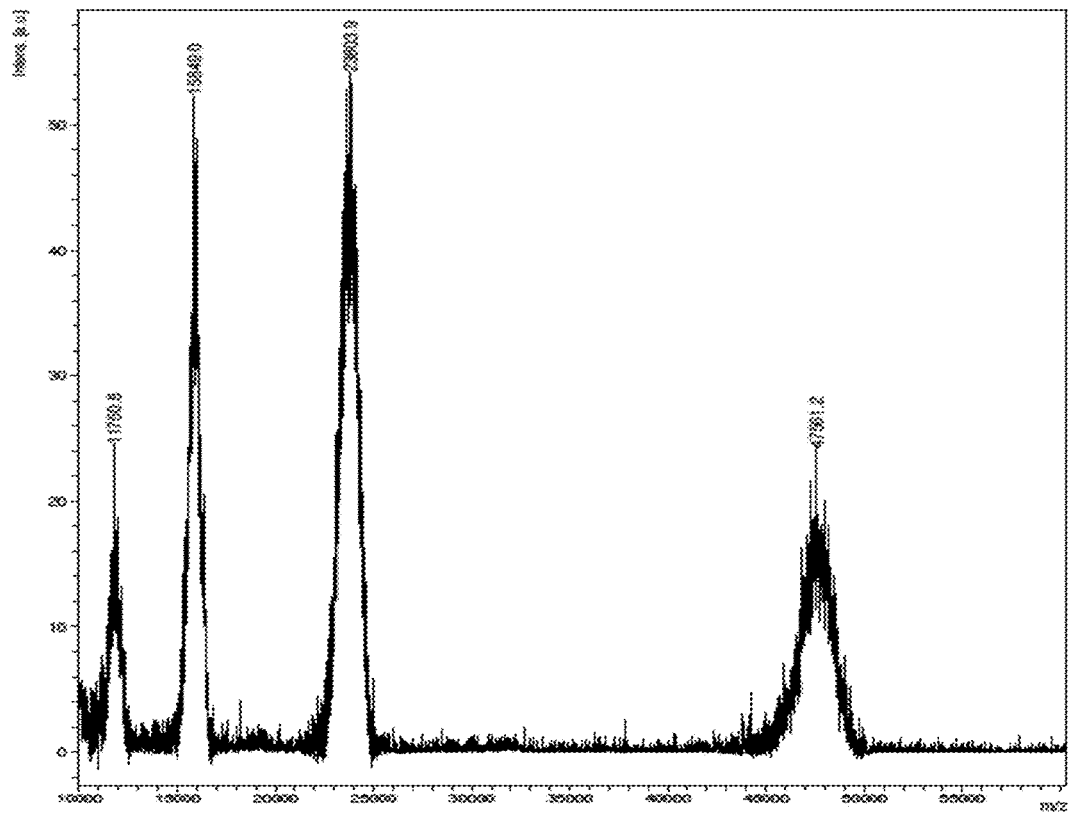
FIG. 12B shows a MALDI-TOF MS of purified, PEGylated Composition D, wherein the x-axis is mass to charge ratio and the y-axis is intensity of the signal.
Figure 12C:
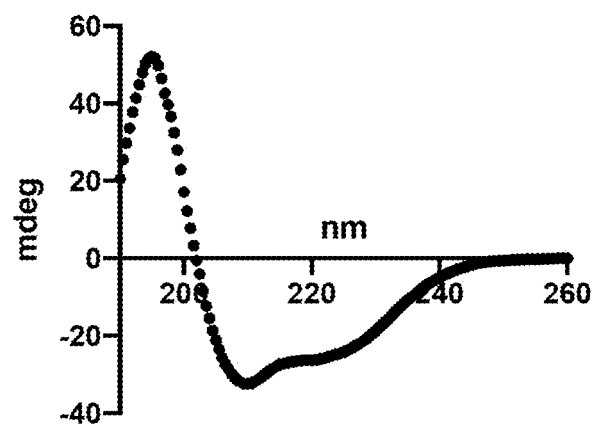
FIG. 12C shows a plot measuring the absorbance of polarized light of a modified IL-2 polypeptide, where the x-axis is wavelength of polarized light and the y-axis is absorbance. The sample shown in this plot is the modified PEGylated IL-2 polypeptide Composition D provided herein.

The general synthesis scheme used to produce the modified IL-2 polypeptides provided herein, which can also be used to synthesize other variants such as those provided in Table 7, is shown in FIG. 11. In particular, any modified IL-2 polypeptide of SEQ ID NOs: 3-22 may be synthesized using the general synthesis protocol provided herein, as can any variant of the sequences. Briefly, linear peptide fragments (Segments 1-4 as shown in FIG. 11) are prepared using SPPS, and any desired modification to the amino acid sequence of wild-type IL-2 (SEQ ID NO:1) is incorporated during the syntheses step. After purification of the individual fragments, segments 1 and 2 are ligated together, and segments 3 and 4 are ligated together separately. Then, resulting segments 12 and 34 are ligated together and universally deprotected to afford crude synthetic IL-2 polypeptide.

The resulting synthetic modified IL-2 polypeptides are then rearranged and folded. The linear polypeptide is then dissolved in aqueous 6M guanidine hydrochloride containing 0.1M Tris and 30 mM reduced glutathione (final polypeptide concentration of 15 μM, 93.2 mL). The pH is adjusted to 8.0 using 6M HCl. The solution is gently shaken at 50° C. for 3 hours and the folding monitored by analytical reverse phase HPLC using a Shiseido Capcell Pak UG80C18 column (4.6×250 mm) preheated to 60° C., with a gradient of 30 to 95% acetonitrile with 0.1% TFA in 22 min flow rate 1.0 mL/min. The solution is then cooled to room temperature and diluted 3× with a buffer containing 0.2M Tris and 2.5 mM oxidized glutathione, pH 8.0 over 30 minutes (final concentration of polypeptide of 5 μM). The resulting solution is stored at room temperature with shaking for 24 h. Folding progress is monitored by analytical HPLC using a Shiseido Proteonavi C4 column (4.6×250 mm) at room temperature, with a gradient of 30 to 95% acetonitrile with 0.1% TFA in 22 min, flow rate: 1.0 mL/min. After completion of folding (~24 hours), the folding solution is acidified with 10% aqueous TFA to ~pH 3 and purified by preparative HPLC, using a Shiseido Proteonavi C4 column (10×250 mm) with a gradient of 40-95% acetonitrile with 0.1% TFA in 40 min, flow rate: 5.0 mL/min. To the pooled fractions containing the modified IL-2 polypeptide is added mannitol (~3 mg) and the material frozen in liquid nitrogen and lyophilized. After lyophilization, a pure modified IL-2 polypeptide is obtained. It is characterized by circular dichroism to confirm the modified IL-2 polypeptide displays similar tertiary structure to wild-type IL-2. The resulting folded modified IL-2 polypeptide is then purified by HPLC.

9.1 General Procedure for Synthesis of IL-2 Segment 1 (IL-2(1-39)-Leu-α-Ketoacid)

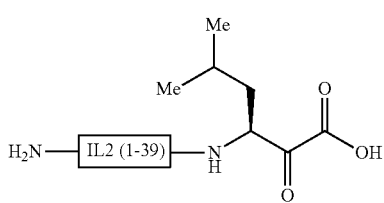

Segment 1

IL2 (1-39)-Leu-α-ketoacid is synthesized on Rink-amide resin pre-loaded with protected Fmoc-α-Leu-ketoacid with a substitution capacity of 0.25 mmol/g. The synthesis is performed up to Alai by automated Fmoc SPPS using the procedure described in the general methods section.

Variants of Segment 1: In some cases, the N-terminus is extended by the sequential coupling of Fmoc-amino-3,6 dioxaoctanoic acid, Fmoc-Lys(Fmoc) and Fmoc-NH-(PEG)$_{27}$-COOH. The progress of the peptide couplings is monitored by performing a microcleavage and analysis of the peptidyl resin using a mixture of (95:2.5:2.5) TFA:DODT:H$_2$O for 1.5 h. HPLC analysis is performed on a C18 column at 60° C. Once confirmed, a bigger batch is cleaved from the resin using a mixture of 95:2.5:2.5 TFA:DODT:H$_2$O (15 mL/g resin) for 2 h, following the procedure described in the general methods. Purification of crude IL2 (1-39) is performed by preparative HPLC using Shiseido capcell pak C18 column (50×250 mm) with a gradient of 30 to 80% CH$_3$CN with 0.1% TFA in 30 min. The N-terminus modified segment is purified using a gradient of 20 to 80% CH$_3$CN with 0.1% TFA in 30 min. The pure product fractions are pooled and lyophilized to obtain the pure IL2 (1-39) (Seg1) (31-69% yield for peptide synthesis, resin cleavage and purification steps). Analytical HPLC and HRMS are used to confirm the purity and exact mass of the product.

General Procedure for Synthesis of IL-2 Segment 2 [Opr-IL2 (42-69) Photoprotected-Leu-α-Ketoacid]

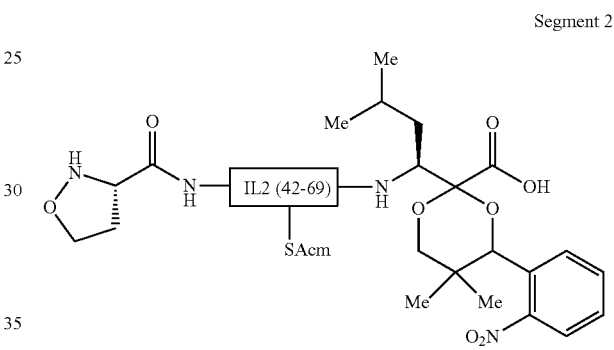

Segment 2

Opr-IL2 (42-69) Photoprotected-Leu-α-ketoacid segment is prepared on Rink Amide MBHA resin preloaded with Fmoc-Leucine-photoprotected-α-ketoacid with a substitution capacity of 0.25 mmol/g. The synthesis is performed up to Nle46 by automated Fmoc SPPS using the procedure described in the general methods section.

From position 45 to 42, the amino acid residues are varied to prepare various modified IL-2 segment 2. In all the cases, Boc-5-(S)-Oxaproline is manually coupled on the N-terminus of the segment.

Variants of Segment 2. In some cases, Tyr 45 or Phe 42 are substituted with non-canonical amino acids represented by, but not limited to N-alpha-(9-Fluorenylmethyloxycarbonyl)-L-biphenylalanine (Fmoc-L-Bip-OH) or N-alpha-(9-Fluorenylmethyloxycarbonyl)-O-benzyl-L-tyrosine (Fmoc-L-Tyr(Bzl)-OH. In some cases, modified tyrosine residues bearing PEG groups or azido groups as described in the detailed description are added by manual or automated SPPS. In some cases, a modified tyrosine residue bearing an O-allylic ester functionality (Structure 5) is used to couple a desired PEG group. The O-allyl group is then removed during an on-resin deprotection step, and the resulting free acid is coupled with the corresponding desired group, for example a PEG group or PEG group bearing an azide or alkyne functionality. In some cases, an amine bearing PEG group is coupled by manual SPPS, followed by further extension with sequential coupling of 3×Fmoc-Lys(Fmoc)-OH and [Fmoc-NH-(PEG)$_{27}$-COOH].

The progress of the peptide coupling is monitored by performing a microcleavage and analysis using a mixture of (95:2.5:2.5) TFA:DODT:H₂O for 1.5 h. HPLC analysis is performed on a C18 column at 60° C. Once confirmed, the entire batch is cleaved from the resin using a mixture of 95:2.5:2.5 TFA:DODT:H₂O (15 mL/g resin) for 2 h, following the procedure described in the general methods. Purification of crude IL2 (41-70) is performed by preparative HPLC using Shiseido capcell pak C18 column (50×250 mm) with a gradient of 30 to 40% or 40 to 60% CH₃CN with 0.1% TFA in 30 min. The pure product fractions are pooled and lyophilized to obtain the pure modified IL2 segment 2 (Seg2) (4-18% yield for peptide synthesis, resin cleavage and purification steps). Analytical HPLC and HRMS are used to confirm the purity and exact mass of the product.

General Procedure for Synthesis of IL-2 Segment 3
[Fmoc-Opr IL2 (72-102)-Phe-α-Ketoacid]

Segment 3

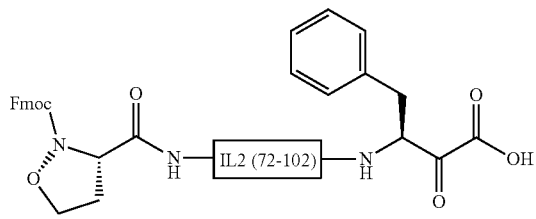

Fmoc-Opr IL2 (72-102)-Phenylalanine-α-ketoacid is synthesized on Rink Amide ChemMatrix resin pre-loaded with Fmoc-Phe-protected-α-ketoacid with a substitution capacity of ~0.25 mmol/g. Automated Fmoc SPPS is performed using the procedure described in the General Methods section up to Leu72. Fmoc-5-(S)-Oxaproline is manually coupled to the sequence. The progress of the peptide synthesis is monitored by performing a microcleavage and analysis using a mixture of (95:2.5:2.5) TFA:DODT:H₂O for 1.5 h. HPLC analysis is performed on a C18 column at 60° C. The peptide is cleaved from resin using a mixture of 95:2.5:2.5 TFA:DODT:H₂O (15 mL/g resin) for 2.0 h. Purification of crude Fmoc-Opr IL2 (72-102) is performed by preparative HPLC using Shiseido Capcell Pak C18 column (50×250 mm) preheated at 60° C., with a gradient of 20 to 75% CH₃CN with 0.1% TFA in 30 min. The pure product fractions are pooled and lyophilized to obtain Fmoc-Opr IL2 (72-102)-Phe-α-ketoacid (Seg3) in >98% purity.

General Procedure for Synthesis of IL-2 Segment 4
[Opr-IL2(105-133)]

Segment 4

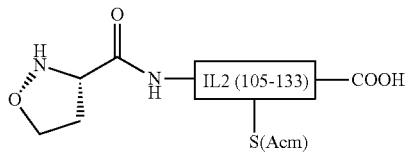

Opr-IL2(105-133) is synthesized on 2-Chlorotrityl-resin pre-loaded with Fmoc-Thr-OH with a substitution capacity of 0.25 mmol/g. After capping (diisopropylethylamine, methanol), the synthesis is performed by automated Fmoc SPPS up to Cys(Acm), residue 105. Then, Boc-5-oxaproline (2.00 equiv to resin) is coupled to the free amine on-resin. The progress of the peptide synthesis is monitored by performing a microcleavage and analysis using a mixture of (95:2.5:2.5) TFA:TIPS:H₂O for 1.5 h. HPLC analysis are performed on a C18 column at 60° C. The peptide is cleaved from resin using a mixture of 95:2.5:2.5 TFA:TIPS:H2O (15 mL/g resin) for 2.0 h. Purification of crude Opr-IL2(105-133) is performed by preparative HPLC using Shiseido Capcell Pak C4 column (50×250 mm) preheated at 60° C., with a gradient of 10 to 65% CH₃CN with 0.1% TFA in 10 min, then 65 to 95% CH₃CN with 0.1% TFA in 20 min. The pure product fractions are pooled and lyophilized to obtain Opr-IL2(105-133)) (Seg4) in >98% purity.

Synthesis of IL2 (1-69)-Protected Leu-α-Ketoacid

Segment 5

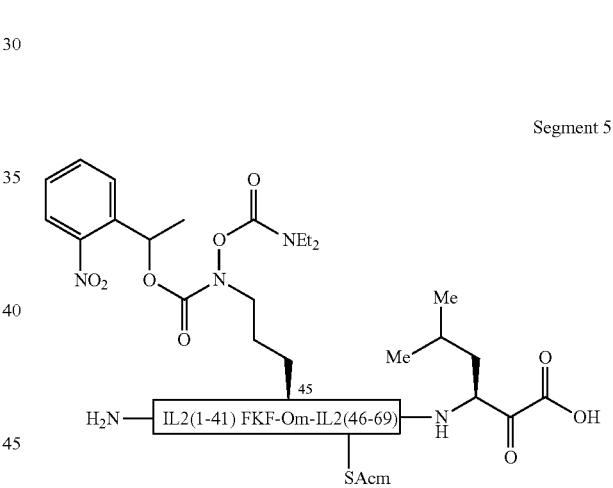

In some cases, an IL2 segment comprising residues (1-70) is synthesized by Fmoc-SPPS. IL2 (1-69)-protected Leu-α-ketoacid (Seg12) was synthesized on Rink-amide resin pre-loaded with protected Fmoc-α-Leu-ketoacid with a substitution capacity of 0.25 mmol/g. The synthesis is performed up to Alai by automated Fmoc SPPS using the procedure described in the general methods section. In some cases, all the methionines in the sequence are substituted with norleucine (Nle) or kept as methionine at the respective position. In some cases, Fmoc-amino acid with a backbone amine bearing —O—C(=O)NEt₂ and —(C=O)-nitrobenzylester protecting groups is coupled in position 45.

KAHA Ligations for the Synthesis of IL2 Linear Protein

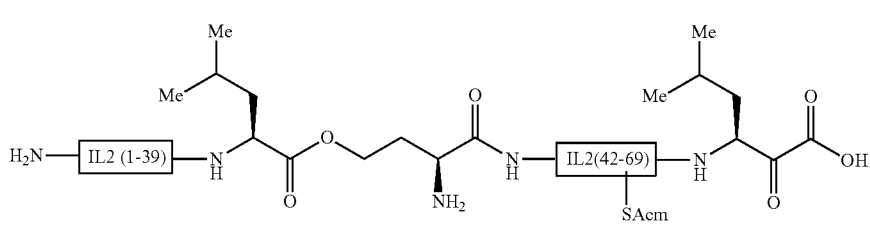

Segment 12

Ligation: Seg1 (1.2 equiv) and Seg2 (1 equiv) are dissolved in DMSO:H$_2$O (9:1) containing 0.1 M oxalic acid (20 mM peptide concentration) and allowed to react at 60° C. for 22 h. The ligation vial is protected from light by wrapping it in aluminum foil. The progress of the KAHA ligation is monitored by uHPLC using a Phenomenex C18 column (150×4.6 mm) at 60° C. with CH$_3$CN/H$_2$O containing 0.1% TFA as mobile phase, with a gradient of 5 to 95% CH$_3$CN in 7 min.

Photodeprotection and purification: After completion of the ligation the mixture is diluted with CH$_3$CN/H$_2$O (1:1) containing 0.1% TFA and irradiated at a wavelength of 365 nm for 1 h. The completion of photolysis reaction is confirmed by injecting a sample on uHPLC using previously described method.

The photo-deprotected sample is purified by preparative HPLC using a Shiseido Capcell Pack UG80 C18 column (50×250 mm) kept at 60° C., with a 2-step gradient: double gradient of CH$_3$CN in water with 0.1% TFA: 10 to 35% in 5 min, then 35 to 65% in 35 min, with a flow of 40 mL/min with CH$_3$CN and MQ-H$_2$O containing 0.1% TFA as the eluents. The fractions containing the product are pooled and lyophilized to give pure IL2-Seg12 (40% yield for ligation and purification steps). The purity and identity of the segment was confirmed by HPLC and HRMS.

KAHA Ligation for the Preparation of IL2-Seg34 (Representative Protocol)

Fmoc deprotection and purification: After completion of ligation, the reaction mixture is diluted with DMSO (6 mL), 5% of diethylamine (300 µL) is added and the reaction mixture is shaken for 7 min at room temperature. To prepare the sample for purification, it is diluted with DMSO (4 mL) containing TFA (300 µL).

The sample is purified by preparative HPLC on a Shiseido Capcell Pack UG80 C18 column (50×250 mm) kept at 60° C., using a gradient of 30 to 70% CH$_3$CN in water with 0.1% TFA in 35 min, with a flow of 40 mL/min. The fractions containing the product are pooled and lyophilized to give pure IL2-Seg34. The purity and identity of the segment 34 is confirmed by HPLC and HRMS.

Final KAHA Ligation for the Preparation of IL2 Linear Protein (Representative Protocol)

Ligation: IL2-Seg12 (1.2 equiv) and IL2-Seg34 (1 equiv) are dissolved in DMSO/H$_2$O (9:1) or (9.8:0.2) containing 0.1 M oxalic acid (15 mM peptide concentration) and the ligation is allowed to proceed for 24 h at 60° C. The progress of the KAHA ligation is monitored by analytical HPLC using a Shiseido Capcell Pak UG80 C18 column (250×4.6 mm) at 60° C. and CH$_3$CN/H$_2$O containing 0.1% TFA as mobile phase, with a gradient of 30 to 95% CH$_3$CN in 14 min.

Purification: After completion of ligation, the reaction mixture is diluted with DMSO followed by further dilution with a mixture of (1:1) CH$_3$CN:H$_2$O containing 0.1% TFA

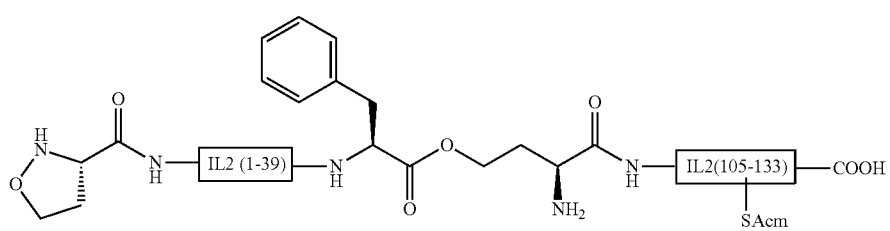

Segment 34

Ligation: IL2-Seg3 (1.2 equiv) and IL2-Seg4 (1 equiv) are dissolved in DMSO/H$_2$O (9:1) or (9.8:0.2) containing 0.1 M oxalic acid (15 mM) and allowed to react for 16 h at 60° C. The progress of the KAHA ligation is monitored by uHPLC using a Phenomenex C18 column (150×4.56 mm) at 60° C. using CH$_3$CN/H$_2$O containing 0.1% TFA as mobile phase, with a gradient of 30 to 70% CH$_3$CN in 7 min.

Fmoc deprotection and purification: After completion of ligation, the reaction mixture is diluted with DMSO (6 mL), 5% of diethylamine (300 µL) is added and the reaction mixture is shaken for 7 min at room temperature. To prepare the sample for purification, it is diluted with DMSO (4 mL) containing TFA (300 µL).

(7 mL). The sample is purified by injecting on a preparative HPLC using a Shiseido Capcell Pack UG80 C18 column (50×250 mm) preheated at 60° C., with a 2-step gradient: 10 to 40% in 5 min and 40 to 80% in 35 min, flow rate: 40 mL/min with CH$_3$CN and MQ-H$_2$O containing 0.1% TFA as the eluents. The fractions containing the product are pooled and lyophilized to give pure IL2 linear protein with Acm. The purity and identity of the IL-2 linear protein with 2×Acm are confirmed by HPLC and HRMS.

Acm deprotection: IL2 linear protein with 2×Acm is dissolved in AcOH/H$_2$O (1:1) (0.25 mM protein concentration) and AgOAc (1% m/v) is added to the solution. The mixture is shaken for 2.5 h at 50° C. protected from light. After completion of reaction as ascertained by HPLC, the sample is diluted with CH$_3$CN:H$_2$O (1:1) containing 0.1% TFA, and purified by preparative HPLC using a Shiseido CapCell Pak UG80 C18 column (20×250 mm) kept at 60° C. A 2-step gradient is used for purification: 10 to 40% in 5 min and 40 to 95% in 30 min, flow rate: 10 mL/min, with CH$_3$CN and MQ-H$_2$O containing 0.1% TFA as the eluents. The fractions containing the product are pooled and lyophilized to give pure IL2 linear protein with 2× free cysteines.

Folding of IL-2 Linear Protein (Representative Protocol)

Rearrangement of linear protein: the linear protein is dissolved in aqueous 6M Gu.HCl containing 0.1 M Tris and 30 mM reduced glutathione (15 μM protein concentration), which is adjusted to pH 8.0 by solution of 6M aq. HCl. The mixture is gently shaken at 50° C. for 2 h and rearrangement is monitored by analytical reverse phase HPLC using a bioZen™ 3.6 μm Intact C4 column (150×4.6 mm) at 25° C., with a gradient of 30 to 95% CH$_3$CN in H$_2$O with 0.1% TFA in 18 min, flow rate: 1.0 mL/min.

Folding of the linear rearranged protein: The solution is cooled to room temperature and diluted 3-fold with a second buffer solution containing 0.1 M Tris and 1.5 mM oxidized glutathione at pH 8.0. The mixture is stored at room temperature and the progress is monitored by analytical HPLC using a bioZen™ 3.6 μm Intact C4 column (150×4.6 mm) at 25° C., with a gradient of 30 to 95% acetonitrile in water with 0.1% TFA in 18 min, flow rate: 1.0 mL/min. After 20 h, the folding solution is acidified with 10% aqueous TFA to pH 3-4 and purified on preparative HPLC, using a Shiseido Proteonavi C4 column (20×250 mm) with a two-step gradient of 5 to 40 to 95% acetonitrile in water with 0.1% TFA in 60 min, flow rate: 10.0 mL/min. The fractions containing the folded IL2 protein are pooled together and lyophilized. The Purity and identity of the pure folded protein is further confirmed by analytical RP-HPLC, high-resolution ESI mass spectrometry and a variety of other protein characterization methods.

Further Modification of the Folded IL2

In some cases, the folded protein IL2 is further modified by reaction with a DBCO-polyethylene glycol polymer. The folded IL2 is dissolved in a CH$_3$CN:H$_2$O (1:1) (50 μM protein concentration) and DBCO-PEG (3 equiv) are added. The reaction is gently mixed at 25° C. for 20 h, monitoring the progress using analytical HPLC with a bioZen™ 3.6 μm Intact C4 column (150×4.6 mm) at 25° C., using a gradient of 30 to 95% CH$_3$CN in water with 0.1% TFA in 18 min, flow rate: 1.0 mL/min. after 20 h, the reaction mixture is diluted with (1:1) CH$_3$CN/H$_2$O+0.1% TFA and purified on preparative HPLC, using a Shiseido Proteonavi C4 column (20×250 mm) with a two-step gradient of 5 to 40 to 95% CH$_3$CN in water with 0.1% TFA in 60 min, flow rate: 10.0 mL/min. The fractions containing the pegylated IL2 protein are pooled together and lyophilized. The Purity and identity of the pure folded protein is further confirmed by analytical RP-HPLC, high-resolution ESI mass spectrometry and a variety of other protein characterization methods.

Formulation of IL2 Synthetic Variants

In some cases, the lyophilized folded protein is directly resuspended in (a) PBS or (b) 10 mM Na$_2$HPO$_4$ buffer solution pH 7.5, containing 0.022% SDS and 50 mg/mL mannitol. In some cases, the sample is resuspended in 0.05 M Na$_2$HPO$_4$ buffer solution (pH 7.5), containing 1% SDS and 50 mg/mL mannitol and sequentially dialyzed against solutions containing decreasing SDS concentration for 24-48 h. The final formulated protein consisted is in 10 mM Na$_2$HPO$_4$ buffer pH 7.5, 0.022% SDS and 50 mg/mL mannitol. The formulated protein is directly used for further studies or assays or stored at −80° C.

What is claimed is:

1. A modified interleukin-2 (IL-2) polypeptide, comprising:
a first polymer covalently attached at residue F42Y and a second polymer covalently attached at residue Y45 of the modified IL-2 polypeptide, and wherein residue position numbering of the modified IL-2 polypeptide is based on SEQ ID NO:1 as a reference sequence.

2. The modified IL-2 polypeptide of claim 1, wherein the first polymer comprises a water-soluble polymer.

3. The modified IL-2 polypeptide of claim 1, wherein the first polymer has a weight average molecular weight of at most 50,000 Daltons, at most 25,000 Daltons, at most 10,000 Daltons, or at most 6,000 Daltons.

4. The modified IL-2 polypeptide of claim 1, wherein the first polymer has a weight average molecular weight of from 250 Daltons to 50,000 Daltons.

5. The modified IL-2 polypeptide of claim 4, wherein the second polymer has a weight average molecular weight of from 250 Daltons to 50,000 Daltons.

6. The modified IL-2 polypeptide of claim 1, wherein the first polymer has a weight average molecular weight of from 5,000 Daltons to 40,000 Daltons and the second polymer has a weight average molecular weight of from 250 Daltons to 1,000 Daltons.

7. The modified IL-2 polypeptide of claim 1, wherein each of the first polymer and the second polymer independently comprises a water-soluble polymer.

8. The modified IL-2 polypeptide of claim 7, wherein each water-soluble polymer comprises poly(alkylene oxide), polysaccharide, poly(vinyl pyrrolidone), poly(vinyl alcohol), polyoxazoline, poly(acryloylmorpholine), or a combination thereof.

9. The modified IL-2 polypeptide of claim 1, wherein the modified IL-2 polypeptide comprises one or more PEGylated tyrosine having a structure of formula (I),

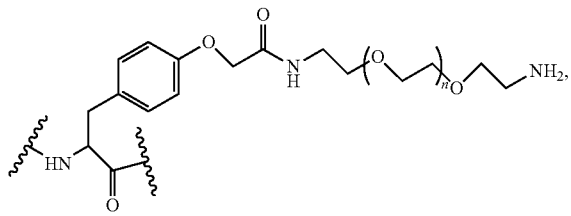

Formula (I)

wherein n is an integer selected from 4 to 30.

10. The modified IL-2 polypeptide of claim 9, wherein the one or more PEGylated tyrosine is located at residue 42, residue 45, or both.

11. The modified IL-2 polypeptide of claim 1, wherein the modified IL-2 polypeptide comprises at least two amino acid substitutions, wherein the at least two amino acid substitutions are selected from:
a) a homoserine (Hse) residue located in any one of residues 35-45;
b) a homoserine residue located in any one of residues 61-81; and
c) a homoserine residue located in any one of residues 94-114.

12. The modified IL-2 polypeptide of claim 11, wherein the modified IL-2 polypeptide comprises Hse41, Hse71, Hse104, or a combination thereof.

13. The modified IL-2 polypeptide of claim 11, wherein the modified IL-2 polypeptide further comprises a norleucine (Nle) substitution, wherein the Nle substitution is located at residue 23, 39, 46, or any combination thereof.

14. The modified IL-2 polypeptide of claim 13, wherein the modified IL-2 polypeptide comprises a polypeptide sequence identical to that of SEQ ID NO: 3.

15. The modified IL-2 polypeptide of claim 1, wherein binding between the modified IL-2 polypeptide and IL-2 Receptor β (IL-2Rβ) is increased by at least 0.1%, at least 1%, at least 2%, at least 5%, at least 10%, at least 15%, or at least 20% compared to the binding between a wild-type IL-2 polypeptide and IL-2Rβ.

16. The modified IL-2 polypeptide of claim 1, wherein binding between the modified IL-2 polypeptide and IL-2 Receptor α (IL-2Rα) is reduced by at least 99% compared to the binding between a wild-type IL-2 polypeptide and IL-2Rα.

17. The modified IL-2 polypeptide of claim 14, wherein the first polymer has a weight average molecular weight of from 250 Daltons to 50,000 Daltons and the second polymer has a weight average molecular weight of from 250 Daltons to 50,000 Daltons, and wherein each polymer independently comprises a water-soluble polymer.

18. The modified IL-2 polypeptide of claim 14, wherein the first polymer has a weight average molecular weight of from 120 Daltons to 1000 Daltons and the second polymer has a weight average molecular weight of from 120 Daltons to 1000 Daltons, and wherein each polymer comprises polyethylene glycol.

19. The modified IL-2 polypeptide of claim 14, wherein residue F42Y with the first polymer attached and residue Y45 with the second polymer attached each comprise a structure of Formula D,

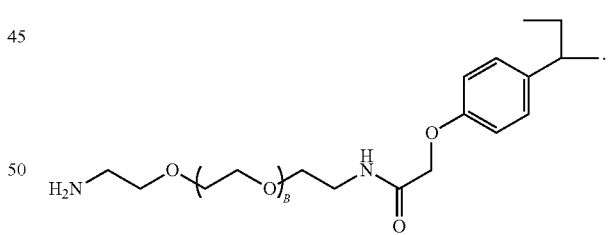

Formula D

20. The modified IL-2 polypeptide of claim 14, wherein the first polymer has a weight average molecular weight of from 5,000 Daltons to 40,000 Daltons and the second polymer has a weight average molecular weight of from 250 Daltons to 1,000 Daltons, and wherein each polymer comprises polyethylene glycol.

* * * * *